US010619156B2

(12) United States Patent
Yu et al.

(10) Patent No.: US 10,619,156 B2
(45) Date of Patent: *Apr. 14, 2020

(54) HYBRID TRNA/PRE-MIRNA MOLECULES AND METHODS OF USE

(71) Applicant: The Regents of the University of California, Oakland, CA (US)

(72) Inventors: Aiming Yu, Granite Bay, CA (US); Weipeng Wang, Davis, CA (US); Qiuxia Chen, Sacramento, CA (US); Meimei Li, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 205 days.

This patent is subject to a terminal disclaimer.

(21) Appl. No.: 15/313,555

(22) PCT Filed: May 21, 2015

(86) PCT No.: PCT/US2015/031861
§ 371 (c)(1),
(2) Date: Nov. 23, 2016

(87) PCT Pub. No.: WO2015/183667
PCT Pub. Date: Dec. 3, 2015

(65) Prior Publication Data
US 2018/0237772 A1 Aug. 23, 2018

Related U.S. Application Data

(60) Provisional application No. 62/003,806, filed on May 28, 2014.

(51) Int. Cl.
C12N 15/11 (2006.01)

(52) U.S. Cl.
CPC ............ *C12N 15/111* (2013.01); *C12N 15/11* (2013.01); *C12N 2310/141* (2013.01); *C12N 2310/3519* (2013.01)

(58) Field of Classification Search
CPC ............ A01K 2207/05; C12N 115/113; C12N 2310/141
See application file for complete search history.

(56) References Cited

U.S. PATENT DOCUMENTS

| | | | |
|---|---|---|---|
| 2005/0075492 A1 | 4/2005 | Chen et al. | |
| 2007/0287678 A1* | 12/2007 | Slack | C12N 15/113 514/44 A |
| 2009/0004668 A1 | 1/2009 | Chen et al. | |
| 2009/0081802 A1* | 3/2009 | Ritt | C12N 15/101 436/94 |
| 2009/0298920 A1 | 12/2009 | Dardel et al. | |
| 2010/0144831 A1 | 6/2010 | Fakhral et al. | |
| 2012/0219958 A1 | 8/2012 | Weidhaas | |
| 2013/0338215 A1 | 12/2013 | Lieberman et al. | |
| 2017/0049909 A1* | 2/2017 | Cullen | C12N 15/111 |

FOREIGN PATENT DOCUMENTS

| | | | | |
|---|---|---|---|---|
| EP | 2566515 A2 | 3/2013 | | |
| WO | WO-9951755 A2 * | 10/1999 | ......... | A01K 67/0278 |
| WO | WO 2013/106766 A2 | 7/2013 | | |
| WO | WO 2013/170365 A1 | 11/2013 | | |
| WO | WO 2015/183667 A1 | 12/2015 | | |
| WO | WO 2016/153880 A2 | 9/2016 | | |

OTHER PUBLICATIONS

PCT International Search Report and Written Opinion dated Sep. 16, 2015 issued in PCT/US2015/031861.
PCT International Preliminary Report on Patentability and Written Opinion dated Dec. 8, 2016 issued in PCT/US2015/031861.
PCT Invitation to Pay Additional Fees and, Where Applicable, Protest Fee dated Aug. 3, 2016 issued in PCT/US16/22681.
PCT International Search Report and Written Opinion dated Oct. 5, 2016 issued in PCT/US16/22681.
Chen et al., (2014) "A general approach to high-yield biosynthesis of chimeric RNAs bearing various types of functional small RNAs for broad applications," *SCHOLARONE Manuscripts*, Oxford University Press, [for Peer Review] 27pp.
Chen et al., (2015) "A general approach to high-yield biosynthesis of chimeric RNAs bearing various types of functional small RNAs for broad applications," *Nucleic Acids Research*, 43(7):3857-3869 [retrieved on Mar. 23, 2015 at http://nar.oxfordjournals.org/], 13pp.
Duan et al., (Nov. 2016) "Bioengineered non-coding RNA agent (BERA) in action," *Bioengineered*, 7(6):411-417.
Ho et al., (Mar. 2016) "Bioengineering of noncoding RNAs for research agents and therapeutics," *Wiley Interdiscip Rev RNA*, 7(2):186-197.
Han et al., (2017) "Co targeting of DNA, RNA, and protein molecules provides optimal outcomes for treating osteosarcoma and pulmonary metastasis in spontaneous and experimental metastasis mouse models," *Oncotarget*, 8(19):30742-30755.
Li et al., (Nov. 2014) "Rapid Production of Novel Pre-MicroRNA Agent hsa-mir-27b in *Escherichia coli* Using Recombinant RNA Technology for Functional Studies in Mammalian Cells," *Drug Metab Dispos*, 42(11):1791-1795 [Downloaded from dmd.aspetjournals. org at ASPET Journals on Jul. 27, 2016].
Li et al., (Jul. 2015) "Chimeric MicroRNA-1291 Biosynthesized Efficiently in *Escherichia coli* Is Effective to Reduce Target Gene Expression in Human Carcinoma Cells and Improve Chemosensitivity," *Drug Metabolism and Disposition*, 43(7): 1129-1136.
Liu et al., (2010) "DNAzyme-mediated recovery of small recombinant RNAs from a 5S rRNA-derived chimera expressed in *Escherichia coli*," *BMC Biotechnology*, 10:85, 9pp.
Nelissen et al., (2012) "Fast production of homogeneous recombinant RNA—towards large-scale production of RNA," *Nucleic Acids Research*, 40(13):e102, 12pp [Downloaded on Mar. 19, 2013 at http://nar.oxfordjournals.org/ at Kainan University].

(Continued)

*Primary Examiner* — Brian Whiteman
(74) *Attorney, Agent, or Firm* — Brian E. Davy; Bozicevic, Field & Francis LLP

(57) ABSTRACT

Provided are hybrid tRNA/pre-microRNA and tRNA/shRNA molecules and methods of making and using.

17 Claims, 32 Drawing Sheets

Specification includes a Sequence Listing.

(56) References Cited

OTHER PUBLICATIONS

Pan et al., (Oct. 2013) "Small Nucleolar RNA-Derived MicroRNA hsa-miR-1291 Modulates Cellular Drug Disposition through Direct Targeting of ABC Transporter ABCC1," *Special Section on Epigenetic Regulation of Drug Metabolizing Enzymes and Transporter, Drug Metabolism and Disposition*, 41(10): 1744-1751.

Pavon-Eternod et al., (2013) "Overexpression of initiator methionine tRNA leads to global reprogramming of tRNA expression and increased proliferation in human epithelial cells," *RNA*, 19(4):461-466 [Downloaded from rnajournal.cshlp.org on Oct. 11, 2016—Published by Cold Spring Harbor Laboratory Press].

Ponchon et al., (Jul. 2007) "Recombinant RNA technology: the tRNA scaffold," *Nature Methods*, 4(7):571-576.

Ponchon et al., (2009) "A generic protocol for the expression and purification of recombinant RNA in *Escherichia coli* using a tRNA scaffold," *Nature Protocols*, 4(6):947-959.

Reese et al., (2010) "Identification of Novel MicroRNA-Like Molecules Generated from Herpesvirus and Host tRNA Transcripts," *Journal of Virology*, 84(19):10344-10353.

Scherer et al., (2007) "Optimization and characterization of tRNA-shRNA expression constructs," *Nucleic Acids Research*, 35(8):2620-2628.

Tarasov et al., (2007) "Differential Regulation of microRNAs by p53 Revealed by Massively Parallel Sequencing: MiR-34a is a p53 Target That Induces Apoptosis and G1-arrest," *Cell Cycle*, 6(13):1586-1593.

Urayama et al., (2015) "Application of novel RNA aptamer-based Rnase I activity assay for pancreatic cancer biomarker development," *American Association for Cancer Research*, Annual Meeting Apr. 18-22, 2015, Philadelphia, Presentation Abstract, 2 pp [retrieved on Mar. 21, 2015 at http://www.abstractsonline.com/Plan/AbstractPrintView.aspx?mID=3682&sKey=cae555b . . . ].

Wang et al., (Aug. 2015) "Bioengineering Novel Chimeric microRNA-34a for Prodrug Cancer Therapy: High-Yield Expression and Purification, and Structural and Functional Characterization," *The Journal of Pharmacology and Experimental Therapeutics*, 354(2): 131-141.

Zhao et al., (May 24, 2016) "Genetically engineered pre-microRNA-34a prodrug suppresses orthotopic osteosarcoma xenograft tumor growth via the induction of apoptosis and cell cycle arrest," *Scientific Reports*, 6:26611, 11pp.

Zhao et al., (Dec. 15, 2016) "Combination therapy with bioengineered miR-34a prodrug and doxorubicin synergistically suppresses osteosarcoma growth," HHS Public Access, Author Manuscript; available in PMC Dec. 15, 2016 24pp [Published in final edited form as: *Biochem Parmacol.*, Dec. 2015; 98(4):602-613].

U.S. Appl. No. 15/558,563, filed Sep. 15, 2017, Yu.

Extended European Search Report dated Feb. 20, 2018 issued in EP 15800458.0.

PCT International Preliminary Report on Patentability and Written Opinion dated Oct. 5, 2017 issued in PCT/US2016/22681.

Bogerd et al., (2010) "A Mammalian Herpesvirus Uses Noncanonical Expression and Processing Mechanisms to Generate Viral MicroRNAs," Molecular Cell., vol. 37, No. 1, Jan. 1, 2010, pp. 135-142.

\* cited by examiner

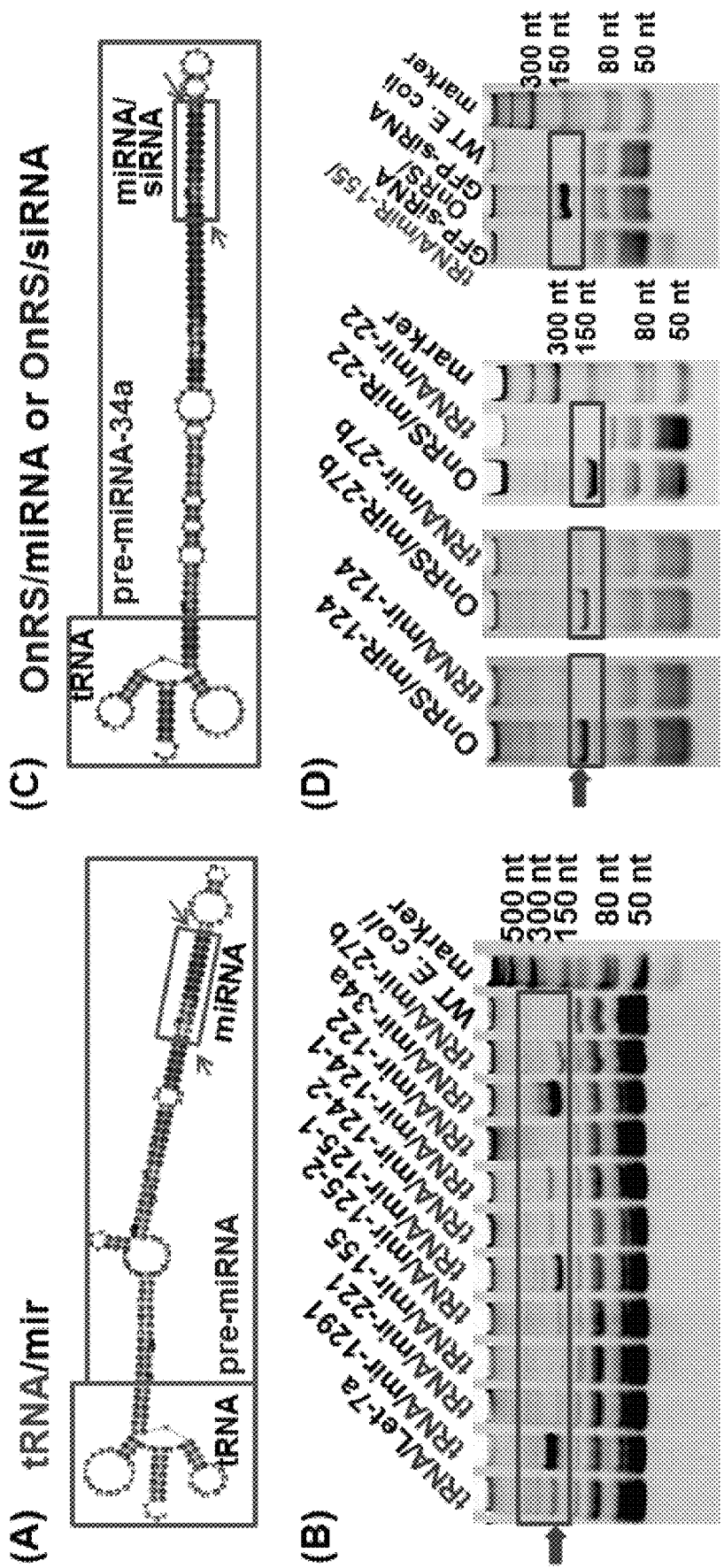
Fig. 1A-D

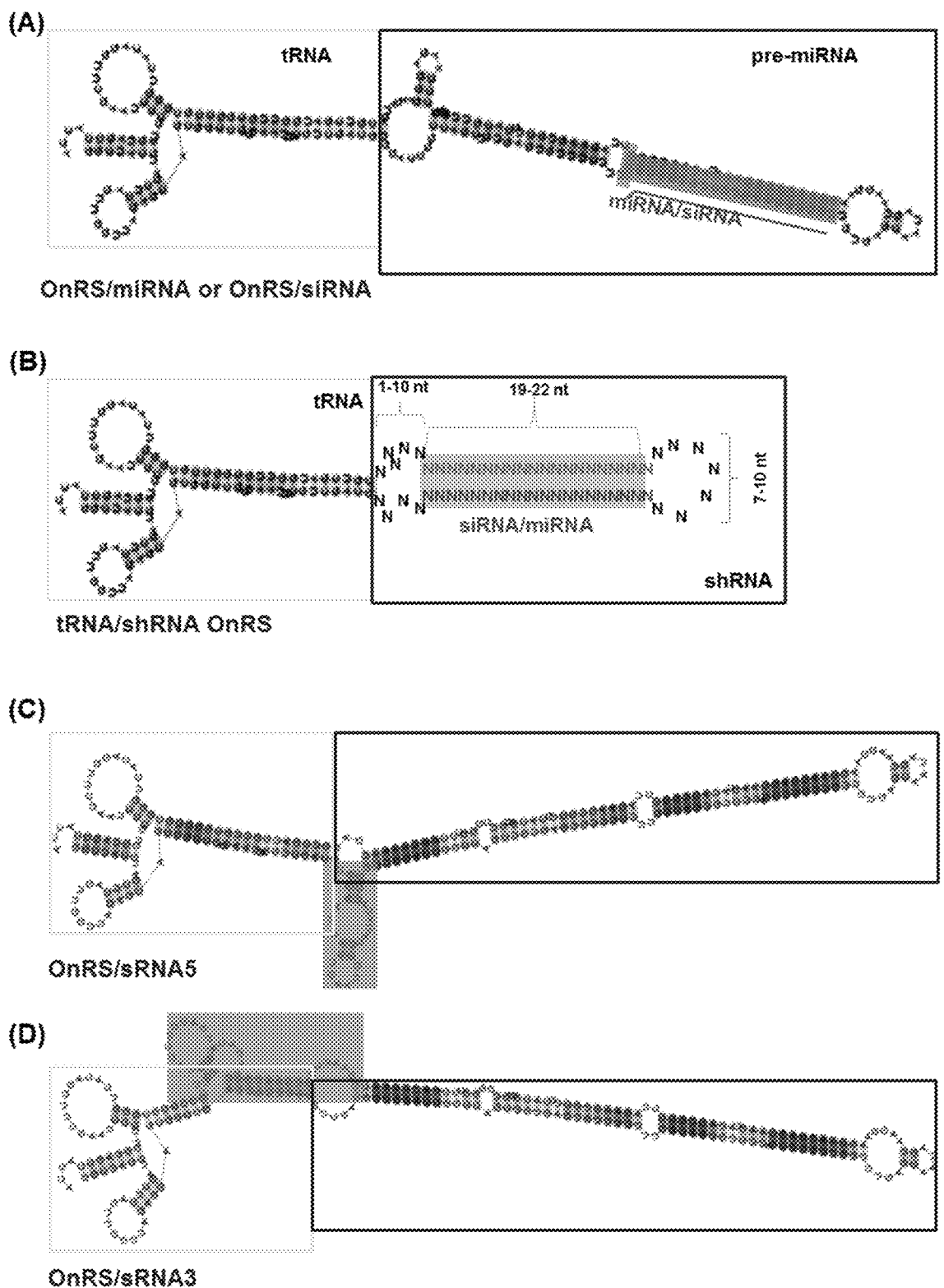
Fig. 2A-D

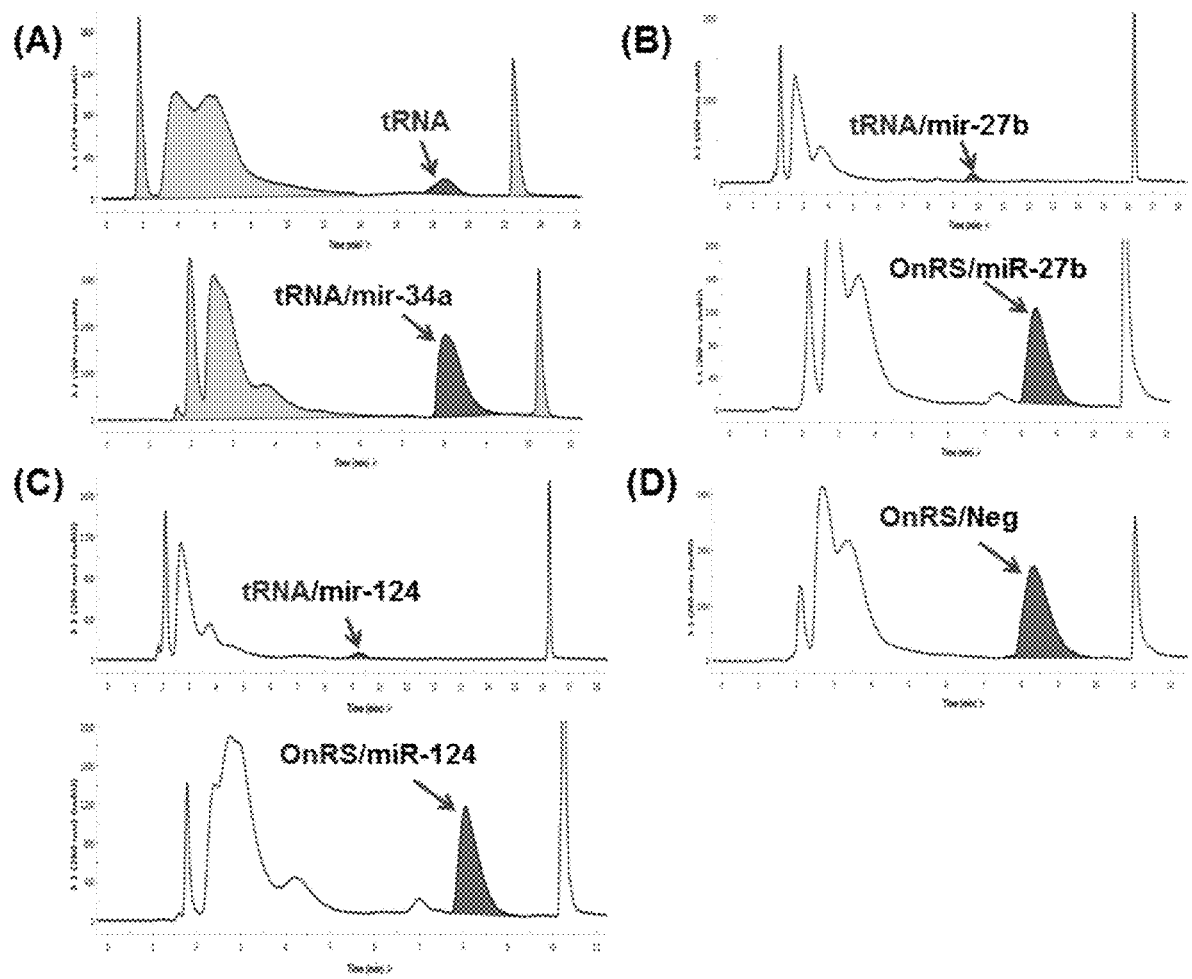
Fig. 3A-D

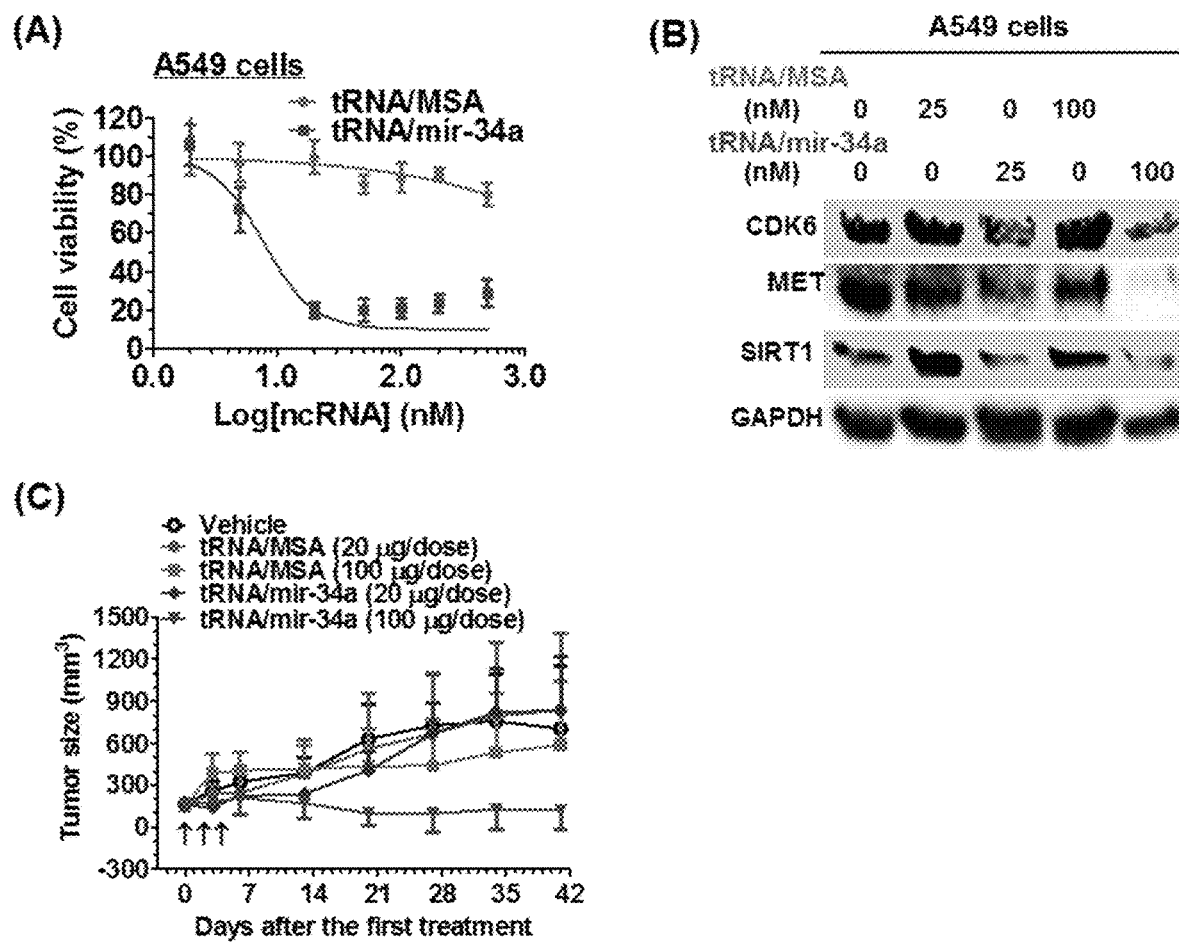
Fig. 4A-C

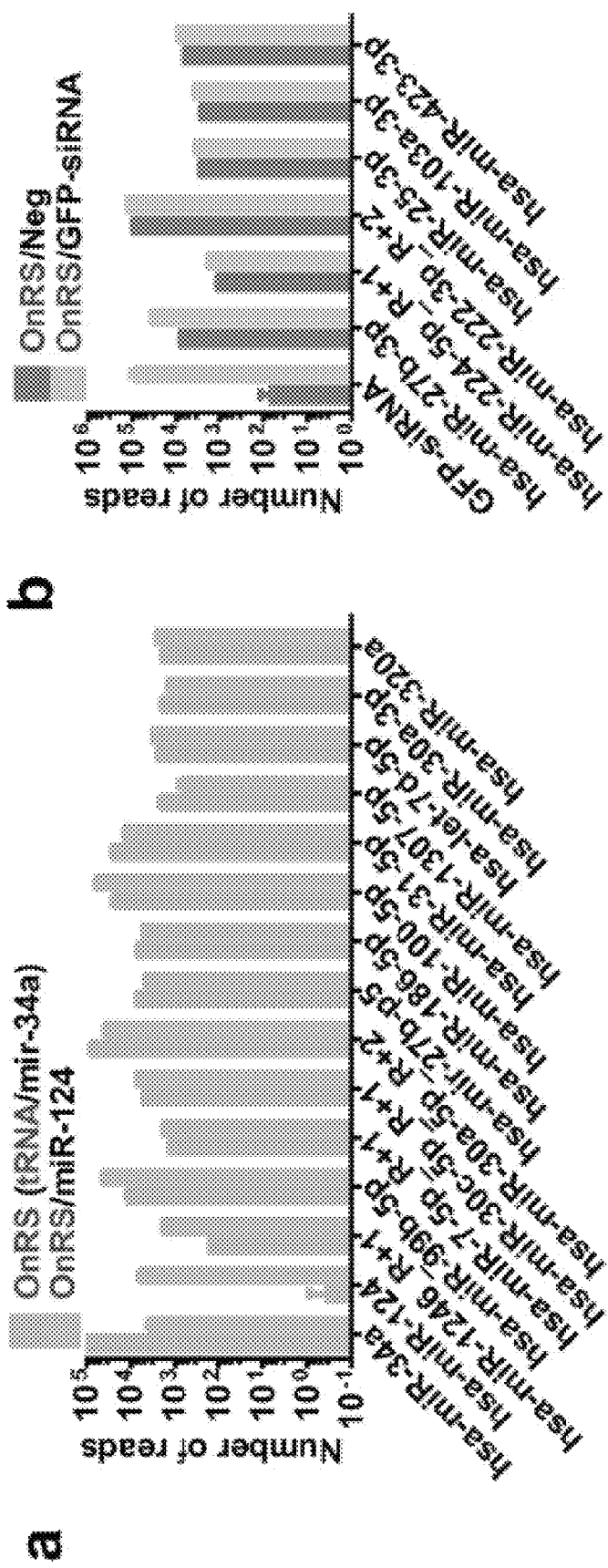
Fig. 5A-B c

OnRS/miR-124: 5'-GGCUACGUAGCUCA...AGUUGGUUAGAGCAGCGGCCCGAGU.....AGGUUCGAAUCCCGUCGUAGCCACCA-3'
tRNA/mir-34a

| Reads | Sequence (left) | Sequence (right) |
|---|---|---|
| 14,215 reads | | |
| 17,069 reads | | |
| 10,147 reads | | |
| 7,810 reads | | |
| 10,655 reads | AGUUGGUUAGAGCAGCGGC | |
| 4,729 reads | AGUUGGUUAGAGCAGCGGCC | |
| 4,682 reads | AGUUGGUUAGAGCAGCGGCCC | |
| 4,247 reads | AGUUGGUUAGAGCAGCGGCCCG | |
| 9,588 reads | AGUUGGUUAGAGCAGCGGCCCGAG | |
| 3,230 reads | | |
| 4,115 reads | | |
| 3,405 reads | | |

Right column sequences:
AAUCCCGUCGUAGCCACCA
AUCCCGUCGUAGCCACCA
CCCGUCGUAGCCACCA
AAUCCCGUCGUAGCC
GAAUCCCGUCGUAGCCACCA
GUUCGAAUCCCGUCGUAGCC

Fig. 5C d

| OnRS/GFP-siRNA: | OnRS/Neg |
|---|---|
| 3,003 reads | 5,662 reads |
| 1,422 reads | 1,212 reads |
| 3,914 reads | 2,156 reads |
| 1,771 reads | 1,116 reads |
| 1,385 reads | 1,073 reads |
| 3,524 reads | 2,333 reads |
| 1,916 reads | 1,242 reads |
| 1,387 reads | 1,075 reads |

5'-GGCUACGUAGCUCAGUUGGUUAGAGCAGCGGC....GUUCGAAUCCCGUCGUAGCCACCA-3'

GGCUACGUAGCUCAGUUGGUUAGAGCAGCGGC
GGCUACGUAGCUCAGUUGGUUAGAGCAGCG

GUUCGAAUCCCGUCGUAGCC
CGAAUCCCGUCGUAGCCACCA
GAAUCCCGUCGUAGCCACCA
AAUCCCGUCGUAGCCACCA
AUCCCGUCGUAGCCACCA
CCCGUCGUAGCCACCA

Fig. 5D

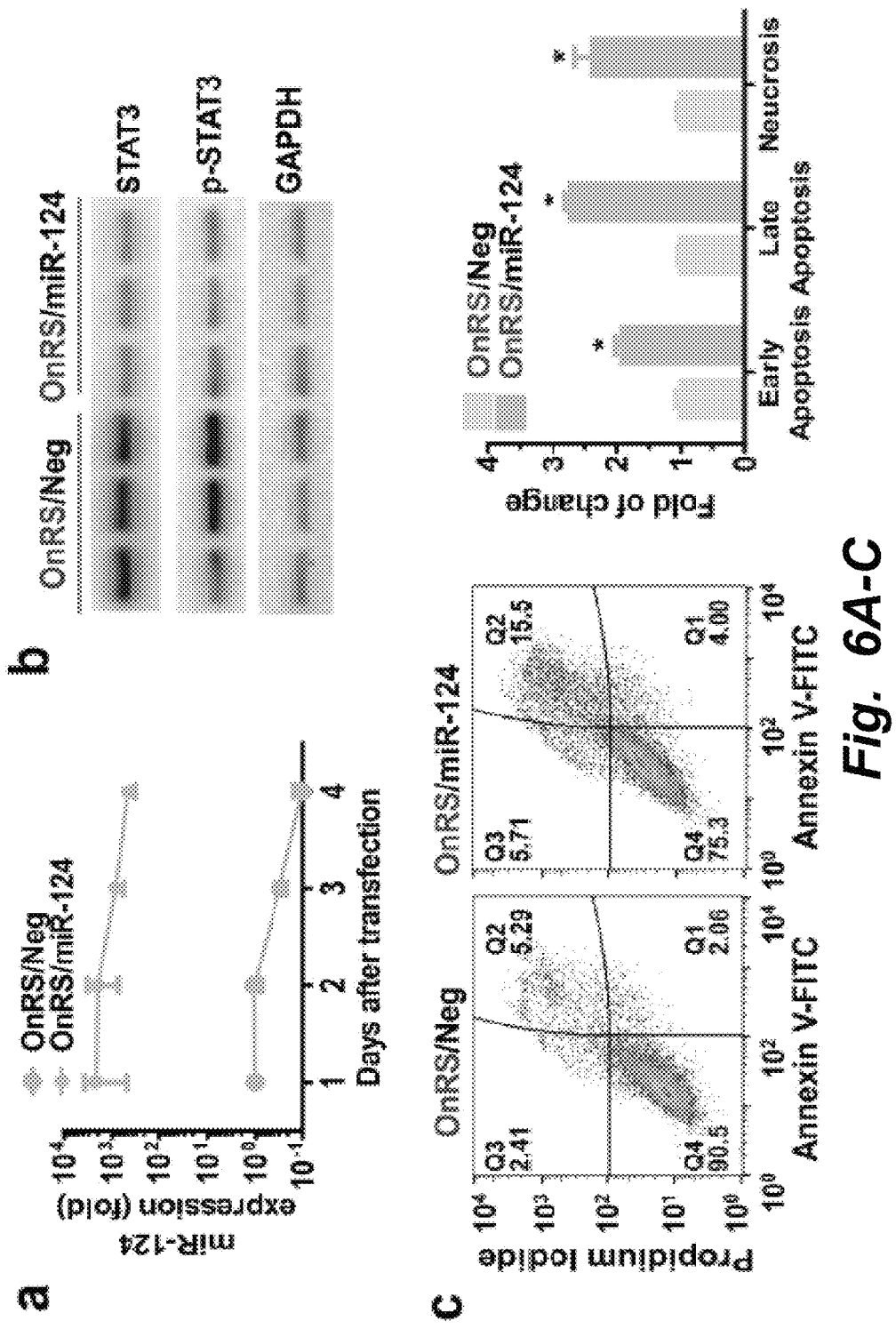
Fig. 6A-C

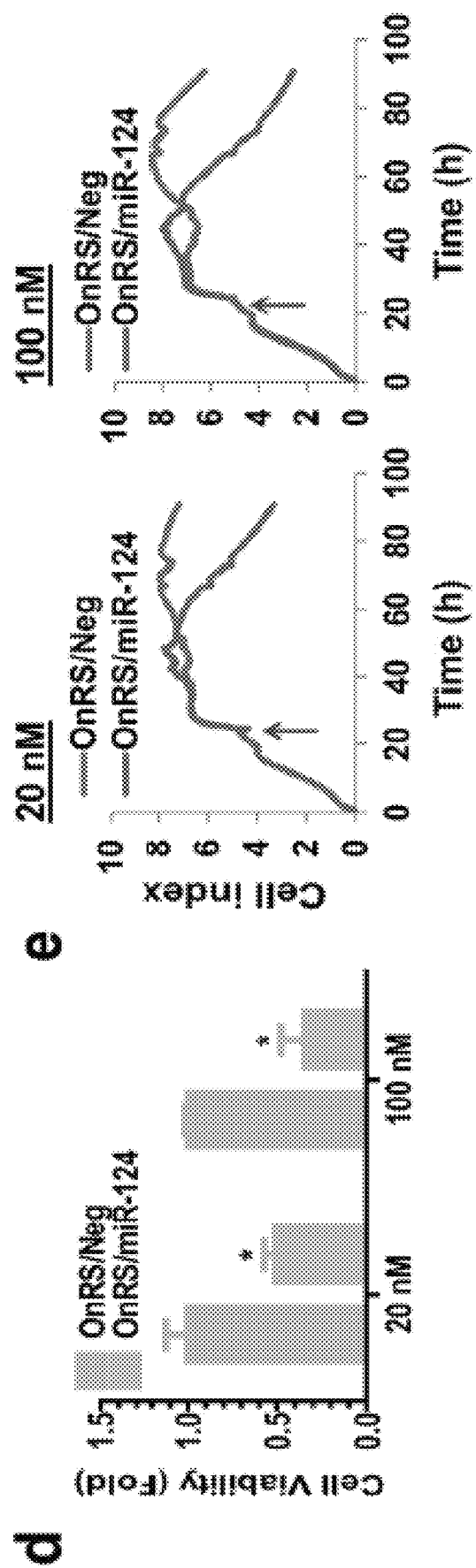
Fig. 6D-E

*In vitro*
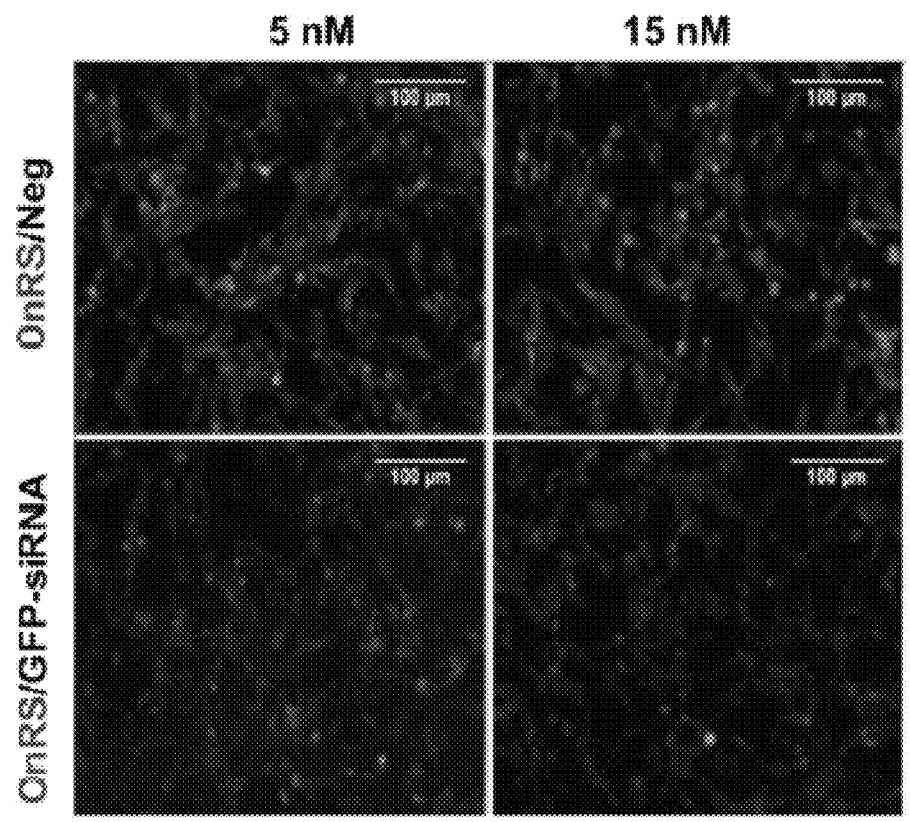
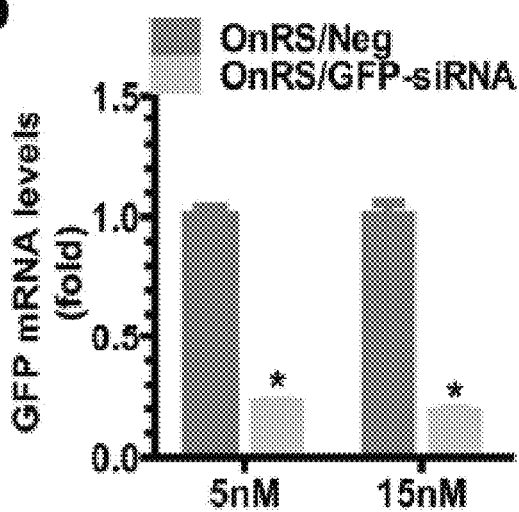
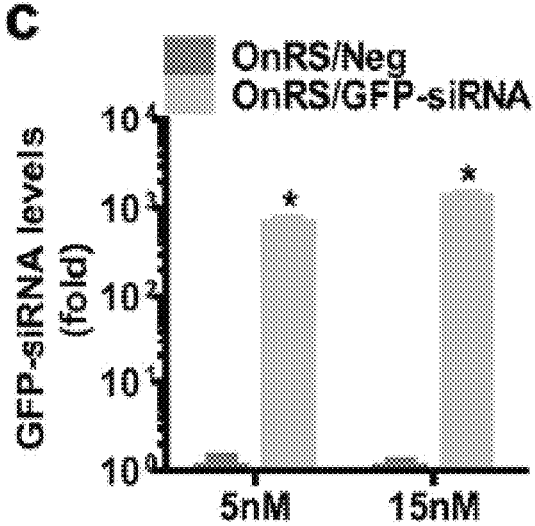
*Fig. 7A-C*

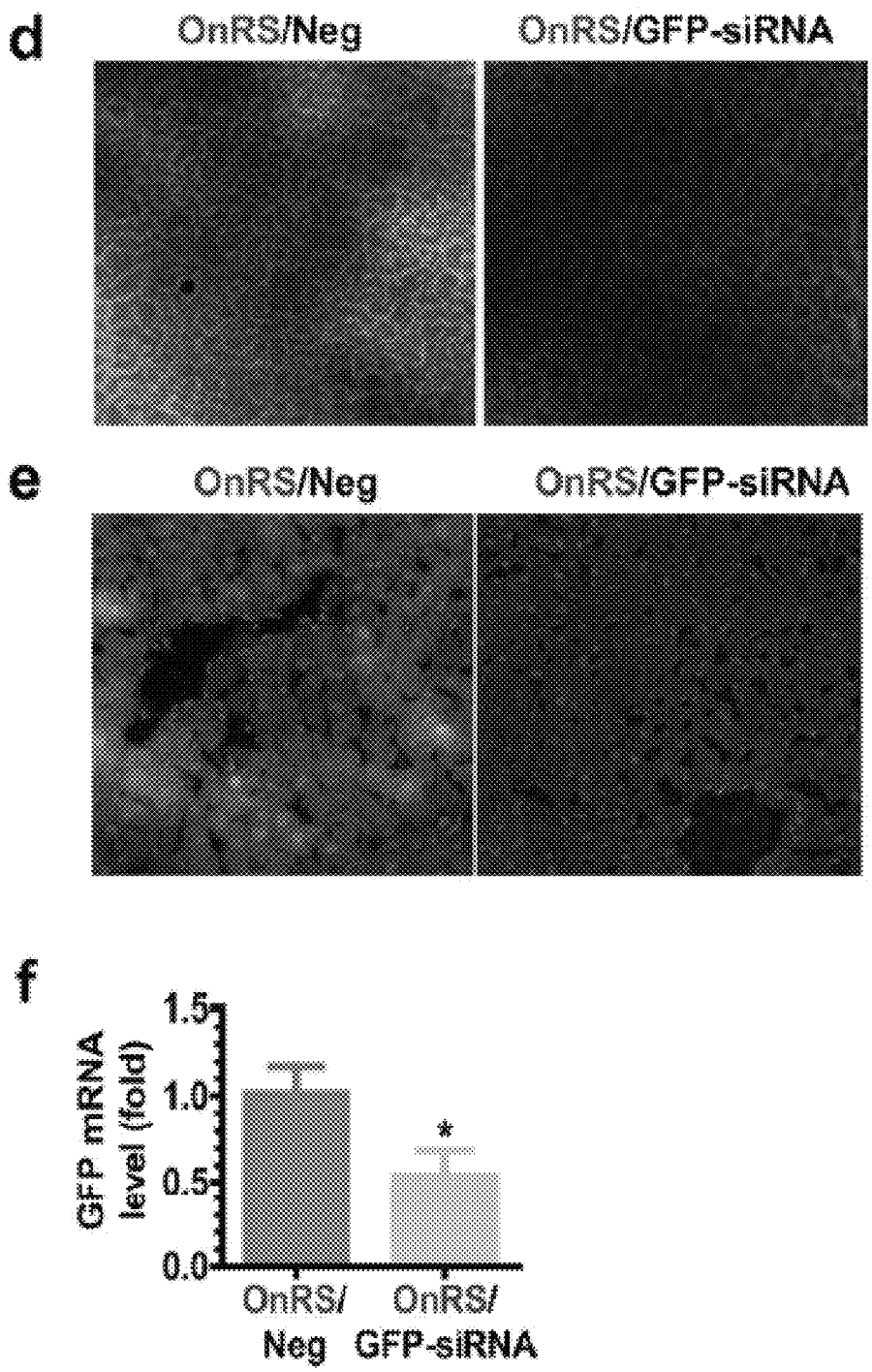
Fig. 7D-F

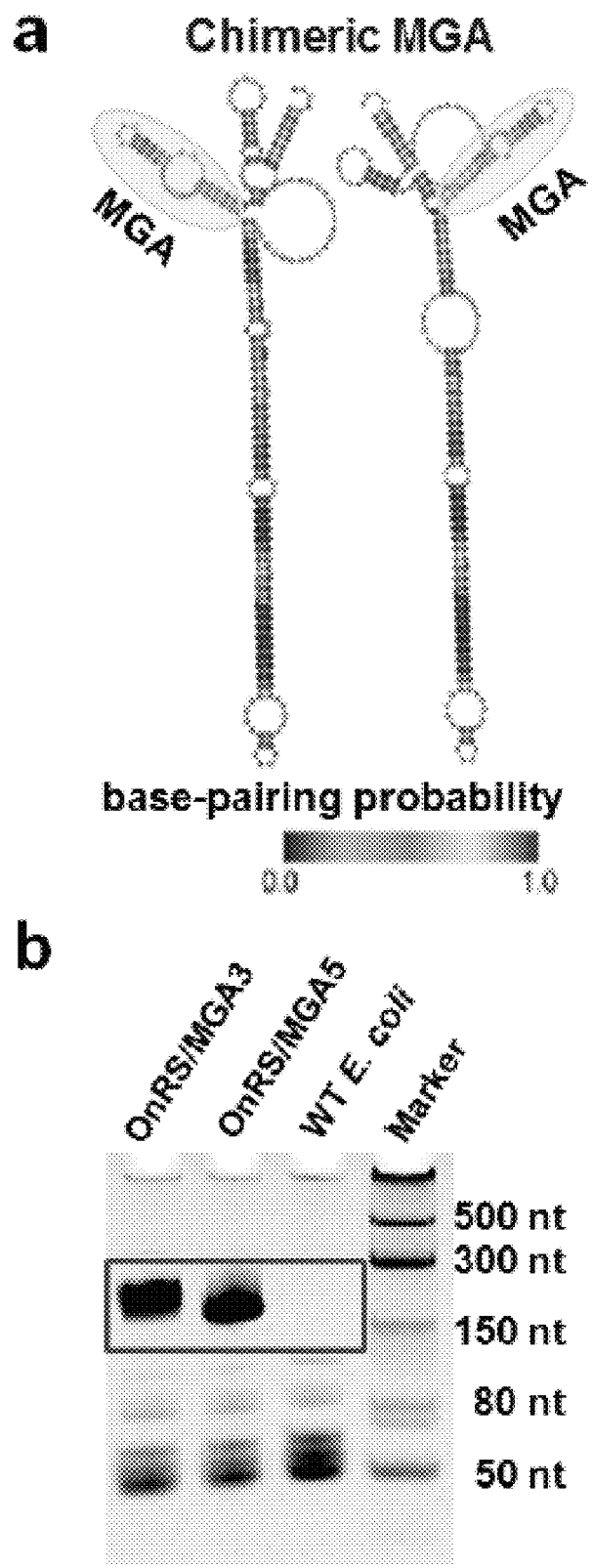
Fig. 9A-B

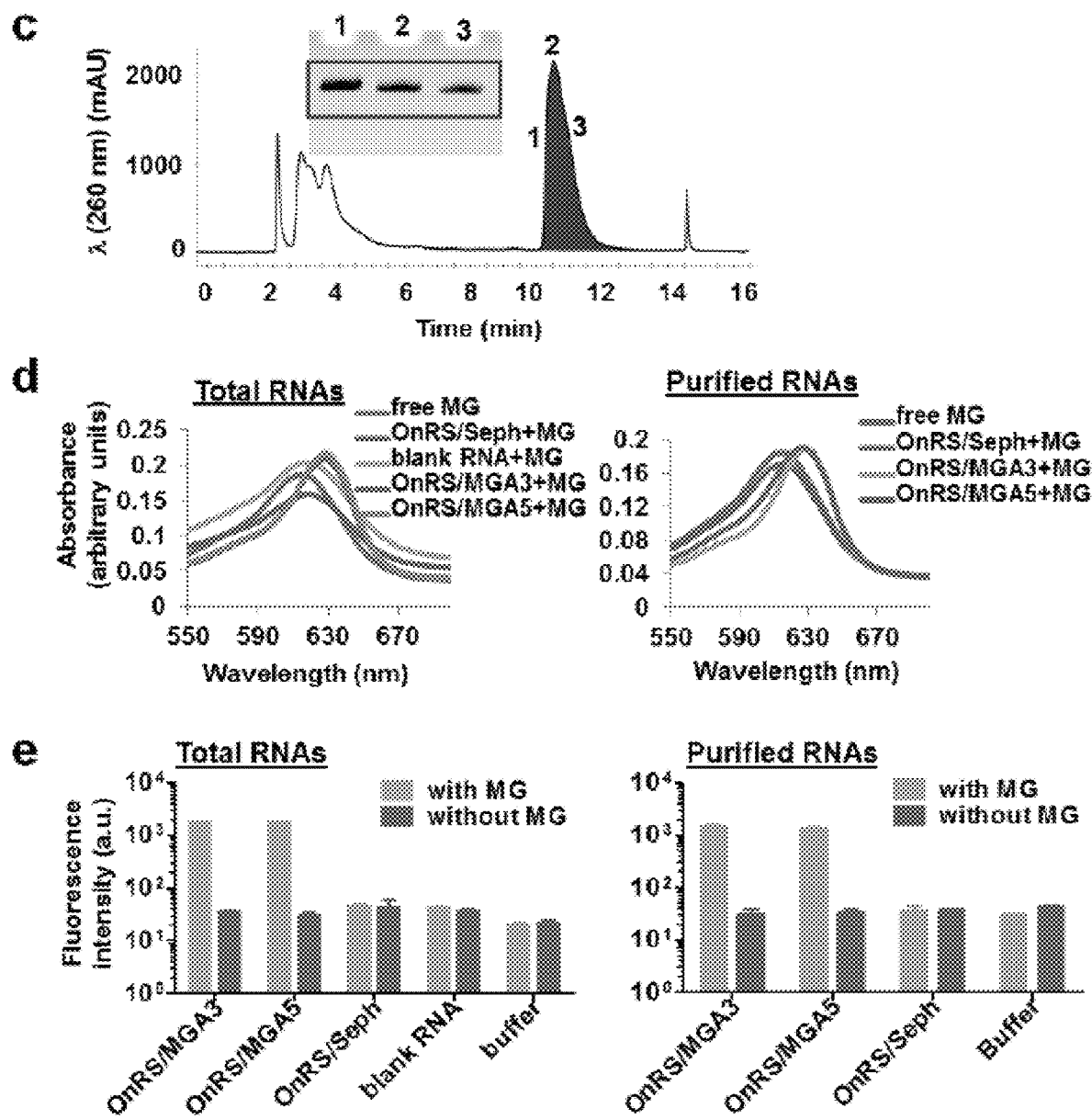
Fig. 9C-E

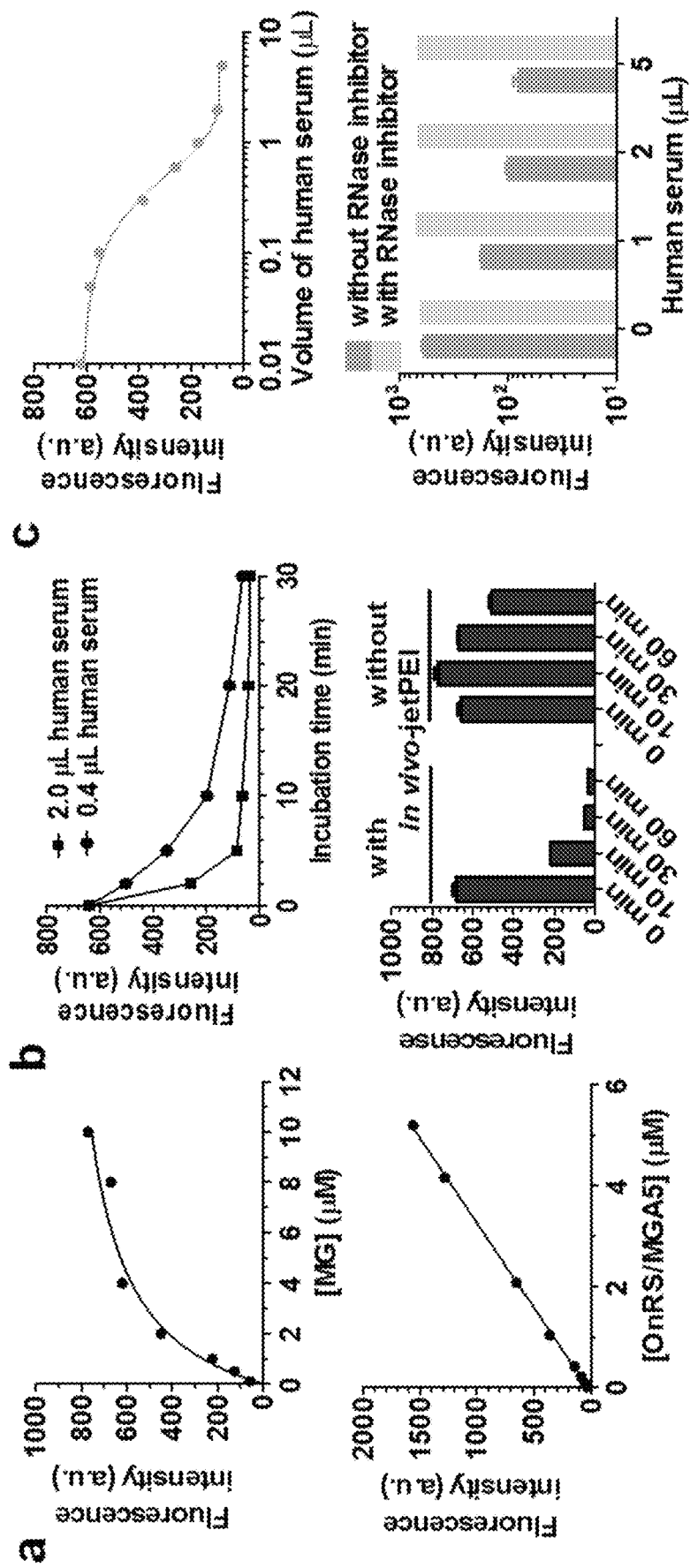
Fig. 10A-C

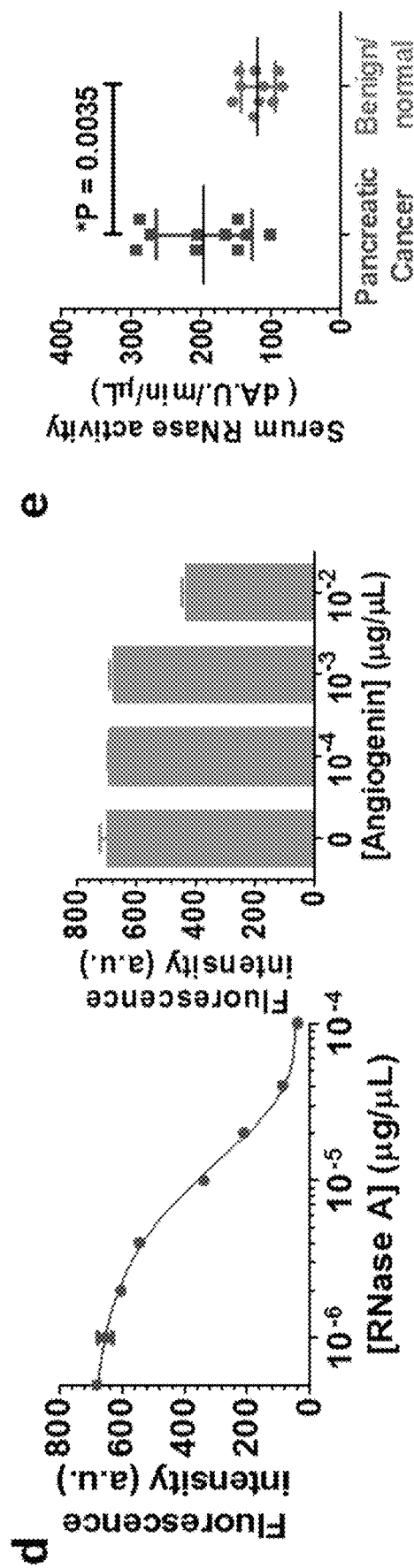
Fig. 10D-E

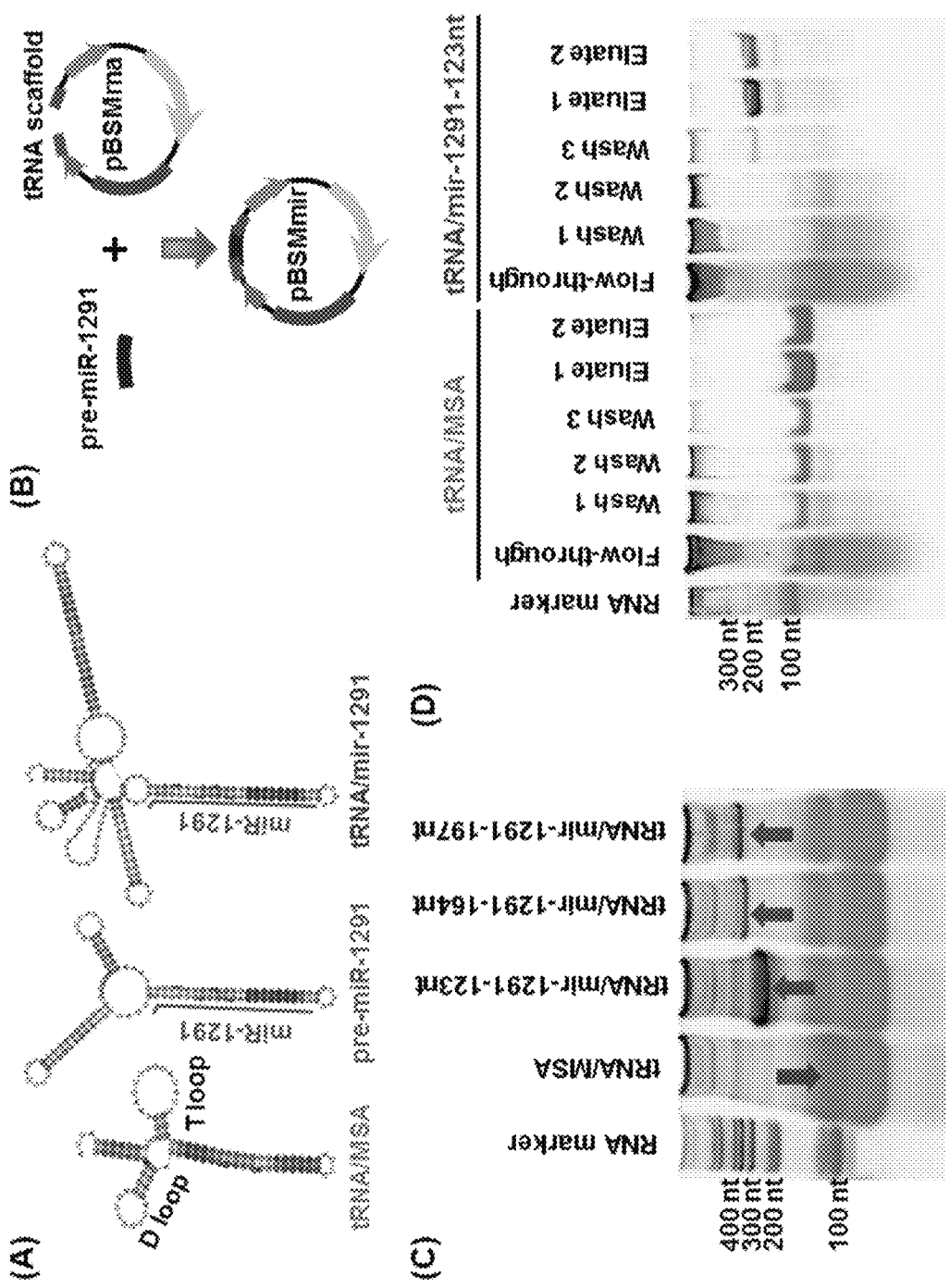
Fig. 11A-D

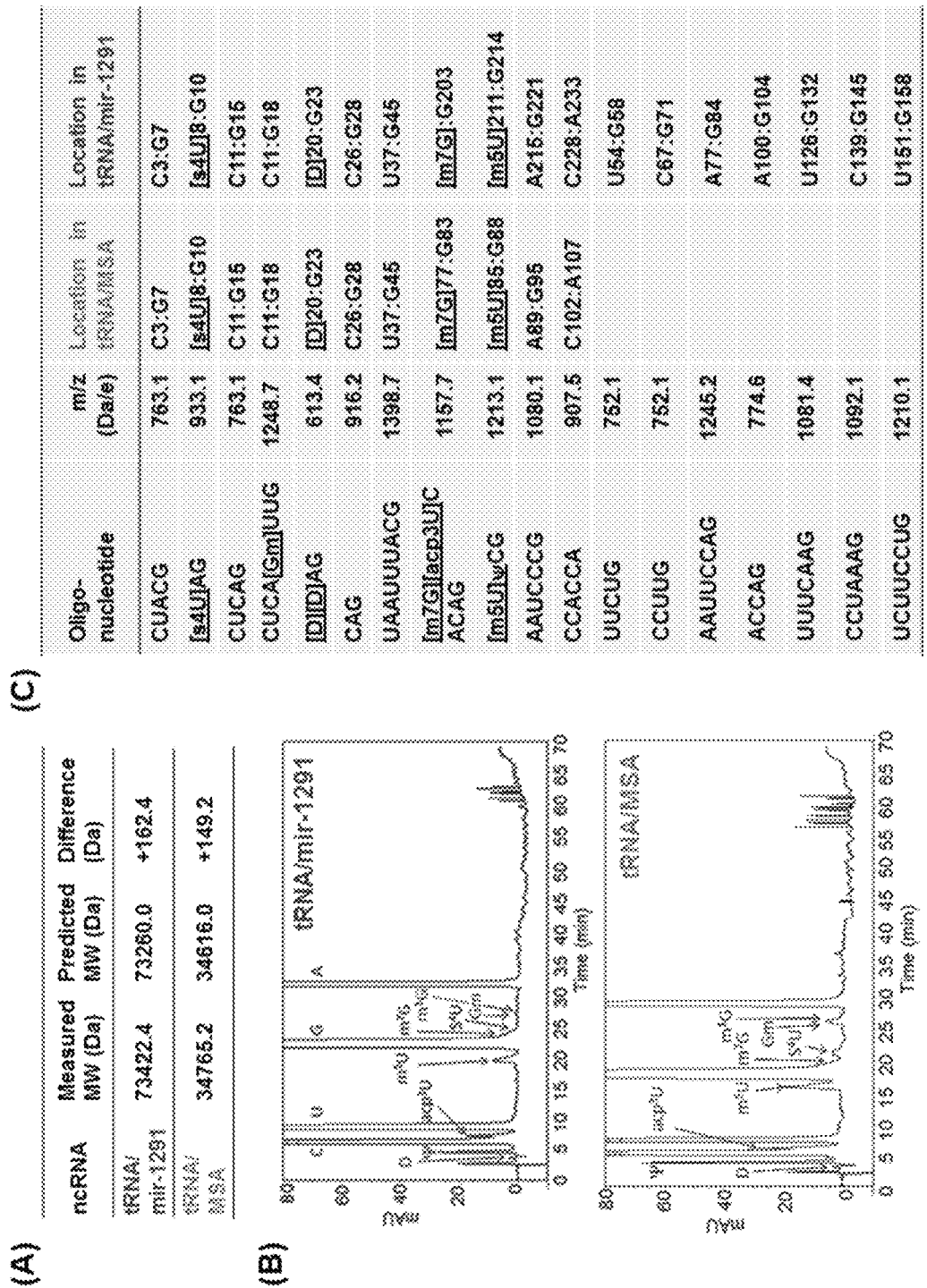
Fig. 12A-C

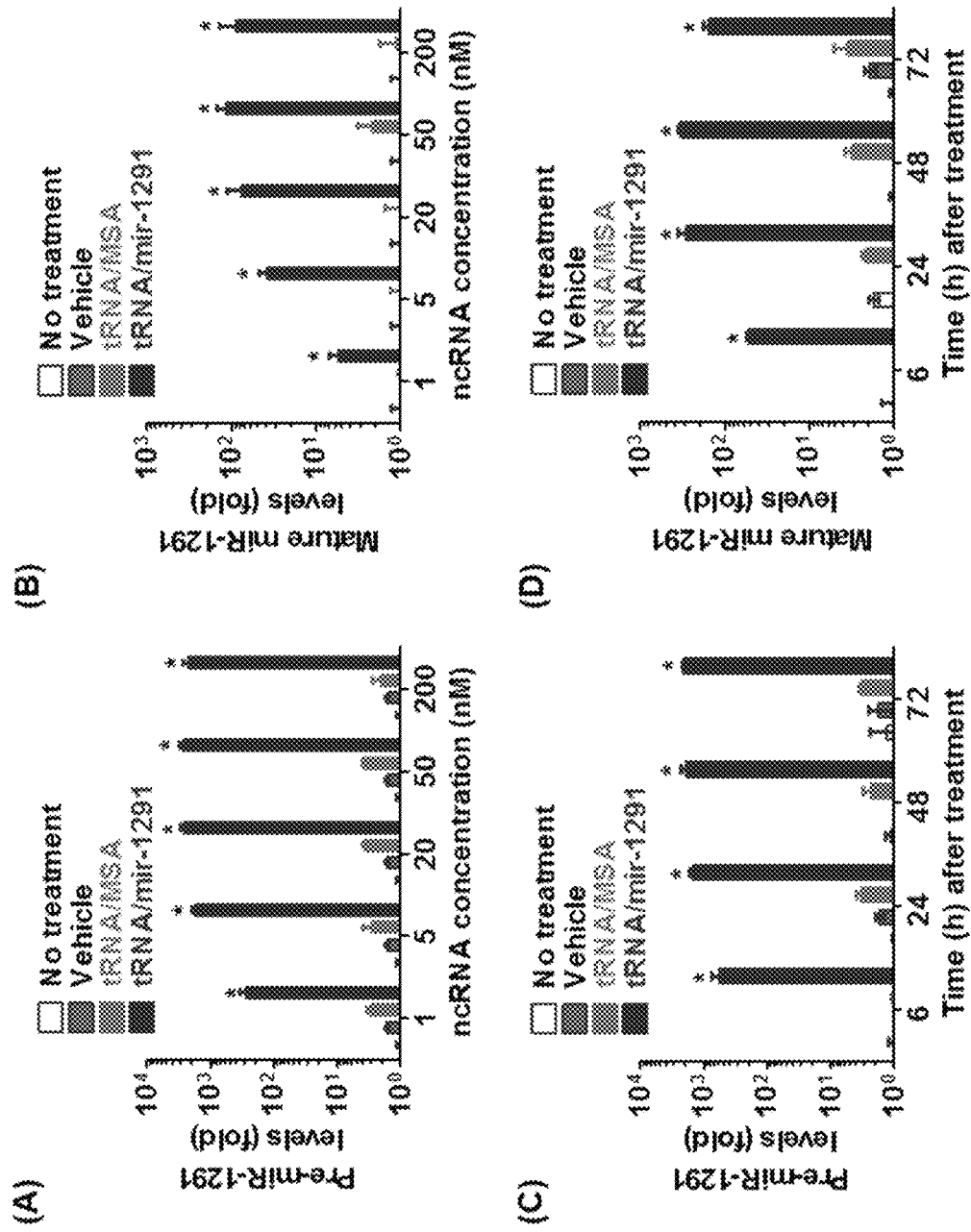
Fig. 13A-D

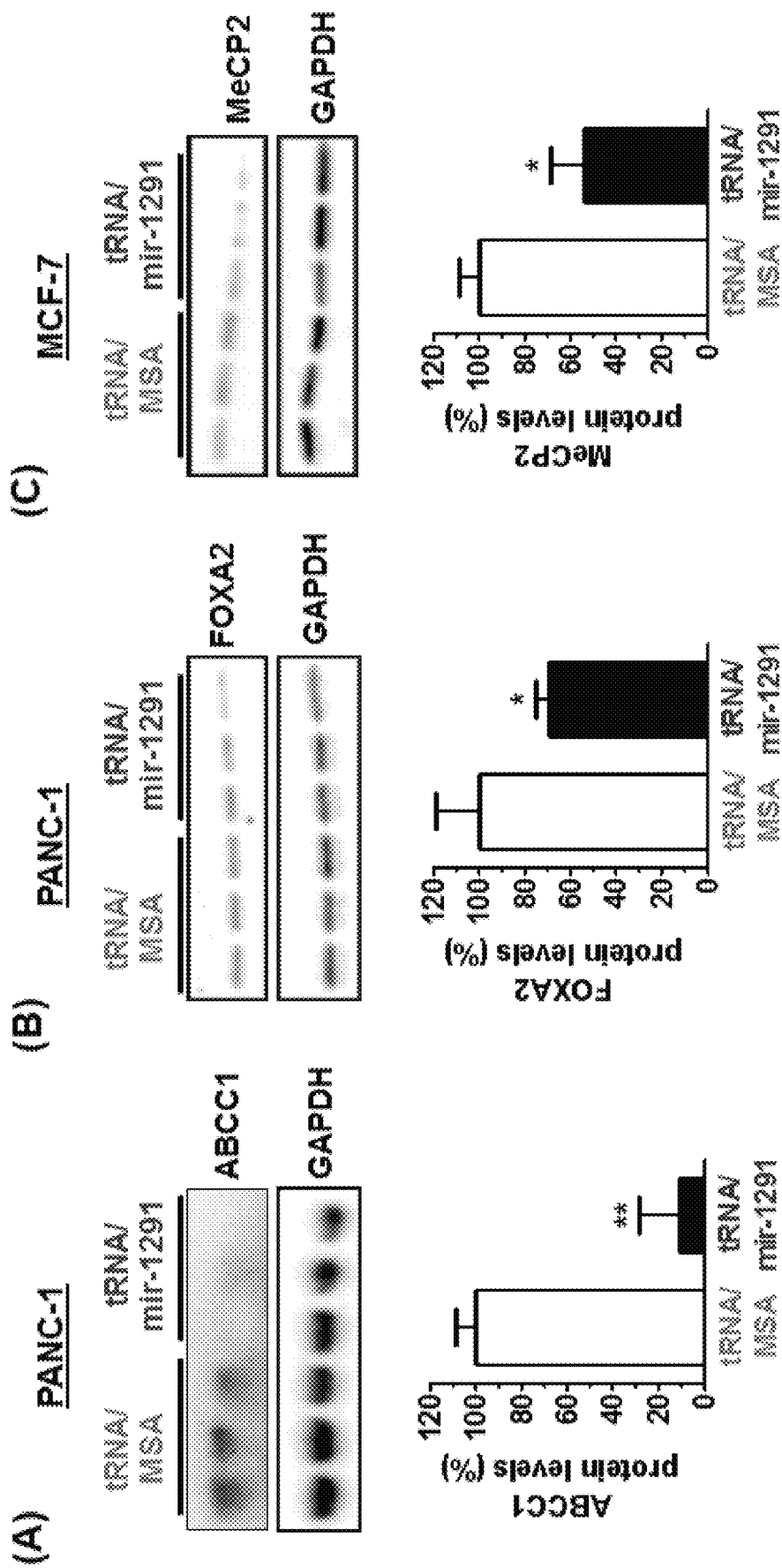
Fig. 14A-C

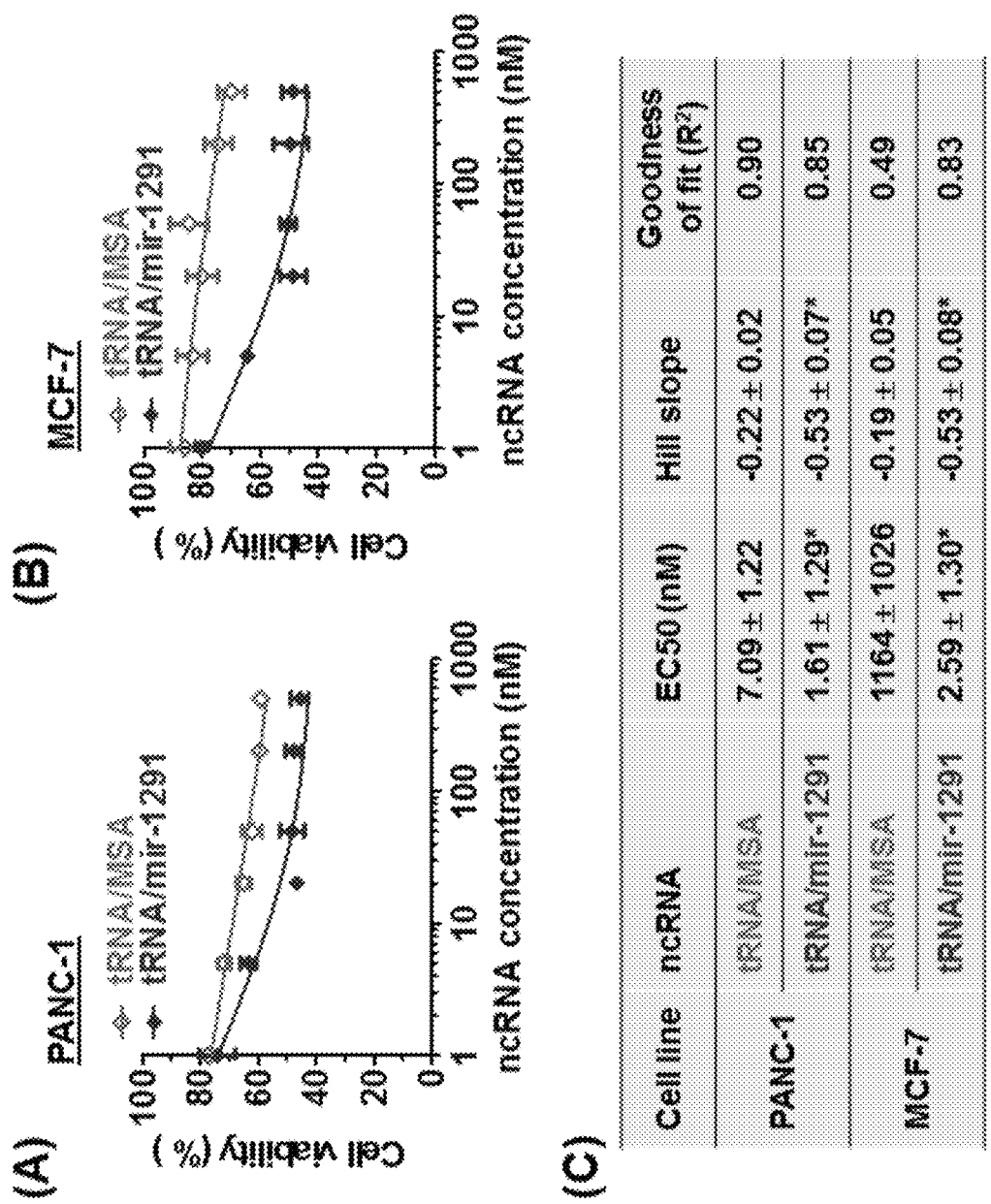
Fig. 15A-C

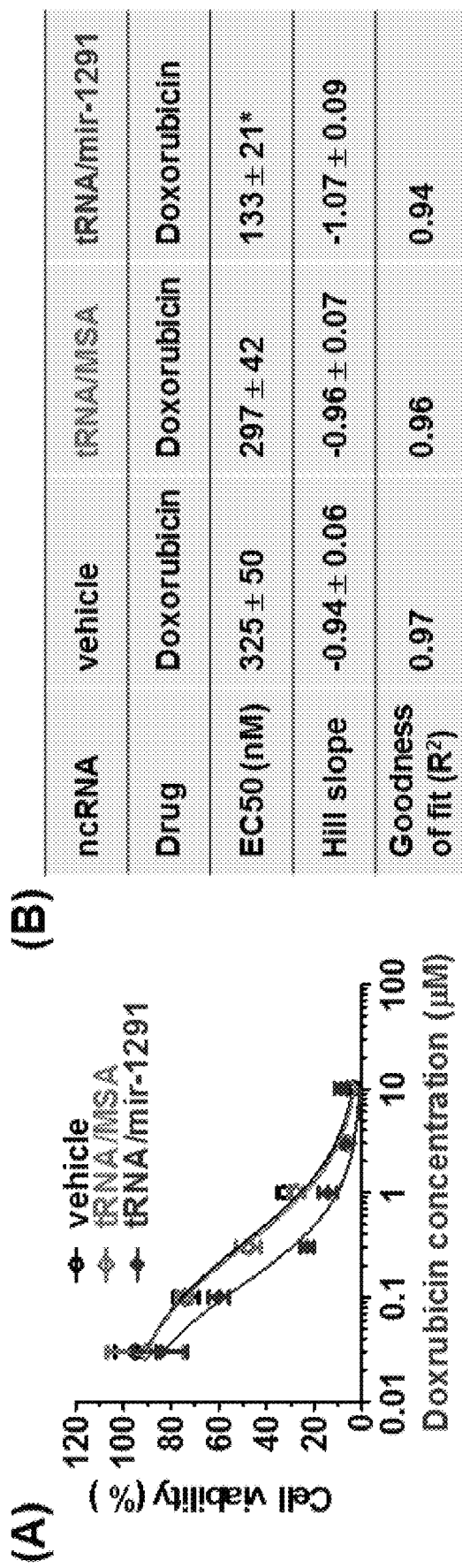
Fig. 16A-B

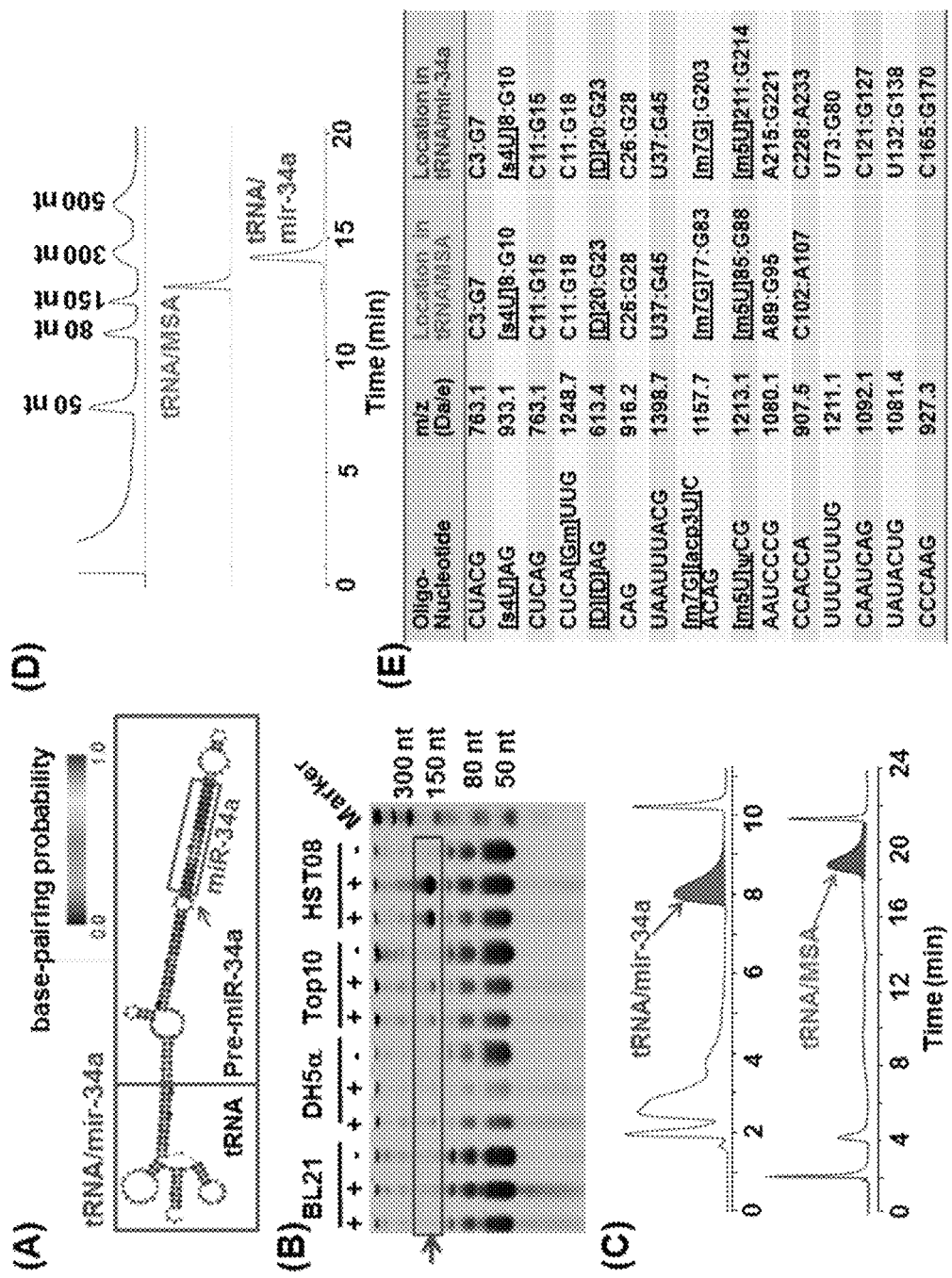
Fig. 17A-E

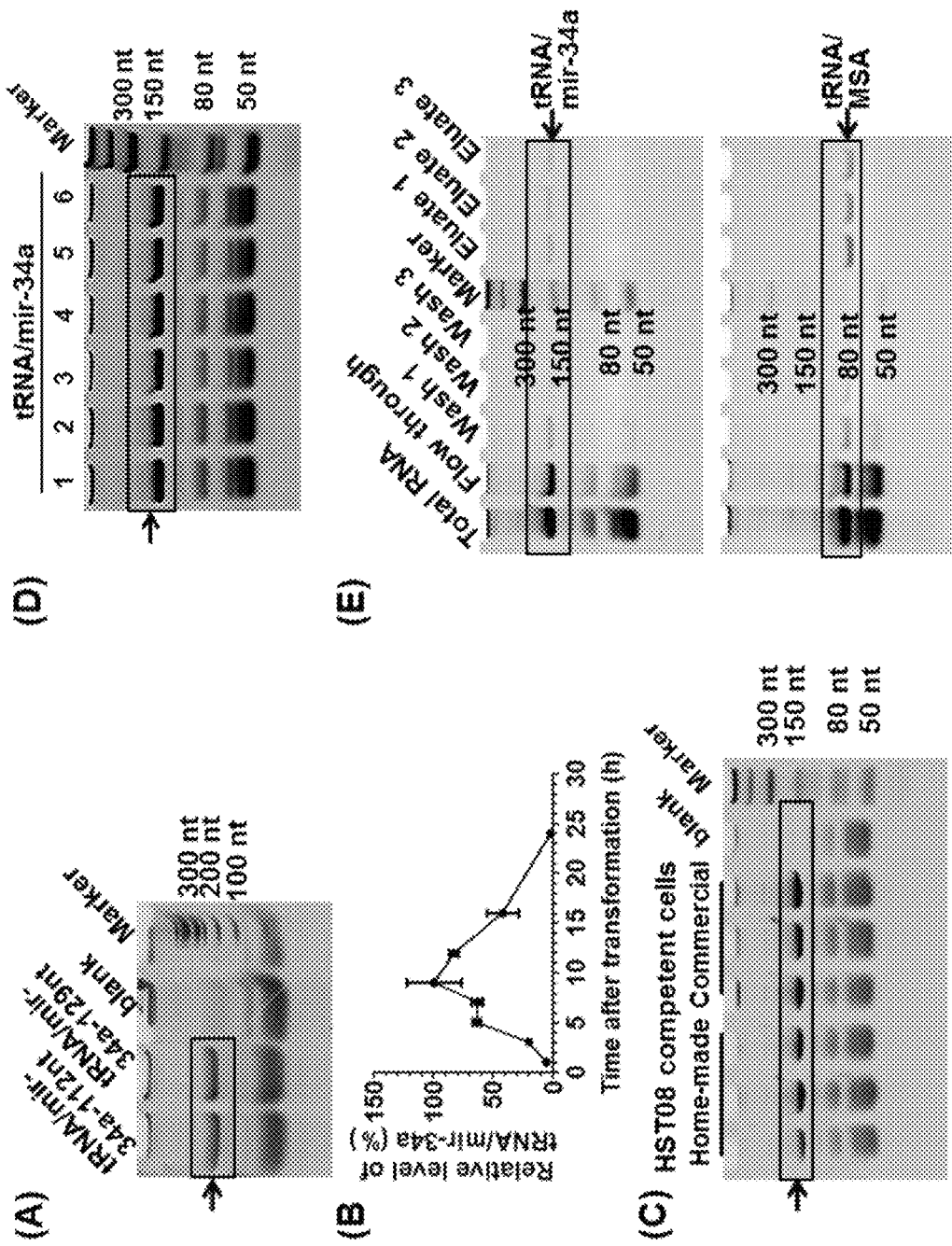
Fig. 18A-E

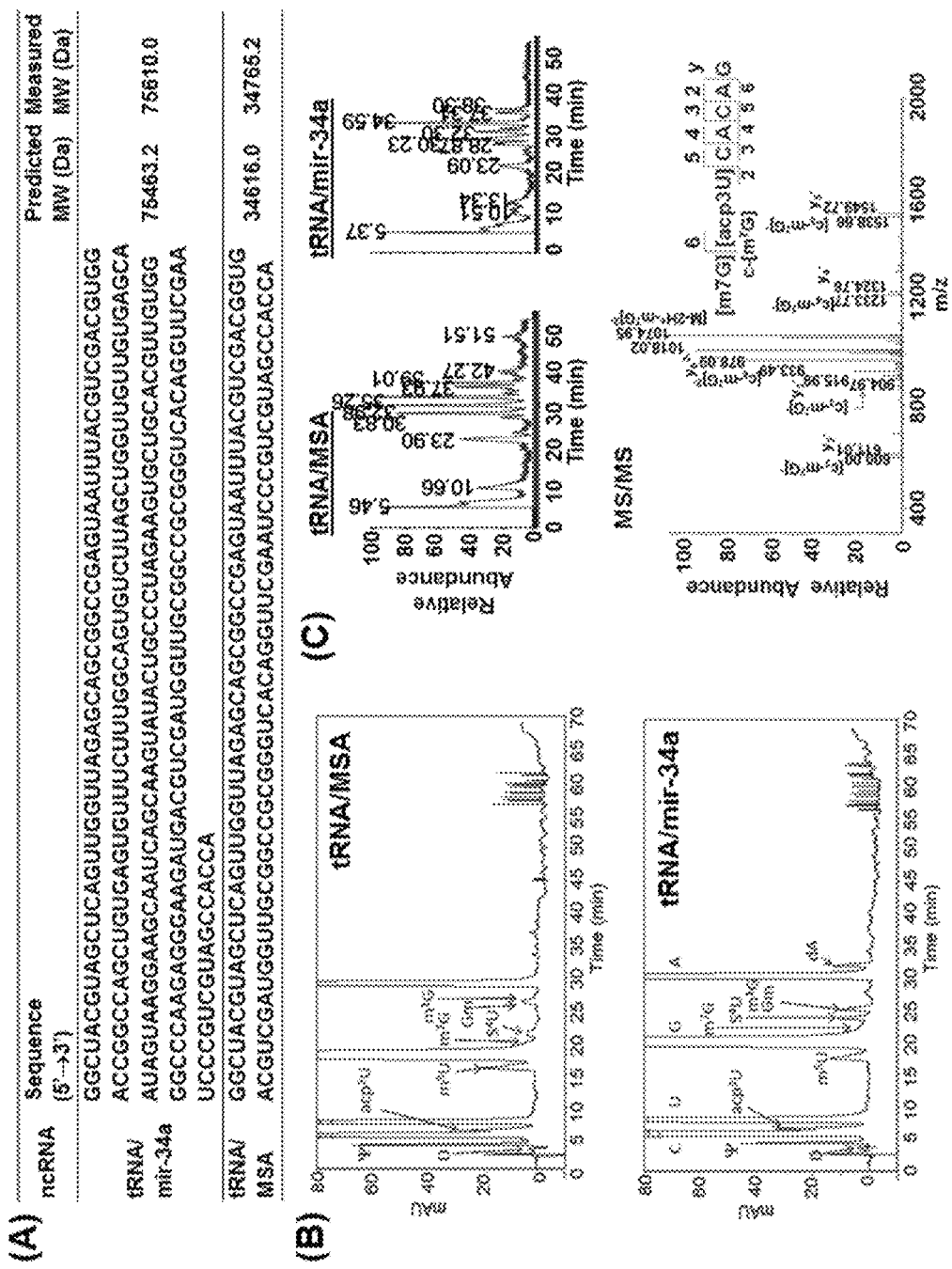
Fig. 19A-C

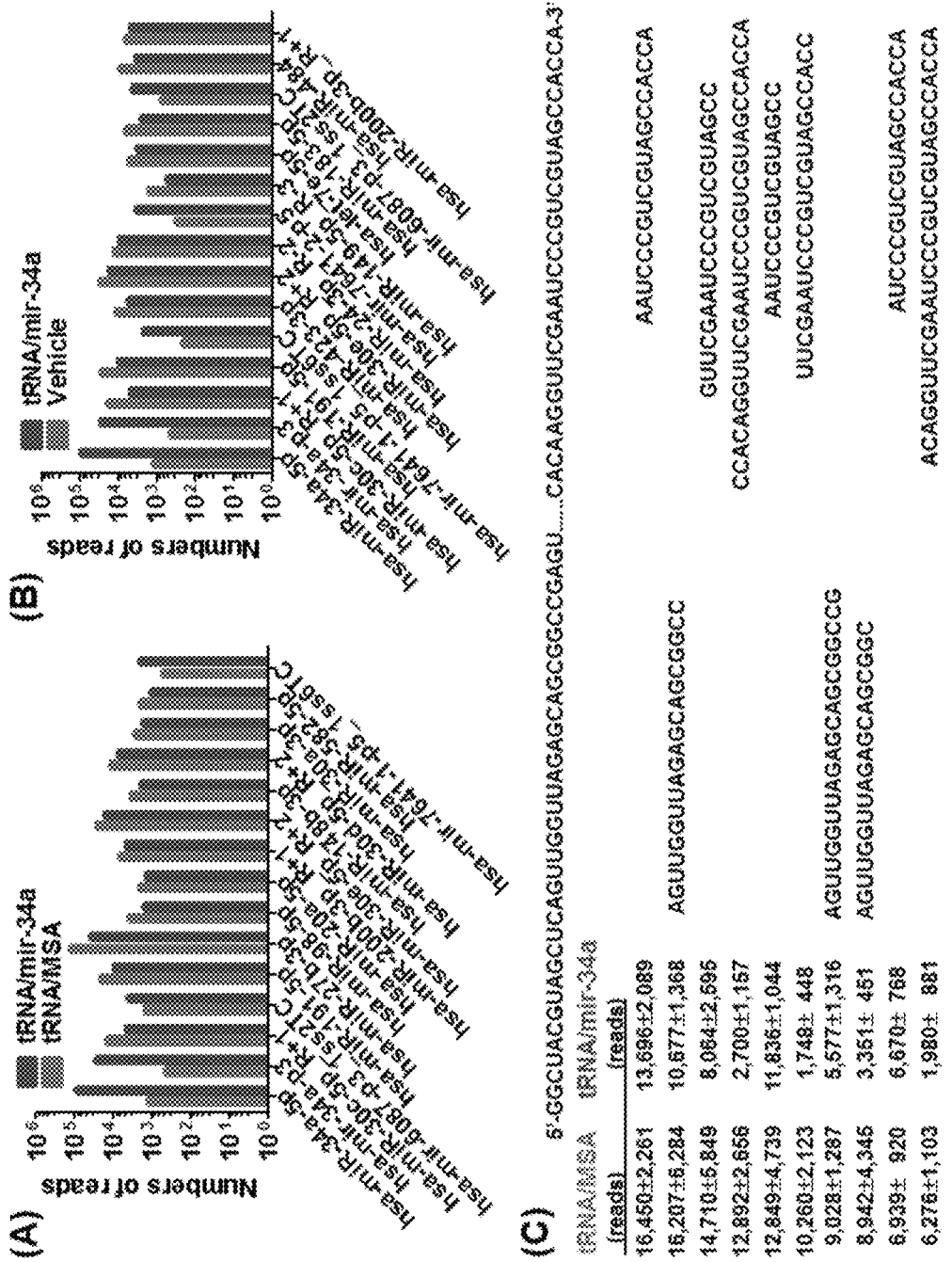
Fig. 20A-C

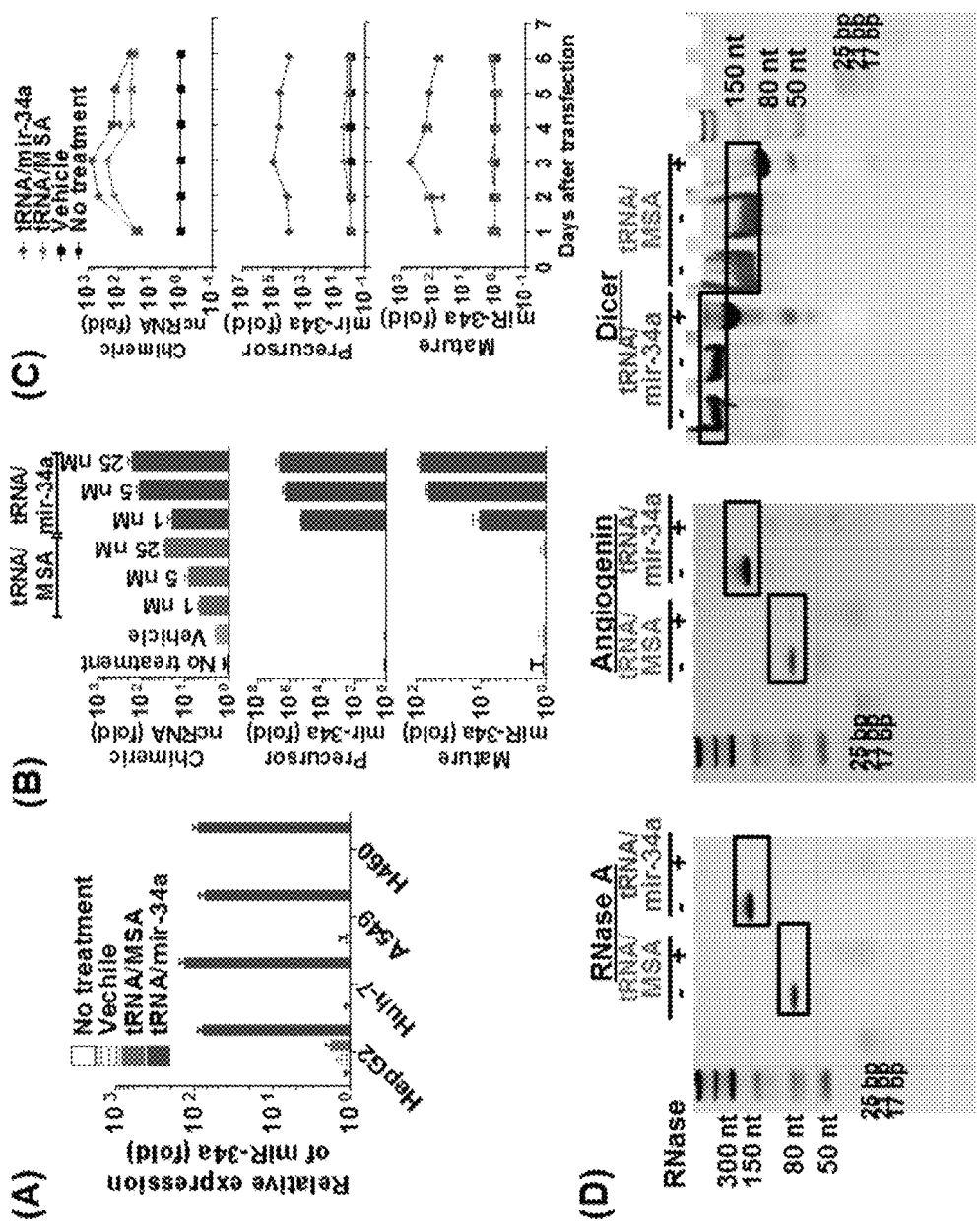
Fig. 21A-D

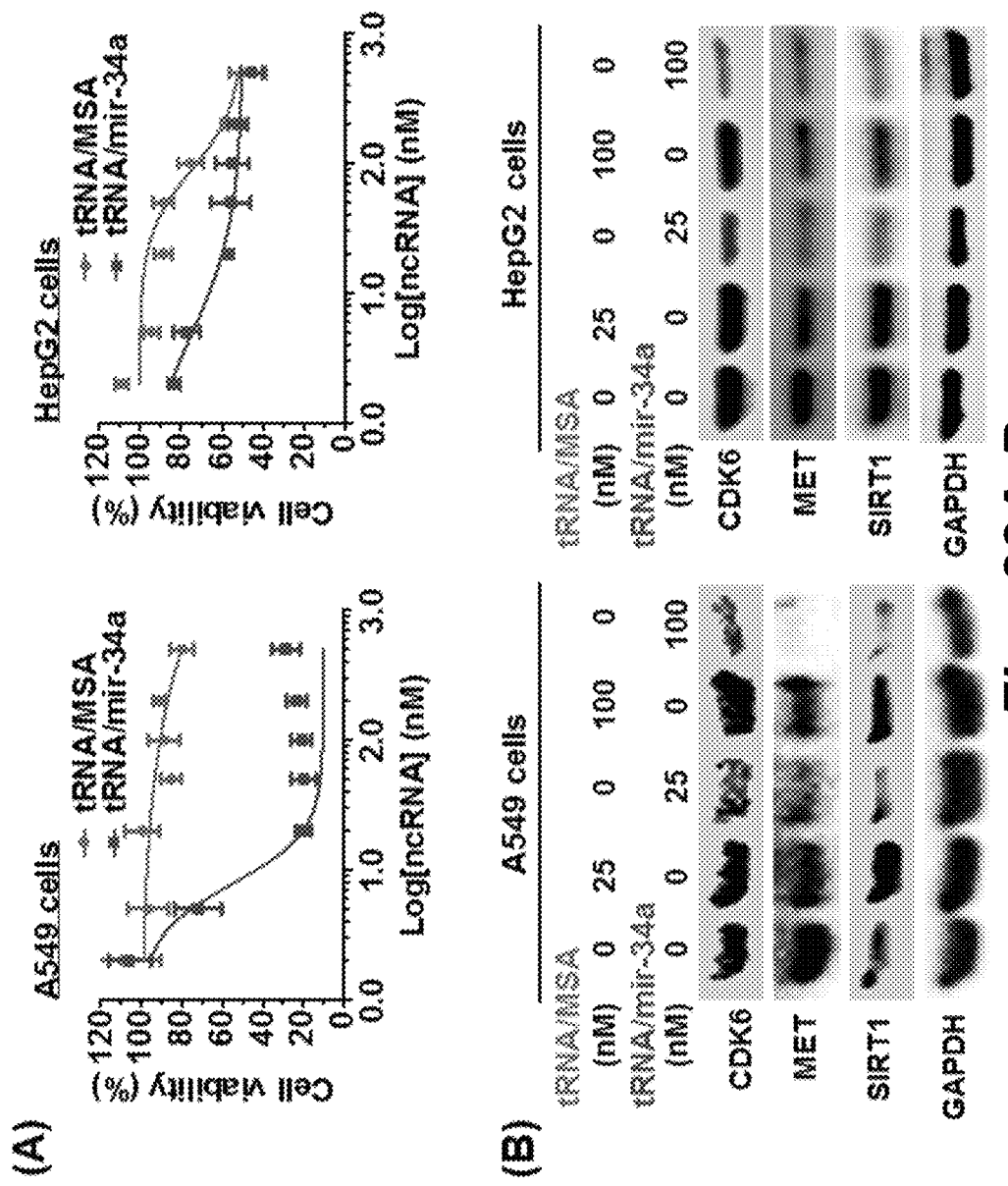
Fig. 22A-B

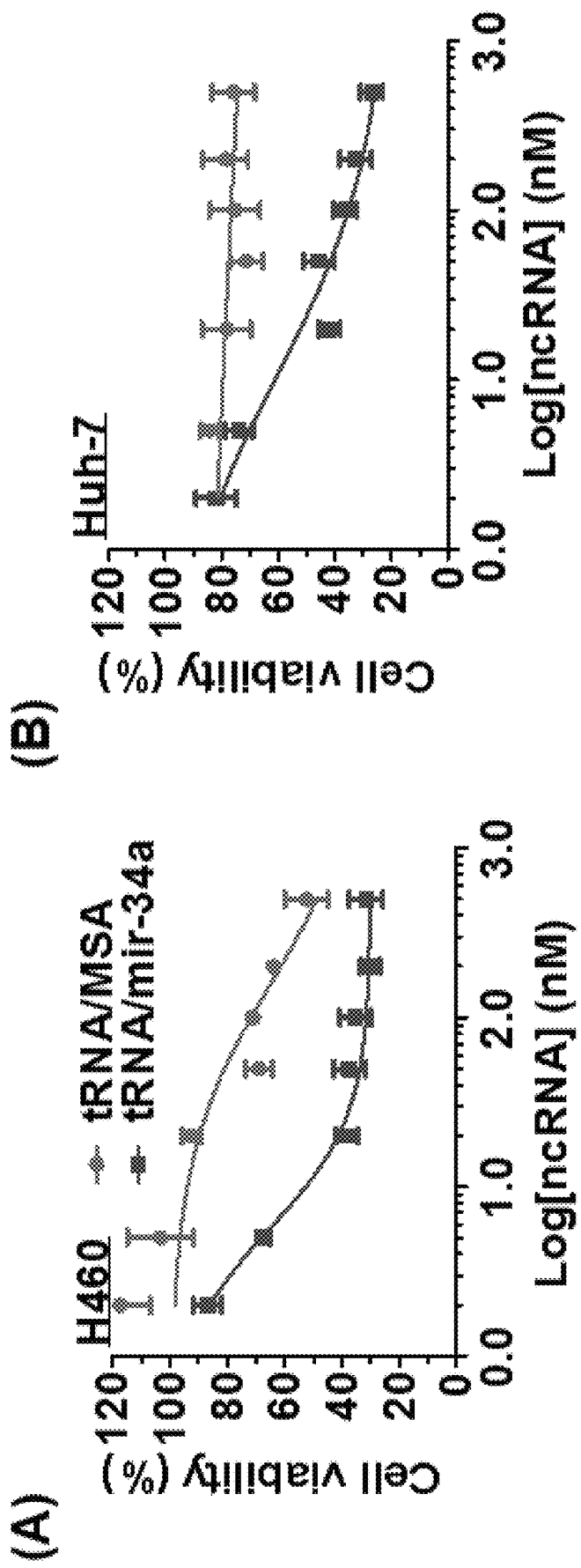
Fig. 23A-B

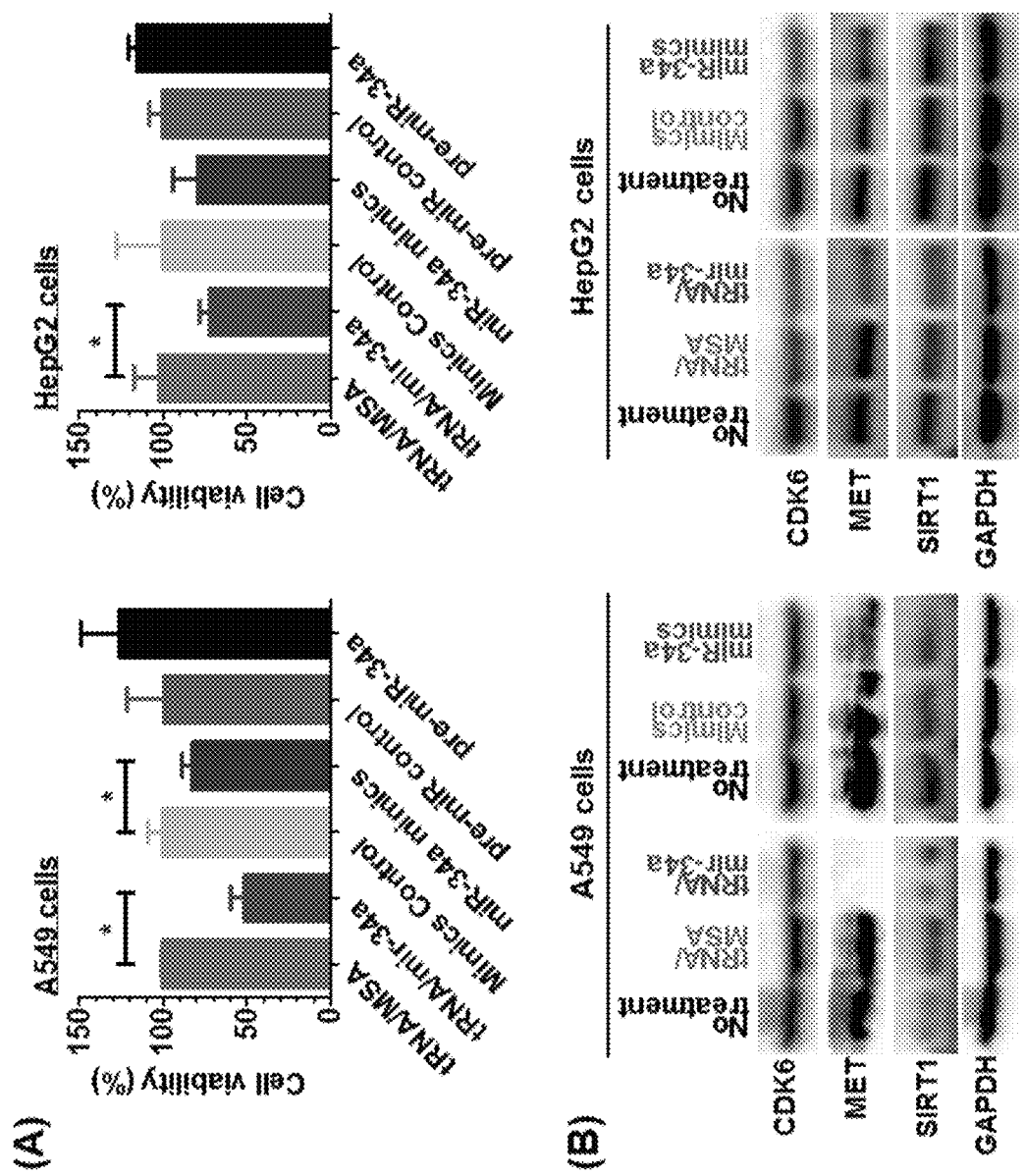
Fig. 24A-B

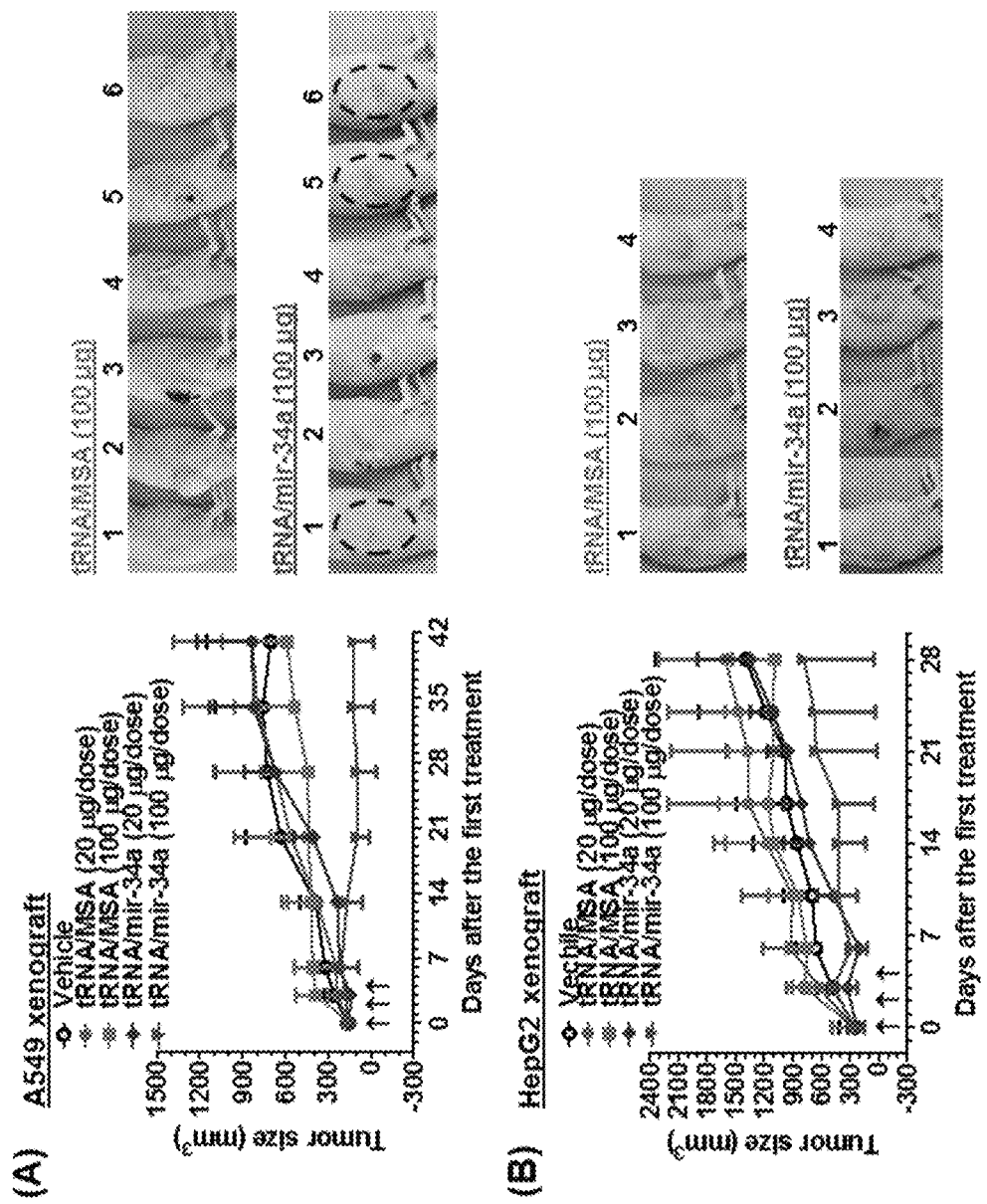
Fig. 25A-B

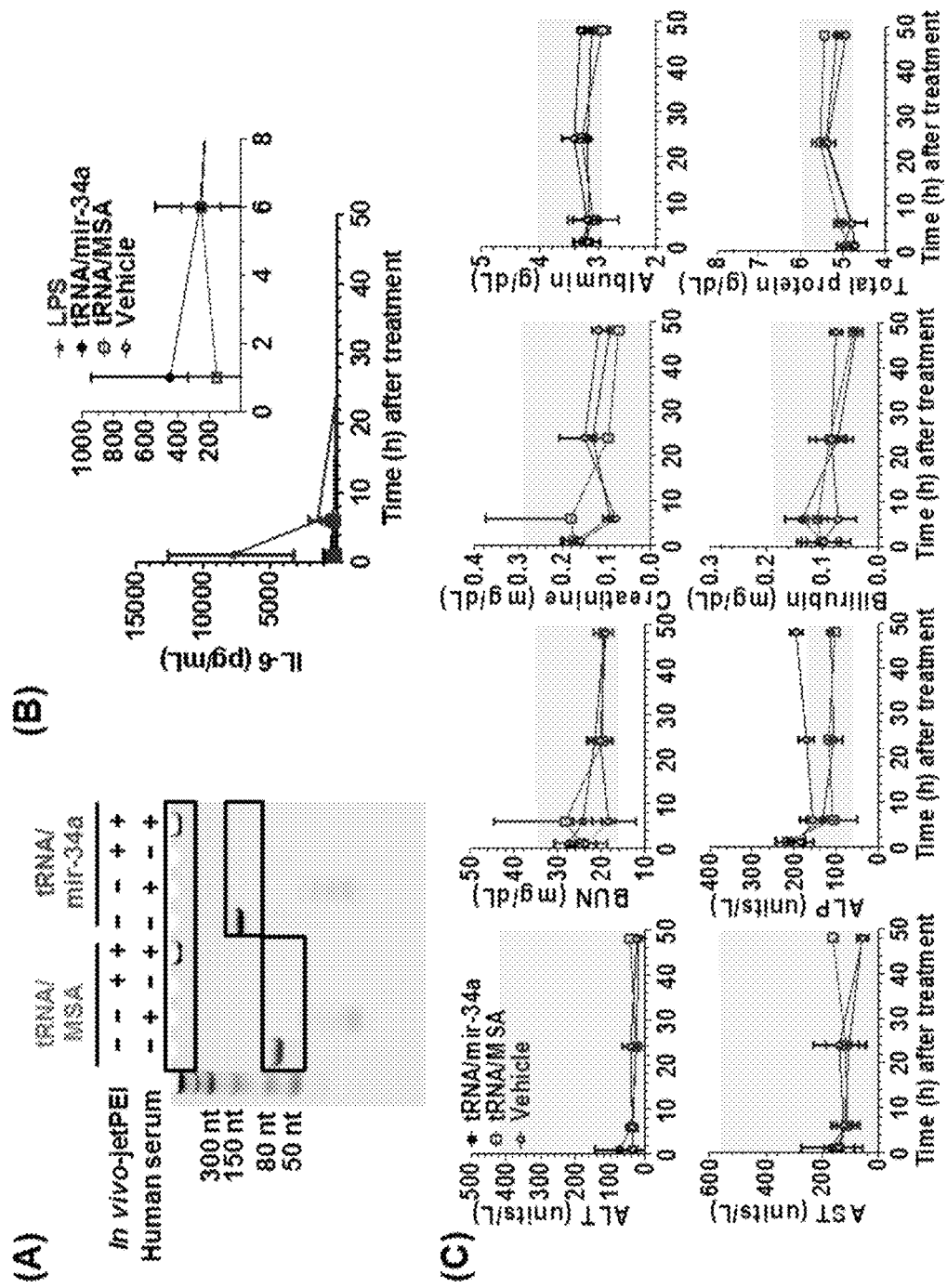
Fig. 26A-C

HYBRID TRNA/PRE-MIRNA MOLECULES AND METHODS OF USE

CROSS-REFERENCE TO RELATED APPLICATIONS

This application is the U.S. National Phase under 35 U.S.C. § 371 of International Appl. No. PCT/US2015/031861, filed on May 21, 2015, which claims the benefit under 35 U.S.C. § 119(e) of U.S. Provisional Application No. 62/003,806, filed on May 28, 2014, which is hereby incorporated herein by reference in its entirety for all purposes.

FIELD

Provided are hybrid tRNA/pre-microRNA and tRNA/shRNA molecules and methods of making and using.

BACKGROUND

The discovery of several superfamilies of genomically-encoded, functional noncoding RNAs (ncRNAs) such as microRNAs (miRNAs or miRs) and long noncoding RNAs (lncRNAs) in the control of various cellular processes has expanded our knowledge of "genes" in the cells. It also provides insights into developing novel therapeutic strategies. For instance, the tumor suppressive ncRNAs (e.g., miR-34a) that are depleted in carcinoma tissues may be reintroduced into cancer cells to manage tumor progression (He, et al. (2007) Nature, 447, 1130-1134; Welch, et al., (2007) Oncogene, 26, 5017-5022; and Liu, et al. (2011) Nature Medicine, 17, 211-215). Indeed, a liposome formulated miR-34a, namely "MRX34", has entered Phase I clinical trial for the treatment of unresectable primary liver cancer or those with liver metastasis from other cancers (Kelnar, et al., (2014) Anal Chem. 86(3):1534-42; and Ling, et al. (2013) Nature Reviews. Drug Discovery, 12, 847-865). However, the lack of efficient method for producing large quantities of inexpensive, naturally-occurring and biologically-functional ncRNA agents hinders the basic research on ncRNA structures and functions as well as the translational research on ncRNA-based therapies. Currently, miRNA agents such as the mimics, precursors and antagomirs are mainly produced via chemical synthesis (Kelnar, et al., (2014) Anal Chem. 86(3):1534-42; Ling, et al., (2013) Nature Reviews. Drug Discovery, 12, 847-865; Takahashi, et al., (2013) Nucleic Acids Research, 41, 10659-10667; and Gebert, et al. (2014) Nucleic Acids Research, 42, 609-621). Although organic synthesis of oligonucleotides may be automated, a projected test or therapeutic dose of 22-nt small RNA agents is astonishingly costly. It is also unclear to what extent chemical modifications would alter RNA structure, biological activity and safety profile despite that the mimics show some favorable pharmacokinetic properties such as a longer half-life. Furthermore, it is extremely difficult to accomplish some naturally-occurring modifications (Cantara, et al. (2011) Nucleic Acids Research, 39, D195-201; Limbach, et al., (1994) Nucleic Acids Research, 22, 2183-2196; Liu, et al., (2013) PloS One, 8, e81922; and Dominissini, et al. (2012) Nature, 485, 201-206) via chemical synthesis, which may be crucial for the biodegradation, function and safety of natural RNAs. In vitro transcription (Beckert, et al., (2011) Methods in Molecular Biology, 703, 29-41) is another way to produce RNA agents in variable lengths. However, in vitro transcription generally generates RNA molecules in a test tube on microgram scale, and the production of larger quantities of RNAs requires more but inexpensive RNA polymerases. Recently, tRNA (Ponchon, et al., (2007) Nature Methods, 4, 571-576; Ponchon, et al., (2009) Nature Protocols, 4, 947-959; Nelissen, et al., (2012) Nucleic Acids Research, 40, e102) and rRNA (Liu, et al., (2010) BMC Biotechnology, 10, 85) have been successfully employed as scaffolds for the production of RNAs, given the fact that tRNAs and rRNAs are present as stable RNA molecules in the cells. The recombinant RNA chimeras are thus isolated, and the target RNAs may be released in demand for structural and biophysical analyses. This recombinant RNA technology provides a novel way for cost-effective and fast production of large quantities of recombinant RNAs (e.g., multimilligrams of RNA species from 1 L bacterial culture). Nevertheless, it has not been shown whether recombinant RNAs comprise any natural modifications (e.g., methylation of a base and pseudouridylation), and whether they are biologically functional in human cells.

SUMMARY

We produced pre-miRNA chimeras in common strains of E. coli using tRNA scaffolds. While the majority of tRNA/pre-miRNA chimeras did not accumulate in bacteria or only at a negligible level, a few chimeras, such as tRNA/pre-miRNA-34a, tRNA/pre-miRNA-1291 and tRNA/pre-miRNA-125-1 were expressed at high levels. Thus, we developed a high expressing non-coding ncRNA scaffold (hereinafter "OnRS")-based strategy to achieve a consistently high-yield production of chimeric RNAs in E. coli that offers the versatility to carry various types of functional small RNAs of interests such as miRNAs, siRNAs, RNA aptamers, guide RNAs, catalytic RNAs and riboswitches, where the OnRS may be a highly expressed tRNA fusion pre-miRNA or modified/artificial short hairpin RNA (shRNA). As demonstrated herein, this approach is proven robust and has broad applications to engineering of target chimeric RNAi agents and RNA sensors that may be utilized, e.g., as research tools and further developed as therapeutic agents and diagnostic tools.

Accordingly, in one aspect, polynucleotides comprising a tRNA operably linked to a pre-microRNA (pre-miRNA) or short hairpin RNA (shRNA) are provided. In varying embodiments, the tRNA is a methionyl tRNA. In varying embodiments, the tRNA has a nucleic acid sequence having at least 90% sequence identity, e.g., at least 91%, 92%, 93%, 94%, 95%, 96%, 97%, 98%, 99% or 100% sequence identity, to SEQ ID NO:1. In varying embodiments, the pre-miRNA or shRNA is naturally or artificially/synthetically derived. In varying embodiments, the pre-miRNA (or shRNA) is selected from pre-miRNA-1291, pre-miRNA-34a, pre-miRNA-125b, pre-miRNA-124, pre-miRNA-27b, and pre-miRNA-22.

In varying embodiments:
a) the pre-miRNA (or shRNA)-1291 comprises a nucleic acid sequence having at least 90% sequence identity, e.g., at least 91%, 92%, 93%, 94%, 95%, 96%, 97%, 98%, 99% or 100% sequence identity to the miRBase Accession No. MI0006353;
b) the pre-miRNA (or shRNA)-34a comprises a nucleic acid sequence having at least 90% sequence identity, e.g., at least 91%, 92%, 93%, 94%, 95%, 96%, 97%, 98%, 99% or 100% sequence identity to miRBase Accession No. MI0000268;
c) the pre-miRNA (or shRNA)-125b-1 comprises a nucleic acid sequence having at least 90% sequence identity, e.g., at least 91%, 92%, 93%, 94%, 95%, 96%, 97%, 98%, 99% or 100% sequence identity to miRBase Accession No. MI0000446;

d) the pre-miRNA (or shRNA)-124 comprises a nucleic acid sequence having at least 90% sequence identity, e.g., at least 91%, 92%, 93%, 94%, 95%, 96%, 97%, 98%, 99% or 100% sequence identity to miRBase Accession No. MI0000443;

e) the pre-miRNA (or shRNA)-27b comprises a nucleic acid sequence having at least 90% sequence identity, e.g., at least 91%, 92%, 93%, 94%, 95%, 96%, 97%, 98%, 99% or 100% sequence identity to miRBase Accession No. MI0000440; and/or f) the pre-miRNA (or shRNA)-22 comprises a nucleic acid sequence having at least 90% sequence identity, e.g., at least 91%, 92%, 93%, 94%, 95%, 96%, 97%, 98%, 99% or 100% sequence identity to miRBase Accession No. MI0000078.

In varying embodiments:

a) the pre-miRNA (or shRNA)-34a comprises a nucleic acid sequence having at least 90% sequence identity, e.g., at least 91%, 92%, 93%, 94%, 95%, 96%, 97%, 98%, 99% or 100% sequence identity, to SEQ ID NO:2;

b) the pre-miRNA (or shRNA)-1291 comprises a nucleic acid sequence having at least 90% sequence identity, e.g., at least 91%, 92%, 93%, 94%, 95%, 96%, 97%, 98%, 99% or 100% sequence identity, to SEQ ID NO:9;

c) the pre-miRNA (or shRNA)-125-1 comprises a nucleic acid sequence having at least 90% sequence identity, e.g., at least 91%, 92%, 93%, 94%, 95%, 96%, 97%, 98%, 99% or 100% sequence identity, to SEQ ID NO:17;

d) the pre-miRNA (or shRNA)-124 comprises a nucleic acid sequence having at least 90% sequence identity, e.g., at least 91%, 92%, 93%, 94%, 95%, 96%, 97%, 98%, 99% or 100% sequence identity, to SEQ ID NO:26;

e) the pre-miRNA (or shRNA)-27b comprises a nucleic acid sequence having at least 90% sequence identity, e.g., at least 91%, 92%, 93%, 94%, 95%, 96%, 97%, 98%, 99% or 100% sequence identity, to SEQ ID NO:29; and/or f) the pre-miRNA (or shRNA)-22 comprises a nucleic acid sequence having at least 90% sequence identity, e.g., at least 91%, 92%, 93%, 94%, 95%, 96%, 97%, 98%, 99% or 100% sequence identity, to SEQ ID NO:32.

In varying embodiments, the polynucleotide comprises a methionyl tRNA operably linked to a pre-miRNA (or shRNA), or mutants or variants thereof, selected from the group consisting of pre-miRNA-1291, pre-miRNA-34a, pre-miRNA-125b, pre-miRNA-124, pre-miRNA-27b and pre-miRNA-22.

In varying embodiments, the polynucleotide comprises:

a) the methionyl tRNA operably linked to the pre-miRNA (or shRNA)-34a has a nucleic acid sequence having at least 90% sequence identity, e.g., at least 91%, 92%, 93%, 94%, 95%, 96%, 97%, 98%, 99% or 100% sequence identity, to a polynucleotide selected from the group consisting of SEQ ID NO:3, SEQ ID NO:4, SEQ ID NO:5, SEQ ID NO:6; SEQ ID NO:7, SEQ ID NO:8, SEQ ID NO:28, SEQ ID NO:31, SEQ ID NO:34, SEQ ID NO:35, SEQ ID NO:36, SEQ ID NO:39 and SEQ ID NO:40;

b) the methionyl tRNA operably linked to the pre-miRNA (or shRNA)-1291 has a nucleic acid sequence having at least 90% sequence identity, e.g., at least 91%, 92%, 93%, 94%, 95%, 96%, 97%, 98%, 99% or 100% sequence identity, to a polynucleotide selected from the group consisting of SEQ ID NO:10, SEQ ID NO:11, SEQ ID NO:12, SEQ ID NO:13; SEQ ID NO:14, SEQ ID NO:15 and SEQ ID NO:16;

c) the methionyl tRNA operably linked to the pre-miRNA (or shRNA)-125 has a nucleic acid sequence having at least 90% sequence identity, e.g., at least 91%, 92%, 93%, 94%, 95%, 96%, 97%, 98%, 99% or 100% sequence identity, to a polynucleotide selected from the group consisting of SEQ ID NO:18, SEQ ID NO:19, SEQ ID NO:20, SEQ ID NO:21; SEQ ID NO:22, SEQ ID NO:23, SEQ ID NO:24 and SEQ ID NO:25;

d) the methionyl tRNA operably linked to the pre-miRNA (or shRNA)-124 has a nucleic acid sequence having at least 90% sequence identity, e.g., at least 91%, 92%, 93%, 94%, 95%, 96%, 97%, 98%, 99% or 100% sequence identity, to a polynucleotide selected from the group consisting of SEQ ID NO:27 and SEQ ID NO:28;

e) the methionyl tRNA operably linked to the pre-miRNA (or shRNA)-27b has a nucleic acid sequence having at least 90% sequence identity, e.g., at least 91%, 92%, 93%, 94%, 95%, 96%, 97%, 98%, 99% or 100% sequence identity, to a polynucleotide selected from the group consisting of SEQ ID NO:30 and SEQ ID NO:31; and/or f) the methionyl tRNA operably linked to the pre-miRNA (or shRNA)-155 has a nucleic acid sequence having at least 90% sequence identity, e.g., at least 91%, 92%, 93%, 94%, 95%, 96%, 97%, 98%, 99% or 100% sequence identity, to a polynucleotide selected from the group consisting of SEQ ID NO:33 and SEQ ID NO:34.

In varying embodiments, the tRNA comprises or comprised a stem-loop anticodon and all or part of the stem-loop anticodon of the tRNA is replaced with the pre-miRNA (or shRNA). In varying embodiments, the tRNA operably linked to the short hairpin RNA (shRNA) comprises a nucleic acid sequence having at least 90% sequence identity, e.g., at least 91%, 92%, 93%, 94%, 95%, 96%, 97%, 98%, 99% or 100% sequence identity, to a polynucleotide selected from the group consisting of SEQ ID NOs:41-45. In varying embodiments, the tRNA and/or pre-miRNA (or shRNA) are further operably linked to one or more inserted RNA molecules. In varying embodiments, the inserted RNA molecule is inserted at, abutted with or operably linked to: a) the 5' end of the pre-miRNA (or shRNA); b) the 3' end of the pre-miRNA (or shRNA); c) 5' of a dicer cleavage site of the pre-miRNA (or shRNA); or d) 3' of a dicer cleavage site of the pre-miRNA (or shRNA). In varying embodiments, the inserted RNA has at least about 18 nucleotides and up to about 200 nucleotides, e.g., at least about 18 nucleotides and up to about 50 nucleotides. In varying embodiments, the inserted RNA is selected from the group consisting of a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), a guide RNA (gRNA), a catalytic RNA, a riboswitch, and an RNA aptamer. In varying embodiments, the inserted RNA is a noncoding RNA. In some embodiments, the noncoding RNA is HOX antisense intergenic RNA (HOTAIR). In some embodiments, the inserted RNA is a mature miRNA selected from the group consisting of miR-21, miR-22, miR-27b, miR-33, miR-34a, miR 122, miR 124-1, miR-125-1, miR-1291 and let-7a. In some embodiments, the inserted RNA prevents, reduces or inhibits the expression of a target polypeptide. In some embodiments, the inserted RNA is an aptamer that binds to a target molecule or a target polypeptide. In some embodiments, the target polypeptide is selected from the group consisting of a fluorescent protein, a cytokine, a growth factor, a hormone, an enzyme, an ion channel, a kinase, a nuclear receptor, a G protein-coupled receptor, an epigenetic regulator, a transcription factor. In some embodiments, the fluorescent protein is selected from the group consisting of a violet fluorescent protein, a blue fluorescent protein (BFP), a cyan fluorescent protein, a green fluorescent protein (GFP), a yellow fluorescent protein (YFP), an orange fluorescent protein (OFP), a red fluorescent protein (RFP) and a sapphire-type protein. In some embodiments, the cytokine is selected from the group consisting of interleukin (IL)-1α, IL-1β, tumor necrosis factor (TNF)α, interferon (IFN)α, IFNβ, IFNγ, TGFβ1, IL-5, IL-6, IL-8, IL-10, IL-12, IL-17, IL-18, IL-22, IL-23 and migration inhibitory factor (MIF). In some embodiments, the nuclear receptor is Peroxisome proliferator-activated receptor gamma (PPAR-γ or PPARG). In some embodiments, the growth factor is vascular endothelial growth factor (VEGF). In some embodiments, the kinase is epidermal growth factor receptor (EGFR). In varying embodiments, the polynucleotide has a nucleic acid sequence having at least 90% sequence identity, e.g., at least 91%, 92%, 93%, 94%, 95%, 96%, 97%, 98%, 99% or 100% sequence identity, to a polynucleotide selected from the group consisting of SEQ ID NO:3, SEQ ID NO:4, SEQ ID NO:5, SEQ ID NO:6; SEQ ID NO:7, SEQ ID NO:8, SEQ ID NO:10, SEQ ID NO:11, SEQ ID NO:12, SEQ ID NO:13; SEQ ID NO:14, SEQ ID NO:15, SEQ ID NO:16; SEQ ID NO:18, SEQ ID NO:19, SEQ ID NO:20, SEQ ID NO:21; SEQ ID NO:22, SEQ ID NO:23, SEQ ID NO:24, SEQ ID NO:25; SEQ ID NO:27, SEQ ID NO:28; SEQ ID NO:30, SEQ ID NO:31, SEQ ID NO:33, SEQ ID NO:34, SEQ ID NO:35, SEQ ID NO:36, SEQ ID NO:37, SEQ ID NO:39 and SEQ ID NO:40.

In a further aspect, provided are expression cassettes comprising a polynucleotide comprising a tRNA operably linked to a pre-microRNA (pre-miRNA) or short-hairpin RNA (shRNA) as described above and herein In another aspect, provided is a liposome, a polymer or a nanoparticle comprising a polynucleotide or an expression cassette comprising a tRNA operably linked to a pre-microRNA (pre-miRNA) or short-hairpin RNA (shRNA) as described above and herein In another aspect, provided is a viral vector comprising a polynucleotide or an expression cassette comprising a tRNA operably linked to a pre-microRNA (pre-miRNA) or short-hairpin RNA (shRNA) as described above and herein.

In another aspect, provided are host cells transfected or transformed with a polynucleotide encoding a hybrid tRNA/pre-microRNA or tRNA/shRNA molecule, as described above and herein, or an expression cassette, liposome, polymer, nanoparticle, viral vector comprising a hybrid tRNA/pre-microRNA or tRNA/shRNA molecule. In varying embodiments, the host cell is a prokaryotic cell or a eukaryotic cell. In varying embodiments, the host cell is selected from a bacterial cell (e.g., E. coli), a mammalian cell (e.g., a human cell), an insect cell or a plant cell.

In a further aspect, provided are methods of producing a hybrid tRNA/pre-microRNA or tRNA/shRNA molecule, comprising expressing in a population of host cells the hybrid tRNA/pre-microRNA or tRNA/shRNA molecule from a polynucleotide, expression cassette, liposome, polymer, nanoparticle or viral vector as described above and herein. In varying embodiments, at least 1 mg e.g., at least about 2 mg, 3 mg, 4 mg, 5 mg, 6 mg, 7 mg, 8 mg, 9 mg, 10 mg, 12 mg, 15 mg, 20 mg, 30 mg, 40 mg, 50 mg, or more, of the hybrid tRNA/pre-microRNA or tRNA/shRNA molecule are produced from a 1 liter culture comprising the population of host cells. In some embodiments, the host cell is selected from a bacterial cell, a mammalian cell, an insect cell or a plant cell. In varying embodiments, at least about 1 mg, e.g., at least about 2 mg, 3 mg, 4 mg, 5 mg, 6 mg, 7 mg, 8 mg, 9 mg, 10 mg, 12 mg, 15 mg, 20 mg, 30 mg, 40 mg, 50 mg, or more, of the hybrid tRNA/pre-microRNA or tRNA/shRNA molecule are produced from a 1 liter culture of E. coli host cells over a period of about 24 hours. In varying embodiments at least about 1 mg, e.g., at least about 2 mg, 3 mg, 4 mg, 5 mg, 6 mg, 7 mg, 8 mg, 9 mg, 10 mg, 12 mg, 15 mg, 20 mg, 30 mg, 40 mg, 50 mg, or more, of the hybrid tRNA/pre-microRNA or tRNA/shRNA molecule are produced from a 1 liter culture of yeast host cells, e.g., over a period of about 24 hours. In varying embodiments, the hybrid tRNA/pre-microRNA or tRNA/shRNA molecule produced comprises at least about 5%, e.g., at least about 6%, 7%, 8%, 9%, 10%, 11%, 12%, 15%, 20%, or more, of the total RNA.

In a further aspect, provided are methods of producing an RNA molecule, comprising expressing the RNA molecule from a a hybrid tRNA/pre-microRNA or tRNA/shRNA polynucleotide, expression cassette, liposome, polymer, nanoparticle or viral vector as described above and herein. In varying embodiments, at least 1 mg e.g., at least about 2 mg, 3 mg, 4 mg, 5 mg, 6 mg, 7 mg, 8 mg, 9 mg, 10 mg, 12 mg, 15 mg, 20 mg, 30 mg, 40 mg, 50 mg, or more, of the RNA molecule are produced from a 1 liter culture comprising the population of host cells. In some embodiments, the host cell is selected from a bacterial cell, a mammalian cell, an insect cell or a plant cell. In varying embodiments, at least about 1 mg, e.g., at least about 2 mg, 3 mg, 4 mg, 5 mg, 6 mg, 7 mg, 8 mg, 9 mg, 10 mg, 12 mg, 15 mg, 20 mg, 30 mg, 40 mg, 50 mg, or more, of the RNA molecule are produced from a 1 liter culture of E. coli host cells over a period of about 24 hours. In varying embodiments at least about 1 mg, e.g., at least about 2 mg, 3 mg, 4 mg, 5 mg, 6 mg, 7 mg, 8 mg, 9 mg, 10 mg, 12 mg, 15 mg, 20 mg, 30 mg, 40 mg, 50 mg, or more, of the RNA molecule are produced from a 1 liter culture yeast host cells, e.g., over a period of about 24 hours. In varying embodiments, the RNA molecule produced comprises at least about 5%, e.g., at least about 6%, 7%, 8%, 9%, 10%, 11%, 12%, 15%, 20%, or more, of the total RNA.

In another aspect, provided are methods of preventing, reducing or inhibiting the expression of a target polynucleotide in a subject in need thereof, comprising administering to the subject a polynucleotide, expression cassette, liposome, polymer, nanoparticle or viral vector as described above and herein. In varying embodiments, at least about 1 mg, e.g., at least about 2 mg, 3 mg, 4 mg, 5 mg, 6 mg, 7 mg, 8 mg, 9 mg, 10 mg, 12 mg, 15 mg, 20 mg, 30 mg, 40 mg, 50 mg, or more, of the hybrid tRNA/pre-microRNA or tRNA/shRNA molecule are produced from a 1 liter culture of E. coli host cells over a period of about 24 hours. In varying embodiments at least about 1 mg, e.g., at least about 2 mg, 3 mg, 4 mg, 5 mg, 6 mg, 7 mg, 8 mg, 9 mg, 10 mg, 12 mg, 15 mg, 20 mg, 30 mg, 40 mg, 50 mg, or more, of the hybrid tRNA/pre-microRNA or tRNA/shRNA molecule are produced from a 1 liter culture yeast host cells, e.g., over a period of about 24 hours. In varying embodiments, the hybrid tRNA/pre-microRNA or tRNA/shRNA molecule produced comprises at least about 5%, e.g., at least about 6%, 7%, 8%, 9%, 10%, 11%, 12%, 15%, 20%, or more, of the total RNA.

In another aspect, provided are methods of preventing, mitigating, reducing and/or inhibiting the growth, proliferation, and/or progression of a cancer in a subject in need thereof, comprising administering to the subject a polynucleotide, expression cassette, liposome, polymer, nanoparticle or viral vector as described above and herein. In varying embodiments, the cancer is selected from the group consisting of breast cancer, lymphoma, colorectal cancer, hepatocellular carcinoma, pancreatic cancer, prostate cancer, and lung cancer.

In another aspect, provided are methods of identifying the presence of a target molecule in a sample, comprising contacting a sample suspected of containing the target molecule under conditions that allow binding an inserted RNA expressed from the a polynucleotide, expression cassette, liposome, polymer, nanoparticle or viral vector as described above and herein, wherein binding of the inserted RNA to the target molecule in the sample identifies its presence.

In another aspect, provided are kits comprising a polynucleotide, expression cassette, liposome, polymer, nanoparticle or viral vector as described above and herein.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 4th ed., Cold Spring Harbor Laboratory Press, Cold Spring Harbor, N.Y. (2012) and Ausubel, ed., Current Protocols in Molecular Biology, John Wiley Interscience, (1990-2014)), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

The term "polynucleotide" refers to polymers composed of deoxyribonucleotides, ribonucleotides or any combination thereof.

As used herein, the term "nucleotide" refers to a chemical moiety having a sugar (modified, unmodified, or an analog thereof), a nucleotide base (modified, unmodified, or an analog thereof), and a phosphate group (modified, unmodified, or an analog thereof). Nucleotides include deoxyribonucleotides, ribonucleotides, and modified nucleotide analogs including, for example, locked nucleic acids ("LNAs"), peptide nucleic acids ("PNAs"), L-nucleotides, ethylene-bridged nucleic acids ("EN As"), arabinoside, and nucleotide analogs (including abasic nucleotides). Similarly, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. RNA may be used in the methods described herein and/or may be converted to cDNA by reverse-transcription and/or RNA for use in the methods described herein.

As used herein interchangeably, a "microRNA," "miR," or "miRNA" refer to the unprocessed or processed RNA transcript from a miRNA gene. The unprocessed miRNA gene transcript is also called a "miRNA precursor," and typically comprises an RNA transcript of about 70-100 nucleotides in length. The miRNA precursor can be processed by digestion with an RNAse (for example, Dicer, Argonaut, or RNAse III) into an active 19-25 nucleotide RNA molecule. This active 19-25 nucleotide RNA molecule is also called the "processed" miRNA gene transcript or "mature" miRNA.

The terms "pre-microRNA" or "pre-miR" or pre-miRNA" interchangeably refer to an RNA hairpin comprising within its polynucleotide sequence at least one mature micro RNA sequence and at least one dicer cleavable site.

The terms "pre-miRNA-1291" or "hsa-mir-1291" or "HGNC:MIR1291" interchangeable refer to an RNA polynucleotide having at least 90% sequence identity, e.g., at least 91%, 92%, 93%, 94%, 95%, 96%, 97%, 98%, 99% or 100% sequence identity, to miRBase Accession No. MI0006353 (www.mirbase.org) or SEQ ID NO:9.

The terms "pre-miRNA-34a" or "hsa-mir-34a" or "HGNC:MIR34A" interchangeable refer to an RNA polynucleotide having at least 90% sequence identity, e.g., at least 91%, 92%, 93%, 94%, 95%, 96%, 97%, 98%, 99% or 100% sequence identity, to miRBase Accession No. MI0000268 (www.mirbase.org) or SEQ ID NO:2.

The terms "pre-miRNA-125-1" or "hsa-mir-125b-1" or "HGNC:MIR125B1" interchangeable refer to an RNA polynucleotide having at least 90% sequence identity, e.g., at least 91%, 92%, 93%, 94%, 95%, 96%, 97%, 98%, 99% or 100% sequence identity, to miRBase Accession No. MI0000446 (www.mirbase.org) or SEQ ID NO:17.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., the tRNA, pre-microRNA and tRNA/microRNA hybrid polynucleotide molecules described herein, e.g, SEQ ID NOs:1-45, when compared and aligned for maximum correspondence over a comparison window, or designated region as measured using a sequence comparison algorithms (e.g., BLAST, ALIGN, FASTA or any other known alignment algorithm) or by manual alignment and visual inspection. Such sequences are then said to be "substantially identical." This definition also refers to the compliment of a test sequence. Preferably, the identity exists over a region that is at least about 10, 15, 20, 25, 35, 40, 45, 50, 60, 70, 80, 90, 100, 110, 120 nucleotides in length, or over the full-length of a reference sequence.

As used herein, the term "short interfering nucleic acid" or "siRNA" refers to any nucleic acid molecule capable of down regulating {i.e., inhibiting) gene expression in a mammalian cells (preferably a human cell). siRNA includes without limitation nucleic acid molecules that are capable of mediating sequence specific RNAi, for example short interfering RNA (siRNA), double-stranded RNA (dsRNA), micro-RNA (miRNA), and short hairpin RNA (shRNA). Likewise, the term "sense region" refers to a nucleotide sequence of a siRNA molecule complementary (partially or fully) to an antisense region of the siRNA molecule. Optionally, the sense strand of a siRNA molecule may also include additional nucleotides not complementary to the antisense region of the siRNA molecule. Conversely, as used herein, the term "antisense region" refers to a nucleotide sequence of a siRNA molecule complementary (partially or fully) to a target nucleic acid sequence. Optionally, the antisense strand of a siRNA molecule may include additional nucleotides not complementary to the sense region of the siRNA molecule.

The terms "piRNA" and "Piwi-interacting RNA" are interchangeable and refer to a class of small RNAs involved in gene silencing. PiRNA molecules typically are between 26 and 31 nucleotides in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against the ncRNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of any one or more of transcription of a microRNA, siRNA, piRNA, snRNA, lncRNA, antisense nucleic acid, or mRNA from a DNA or RNA template and can further include translation of a protein from an mRNA template. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequence. Homologous regions may vary in length, but will typically be between 4 and 40 nucleotides (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.).

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

A "target site" or "target sequence" is the nucleic acid sequence recognized (i.e., sufficiently complementary for hybridization) by an antisense oligonucleotide or inhibitory RNA molecule.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a subject who is, or is suspected to be, afflicted with a disease.

As used herein, the terms "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

The terms "cancer-associated antigen" or "tumor-associated antigen" or "tumor-specific marker" or "tumor marker" interchangeably refers to a molecule (typically protein, carbohydrate or lipid) that is preferentially expressed on the surface of a cancer cell in comparison to a normal cell, and which is useful for the preferential targeting of a pharmacological agent to the cancer cell. Oftentimes, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal.

BRIEF DESCRIPTION OF THE DRAWINGS

FIGS. 1A-D illustrate the establishment of OnRS for high-level expression of recombinant RNAs in E. coli. (A) and (B) When only the tRNA scaffold was used, the majority of pre-miRNAs were not expressed or at a limited level despite that mir-34a, mir-1291 and mir-125 etc. were expressed at very high levels. (C) and (D) Therefore, the tRNA/mir-34a, tRNA/mir-1291 and tRNA/mir-125, etc. were developed as new scaffolds that allow a consistent, high-level production of miRNAs or siRNAs (or other small RNAs; please see the following figures).

FIGS. 2A-D illustrate the design of recombinant RNAs using the tRNA/pre-miRNA or tRNA/shRNA non-coding RNA (ncRNA) scaffolds (OnRS). Shown are the secondary structures of OnRS such as tRNA/pre-miRNA hybrid carrying a miRNA or siRNA (A), or tRNA/shRNA OnRS bearing a siRNA or miRNA (B), the OnRS carrying a small RNA (e.g., an aptamer) or other RNA species at the 5' of the pre-miRNA or shRNA (C), and the OnRS carrying a small RNA (e.g., an aptamer) or other target RNA species at the 3' of the pre-miRNA or shRNA (D). The shaded highlights the small RNAs inserted in the OnRS carrier.

FIGS. 3A-D illustrate the consistently high-level expression of recombinant miRNAs using OnRS, which are also indicated by their FPLC traces during purification. Approximately the same amount of total RNAs were loaded onto the column. (A) The level of tRNA/pre-mir-34a scaffold (A) is about 5- to 10-fold higher than tRNA scaffold. (B) Expression levels of miR-27b using a tRNA/pre-mir-34a scaffold versus tRNA alone. (C) Expression of miR-124 using a tRNA/pre-mir-34a scaffold versus tRNA alone. (D) Expression of a scrambled RNA using OnRS (OnRS/Neg).

FIGS. 4A-C illustrate the effectiveness of recombinant mir-34a in suppressing cancer cell proliferation and target gene expression, and controlling xenograft tumor progression. (A) tRNA/mir-34a inhibited the growth of human carcinoma A549 cells in a dose dependent manner and to a much greater degrees than the control tRNA/MSA (P<0.001, two-way ANOVA). Cell viability was determined using MTT assay at 72 h post-transfection. Values are mean±SD of triplicate cultures. (B) Compared to the control tRNA/MSA, recombinant tRNA/mir-34a sharply reduced the protein levels of a number of miR-34a target genes including CDK6, MET and SIRT1 in A549 cells. Western blots were conducted using protein selective antibodies. GAPDH was used as a loading control. (C) Compared to the same dose of tRNA/MSA or vehicle control, tRNA/mir-34a (100 µs) significantly (P<0.001, unpaired t test) suppressed the growth of A549 xenograft tumors in mouse models. FPLC-purified ncRNAs were administered intratumorally every the other day for three times. Values are mean±SD (N=6 per group except N=4 for vehicle treatment).

FIG. 5A-D illustrate the fate of recombinant ncRNAs in human cells. (a and b) Unbiased deep sequencing study revealed that OnRS-carried miR-124 and GFP-siRNA were precisely processed to target small RNAs, leading to 3 orders of magnitude increase in miR-124 in A549 cells and GFP siRNA in ES-2/GFP cells, respectively. Note the presence of miRNA and siRNA isoforms as well as corresponding passenger strands and other small RNAs at much lower levels. In contrast, the levels of other cellular miRNAs showed no or minor changes. Values are mean ±SD of triplicated treatments that were sequenced separately. (c and d) Mapping major cellular tRFs derived from OnRS/miR-124 versus OnRS (tRNA/mir-34a) in A549 cells and OnRS/GFP-siRNA versus OnRS/Neg in ES-2/GFP cells, respectively. Shown are the mean numbers of reads of triplicated treatments. 3,000 reads was used as a cut off. FIG. 5C amino acid sequences from Top to Bottom: SEQ ID Nos: 140-50. FIG. 5D amino acid sequences from Top to Bottom: SEQ ID NOs: 151-159.

FIGS. 6A-E illustrate OnRS-carried miRNA is biologically/pharmacologically active in regulating target gene expression and controlling cellular processes in human cells. (a) RT-qPCR analysis revealed that mature miR-124 levels retained 3 orders of magnitude higher in A549 cells for 4 days since transfection with OnRS/miR-124, as compared with OnRS/Neg. (b) Western blots showed that OnRS/miR-124 was effective in reducing the protein expression level of miR-124 target gene STAT3 in A549 cells at 72 h post-transfection. (c) Flow cytometric analyses demonstrated that OnRS/miR-124 was effective in inducing apoptosis in A549 cells at 48 h post-transfection. Cells treated with OnRS/Neg were used as controls. (d) MTT assay showed that OnRS/miR-124 significantly suppressed the proliferation of A549 cells at 72 h post-treatment, as compared to OnRS/Neg. (e) Inhibition of A549 cell proliferation by OnRS/miR-124 was also demonstrated when cell growth was monitored using Icelligence Real-Time Cell analyzer. The arrow points to the time point of ncRNA treatment. Values are mean±SD of triplicated treatments. *P<0.01.

FIGS. 7A-F illustrate OnRS-carried siRNA is effective for RNAi in vitro and in vivo. GFP fluorescence intensity was sharply reduced in ES-2/GFP cells in vitro at 72 h after transfected with OnRS/GFP-siRNA (a), which was associated with (b) 70-80% lower GFP mRNA levels and (c) 1000-fold higher GFP siRNA levels. Following i.v. administration of OnRS/GFP-siRNA, hepatic GFP fluorescence was significantly suppressed in the GFP-transgenic mouse models in vivo, as demonstrated by microscopic examination of (d) non-fixed and (e) fixed liver slices, as well as (f) RT-qPCR analysis of hepatic GFP mRNA levels. Fixed liver slices were stained with DAPI, and GFP fluorescence and DAPI-stained nuclei (blue) images were merged together (e). Control RS-2/GFP cells (N=3 per group) or GFP-transgenic mice (N=3-4 per group) were treated with the same doses of OnRS/Neg. Values are mean±SD. *P<0.01, compared with OnRS/Neg treatment.

FIGS. 9A-E illustrate high-yield large-scale production of chimeric MGA sensor that produces strong and selective fluorescence upon binding to MG. (a) MGA may be inserted at the 5' or 3' end of the OnRS scaffold to offer OnRS/MGA5 and OnRS/MGA3, respectively. The heat color gradation indicates the base-pairing probability from 0 to 1. (b) A consistent high-level expression of chimeric MGA in E. coli, e.g., over 50% of OnRS/MGA5 and OnRS/MGA3 in total RNAs. (c) Representative FPLC traces of OnRS/MGA5 during FPLC purification. Insert is urea-PAGE analysis of the collected RNA fractions (1, 2 and 3) eluted at 10.6 min. (d) Binding to OnRS/MGA5 and OnRS/MGA3 led to a shift of the wavelength of MG maximum absorbance from 618 to 630 nm. The same shift was observed when FPLC-purified OnRS/MGA and total RNAs isolated from OnRS/MGA-expressing bacteria were used. The SEPHADEX™-purified aptamer (OnRS/Seph) and corresponding total RNAs were used as additional controls. (e) Strong and selective fluorescence was shown when MG bound to OnRS/MGA5 or OnRS/MGA3. The same results were obtained when using FPLC-purified OnRS/MGA and OnRS/MGA-containing total RNAs.

FIG. 10A-E illustrate methods to determine RNase activity using chimeric MGA sensor. (a) Change in MGA-bound-MG fluorescent intensity with the increase in MG and MGA concentrations. Corresponding MGA and MG concentrations were fixed at 1.6 µg/mL and 10 µM, respectively. (b) The fluorescent intensity was decreased over time when incubated with human serum, and in vivo-jetPEI formulated OnRS/MGA was protected from cleavage by serum RNases. (c) Dose response was obvious for the exposure to human serum RNases and the intensity of OnRS/MGA-bound MG fluorescence, and addition of RNase inhibitor completely blocked the cleavage of OnRS/MGA by serum RNases. (d) OnRS/MGA was much more susceptible to human RNase A (10 min incubation) than angiogenin (RNase 5; 30 min incubation). (e) Human pancreatic cancer patients showed significantly higher serum RNase activities than benign/normal patients, as determined by the decrease in MGA-bound MG fluorescence intensity (ΔA.U./min/μL). N=10 in each group. OnRS/MGA5 was used in this study.

FIGS. 11A-D illustrate design, expression and purification of recombinant chimeric miR-1291. (A) Secondary structures of tRNA/MSA, pre-miR-1291 and chimeric tRNA/mir-1291-123nt were predicted with CentroidFold. (B) Target pre-miR-1291 inserts were cloned into the pBSMrna vector linearized with endonucleases Sal I and Aat II. (C) Successful expression of recombinant tRNA/mir-1291 in *E. coli* was demonstrated by the appearance of new RNA band (indicated by the arrow) at expected size/mobility after urea-PAGE separation. (D) Recombinant ncRNAs bearing a sephadex aptamer were purified by affinity chromatography. The cell lysate flow-though and individual fractions were analyzed by urea-PAGE. The flow-through and Wash 1-3 mainly comprised the unbound RNAs. Eluate1 and Eluate 2 contained >85% pure recombinant ncRNAs.

FIGS. 12 A-C illustrate structural characterization of recombinant ncRNAs. (A) MWs of intact ncRNAs were determined by ESI-MS analyses, and the differences between measured and predicted MWs suggest the presence of post-transcriptionally-modified nucleosides. (B) Post-transcriptionally modified nucleosides were identified by LC-UV-MS analyses of the hydrolysates of recombinant ncRNAs. Shown are LC-UV traces of the hydrolysates of tRNA/MSA and tRNA/mir-1291, and individual peaks were annotated according to their retention times and mass spectra. D, dihydrouridine; Ψpseudouridine; C, cytidine; acp$^3$U, 3-(3-amino-3-carboxypropyl)uridine; U, uridine; m$^5$U, 5-methyluridine; G, guanosine; m$^7$G, 7-methylguanosine; S$^4$U, 4-thiouridine; Gm, 2'-O-methylguanosine; m$^1$G, 1-methylguanosine; A, adenosine. (C) Mapping and sequencing of tRNA/MSA and tRNA/mir-1291 was achieved by LC-MS/MS analyses of RNase T1 digestions. Modified nucleosides were also localized, based upon their MS/MS fragmentations.

FIGS. 13A-D illustrate tRNA-carried pre-miR-1291 is processed to mature miR-1291 in in human MCF-7 breast cancer cells. (A-B) The levels of pre-miR-1291 and mature miR-1291 were increased in a dose dependent manner in MCF-7 cells after transfection with purified tRNA/mir-1291. (C-D) The time courses of pre-miR-1291 and mature miR-1291 were monitored in MCF-7 cells at 6, 24, 48 and 72 h post-transfection with 20 nM recombinant tRNA/mir-1291. Cells without treatment or treated with the same doses of tRNA/MSA or vehicle were used as controls. RNA levels were determined by selective qPCR assays. Values are mean±SD of triplicate treatments. *P<0.05, compared to cells treated with the same doses of tRNA/MSA or vehicle or cells without treatment that were harvested at the same time points.

FIGS. 14A-C illustrate recombinant tRNA/mir-1291 is effective to regulate miR-1291 target gene expression in human carcinoma cells. MRP1 (A), FOXA2 (B) and MeCP2 (C) protein levels were significantly reduced in human carcinoma cells at 48 h post-transfection with 20 nM of tRNA/mir-1291. Western blot analyses were conducted with selective antibodies. GAPDH was used as a loading control. Values are mean±SD of triplicate treatments. *P<0.05 and **P<0.01, compared to the control tRNA/MSA treatment.

FIGS. 15A-C illustrate chimeric miR-1291 is effective to suppress human carcinoma cell proliferation. PANC-1 (A) and MCF-7 (B) cells were sensitive to recombinant tRNA/mir-1291 in a dose dependent manner, to a significantly (P<0.01, two-way ANOVA) greater degree than tRNA/MSA. This is also indicated by the estimated EC50 and Hill slope values (C). Cell viability was determined with MTT assay. Values are mean±SD (N=3) of triplicate treatments.*Significantly (P<0.05) different from the control tRNA/MSA in the same cell line.

FIGS. 16A-B illustrate tRNA-carried pre-miR-1291 enhances the chemosensitivity of PANC-1 cells. (A) tRNA/mir-1291 significantly (P<0.01, two-way ANOVA) sensitized PANC-1 cells to doxorubicin, as compared with tRNA/MSA or vehicle treatment. (B) Estimated EC50 and Hill slope values for doxorubicin cytotoxicity in vehicle-, tRNA/MSA- and tRNA/mir-1291-transfected PANC-1 cells. Cell viability was determined with MTT assay. Values are mean±SD (N=3) of triplicate treatments. *Significantly (P<0.05) different from tRNA/MSA and vehicle treatment.

FIGS. 17A-E illustrate production and structural characterization of recombinant tRNA/mir-34a agents. (A) The secondary structure of chimeric tRNA/mir-34a (233 nt) predicted by CentroidFold showed that the stem-loop structure of mir-34a retained within the chimeric ncRNA. The heat color gradation indicates the base-pairing probability from 0 to 1. (B) Expression of tRNA/mir-34a in various strains of *E. coli*. Among those tested, the highest levels of recombinant ncRNAs were found in HST08. (C) FPLC traces of tRNA/mir-34a and tRNA/MSA during the purification. Total RNAs were separated using anion-exchange FPLC and monitored at 260 nm. (D) HPLC analysis confirmed the high homogeneity (>98%) of purified tRNA/mir-34a and tRNA/MSA. (E) LC-MS/MS mapping/sequencing of purified tRNA/mir-34a and tRNA/MSA after the digestion with RNase T1. All posttranscriptional modifications except deoxyadenosine identified by nucleoside analysis (FIG. 18) could be mapped to RNase T1 digestion products and assigned to specific sites.

FIGS. 18A-E illustrate expression and affinity purification of recombinant tRNA/mir-34a. (A) tRNA/mir-34a-129nt (233 nt in total) and tRNA/mir-34a-112nt (216 nt in total) chimeras were expressed at comparably high levels in HST08 *E. coli*. The tRNA/mir-34a-129nt was chosen for further investigation which is simply named tRNA/mir-34a. (B) Time course of tRNA/mir-34a levels accumulated within HST08 cells after transformation indicated that higher ncRNA levels were achieved at 9-14 hr post-transformation. Chimeric tRNA/mir-34a levels were determined by qPCR assay, normalized to bacterial 16S, and then multiplied by the quantities of total RNAs isolated from corresponding cultures. Values are mean±SD of triplicate cultures. (C) Expression/accumulation levels of tRNA/mir-34a using home-made and commercial HST08 competent cells were comparable. (D) Consistent high-level expression of recombinant ncRNAs in different batches of 0.5 L bacterial cultures. (E) Urea-PAGE analysis of RNA fractions during affinity purification using Sephadex G-100 beads. While pure recombinant ncRNAs were readily obtained, the overall purification yields were very low (e.g., ~2% recombinant ncRNAs/total RNAs) due to an obvious poor binding to the Sephadex aptamer.

FIGS. 19A-C illustrate structural characterization of recombinant tRNA/mir-34a and tRNA/MSA purified by anion-exchange FPLC. (A) The molecular weight (MW) of intact ncRNA was determined by electrospray ionization mass spectrometry (ESI-MS) analyses, followed by deconvolution of multiply protonated ions. The differences between the measured and predicted MWs of tRNA/mir-34a and tRNA/MSA suggest the presence of posttranscriptionally modified nucleosides. tRNA/mir-34a amino acid sequence: SEQ ID NO:3; tRNA/NISA amino acid sequence:

Figure 8:
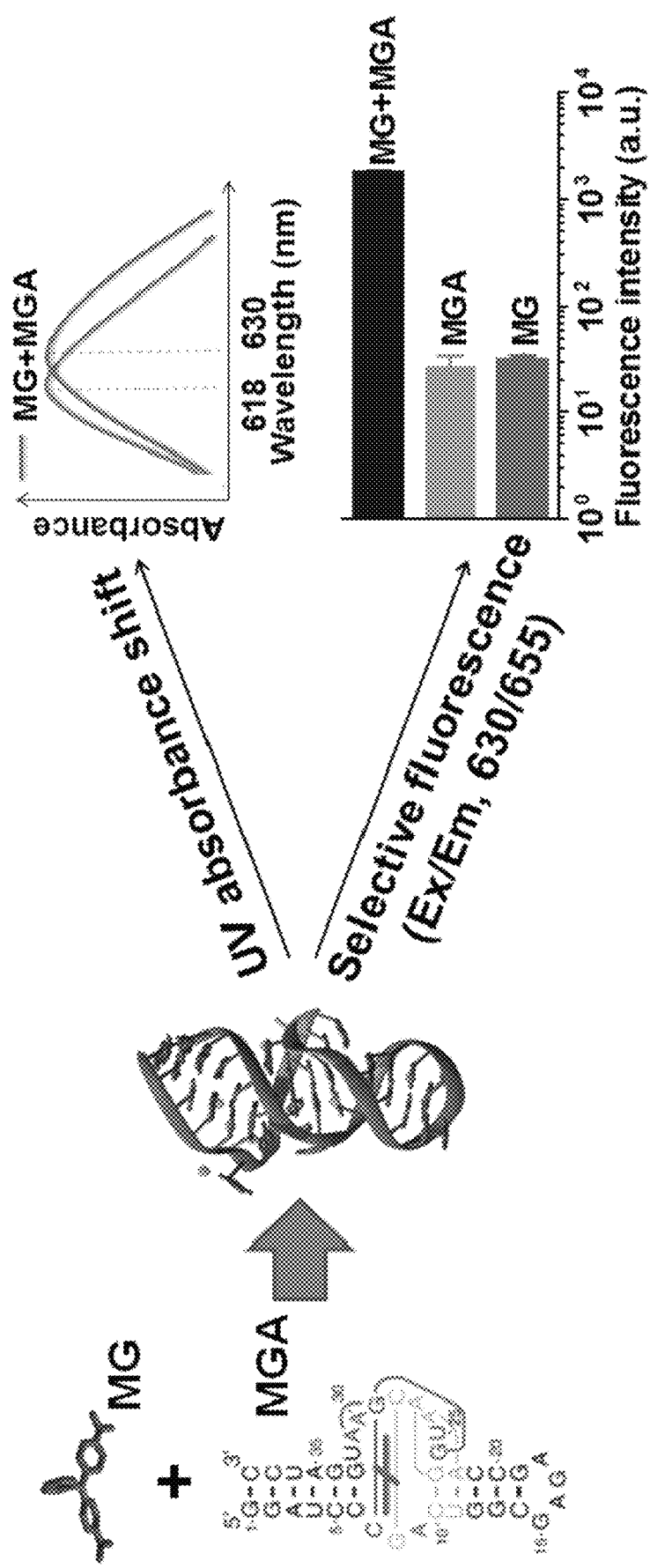
FIG. 8 illustrates the basic principle of the herein described RNase assay method using a malachite green aptamer (MGA) sensor. MGA amino acid sequence: SEQ ID NO:166.

SEQ ID NO:160. (B) Identification of posttranscriptionally modified nucleosides through LC-UV-MS analyses of the hydrolysates of recombinant ncRNAs. Shown are LC-UV traces of the hydrolysates of tRNA/MSA and tRNA/mir-34a, and individual peaks were assigned to natural nucleosides based on their retention times and mass spectra. D, dihydrouridine; Ψ, pseudouridine; C, cytidine; acp$^3$U, 3-(3-amino-3-carboxypropyl)uridine; U, uridine; m$^5$U, 5-methyluridine; G, guanosine; m$^7$G, 7-methylguanosine; S$^4$U, 4-thiouridine; Gm, 2'-O-methylguanosine; m$^1$G, 1-methylguanosine; A, adenosine; dA, deoxyadenosine. (C) RNase T1 mapping tRNA/mir-34a and tRNA/MSA. Shown are the total ion LC-MS chromatograms of RNase T1-digested tRNA/MSA and tRNA/mir-34a, and the identification of an example fragment [m$^7$G][acp$^3$U]CACAG (m/z 1157.76, [M−2H+]$^{2-}$) eluted at 33.0 min based upon the MS/MS fragment ions.

FIGS. 20A-C illustrate tRNA-carried pre-miR-34a was selectively processed to mature miR-34a in human carcinoma cells while tRNA scaffold was degraded to tRFs, as revealed by unbiased deep sequencing studies. Mature miR-34a levels were over 70-fold higher in A549 cells treated with 5 nM tRNA/mir-34a, as compared to cells treated with the control tRNA/MSA (A) or vehicle (B). This was associated with a 60- to 65-fold increase in the numbers of reads of 15-nt miR-34a-p3 fragment (5'-CACGUU-GUGGGGCCC-3') (SEQ ID NO:46). In contrast, changes in other miRNAs were small or insignificant, except several undefined small RNAs (e.g., hsa-mir-7641-1-p5 _1ss6TC). Values are mean ±SD of triplicate treatments that were sequenced separately. (C) Mapping major tRFs derived from tRNA/mir-34a and tRNA/MSA in A549 cells. Amino acid sequences from top to bottom: SEQ ID NOs: 161, 145, 142, 150, 162, 163, 164, 143, 141, 146, and 165.

FIGS. 21A-D illustrate cellular stability and RNase susceptibility of chimeric tRNA/mir-34a. (A) Chimeric tRNA/mir-34a was processed to mature miR-34a in various types of human carcinoma cells, as determined by selective stem-loop RT-qPCR analyses. Values are mean±SD of triplicate treatments. (B) The levels of chimeric ncRNA (tRNA/mir-34a or tRNA/MSA), pre-miRNA mir-34a, and mature miRNA miR-34a were increased in a dose dependent manner (P<0.001, one-way ANOVA) in A549 cells at 24 h after transfection with 1, 5 or 25 nM of FPLC-purified tRNA/mir-34a or tRNA/MSA. Note that mir-34a and miR-34a levels were only elevated in cells treated with tRNA/mir-34a. (C) Chimeric ncRNA (tRNA/mir-34a or tRNA/MSA; 5 nM) exhibited a good stability in A549 cells. Note that change in mature miR-34a levels was dependent upon tRNA/mir-34a treatment. (D) Chimeric tRNA/mir-34a and the tRNA/MSA were susceptible to a number of human RNases including RNase A, angiogenin and Dicer. RNase digestions were analyzed with 8% Urea PAGE.

FIGS. 22A-B that recombinant mir-34a was biologically/pharmacologically active in suppressing cancer cell proliferation and target gene expression. (A) tRNA/mir-34a inhibited the growth of human carcinoma A549 and HepG2 cells in a dose dependent manner and to much greater degrees than the control tRNA/MSA (P<0.001, two-way ANOVA). Antiproliferative activities against H460 and Huh-7 cells are shown in FIG. 23, and the estimated ED50 and Hill Slope values are provided in Table 2. Cell viability was determined using MTT assay at 72 h post-transfection. Values are mean±SD of triplicate cultures. (B) Compared to the control tRNA/MSA, recombinant tRNA/mir-34a sharply reduced the protein levels of a number of miR-34a target genes including CDK6, MET and SIRT1 in A549 and HepG2 cells. Western blots were conducted using protein selective antibodies. GAPDH was used as a loading control.

FIGS. 23A-B illustrate recombinant tRNA/mir-34a inhibited the growth of lung H460 (A) and liver Huh-7 (B) human carcinoma cells in a dose dependent manner and to greater degree than the control tRNA/MSA (P<0.001, two-way ANOVA). Cells transfected with the same doses of tRNA/MSA were used as controls. Cell viability was determined using MTT assay at 72 h post-transfection. Values are mean±SD of triplicate treatments.

FIGS. 24A-B illustrate that recombinant mir-34a was equally or more effective than synthetic miR-34a mimics to reduce human carcinoma cell proliferation and target gene expression. (A) The effects of 5 nM biologic tRNA/mir-34a, and synthetic miR-34a precursor and mimics on the growth of A549 and HepG2 carcinoma cells. Cell viability was determined using MTT assay at 72 h post-transfection. Values are mean±SD of triplicate treatments. *P<0.05, compared to corresponding control. (B) The effects of 25 nM recombinant mir-34a and synthetic miR-34a mimics on the protein levels of miR-34a target genes CDK6, MET, and SIRT1 in A549 and HepG2 carcinoma cells, as determined by Western blots at 72 h post-transfection.

FIGS. 25A-B illustrate that recombinant mir-34a was effective to control xenograft tumor progression in mouse models. (A) Compared to the same dose of tRNA/MSA or vehicle control, tRNA/mir-34a (100 µg) significantly (P<0.001, unpaired t test) suppressed the growth of A549 xenograft tumors. Note that the tumors in three mice completely disappeared after the treatment with 100 µs of tRNA/mir-34a. (B) Growth of HepG2 xenograft tumors were also significantly (P<0.01, unpaired t test) suppressed by the 100 µg dose tRNA/mir-34a treatment, as compared with the same dose of tRNA/MSA or vehicle. FPLC-purified ncRNAs were administered intratumorally every the other day for three times. Values are mean±SD (N=6 per group for A549 xenografts; N=4 per group for HepG2 xenografts). Separate groups of mice (N=4) were treated with vehicle as additional controls.

FIGS. 26A-C illustrate that biologic ncRNAs were well tolerated in mouse models. (A) In vivo-jetPEI-loaded ncRNAs were protected against the degradation by serum RNases. (B) Compared with vehicle control treatment, in vivo-jetPEI formulated recombinant ncRNAs (100 µg, i.v.) did not cause significant change in mouse serum IL-6 levels while LPS did (two-way ANOVA with Bonferroni post-tests). (C) Recombinant ncRNAs (100 µg, i.v.) had no significant influence on blood chemistry profiles including alanine aminotransferase (ALT), aspartate aminotransferase (AST), blood urea nitrogen (BUN), alkaline phosphatase (ALP), creatinine, total bilirubin, albumin and total protein. The gray-shaded area indicates the guideline ranges reported by the Comparative Pathology Laboratory at UC Davis. Values are mean±SD (N=3-4 mice per time point and treatment).

DETAILED DESCRIPTION

1. Introduction

Provided are tRNA/pre-microRNA and tRNA/shRNA scaffolds, based in part, on the unexpected observation that the majority pre-miRNAs and tRNA/shRNAs are not expressed or at limited levels only using a tRNA scaffold. The present tRNA/pre-microRNA and tRNA/shRNA scaffolds find use for high-level production of recombinant RNAs bearing target small RNAs (e.g., miRNAs, siRNAs, RNA aptamers, catalytic RNAs, riboswitches, guide RNAs and other RNA species).

Provided herein are tRNA/pre-miRNA and tRNA/shRNA hybrid molecules based non-coding RNA (ncRNA) scaffolds (OnRS) for a consistent high-level expression of recombinant ncRNAs consisting of target RNAs on a large scale. After purification and structural characterization, the tRNA/pre-microRNA and tRNA/shRNA scaffold chimeras were confirmed to bind directly to Dicer and processed to target RNAs (e.g., siRNAs and miRNAs). Most importantly, the OnRS-carried RNAs (i.e., inserted RNAs) are biologically active in regulating target gene expression and controlling cellular processes, even to a greater degree than the same concentration of chemically modified RNAs (e.g., miRNA mimics or pre-microRNAs). The tRNA/pre-microRNA and tRNA/shRNA scaffolds allow for the consistent high-level expression of biologically-active target miRNAs, siRNA and RNA aptamers (as well as a scrambled small RNA). Consequently, the OnRS-carried recombinant RNAs find use as therapeutic, diagnostic or prognostic agents and used as research materials.

An inserted or target RNA molecule, e.g., a siRNA, an aptamer or diagnostic RNA agent, may be attached to an appropriate site of the OnRS such as the Dicer-cleavable site, 5' and 3' flanking region.

Further provided is the design, establishment and application of a series of tRNA/pre-microRNA scaffolds for high-level and large-scale production of target RNA agents. It is also related to the purification and delivery of these recombinant ncRNAs.

Further provided is the design, production and purification of ncRNAs expressed from the present tRNA/pre-microRNA and tRNA/shRNA scaffolds as the precursors or carriers for the delivery of RNA therapeutics, and thus the recombinant OnRS/RNA themselves may be used as "pre-RNAdrugs" and/or research agents.

Further provided is the design, preparation and application of the present tRNA/pre-microRNA and tRNA/shRNA scaffolds for the production and delivery of a siRNA, miRNA and/or miRNA antagomir.

Further provided is the design, production and application of the present tRNA/pre-microRNA and tRNA/shRNA scaffolds for the production and delivery of a RNA molecule such as RNA aptamer against a drug target.

Further provided is the design, production and application of the present tRNA/pre-microRNA and tRNA/shRNA scaffolds for the production of a druggable RNA target for the identification of new therapeutic agents, as well as diagnostic/prognostic RNA molecule for the development of new diagnostic/prognostic agent or kit.

Further provided is the design, production and delivery of an OnRS-based ncRNA and/or OnRS-generated RNA for combination therapeutics such as co-administration of this recombinant RNA with a small molecule and/or protein agent.

Further provided is the design, preparation and application of OnRS for the production of RNA agents for imaging or development of new imaging agents and/or methods.

Further provided is the design, preparation and application of OnRS for the production of RNA sensors for the quantification of specific small molecule compounds (e.g., drug, hormones, etc.) or biological molecules (e.g., proteins).

Further provided is the design, preparation and application of OnRS for the production of RNA species for selective or nonselective knocking out of knocking down of specific genes or blocking particular proteins or other biological molecules.

Further provided is the design and production of RNA materials as diagnostic or prognostic biomarkers as well as assay kits.

Further provided is the design, preparation and application of OnRS for the production of RNA species as catalysts for the production of organic compounds and/or other biological molecules.

Further provided is the design, preparation and application of OnRS for the production of RNA species as riboswitch for the control of gene expression and cellular processes and use as therapeutics or research agents.

Further provided is the design, preparation and application of OnRS for the production of RNA species as guide RNAs for the genome editing and disease treatment.

Further provided is the engineering of new RNA molecules including consequent chemical modifications and/or formulations as research materials, reagents, catalysts, diagnostic, prognostic and/or therapeutic treatments.

Further provided is the design, preparation, purification and delivery of therapeutic microRNAs such as mir-34a, mir-1291, mir-125-1 and mir-124-1, etc. for the treatment or control of cancers or other diseases.

Further provided is the design, preparation, purification and delivery of microRNAs such as mir-125-1 and mir-33, etc. for the development of new treatment, diagnosis, and/or prognosis.

2. tRNA/Pre-microRNA Scaffolds

Generally, the polynucleotides comprise a tRNA operably linked to a pre-microRNA. In varying embodiments, the anticodon of the tRNA is replaced with a pre-microRNA molecule. For example, in some embodiments, the 3'-terminus and the 5'-terminus of the pre-microRNA are ligated or fused to the 3'-terminus and the 5'-terminus of the tRNA that are created when the anticodon is removed. The tRNA molecule and the pre-microRNA molecule can be, but need not be directly ligated or fused to one another to be operably linked. In varying embodiments, the pre-microRNA can contain one or more dicer cleavable sites to allow for the high level expression and efficient cleavage of an inserted RNA molecule desired to be expressed from the hybrid tRNA/pre-microRNA polynucleotide.

The hybrid tRNA/pre-microRNA molecules can be produced by standard recombinant methods, or can be synthetically prepared. In varying embodiments, the polynucleotides can have one or more chemical modifications, including without limitation, e.g., internucleotide linkages, internucleoside linkages, dideoxyribonucleotides, 2'-sugar modification, 2'-amino groups, 2'-fluoro groups, 2'-methoxy groups, 2'-alkoxy groups, 2'-alkyl groups, 2'-deoxyribonucleotides, 2'-O-methyl ribonucleotides, 2'-deoxy-2'-fluoro ribonucleotides, universal base nucleotides, acyclic nucleotides, 5-C-methyl nucleotides, biotin groups, terminal glyceryl incorporation, inverted deoxy abasic residue incorporation, sterically hindered molecules, 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidi-ne (d4T), monophosphate nucleotide modification (MNM) of 3'-azido-3'-deoxythymidine (AZT), MNM-2',3'-dideoxy-3'-thiacytidine (3TC), MNM-2',3'-didehydro-2',3'-dide-oxythymidine (d4T), capping moieties, L-nucleotides locked nucleic acid (LNA) nucleotides, 2'-methoxyethoxy (MOE) nucleotides, 2'-methyl-thio-ethyl, 2'-deoxy-2'-fluoro nucleotides, 2'-deoxy-2'-chloro nucleotides, 2'-azido nucleotides, 2'-O-methyl, cholesterol groups, 2'-O-methyl groups, phosphorothioate groups, 2'-fluoro groups, 2'-O-methyoxyethyl groups, boranophosphate groups, 4'-thioribose groups, bile acid, lipids, and bridges connecting the 2'-oxygen and 4'-carbon.

In varying embodiments, the hybrid tRNA/pre-microRNA molecules comprise analog ribonucleotide bases. As used herein, the term "analog" defines possible derivatives of the ribonucleotide originating from the activity of tRNA post-transcriptional modification enzymes of the cell in which they are produced. The analogs of the ribonucleotides A, C, G and U which may be found in a tRNA depend on the cell in which that tRNA is produced and on the position of the ribonucleotide in question in the tRNA. A large number of analogs are given in Sprinzl et al. (1998) "Compilation of tRNA sequences and sequences of tRNA genes". Nucleic Acids Res., 26, 148-153 and on the basis of "RNA modification database" data (http://medstat.med.utah.edu/RNAmods/). The analogs of A may be selected more particularly from the group constituted by 1-methyl-A, inosine and 2'-O-methyl-A. The analogs of C may be selected more particularly from the group constituted by 5-methyl-C and 2'-O-methyl-C. The analogs of G may be selected more particularly from the group constituted by 7-methyl-G and 2'-O-methyl-G. The analogs of U may be selected more particularly from the group constituted by pseudouridine, ribothymidine, 2'-O-methyl-ribothymidine, dihydrouridine, 4-thiouridine and 3-(3-amino-3-carboxypropyl)-uridine.

a. tRNA

The general characteristics of a tRNA are well-known to the person skilled in the art. In some embodiments, a tRNA is formed of a single ribonucleotide chain which is capable of folding to adopt a characteristic, so-called cloverleaf secondary structure. This characteristic secondary structure comprises:

(i) an acceptor stem composed of the first 7 ribonucleotides of the 5' end of the ribonucleotide chain and the 7 ribonucleotides that precede the last 4 ribonucleotides of the 3' end of the ribonucleotide chain, thus forming a double-stranded structure comprising 6 or 7 pairs of ribonucleotides, it being possible for the ribonucleotides constituted by the first ribonucleotide of the 5' end of the ribonucleotide chain and the ribonucleotide that precedes the last 4 ribonucleotides of the 3' end of the ribonucleotide chain not to be paired;

(ii) a D arm constituted by 4 pairs of ribonucleotides and a D loop constituted by 8 to 10 ribonucleotides, formed by the folding of a part of the ribonucleotide chain that follows the first 7 ribonucleotides of the 5' end of the ribonucleotide chain;

(iii) a stem of the anticodon constituted by 5 pairs of ribonucleotides, and a loop of the anticodon constituted by 7 ribonucleotides (stem-loop of the anticodon), formed by the folding of a part of the ribonucleotide chain that follows the D arm and the D loop;

(iv) a variable loop constituted by from 4 to 21 ribonucleotides and formed by a part of the ribonucleotide chain that follows the stem of the anticodon and the loop of the anticodon;

(v) a T arm constituted by 5 pairs of ribonucleotides, and a T loop constituted by 8 ribonucleotides, formed by the folding of a part of the ribonucleotide chain that follows the variable loop and precedes the ribonucleotides of the 3' end of the ribonucleotide chain which are involved in the constitution of the acceptor stem.

The hybrid tRNA/pre-microRNA polynucleotides can contain any tRNA known in the art, e.g., for encoding any amino acid. The selection of an appropriate tRNA molecule may be, in part, driven by the host cells to be used for expression of the inserted RNA. For example, when seeking to produce high expression levels of a desired inserted RNA molecule, the tRNA selected can be from a tRNA encoding for codon preferred by the species of host cell rather than from a rare codon in that species of host cell. In varying embodiments, the tRNA is a methionyl-tRNA. In varying embodiments, the tRNA is derived from the host cell used for expression. In varying embodiments, the tRNA is a mammalian tRNA. In varying embodiments, the tRNA is a human tRNA.

In some embodiments, the chimeric tRNA defined above does not comprise the substantially intact stem of the anticodon of the tRNA from which it is derived. For example, in the chimeric tRNA, between the ribonucleotide that precedes the stem-loop of the anticodon in the tRNA before modification and the ribonucleotide that follows the stem-loop of the anticodon in the tRNA before modification, the stem of the anticodon of the tRNA before modification is no longer present.

b. Pre-microRNA

The hybrid tRNA/pre-microRNA and tRNA/shRNA polynucleotides can contain any pre-microRNA molecule known in the art, and can be obtained from naturally occurring sources (e.g., pre-miRNAs or miRNAs), or artificially derived (e.g., shRNAs). In varying embodiments the pre-microRNA is selected from human pre-miRNA-1291, human pre-miRNA-34a, human pre-miRNA-125-1, human pre-miRNA-124, human pre-miRNA-27b, human pre-miRNA-22, and mutants or variants thereof. Other pre-microRNA molecules that can be used in the hybrid tRNA/pre-microRNA polynucleotides include pre-microRNA molecules that express in the host cell (e.g., *E. coli* host cell) at or above the levels of expression of human pre-miRNA-1291, human pre-miRNA-34a, human pre-miRNA-125-1, human pre-miRNA-124, human pre-miRNA-27b, human pre-miRNA-22, in the same host cell (e.g., *E. coli* host cell). In varying embodiments, the pre-microRNA molecule is from a mammalian pre-microRNA molecule. In varying embodiments, the pre-microRNA molecule is from a human pre-microRNA molecule. In varying embodiments, the pre-microRNA component of the hybrid tRNA/pre-microRNA polynucleotides is from about 80 nucleotides to about 120 nucleotides in length, e.g., from about 80 nucleotides to about 100 nucleotides in length, e.g., about 80, 85, 90, 95, 100, 105, 110, 115 or 120 nucleotides in length.

In varying embodiments, the pre-microRNA is a human pre-microRNA selected from the group consisting of hsa-let-7a-1 (miRBase.org accession no.: MI0000060), hsa-let-7a-2 (MI0000061), hsa-let-7a-3 (MI0000062), hsa-let-7b (MI0000063), hsa-let-7c (MI0000064), hsa-let-7d (MI0000065), hsa-let-7e (MI0000066), hsa-let-7f-1 (MI0000067), hsa-let-7f-2 (MI0000068), hsa-let-7g (MI0000433), hsa-let-7i (MI0000434), hsa-mir-1-1 (MI0000651), hsa-mir-1-2 (MI0000437), hsa-mir-7-1 (MI0000263), hsa-mir-7-2 (MI0000264), hsa-mir-7-3 (MI0000265), hsa-mir-9-1 (MI0000466), hsa-mir-9-2 (MI0000467), hsa-mir-9-3 (MI0000468), hsa-mir-10a (MI0000266), hsa-mir-10b (MI0000267), hsa-mir-15a (MI0000069), hsa-mir-15b (MI0000438), hsa-mir-16-1 (MI0000070), hsa-mir-16-2 (MI0000115), hsa-mir-17 (MI0000071), hsa-mir-18a (MI0000072), hsa-mir-18b (MI0001518), hsa-mir-19a (MI0000073), hsa-mir-19b-1 (MI0000074), hsa-mir-19b-2 (MI0000075), hsa-mir-20a (MI0000076), hsa-mir-20b (MI0001519), hsa-mir-21 (MI0000077), hsa-mir-22 (MI0000078), hsa-mir-23a (MI0000079), hsa-mir-23b (MI0000439), hsa-mir-23c (MI0016010), hsa-mir-24-1 (MI0000080), hsa-mir-24-2 (MI0000081), hsa-mir-25 (MI0000082), hsa-mir-26a-1 (MI0000083), hsa-mir-26a-2 (MI0000750), hsa-mir-26b (MI0000084), hsa-mir-27a (MI0000085), hsa-mir-27b (MI0000440), hsa-mir-28 (MI0000086), hsa-mir-29a (MI0000087), hsa-mir-29b-1 (MI0000105), hsa-mir-29b-2 (MI0000107), hsa-mir-29c (MI0000735), hsa-mir-30a (MI0000088), hsa-mir-30b (MI0000441), hsa-mir-30c-1 (MI0000736), hsa-mir-30c-2 (MI0000254), hsa-mir-30d (MI0000255), hsa-mir-30e (MI0000749), hsa-mir-31 (MI0000089), hsa-mir-32 (MI0000090), hsa-mir-33a (MI0000091), hsa-mir-33b (MI0003646), hsa-mir-34a (MI0000268), hsa-mir-34b (MI0000742), hsa-mir-34c (MI0000743), hsa-mir-92a-1 (MI0000093), hsa-mir-92a-2 (MI0000094), hsa-mir-92b (MI0003560), hsa-mir-93 (MI0000095), hsa-mir-95 (MI0000097), hsa-mir-96 (MI0000098), hsa-mir-98 (MI0000100), hsa-mir-99a (MI0000101), hsa-mir-99b (MI0000746), hsa-mir-100 (MI0000102), hsa-mir-101-1 (MI0000103), hsa-mir-101-2 (MI0000739), hsa-mir-103a-1 (MI0000109), hsa-mir-103a-2 (MI0000108), hsa-mir-103b-1 (MI0007261), hsa-mir-103b-2 (MI0007262), hsa-mir-105-1 (MI0000111), hsa-mir-105-2 (MI0000112), hsa-mir-106a (MI0000113), hsa-mir-106b (MI0000734), hsa-mir-107 (MI0000114), hsa-mir-122 (MI0000442), hsa-mir-124-1 (MI0000443), hsa-mir-124-2 (MI0000444), hsa-mir-124-3 (MI0000445), hsa-mir-125a (MI0000469), hsa-mir-125b-1 (MI0000446), hsa-mir-125b-2 (MI0000470), hsa-mir-126 (MI0000471), hsa-mir-127 (MI0000472), hsa-mir-128-1 (MI0000447), hsa-mir-128-2 (MI0000727), hsa-mir-129-1 (MI0000252), hsa-mir-129-2 (MI0000473), hsa-mir-130a (MI0000448), hsa-mir-130b (MI0000748), hsa-mir-132 (MI0000449), hsa-mir-133a-1 (MI0000045), hsa-mir-133a-2 (MI0000451), hsa-mir-133b (MI0000822), hsa-mir-134 (MI0000474), hsa-mir-135a-1 (MI0000452), hsa-mir-135a-2 (MI0000453), hsa-mir-135b (MI0000810), hsa-mir-136 (MI0000475), hsa-mir-137 (MI0000454), hsa-mir-138-1 (MI0000476), hsa-mir-138-2 (MI0000455), hsa-mir-139 (MI0000261), hsa-mir-140 (MI0000456), hsa-mir-141 (MI0000457), hsa-mir-142 (MI0000458), hsa-mir-143 (MI0000459), hsa-mir-144 (MI0000460), hsa-mir-145 (MI0000461), hsa-mir-146a (MI0000477), hsa-mir-146b (MI0003129), hsa-mir-147a (MI0000262), hsa-mir-147b (MI0005544), hsa-mir-148a (MI0000253), hsa-mir-148b (MI0000811), hsa-mir-149 (MI0000478), hsa-mir-150 (MI0000479), hsa-mir-151a (MI0000809), hsa-mir-151b (MI0003772), hsa-mir-152 (MI0000462), hsa-mir-153-1 (MI0000463), hsa-mir-153-2 (MI0000464), hsa-mir-154 (MI0000480), hsa-mir-155 (MI0000681), hsa-mir-181a-1 (MI0000289), hsa-mir-181a-2 (MI0000269), hsa-mir-181b-1 (MI0000270), hsa-mir-181b-2 (MI0000683), hsa-mir-181c (MI0000271), hsa-mir-181d (MI0003139), hsa-mir-182 (MI0000272), hsa-mir-183 (MI0000273), hsa-mir-184 (MI0000481), hsa-mir-185 (MI0000482), hsa-mir-186 (MI0000483), hsa-mir-187 (MI0000274), hsa-mir-188 (MI0000484), hsa-mir-190a (MI0000486), hsa-mir-190b (MI0005545), hsa-mir-191 (MI0000465), hsa-mir-192 (MI0000234), hsa-mir-193a (MI0000487), hsa-mir-193b (MI0003137), hsa-mir-194-1 (MI0000488), hsa-mir-194-2 (MI0000732), hsa-mir-195 (MI0000489), hsa-mir-196a-1 (MI0000238), hsa-mir-196a-2 (MI0000279), hsa-mir-196b (MI0001150), hsa-mir-197 (MI0000239), hsa-mir-198 (MI0000240), hsa-mir-199a-1 (MI0000242), hsa-mir-199a-2 (MI0000281), hsa-mir-199b (MI0000282), hsa-mir-200a (MI0000737), hsa-mir-200b (MI0000342), hsa-mir-200c (MI0000650), hsa-mir-202 (MI0003130), hsa-mir-203a (MI0000283), hsa-mir-203b (MI0017343), hsa-mir-204 (MI0000284), hsa-mir-205 (MI0000285), hsa-mir-206 (MI0000490), hsa-mir-208a (MI0000251), hsa-mir-208b (MI0005570), hsa-mir-210 (MI0000286), hsa-mir-211 (MI0000287), hsa-mir-212 (MI0000288), hsa-mir-214 (MI0000290), hsa-mir-215 (MI0000291), hsa-mir-216a (MI0000292), hsa-mir-216b (MI0005569), hsa-mir-217 (MI0000293), hsa-mir-218-1 (MI0000294), hsa-mir-218-2 (MI0000295), hsa-mir-219a-1 (MI0000296), hsa-mir-219a-2 (MI0000740), hsa-mir-219b (MI0017299), hsa-mir-221 (MI0000298), hsa-mir-222 (MI0000299), hsa-mir-223 (MI0000300), hsa-mir-224 (MI0000301), hsa-mir-296 (MI0000747), hsa-mir-297 (MI0005775), hsa-mir-298 (MI0005523), hsa-mir-299 (MI0000744), hsa-mir-300 (MI0005525), hsa-mir-301a (MI0000745), hsa-mir-301b (MI0005568), hsa-mir-302a (MI0000738), hsa-mir-302b (MI0000772), hsa-mir-302c (MI0000773), hsa-mir-302d (MI0000774), hsa-mir-302e (MI0006417), hsa-mir-302f (MI0006418), hsa-mir-320a (MI0000542), hsa-mir-320b-1 (MI0003776), hsa-mir-320b-2 (MI0003839), hsa-mir-320c-1 (MI0003778), hsa-mir-320c-2 (MI0008191), hsa-mir-320d-1 (MI0008190), hsa-mir-320d-2 (MI0008192), hsa-mir-320e (MI0014234), hsa-mir-323a (MI0000807), hsa-mir-323b (MI001420), hsa-mir-324 (MI0000813), hsa-mir-325 (MI0000824), hsa-mir-326 (MI0000808), hsa-mir-328 (MI0000804), hsa-mir-329-1 (MI0001725), hsa-mir-329-2 (MI0001726), hsa-mir-330 (MI0000803), hsa-mir-331 (MI0000812), hsa-mir-335 (MI0000816), hsa-mir-337 (MI0000806), hsa-mir-338 (MI0000814), hsa-mir-339 (MI0000815), hsa-mir-340 (MI0000802), hsa-mir-342 (MI0000805), hsa-mir-345 (MI0000825), hsa-mir-346 (MI0000826), hsa-mir-361 (MI0000760), hsa-mir-362 (MI0000762), hsa-mir-363 (MI000076), hsa-mir-365a (MI0000767), hsa-mir-365b (MI0000769), hsa-mir-367 (MI0000775), hsa-mir-369 (MI0000777), hsa-mir-370 (MI0000778), hsa-mir-371a (MI0000779), hsa-mir-371b (MI0017393), hsa-mir-372 (MI0000780), hsa-mir-373 (MI0000781), hsa-mir-374a (MI0000782), hsa-mir-374b (MI0005566), hsa-mir-374c (MI0016684), hsa-mir-375 (MI0000783), hsa-mir-376a-1 (MI0000784), hsa-mir-376a-2 (MI0003529), hsa-mir-376b (MI0002466), hsa-mir-376c (MI0000776), hsa-mir-377 (MI0000785), hsa-mir-378a (MI0000786), hsa-mir-378b (MI0014154), hsa-mir-378c (MI0015825), hsa-mir-378d-1 (MI0016749), hsa-mir-378d-2 (MI0003840), hsa-mir-378e (MI0016750), hsa-mir-378f (MI0016756), hsa-mir-378g (MI0016761), hsa-mir-378h (MI0016808 803), hsa-mir-378i (MI0016902), hsa-mir-378j (MI0021273), hsa-mir-379 (MI0000787), hsa-mir-380 (MI0000788), hsa-mir-381 (MI0000789), hsa-mir-382 (MI0000790), hsa-mir-383 (MI0000791), hsa-mir-384 (MI0001145), hsa-mir-409 (MI0001735), hsa-mir-410 (MI0002465), hsa-mir-411 (MI0003675), hsa-mir-412 (MI0002464), hsa-mir-421 (MI0003685), hsa-mir-422a (MI0001444), hsa-mir-423 (MI0001445), hsa-mir-424 (MI0001446), hsa-mir-425 (MI0001448), hsa-mir-429 (MI0001641), hsa-mir-431 (MI0001721), hsa-mir-432 (MI0003133), hsa-mir-433 (MI0001723), hsa-mir-448 (MI0001637), hsa-mir-449a (MI0001648), hsa-mir-449b (MI0003673), hsa-mir-449c (MI0003823), hsa-mir-450a-1 (MI0001652), hsa-mir-450a-2 (MI0003187), hsa-mir-450b (MI0005531), hsa-mir-451a (MI0001729), hsa-mir-451b (MI0017360), hsa-mir-452 (MI0001733), hsa-mir-454 (MI0003820), hsa-mir-455 (MI0003513), hsa-mir-466 (MI0014157), hsa-mir-483 (MI0002467), hsa-mir-484 (MI0002468), hsa-mir-485 (MI0002469), hsa-mir-486 (MI0002470), hsa-mir-486-2

(MI0023622), hsa-mir-487a (MI0002471), hsa-mir-487b (MI0003530), hsa-mir-488 (MI0003123), hsa-mir-489 (MI0003124), hsa-mir-490 (MI0003125), hsa-mir-491 (MI0003126), hsa-mir-492 (MI0003131), hsa-mir-493 (MI0003132), hsa-mir-494 (MI0003134), hsa-mir-495 (MI0003135), hsa-mir-496 (MI0003136), hsa-mir-497 (MI0003138), hsa-mir-498 (MI0003142), hsa-mir-499a (MI0003183), hsa-mir-499b (MI0017396), hsa-mir-500a (MI0003184), hsa-mir-500b (MI0015903), hsa-mir-501 (MI0003185), hsa-mir-502 (MI0003186), hsa-mir-503 (MI0003188), hsa-mir-504 (MI0003189), hsa-mir-505 (MI0003190), hsa-mir-506 (MI0003193), hsa-mir-507 (MI0003194), hsa-mir-508 (MI0003195), hsa-mir-509-1 (MI0003196), hsa-mir-509-2 (MI0005530), hsa-mir-509-3 (MI0005717), hsa-mir-510 (MI0003197), hsa-mir-511 (MI0003127), hsa-mir-512-1 (MI0003140), hsa-mir-512-2 (MI0003141), hsa-mir-513a-1 (MI0003191), hsa-mir-513a-2 (MI0003192), hsa-mir-513b (MI0006648), hsa-mir-513c (MI0006649), hsa-mir-514a-1 (MI0003198), hsa-mir-514a-2 (MI0003199), hsa-mir-514a-3 (MI0003200), hsa-mir-514b (MI0014251), hsa-mir-515-1 (MI0003144), hsa-mir-515-2 (MI0003147), hsa-mir-516a-1 (MI0003180), hsa-mir-516a-2 (MI0003181), hsa-mir-516b-1 (MI0003172), hsa-mir-516b-2 (MI0003167), hsa-mir-517a (MI0003161), hsa-mir-517b (MI0003165), hsa-mir-517c (MI0003174), hsa-mir-518a-1 (MI0003170), hsa-mir-518a-2 (MI0003173), hsa-mir-518b (MI0003156), hsa-mir-518c (MI0003159), hsa-mir-518d (MI0003171), hsa-mir-518e (MI0003169), hsa-mir-518f (MI0003154), hsa-mir-519a-1 (MI0003178), hsa-mir-519a-2 (MI0003182), hsa-mir-519b (MI0003151), hsa-mir-519c (MI0003148), hsa-mir-519d (MI0003162), hsa-mir-519e (MI0003145), hsa-mir-520a (MI0003149), hsa-mir-520b (MI0003155), hsa-mir-520c (MI0003158), hsa-mir-520d (MI0003164), hsa-mir-520e (MI0003143), hsa-mir-520f (MI0003146), hsa-mir-520g (MI0003166), hsa-mir-520h (MI0003175), hsa-mir-521-1 (MI0003176), hsa-mir-521-2 (MI0003163), hsa-mir-522 (MI0003177), hsa-mir-523 (MI0003153), hsa-mir-524 (MI0003160), hsa-mir-525 (MI0003152), hsa-mir-526a-1 (MI0003157), hsa-mir-526a-2 (MI0003168), hsa-mir-526b (MI0003150), hsa-mir-527 (MI0003179), hsa-mir-532 (MI0003205), hsa-mir-539 (MI0003514), hsa-mir-541 (MI0005539), hsa-mir-542 (MI0003686), hsa-mir-543 (MI0005565), hsa-mir-544a (MI0003515), hsa-mir-544b (MI0014159), hsa-mir-545 (MI0003516), hsa-mir-548a-1 (MI0003593). hsa-mir-548a-2 (MI000359), hsa-mir-548a-3 (MI0003612), hsa-mir-548aa-1 (MI0016689), hsa-mir-548aa-2 (MI0016690), hsa-mir-548ab (MI0016752), hsa-mir-548ac (MI0016762), hsa-mir-548ad (MI0016770), hsa-mir-548ae-1 (MI0016779), hsa-mir-548ae-2 (MI0016780), hsa-mir-548ag-1 (MI0016793), hsa-mir-548ag-2 (MI0016794), hsa-mir-548ah (MI0016796), hsa-mir-548ai (MI0016813), hsa-mir-548aj-1 (MI0016814), hsa-mir-548aj-2 (MI0016815), hsa-mir-548ak (MI0016840), hsa-mir-548al (MI0016851), hsa-mir-548am (MI0016904), hsa-mir-548an (MI0016907), hsa-mir-548ao (MI0017871), hsa-mir-548ap (MI0017875), hsa-mir-548aq (MI0019130), hsa-mir-548ar (MI0019131), hsa-mir-548as (MI0019132), hsa-mir-548at (MI0019137), hsa-mir-548au (MI0019145), hsa-mir-548av (MI0019152), hsa-mir-548aw (MI0019283), hsa-mir-548ax (MI0019286), hsa-mir-548ay (MI0022210), hsa-mir-548az (MI0022212), hsa-mir-548b (MI0003596), hsa-mir-548ba (MI0025747), hsa-mir-548c (MI0003630), hsa-mir-548d-1 (MI0003668), hsa-mir-548d-2 (MI0003671), hsa-mir-548e (MI0006344), hsa-mir-548f-1 (MI0006374), hsa-mir-548f-2 (MI0006375), hsa-mir-548f-3 (MI0006376), hsa-mir-548f-4 (MI0006377), hsa-mir-548f-5 (MI0006378), hsa-mir-548g (MI0006395), hsa-mir-548h-1 (MI0006411), hsa-mir-548h-2 (MI0006412), hsa-mir-548h-3 (MI0006413), hsa-mir-548h-4 (MI0006414), hsa-mir-548h-5 (MI0016751), hsa-mir-548i-1 (MI0006421), hsa-mir-548i-2 (MI0006422), hsa-mir-548i-3 (MI0006423), hsa-mir-548i-4 (MI0006424), hsa-mir-548j (MI0006345), hsa-mir-548k (MI0006354), hsa-mir-548l (MI0006361), hsa-mir-548m (MI0006400), hsa-mir-548n (MI0006399), hsa-mir-548o (MI0006402), hsa-mir-548o-2 (MI0016746), hsa-mir-548p (MI0006420), hsa-mir-548q (MI0010637), hsa-mir-548s (MI0014141), hsa-mir-548t (MI0014164), hsa-mir-548u (MI0014168), hsa-mir-548v (MI0014174), hsa-mir-548w (MI0014222), hsa-mir-548x (MI0014244), hsa-mir-548x-2 (MI0016833), hsa-mir-548y (MI0016595), hsa-mir-548z (MI0016688), hsa-mir-549a (MI0003679), hsa-mir-550a-1 (MI0003600), hsa-mir-550a-2 (MI0003601), hsa-mir-550a-3 (MI0003762), hsa-mir-550b-1 (MI0016686), hsa-mir-550b-2 (MI0016687), hsa-mir-551a (MI0003556), hsa-mir-55 1b (MI0003575), hsa-mir-552 (MI0003557), hsa-mir-553 (MI0003558), hsa-mir-554 (MI0003559), hsa-mir-555 (MI0003561), hsa-mir-556 (MI0003562), hsa-mir-557 (MI0003563), hsa-mir-558 (MI0003564), hsa-mir-559 (MI0003565), hsa-mir-561 (MI0003567), hsa-mir-562 (MI0003568), hsa-mir-563 (MI0003569), hsa-mir-564 (MI0003570), hsa-mir-566 (MI0003572), hsa-mir-567 (MI0003573), hsa-mir-568 (MI0003574), hsa-mir-569 (MI0003576), hsa-mir-570 (MI0003577), hsa-mir-571 (MI0003578), hsa-mir-572 (MI0003579), hsa-mir-573 (MI0003580), hsa-mir-574 (MI0003581), hsa-mir-575 (MI0003582), hsa-mir-576 (MI0003583), hsa-mir-577 (MI0003584), hsa-mir-578 (MI0003585), hsa-mir-579 (MI0003586), hsa-mir-580 (MI0003587), hsa-mir-581 (MI0003588), hsa-mir-582 (MI0003589), hsa-mir-583 (MI0003590), hsa-mir-584 (MI0003591), hsa-mir-585 (MI000359), hsa-mir-586 (MI0003594), hsa-mir-587 (MI0003595), hsa-mir-588 (MI0003597), hsa-mir-589 (MI0003599), hsa-mir-590 (MI0003602), hsa-mir-591 (MI0003603), hsa-mir-592 (MI0003604), hsa-mir-593 (MI0003605), hsa-mir-595 (MI0003607), hsa-mir-596 (MI0003608), hsa-mir-597 (MI0003609), hsa-mir-598 (MI0003610 162), hsa-mir-599 (MI0003611), hsa-mir-600 (MI0003613), hsa-mir-601 (MI0003614), hsa-mir-602 (MI0003615), hsa-mir-603 (MI0003616), hsa-mir-604 (MI0003617), hsa-mir-605 (MI0003618), hsa-mir-606 (MI0003619), hsa-mir-607 (MI0003620), hsa-mir-608 (MI0003621), hsa-mir-609 (MI0003622), hsa-mir-610 (MI0003623), hsa-mir-611 (MI0003624), hsa-mir-612 (MI0003625), hsa-mir-613 (MI0003626), hsa-mir-614 (MI0003627), hsa-mir-615 (MI0003628), hsa-mir-616 (MI0003629), hsa-mir-617 (MI0003631), hsa-mir-618 (MI0003632), hsa-mir-619 (MI0003633), hsa-mir-620 (MI0003634), hsa-mir-621 (MI0003635), hsa-mir-622 (MI0003636), hsa-mir-623 (MI0003637), hsa-mir-624 (MI0003638), hsa-mir-625 (MI0003639), hsa-mir-626 (MI0003640), hsa-mir-627 (MI0003641), hsa-mir-628 (MI0003642), hsa-mir-629 (MI0003643), hsa-mir-630 (MI000364), hsa-mir-631 (MI0003645), hsa-mir-632 (MI0003647), hsa-mir-633 (MI0003648), hsa-mir-634 (MI0003649), hsa-mir-635 (MI0003650), hsa-mir-636 (MI0003651), hsa-mir-637 (MI0003652), hsa-mir-638 (MI0003653), hsa-mir-639 (MI0003654), hsa-mir-640 (MI0003655), hsa-mir-641 (MI0003656), hsa-mir-642a (MI0003657), hsa-mir-642b (MI0016685), hsa-mir-643 (MI0003658), hsa-mir-644a (MI0003659), hsa-mir-645 (MI0003660), hsa-mir-646 (MI0003661), hsa-mir-647 (MI0003662), hsa-mir-648 (MI0003663), hsa-mir-649 (MI0003664), hsa-mir-650

(MI0003665), hsa-mir-651 (MI0003666), hsa-mir-652 (MI0003667), hsa-mir-653 (MI0003674), hsa-mir-654 (MI0003676), hsa-mir-655 (MI0003677), hsa-mir-656 (MI0003678), hsa-mir-657 (MI0003681), hsa-mir-658 (MI0003682), hsa-mir-659 (MI0003683), hsa-mir-660 (MI0003684), hsa-mir-661 (MI0003669), hsa-mir-662 (MI0003670), hsa-mir-663a (MI0003672), hsa-mir-663b (MI0006336), hsa-mir-664a (MI0006442), hsa-mir-664b (MI0019134), hsa-mir-665 (MI0005563), hsa-mir-668 (MI0003761), hsa-mir-670 (MI0003933), hsa-mir-671 (MI0003760), hsa-mir-675 (MI0005416), hsa-mir-676 (MI0016436), hsa-mir-708 (MI0005543), hsa-mir-711 (MI0012488), hsa-mir-718 (MI0012489), hsa-mir-744 (MI0005559), hsa-mir-758 (MI0003757), hsa-mir-759 (MI0004065), hsa-mir-760 (MI0005567), hsa-mir-761 (MI0003941), hsa-mir-762 (MI0003892), hsa-mir-764 (MI0003944), hsa-mir-765 (MI0005116), hsa-mir-766 (MI0003836), hsa-mir-767 (MI0003763), hsa-mir-769 (MI0003834), hsa-mir-770 (MI0005118), hsa-mir-802 (MI0003906), hsa-mir-873 (MI0005564), hsa-mir-874 (MI0005532), hsa-mir-875 (MI0005541), hsa-mir-876 (MI0005542), hsa-mir-877 (MI0005561), hsa-mir-885 (MI0005560), hsa-mir-887 (MI0005562), hsa-mir-888 (MI0005537), hsa-mir-889 (MI0005540), hsa-mir-890 (MI0005533), hsa-mir-891a (MI0005524), hsa-mir-891b (MI0005534), hsa-mir-892a (MI0005528), hsa-mir-892b (MI0005538), hsa-mir-892c (MI0022560), hsa-mir-920 (MI0005712), hsa-mir-921 (MI0005713), hsa-mir-922 (MI0005714), hsa-mir-924 (MI0005716), hsa-mir-933 (MI0005755), hsa-mir-934 (MI0005756), hsa-mir-935 (MI0005757), hsa-mir-936 (MI0005758), hsa-mir-937 (MI0005759), hsa-mir-938 (MI0005760), hsa-mir-939 (MI0005761), hsa-mir-940 (MI0005762), hsa-mir-941-1 (MI0005763), hsa-mir-941-2 (MI0005764), hsa-mir-941-3 (MI0005765), hsa-mir-941-4 (MI0005766), hsa-mir-942 (MI0005767), hsa-mir-943 (MI0005768), hsa-mir-944 (MI0005769), hsa-mir-1178 (MI0006271), hsa-mir-1179 (MI0006272), hsa-mir-1180 (MI0006273), hsa-mir-1181 (MI0006274), hsa-mir-1182 (MI0006275), hsa-mir-1183 (MI0006276), hsa-mir-1184-1 (MI0006277), hsa-mir-1184-2 (MI0015971), hsa-mir-1184-3 (MI0015972), hsa-mir-1185-1 (MI0003844), hsa-mir-1185-2 (MI0003821), hsa-mir-1193 (MI0014205), hsa-mir-1197 (MI0006656), hsa-mir-1199 (MI0020340), hsa-mir-1200 (MI0006332), hsa-mir-1202 (MI0006334), hsa-mir-1203 (MI0006335), hsa-mir-1204 (MI0006337), hsa-mir-1205 (MI0006338), hsa-mir-1206 (MI0006339), hsa-mir-1207 (MI0006340), hsa-mir-1208 (MI0006341), hsa-mir-1224 (MI0003764), hsa-mir-1225 (MI0006311), hsa-mir-1226 (MI0006313), hsa-mir-1227 (MI0006316), hsa-mir-1228 (MI0006318), hsa-mir-1229 (MI0006319), hsa-mir-1231 (MI0006321), hsa-mir-1233-1 (MI0006323), hsa-mir-1233-2 (MI0015973), hsa-mir-1234 (MI0006324), hsa-mir-1236 (MI0006326), hsa-mir-1237 (MI0006327), hsa-mir-1238 (MI0006328), hsa-mir-1243 (MI0006373), hsa-mir-1244-1 (MI0006379), hsa-mir-1244-2 (MI0015974), hsa-mir-1244-3 (MI0015975), hsa-mir-1245a (MI0006380), hsa-mir-1245b (MI0017431), hsa-mir-1246 (MI0006381), hsa-mir-1247 (MI0006382), hsa-mir-1248 (MI0006383), hsa-mir-1249 (MI0006384), hsa-mir-1250 (MI0006385), hsa-mir-1251 (MI0006386), hsa-mir-1252 (MI0006434), hsa-mir-1253 (MI0006387), hsa-mir-1254-1 (MI000638), hsa-mir-1254-2 (MI0016747), hsa-mir-1255a (MI0006389), hsa-mir-1255b-1 (MI0006435), hsa-mir-1255b-2 (MI0006436), hsa-mir-1256 (MI0006390), hsa-mir-1257 (MI0006391), hsa-mir-1258 (MI0006392), hsa-mir-1260a (MI0006394), hsa-mir-1260b (MI0014197), hsa-mir-1261 (MI0006396), hsa-mir-1262 (MI0006397), hsa-mir-1263 (MI0006398), hsa-mir-1264 (MI0003758), hsa-mir-1265 (MI0006401), hsa-mir-1266 (MI0006403), hsa-mir-1267 (MI0006404), hsa-mir-1268a (MI0006405), hsa-mir-1268b (MI0016748), hsa-mir-1269a (MI0006406), hsa-mir-1269b (MI0016888), hsa-mir-1270-1 (MI0006407), hsa-mir-1270-2 (MI0015976), hsa-mir-1271 (MI0003814), hsa-mir-1272 (MI0006408), hsa-mir-1273a (MI0006409), hsa-mir-1273c (MI0014171), hsa-mir-1273d (MI0014254), hsa-mir-1273e (MI0016059), hsa-mir-1273f (MI0018002), hsa-mir-1273g (MI0018003), hsa-mir-1273h (MI0025512), hsa-mir-1275 (MI0006415), hsa-mir-1276 (MI0006416), hsa-mir-1277 (MI0006419), hsa-mir-1278 (MI0006425), hsa-mir-1279 (MI0006426), hsa-mir-1281 (MI0006428), hsa-mir-1282 (MI0006429), hsa-mir-1283-1 (MI0003832), hsa-mir-1283-2 (MI0006430), hsa-mir-1284 (MI0006431), hsa-mir-1285-1 (MI0006346), hsa-mir-1285-2 (MI0006347), hsa-mir-1286 (MI0006348), hsa-mir-1287 (MI0006349), hsa-mir-1288 (MI0006432), hsa-mir-1289-1 (MI0006350), hsa-mir-1289-2 (MI0006351), hsa-mir-1290 (MI0006352), hsa-mir-1291 (MI0006353), hsa-mir-1292 (MI0006433), hsa-mir-1293 (MI0006355), hsa-mir-1294 (MI0006356), hsa-mir-1295a (MI0006357), hsa-mir-1295b (MI0019146), hsa-mir-1296 (MI0003780), hsa-mir-1297 (MI0006358), hsa-mir-1298 (MI0003938), hsa-mir-1299 (MI0006359), hsa-mir-1301 (MI0003815), hsa-mir-1302-1 (MI0006362), hsa-mir-1302-10 (MI0015979), hsa-mir-1302-11 (MI0015980), hsa-mir-1302-2 (MI0006363), hsa-mir-1302-3 (MI0006364), hsa-mir-1302-4 (MI0006365), hsa-mir-1302-5 (MI0006366), hsa-mir-1302-6 (MI0006367), hsa-mir-1302-7 (MI0006368), hsa-mir-1302-8 (MI0006369), hsa-mir-1302-9 (MI0015978), hsa-mir-1303 (MI0006370), hsa-mir-1304 (MI0006371), hsa-mir-1305 (MI0006372), hsa-mir-1306 (MI0006443), hsa-mir-1307 (MI0006444), hsa-mir-1321 (MI0006652), hsa-mir-1322 (MI0006653), hsa-mir-1323 (MI0003786), hsa-mir-1324 (MI0006657), hsa-mir-1343 (MI0017320), hsa-mir-1468 (MI0003782), hsa-mir-1469 (MI0007074), hsa-mir-1470 (MI0007075), hsa-mir-1471 (MI0007076), hsa-mir-1537 (MI0007258), hsa-mir-1538 (MI0007259), hsa-mir-1539 (MI0007260), hsa-mir-1587 (MI0016905), hsa-mir-1825 (MI0008193), hsa-mir-1827 (MI0008195), hsa-mir-1908 (MI0008329), hsa-mir-1909 (MI0008330), hsa-mir-1910 (MI0008331), hsa-mir-1911 (MI0008332), hsa-mir-1912 (MI0008333), hsa-mir-1913 (MI0008334), hsa-mir-1914 (MI0008335), hsa-mir-1915 (MI0008336), hsa-mir-1972-1 (MI0009982), hsa-mir-1972-2 (MI0015977), hsa-mir-1973 (MI0009983), hsa-mir-1976 (MI0009986), hsa-mir-2052 (MI0010486), hsa-mir-2053 (MI0010487), hsa-mir-2054 (MI0010488), hsa-mir-2110 (MI0010629), hsa-mir-2113 (MI0003939), hsa-mir-2114 (MI0010633), hsa-mir-2115 (MI0010634), hsa-mir-2116 (MI0010635), hsa-mir-2117 (MI0010636), hsa-mir-2276 (MI0011282), hsa-mir-2277 (MI0011284), hsa-mir-2278 (MI0011285), hsa-mir-2355 (MI0015873), hsa-mir-2392 (MI0016870), hsa-mir-2467 (MI0017432), hsa-mir-2681 (MI0012062), hsa-mir-2682 (MI0012063), hsa-mir-2861 (MI0013006), hsa-mir-2909 (MI0013083), hsa-mir-3064 (MI0017375), hsa-mir-3065 (MI0014228), hsa-mir-3074 (MI0014181), hsa-mir-3115 (MI0014127), hsa-mir-3116-1 (MI0014128), hsa-mir-3116-2 (MI0014129), hsa-mir-3117 (MI0014130), hsa-mir-3118-1 (MI0014131), hsa-mir-3118-2 (MI0014132), hsa-mir-3118-3 (MI0014133), hsa-mir-3118-4 (MI0014207), hsa-mir-3118-5 (MI0014243), hsa-mir-3118-6 (MI0015981), hsa-mir-3119-1 (MI0014134), hsa-mir-3119-2 (MI0014135), hsa-mir-3120 (MI0014136), hsa-mir-3121 (MI0014137), hsa-mir-3122 (MI0014138), hsa-mir-3123

(MI0014139), hsa-mir-3124 (MI0014140), hsa-mir-3125 (MI0014142), hsa-mir-3126 (MI0014143), hsa-mir-3127 (MI0014144), hsa-mir-3128 (MI0014145), hsa-mir-3129 (MI0014146), hsa-mir-3130-1 (MI0014147), hsa-mir-3130-2 (MI0014148), hsa-mir-3131 (MI0014151), hsa-mir-3132 (MI0014152), hsa-mir-3133 (MI0014153), hsa-mir-3134 (MI0014155), hsa-mir-3135a (MI0014156), hsa-mir-3135b (MI0016809), hsa-mir-3136 (MI0014158), hsa-mir-3137 (MI0014160), hsa-mir-3138 (MI0014161), hsa-mir-3139 (MI0014162), hsa-mir-3140 (MI0014163), hsa-mir-3141 (MI0014165), hsa-mir-3142 (MI0014166), hsa-mir-3143 (MI0014167), hsa-mir-3144 (MI0014169), hsa-mir-3145 (MI0014170), hsa-mir-3146 (MI0014172), hsa-mir-3147 (MI0014173), hsa-mir-3148 (MI0014175), hsa-mir-3149 (MI0014176), hsa-mir-3150a (MI0014177), hsa-mir-3150b (MI0016426), hsa-mir-3151 (MI0014178), hsa-mir-3152 (MI0014179), hsa-mir-3153 (MI0014180), hsa-mir-3154 (MI0014182), hsa-mir-3155a (MI0014183), hsa-mir-3155b (MI0016839), hsa-mir-3156-1 (MI0014184), hsa-mir-3156-2 (MI0014230), hsa-mir-3156-3 (MI0014242), hsa-mir-3157 (MI0014185), hsa-mir-3158-1 (MI0014186), hsa-mir-3158-2 (MI0014187), hsa-mir-3159 (MI0014188), hsa-mir-3160-1 (MI0014189), hsa-mir-3160-2 (MI0014190), hsa-mir-3161 (MI0014191), hsa-mir-3162 (MI0014192), hsa-mir-3163 (MI0014193), hsa-mir-3164 (MI0014194), hsa-mir-3165 (MI0014195), hsa-mir-3166 (MI0014196), hsa-mir-3167 (MI0014198), hsa-mir-3168 (MI0014199), hsa-mir-3169 (MI0014200), hsa-mir-3170 (MI0014201), hsa-mir-3171 (MI0014202), hsa-mir-3173 (MI0014204), hsa-mir-3174 (MI0014208), hsa-mir-3175 (MI0014209), hsa-mir-3176 (MI0014210), hsa-mir-3177 (MI0014211), hsa-mir-3178 (MI0014212), hsa-mir-3179-1 (MI0014213), hsa-mir-3179-2 (MI0014216; hsa-mir-3179-3 (MI0014221), hsa-mir-3180-1 (MI0014214), hsa-mir-3180-2 (MI0014215; hsa-mir-3180-3 (MI0014217), hsa-mir-3180-4 (MI0016408), hsa-mir-3180-5 (MI0016409), hsa-mir-3181 (MI0014223), hsa-mir-3182 (MI0014224), hsa-mir-3183 (MI0014225), hsa-mir-3184 (MI0014226), hsa-mir-3185 (MI0014227), hsa-mir-3186 (MI0014229), hsa-mir-3187 (MI0014231), hsa-mir-3188 (MI0014232), hsa-mir-3189 (MI0014233), hsa-mir-3190 (MI0014235), hsa-mir-3191 (MI0014236), hsa-mir-3192 (MI0014237), hsa-mir-3193 (MI0014238), hsa-mir-3194 (MI0014239), hsa-mir-3195 (MI0014240), hsa-mir-3196 (MI0014241), hsa-mir-3197 (MI0014245), hsa-mir-3198-1 (MI0014246), hsa-mir-3198-2 (MI0017335), hsa-mir-3199-1 (MI0014247), hsa-mir-3199-2 (MI0014248), hsa-mir-3200 (MI0014249), hsa-mir-3201 (MI0014250), hsa-mir-3202-1 (MI0014252), hsa-mir-3202-2 (MI0014253), hsa-mir-3529 (MI0017351), hsa-mir-3591 (MI0017383), hsa-mir-3605 (MI0015995), hsa-mir-3606 (MI0015996), hsa-mir-3607 (MI0015997), hsa-mir-3609 (MI0015999), hsa-mir-3610 (MI0016000), hsa-mir-3611 (MI0016001), hsa-mir-3612 (MI0016002), hsa-mir-3613 (MI0016003), hsa-mir-3614 (MI0016004), hsa-mir-3615 (MI0016005), hsa-mir-3616 (MI0016006), hsa-mir-3617 (MI0016007), hsa-mir-3618 (MI0016008), hsa-mir-3619 (MI0016009), hsa-mir-3620 (MI0016011), hsa-mir-3621 (MI0016012), hsa-mir-3622a (MI0016013), hsa-mir-3622b (MI0016014), hsa-mir-3646 (MI0016046), hsa-mir-3648 (MI0016048), hsa-mir-3649 (MI0016049), hsa-mir-3650 (MI0016050), hsa-mir-3651 (MI0016051), hsa-mir-3652 (MI0016052), hsa-mir-3653 (MI0016053), hsa-mir-3654 (MI0016054), hsa-mir-3655 (MI0016055), hsa-mir-3656 (MI0016056), hsa-mir-3657 (MI0016057), hsa-mir-3658 (MI0016058), hsa-mir-3659 (MI0016060), hsa-mir-3660 (MI0016061), hsa-mir-3661 (MI0016062), hsa-mir-3662 (MI0016063), hsa-mir-3663 (MI0016064), hsa-mir-3664 (MI0016065), hsa-mir-3665 (MI0016066), hsa-mir-3666 (MI0016067), hsa-mir-3667 (MI0016068), hsa-mir-3668 (MI0016069), hsa-mir-3669 (MI0016070), hsa-mir-3670-1 (MI0016071), hsa-mir-3670-2 (MI0019112), hsa-mir-3671 (MI0016072), hsa-mir-3672 (MI0016073), hsa-mir-3673 (MI0016074), hsa-mir-3674 (MI0016075), hsa-mir-3675 (MI0016076), hsa-mir-3677 (MI0016078), hsa-mir-3678 (MI0016079), hsa-mir-3679 (MI0016080), hsa-mir-3680-1 (MI0016081), hsa-mir-3680-2 (MI0019113), hsa-mir-3681 (MI0016082), hsa-mir-3682 (MI0016083), hsa-mir-3683 (MI0016084), hsa-mir-3684 (MI0016085), hsa-mir-3685 (MI0016086), hsa-mir-3686 (MI0016087), hsa-mir-3687 (MI0016088), hsa-mir-3688-1 (MI0016089), hsa-mir-3688-2 (MI0017447), hsa-mir-3689a (MI0016090), hsa-mir-3689b (MI0016411), hsa-mir-3689c (MI0016832), hsa-mir-3689d-1 (MI0016834), hsa-mir-3689d-2 (MI0016835), hsa-mir-3689e (MI0016836), hsa-mir-3689f (MI0016837), hsa-mir-3690-1 (MI0016091), hsa-mir-3690-2 (MI0023561), hsa-mir-3691 (MI0016092), hsa-mir-3692 (MI0016093), hsa-mir-3713 (MI0016134), hsa-mir-3714 (MI0016135), hsa-mir-3907 (MI0016410), hsa-mir-3908 (MI0016412), hsa-mir-3909 (MI0016413), hsa-mir-3910-1 (MI0016414), hsa-mir-3910-2 (MI0016431), hsa-mir-3911 (MI0016415), hsa-mir-3912 (MI0016416), hsa-mir-3913-1 (MI0016417), hsa-mir-3913-2 (MI0016418), hsa-mir-3914-1 (MI0016419), hsa-mir-3914-2 (MI0016421), hsa-mir-3915 (MI0016420), hsa-mir-3916 (MI0016422), hsa-mir-3917 (MI0016423), hsa-mir-3918 (MI0016424), hsa-mir-3919 (MI0016425), hsa-mir-3920 (MI0016427), hsa-mir-3921 (MI0016428), hsa-mir-3922 (MI0016429), hsa-mir-3923 (MI0016430), hsa-mir-3924 (MI0016432), hsa-mir-3925 (MI0016433), hsa-mir-3926-1 (MI0016434), hsa-mir-3926-2 (MI0016437), hsa-mir-3927 (MI0016435), hsa-mir-3928 (MI0016438), hsa-mir-3929 (MI0016439), hsa-mir-3934 (MI0016590), hsa-mir-3935 (MI0016591), hsa-mir-3936 (MI0016592), hsa-mir-3937 (MI0016593), hsa-mir-3938 (MI0016594), hsa-mir-3939 (MI0016596), hsa-mir-3940 (MI0016597), hsa-mir-3941 (MI0016598), hsa-mir-3942 (MI0016599), hsa-mir-3943 (MI0016600), hsa-mir-3944 (MI0016601), hsa-mir-3945 (MI0016602), hsa-mir-3960 (MI0016964), hsa-mir-3972 (MI0016990), hsa-mir-3973 (MI0016991), hsa-mir-3974 (MI0016992), hsa-mir-3975 (MI0016993), hsa-mir-3976 (MI0016994), hsa-mir-3977 (MI0016995), hsa-mir-3978 (MI0016996), hsa-mir-4251 (MI0015861), hsa-mir-4252 (MI0015864), hsa-mir-4253 (MI0015860), hsa-mir-4254 (MI0015862), hsa-mir-4255 (MI0015863), hsa-mir-4256 (MI0015855), hsa-mir-4257 (MI0015856), hsa-mir-4259 (MI0015858), hsa-mir-4260 (MI0015859), hsa-mir-4261 (MI0015868), hsa-mir-4262 (MI0015872), hsa-mir-4263 (MI0015876), hsa-mir-4264 (MI0015877), hsa-mir-4265 (MI0015869), hsa-mir-4266 (MI0015870), hsa-mir-4267 (MI0015871), hsa-mir-4268 (MI0015874), hsa-mir-4269 (MI0015875), hsa-mir-4270 (MI0015878), hsa-mir-4271 (MI0015879), hsa-mir-4272 (MI0015880), hsa-mir-4273 (MI0015881), hsa-mir-4274 (MI0015884), hsa-mir-4275 (MI0015883), hsa-mir-4276 (MI0015882), hsa-mir-4277 (MI0015886), hsa-mir-4278 (MI0015888), hsa-mir-4279 (MI0015887), hsa-mir-4280 (MI0015889), hsa-mir-4281 (MI0015885), hsa-mir-4282 (MI0015890), hsa-mir-4283-1 (MI0015892), hsa-mir-4283-2 (MI0015982), hsa-mir-4284 (MI0015893), hsa-mir-4285 (MI0015891), hsa-mir-4286 (MI0015894), hsa-mir-4287 (MI0015895), hsa-mir-4288 (MI0015896), hsa-mir-4289 (MI0015898), hsa-mir-4290 (MI0015899), hsa-mir-4291 (MI0015900), hsa-mir-4292 (MI0015897), hsa-mir-4293 (MI0015826), hsa-mir-4294 (MI0015827), hsa-mir-4295

(MI0015822), hsa-mir-4296 (MI0015823), hsa-mir-4297 (MI0015824), hsa-mir-4298 (MI0015830), hsa-mir-4299 (MI0015829), hsa-mir-4300 (MI0015831), hsa-mir-4301 (MI0015828), hsa-mir-4302 (MI0015833), hsa-mir-4303 (MI0015834), hsa-mir-4304 (MI0015832), hsa-mir-4305 (MI0015835), hsa-mir-4306 (MI0015836), hsa-mir-4307 (MI0015838), hsa-mir-4308 (MI0015839), hsa-mir-4309 (MI0015837), hsa-mir-4310 (MI0015840), hsa-mir-4311 (MI0015841), hsa-mir-4312 (MI0015842), hsa-mir-4313 (MI0015843), hsa-mir-4314 (MI0015846), hsa-mir-4315-1 (MI0015844), hsa-mir-4315-2 (MI0015983), hsa-mir-4316 (MI0015845), hsa-mir-4317 (MI0015850), hsa-mir-4318 (MI0015847), hsa-mir-4319 (MI0015848), hsa-mir-4320 (MI0015849), hsa-mir-4321 (MI0015852), hsa-mir-4322 (MI0015851), hsa-mir-4323 (MI0015853), hsa-mir-4324 (MI0015854), hsa-mir-4325 (MI0015865), hsa-mir-4326 (MI0015866), hsa-mir-4327 (MI0015867), hsa-mir-4328 (MI0015904), hsa-mir-4329 (MI0015901), hsa-mir-4330 (MI0015902), hsa-mir-4417 (MI0016753), hsa-mir-4418 (MI0016754), hsa-mir-4419a (MI0016755), hsa-mir-4419b (MI0016861), hsa-mir-4420 (MI0016757), hsa-mir-4421 (MI0016758), hsa-mir-4422 (MI0016759), hsa-mir-4423 (MI0016760), hsa-mir-4424 (MI0016763), hsa-mir-4425 (MI0016764), hsa-mir-4426 (MI0016765), hsa-mir-4427 (MI0016766), hsa-mir-4428 (MI0016767), hsa-mir-4429 (MI0016768), hsa-mir-4430 (MI0016769), hsa-mir-4431 (MI0016771), hsa-mir-4432 (MI0016772), hsa-mir-4433 (MI0016773), hsa-mir-4433b (MI0025511), hsa-mir-4434 (MI0016774), hsa-mir-4435-1 (MI0016775), hsa-mir-4435-2 (MI0016777), hsa-mir-4436a (MI0016776), hsa-mir-4436b-1 (MI0017425), hsa-mir-4436b-2 (MI0019110), hsa-mir-4437 (MI0016778), hsa-mir-4438 (MI0016781), hsa-mir-4439 (MI0016782), hsa-mir-4440 (MI0016783), hsa-mir-4441 (MI0016784), hsa-mir-4442 (MI0016785), hsa-mir-4443 (MI0016786), hsa-mir-4444-1 (MI0016787), hsa-mir-4444-2 (MI0019111), hsa-mir-4445 (MI0016788), hsa-mir-4446 (MI0016789), hsa-mir-4447 (MI0016790), hsa-mir-4448 (MI0016791), hsa-mir-4449 (MI0016792), hsa-mir-4450 (MI0016795), hsa-mir-4451 (MI0016797), hsa-mir-4452 (MI0016798), hsa-mir-4453 (MI0016799), hsa-mir-4454 (MI0016800), hsa-mir-4455 (MI0016801), hsa-mir-4456 (MI0016802), hsa-mir-4457 (MI0016803), hsa-mir-4458 (MI0016804), hsa-mir-4459 (MI0016805), hsa-mir-4460 (MI0016806), hsa-mir-4461 (MI0016807), hsa-mir-4462 (MI0016810), hsa-mir-4463 (MI0016811), hsa-mir-4464 (MI0016812), hsa-mir-4465 (MI0016816), hsa-mir-4466 (MI0016817), hsa-mir-4467 (MI0016818), hsa-mir-4468 (MI0016819), hsa-mir-4469 (MI0016820), hsa-mir-4470 (MI0016821), hsa-mir-4471 (MI0016822), hsa-mir-4472-1 (MI0016823), hsa-mir-4472-2 (MI0016824), hsa-mir-4473 (MI0016825), hsa-mir-4474 (MI0016826), hsa-mir-4475 (MI0016827), hsa-mir-4476 (MI0016828), hsa-mir-4477a (MI0016829), hsa-mir-4477b (MI0016830), hsa-mir-4478 (MI0016831), hsa-mir-4479 (MI0016838), hsa-mir-4480 (MI0016841), hsa-mir-4481 (MI0016842), hsa-mir-4482 (MI0016843), hsa-mir-4483 (MI0016844), hsa-mir-4484 (MI0016845), hsa-mir-4485 (MI0016846), hsa-mir-4486 (MI0016847), hsa-mir-4487 (MI0016848), hsa-mir-4488 (MI0016849), hsa-mir-4489 (MI0016850), hsa-mir-4490 (MI0016852), hsa-mir-4491 (MI0016853), hsa-mir-4492 (MI0016854), hsa-mir-4493 (MI0016855), hsa-mir-4494 (MI0016856), hsa-mir-4495 (MI0016857), hsa-mir-4496 (MI0016858), hsa-mir-4497 (MI0016859), hsa-mir-4498 (MI0016860), hsa-mir-4499 (MI0016862), hsa-mir-4500 (MI0016863), hsa-mir-4501 (MI0016864), hsa-mir-4502 (MI0016865), hsa-mir-4503 (MI0016866), hsa-mir-4504 (MI0016867), hsa-mir-4505 (MI0016868), hsa-mir-4506 (MI0016869), hsa-mir-4507 (MI0016871), hsa-mir-4508 (MI0016872), hsa-mir-4509-1 (MI0016873), hsa-mir-4509-2 (MI0016874), hsa-mir-4509-3 (MI0016875), hsa-mir-4510 (MI0016876), hsa-mir-4511 (MI0016877), hsa-mir-4512 (MI0016878), hsa-mir-4513 (MI0016879), hsa-mir-4514 (MI0016880), hsa-mir-4515 (MI0016881), hsa-mir-4516 (MI0016882), hsa-mir-4517 (MI0016883), hsa-mir-4518 (MI0016884), hsa-mir-4519 (MI0016885), hsa-mir-4520a (MI0016886), hsa-mir-4520b (MI0017358), hsa-mir-4521 (MI0016887), hsa-mir-4522 (MI0016889), hsa-mir-4523 (MI0016890), hsa-mir-4524a (MI0016891), hsa-mir-4524b (MI0019114), hsa-mir-4525 (MI0016892), hsa-mir-4526 (MI0016893), hsa-mir-4527 (MI0016894), hsa-mir-4528 (MI0016895), hsa-mir-4529 (MI0016896), hsa-mir-4530 (MI0016897), hsa-mir-4531 (MI0016898), hsa-mir-4532 (MI0016899), hsa-mir-4533 (MI0016900), hsa-mir-4534 (MI0016901), hsa-mir-4535 (MI0016903), hsa-mir-4536-1 (MI0016906), hsa-mir-4536-2 (MI0019149), hsa-mir-4537 (MI0016908), hsa-mir-4538 (MI0016909), hsa-mir-4539 (MI0016910), hsa-mir-4540 (MI0016911), hsa-mir-4632 (MI0017259), hsa-mir-4633 (MI0017260), hsa-mir-4634 (MI0017261), hsa-mir-4635 (MI0017262), hsa-mir-4636 (MI0017263), hsa-mir-4637 (MI0017264), hsa-mir-4638 (MI0017265), hsa-mir-4639 (MI0017266), hsa-mir-4640 (MI0017267), hsa-mir-4641 (MI0017268), hsa-mir-4642 (MI0017269), hsa-mir-4643 (MI0017270), hsa-mir-4644 (MI0017271), hsa-mir-4645 (MI0017272), hsa-mir-4646 (MI0017273), hsa-mir-4647 (MI0017274), hsa-mir-4648 (MI0017275), hsa-mir-4649 (MI0017276), hsa-mir-4650-1 (MI0017277), hsa-mir-4650-2 (MI0017278), hsa-mir-4651 (MI0017279), hsa-mir-4652 (MI0017280), hsa-mir-4653 (MI0017281), hsa-mir-4654 (MI0017282), hsa-mir-4655 (MI0017283), hsa-mir-4656 (MI0017284), hsa-mir-4657 (MI0017285), hsa-mir-4658 (MI0017286), hsa-mir-4659a (MI0017287), hsa-mir-4659b (MI0017291), hsa-mir-4660 (MI0017288), hsa-mir-4661 (MI0017289), hsa-mir-4662a (MI0017290), hsa-mir-4662b (MI0017293), hsa-mir-4663 (MI0017292), hsa-mir-4664 (MI001729), hsa-mir-4665 (MI0017295), hsa-mir-4666a (MI0017296), hsa-mir-4666b (MI0019299), hsa-mir-4667 (MI0017297), hsa-mir-4668 (MI0017298), hsa-mir-4669 (MI0017300), hsa-mir-4670 (MI0017301), hsa-mir-4671 (MI0017302), hsa-mir-4672 (MI0017303), hsa-mir-4673 (MI0017304), hsa-mir-4674 (MI0017305), hsa-mir-4675 (MI0017306), hsa-mir-4676 (MI0017307), hsa-mir-4677 (MI0017308), hsa-mir-4678 (MI0017309), hsa-mir-4679-1 (MI0017310), hsa-mir-4679-2 (MI0017311), hsa-mir-4680 (MI0017312), hsa-mir-4681 (MI0017313), hsa-mir-4682 (MI0017314), hsa-mir-4683 (MI0017315), hsa-mir-4684 (MI0017316), hsa-mir-4685 (MI0017317), hsa-mir-4686 (MI0017318), hsa-mir-4687 (MI0017319), hsa-mir-4688 (MI0017321), hsa-mir-4689 (MI0017322), hsa-mir-4690 (MI0017323), hsa-mir-4691 (MI0017324), hsa-mir-4692 (MI0017325), hsa-mir-4693 (MI0017326), hsa-mir-4694 (MI0017327), hsa-mir-4695 (MI0017328), hsa-mir-4696 (MI0017329), hsa-mir-4697 (MI0017330), hsa-mir-4698 (MI0017331), hsa-mir-4699 (MI0017332), hsa-mir-4700 (MI0017333), hsa-mir-4701 (MI0017334), hsa-mir-4703 (MI0017336), hsa-mir-4704 (MI0017337), hsa-mir-4705 (MI0017338), hsa-mir-4706 (MI0017339), hsa-mir-4707 (MI0017340), hsa-mir-4708 (MI0017341), hsa-mir-4709 (MI0017342), hsa-mir-4710 (MI0017344), hsa-mir-4711 (MI0017345), hsa-mir-4712 (MI0017346), hsa-mir-4713 (MI0017347), hsa-mir-4714 (MI0017348), hsa-mir-4715 (MI0017349), hsa-mir-4716 (MI0017350), hsa-mir-4717 (MI0017352), hsa-mir-4718 (MI0017353), hsa-mir-4719 (MI0017354), hsa-mir-4720 (MI0017355), hsamir-4721 (MI0017356), hsa-mir-4722 (MI0017357), hsa-mir-4723 (MI0017359), hsa-mir-4724 (MI0017361), hsa-mir-4725 (MI0017362), hsa-mir-4726 (MI0017363), hsa-mir-4727 (MI0017364), hsa-mir-4728 (MI0017365), hsa-mir-4729 (MI0017366), hsa-mir-4730 (MI0017367), hsa-mir-4731 (MI0017368), hsa-mir-4732 (MI0017369), hsa-mir-4733 (MI0017370), hsa-mir-4734 (MI0017371), hsa-mir-4735 (MI0017372), hsa-mir-4736 (MI0017373), hsa-mir-4737 (MI0017374), hsa-mir-4738 (MI0017376), hsa-mir-4739 (MI0017377), hsa-mir-4740 (MI0017378), hsa-mir-4741 (MI0017379), hsa-mir-4742 (MI0017380), hsa-mir-4743 (MI0017381), hsa-mir-4744 (MI0017382), hsa-mir-4745 (MI0017384), hsa-mir-4746 (MI0017385), hsa-mir-4747 (MI0017386), hsa-mir-4748 (MI0017387), hsa-mir-4749 (MI0017388), hsa-mir-4750 (MI0017389), hsa-mir-4751 (MI0017390), hsa-mir-4752 (MI0017391), hsa-mir-4753 (MI0017392), hsa-mir-4754 (MI0017394), hsa-mir-4755 (MI0017395), hsa-mir-4756 (MI0017397), hsa-mir-4757 (MI0017398), hsa-mir-4758 (MI0017399), hsa-mir-4759 (MI0017400), hsa-mir-4760 (MI0017401), hsa-mir-4761 (MI0017402), hsa-mir-4762 (MI0017403), hsa-mir-4763 (MI0017404), hsa-mir-4764 (MI0017405), hsa-mir-4765 (MI0017406), hsa-mir-4766 (MI0017407), hsa-mir-4767 (MI0017408), hsa-mir-4768 (MI0017409), hsa-mir-4769 (MI0017410), hsa-mir-4770 (MI0017411), hsa-mir-4771-1 (MI0017412), hsa-mir-4771-2 (MI0017413), hsa-mir-4772 (MI0017414), hsa-mir-4773-1 (MI0017415), hsa-mir-4773-2 (MI0017416), hsa-mir-4774 (MI0017417), hsa-mir-4775 (MI0017418), hsa-mir-4776-1 (MI0017419), hsa-mir-4776-2 (MI0017420), hsa-mir-4777 (MI0017421), hsa-mir-4778 (MI0017422), hsa-mir-4779 (MI0017423), hsa-mir-4780 (MI0017424), hsa-mir-4781 (MI0017426), hsa-mir-4782 (MI0017427), hsa-mir-4783 (MI0017428), hsa-mir-4784 (MI0017429), hsa-mir-4785 (MI0017430), hsa-mir-4786 (MI0017433), hsa-mir-4787 (MI0017434), hsa-mir-4788 (MI0017435), hsa-mir-4789 (MI0017436), hsa-mir-4790 (MI0017437), hsa-mir-4791 (MI0017438), hsa-mir-4792 (MI0017439), hsa-mir-4793 (MI0017440), hsa-mir-4794 (MI0017441), hsa-mir-4795 (MI0017442), hsa-mir-4796 (MI0017443), hsa-mir-4797 (MI0017444), hsa-mir-4798 (MI0017445), hsa-mir-4799 (MI0017446), hsa-mir-4800 (MI0017448), hsa-mir-4801 (MI0017449), hsa-mir-4802 (MI0017450), hsa-mir-4803 (MI0017451), hsa-mir-4804 (MI0017452), hsa-mir-4999 (MI0017865), hsa-mir-5000 (MI0017866), hsa-mir-5001 (MI0017867), hsa-mir-5002 (MI0017868), hsa-mir-5003 (MI0017869), hsa-mir-5004 (MI0017870), hsa-mir-5006 (MI0017873), hsa-mir-5007 (MI0017874), hsa-mir-5008 (MI0017876), hsa-mir-5009 (MI0017877), hsa-mir-5010 (MI0017878), hsa-mir-5011 (MI0017879), hsa-mir-5047 (MI0017932), hsa-mir-5087 (MI0017976), hsa-mir-5088 (MI0017977), hsa-mir-5089 (MI0017978), hsa-mir-5090 (MI0017979), hsa-mir-5091 (MI0017980), hsa-mir-5092 (MI0017981), hsa-mir-5093 (MI0017982), hsa-mir-5094 (MI0017983), hsa-mir-5095 (MI0018001), hsa-mir-5096 (MI0018004), hsa-mir-5100 (MI0019116), hsa-mir-5186 (MI0018165), hsa-mir-5187 (MI0018166), hsa-mir-5188 (MI0018167), hsa-mir-5189 (MI0018168), hsa-mir-5190 (MI0018169), hsa-mir-5191 (MI0018170), hsa-mir-5192 (MI0018171), hsa-mir-5193 (MI0018172), hsa-mir-5194 (MI0018173), hsa-mir-5195 (MI0018174), hsa-mir-5196 (MI0018175), hsa-mir-5197 (MI0018176), hsa-mir-5571 (MI0019115), hsa-mir-5572 (MI0019117), hsa-mir-5579 (MI0019133), hsa-mir-5580 (MI0019135), hsa-mir-5581 (MI0019136), hsa-mir-5582 (MI0019138), hsa-mir-5583-1 (MI0019139), hsa-mir-5583-2 (MI0019140), hsa-mir-5584 (MI0019141), hsa-mir-5585 (MI0019142), hsa-mir-5586 (MI0019143), hsa-mir-5587 (MI0019144), hsa-mir-5588 (MI0019147), hsa-mir-5589 (MI0019148), hsa-mir-5590 (MI0019150), hsa-mir-5591 (MI0019151), hsa-mir-5680 (MI0019280), hsa-mir-5681a (MI0019281), hsa-mir-568 1b (MI0019293), hsa-mir-5682 (MI0019282), hsa-mir-5683 (MI0019284), hsa-mir-5684 (MI0019285), hsa-mir-5685 (MI0019287), hsa-mir-5687 (MI0019291), hsa-mir-5688 (MI0019292), hsa-mir-5689 (MI0019294), hsa-mir-5690 (MI0019295), hsa-mir-5691 (MI0019296), hsa-mir-5692a-1 (MI0019297), hsa-mir-5692a-2 (MI0019298), hsa-mir-5692b (MI0019311), hsa-mir-5692c-1 (MI0019288), hsa-mir-5692c-2 (MI0019289), hsa-mir-5693 (MI0019300), hsa-mir-5694 (MI0019301), hsa-mir-5695 (MI0019302), hsa-mir-5696 (MI0019303), hsa-mir-5697 (MI0019304), hsa-mir-5698 (MI0019305), hsa-mir-5699 (MI0019306), hsa-mir-5700 (MI0019307), hsa-mir-5701-1 (MI0019308), hsa-mir-5701-2 (MI0019593), hsa-mir-5702 (MI0019309), hsa-mir-5703 (MI0019310), hsa-mir-5704 (MI0019312), hsa-mir-5705 (MI0019313), hsa-mir-5706 (MI0019314), hsa-mir-5707 (MI0019315), hsa-mir-5708 (MI0019316), hsa-mir-5739 (MI0019412), hsa-mir-5787 (MI0019797), hsa-mir-6068 (MI0020345), hsa-mir-6069 (MI0020346), hsa-mir-6070 (MI0020347), hsa-mir-6071 (MI0020348), hsa-mir-6072 (MI0020349), hsa-mir-6073 (MI0020350), hsa-mir-6074 (MI0020351), hsa-mir-6075 (MI0020352), hsa-mir-6076 (MI0020353), hsa-mir-6077-1 (MI0020354), hsa-mir-6077-2 (MI0023562), hsa-mir-6078 (MI0020355), hsa-mir-6079 (MI0020356), hsa-mir-6080 (MI0020357), hsa-mir-6081 (MI0020358), hsa-mir-6082 (MI0020359), hsa-mir-6083 (MI0020360), hsa-mir-6084 (MI0020361), hsa-mir-6085 (MI0020362), hsa-mir-6086 (MI0020363), hsa-mir-6087 (MI0020364), hsa-mir-6088 (MI0020365), hsa-mir-6089-1 (MI0020366), hsa-mir-6089-2 (MI0023563), hsa-mir-6090 (MI0020367), hsa-mir-6124 (MI0021258), hsa-mir-6125 (MI0021259), hsa-mir-6126 (MI0021260), hsa-mir-6127 (MI0021271), hsa-mir-6128 (MI0021272), hsa-mir-6129 (MI0021274), hsa-mir-6130 (MI0021275), hsa-mir-6131 (MI0021276), hsa-mir-6132 (MI0021277), hsa-mir-6133 (MI0021278), hsa-mir-6134 (MI0021279), hsa-mir-6165 (MI0021472), hsa-mir-6499 (MI0022209), hsa-mir-6500 (MI0022211), hsa-mir-6501 (MI0022213), hsa-mir-6502 (MI0022214), hsa-mir-6503 (MI0022215), hsa-mir-6504 (MI0022216), hsa-mir-6505 (MI0022217), hsa-mir-6506 (MI0022218), hsa-mir-6507 (MI0022219), hsa-mir-6508 (MI0022220), hsa-mir-6509 (MI0022221), hsa-mir-6510 (MI0022222), hsa-mir-6511a-1 (MI0022223), hsa-mir-6511a-2 (MI0023564), hsa-mir-6511a-3 (MI0023565), hsa-mir-6511a-4 (MI0023566), hsa-mir-6511b-1 (MI0022552), hsa-mir-6511b-2 (MI0023431), hsa-mir-6512 (MI0022224), hsa-mir-6513 (MI0022225), hsa-mir-6514 (MI0022226), hsa-mir-6515 (MI0022227), hsa-mir-6516 (MI0025513), hsa-mir-6715a (MI0022548), hsa-mir-6715b (MI0022549), hsa-mir-6716 (MI0022550), hsa-mir-6717 (MI0022551), hsa-mir-6718 (MI0022553), hsa-mir-6719 (MI0022554), hsa-mir-6720 (MI0022555), hsa-mir-6721 (MI0022556), hsa-mir-6722 (MI0022557), hsa-mir-6723 (MI0022558), hsa-mir-6724 (MI0022559), hsa-mir-6726 (MI0022571), hsa-mir-6727 (MI0022572), hsa-mir-6728 (MI0022573), hsa-mir-6729 (MI0022574), hsa-mir-6730 (MI0022575), hsa-mir-6731 (MI0022576), hsa-mir-6732 (MI0022577), hsa-mir-6733 (MI0022578), hsa-mir-6734 (MI0022579), hsa-mir-6735 (MI0022580), hsa-mir-6736 (MI0022581), hsa-mir-6737 (MI0022582), hsa-mir-6738 (MI0022583), hsa-mir-6739 (MI0022584), hsa-mir-6740 (MI0022585), hsa-mir-6741 (MI0022586), hsa-mir-6742 (MI0022587), hsa-mir-6743 (MI0022588), hsa-mir-6744 (MI0022589), hsa-mir-6745 (MI0022590), hsamir-6746 (MI0022591), hsa-mir-6747 (MI0022592), hsa-mir-6748 (MI0022593), hsa-mir-6749 (MI0022594), hsa-mir-6750 (MI0022595), hsa-mir-6751 (MI0022596), hsa-mir-6752 (MI0022597), hsa-mir-6753 (MI0022598), hsa-mir-6754 (MI0022599), hsa-mir-6755 (MI0022600), hsa-mir-6756 (MI0022601), hsa-mir-6757 (MI0022602), hsa-mir-6758 (MI0022603), hsa-mir-6759 (MI0022604), hsa-mir-6760 (MI0022605), hsa-mir-6761 (MI0022606), hsa-mir-6762 (MI0022607), hsa-mir-6763 (MI0022608), hsa-mir-6764 (MI0022609), hsa-mir-6765 (MI0022610), hsa-mir-6766 (MI0022611), hsa-mir-6767 (MI0022612), hsa-mir-6768 (MI0022613), hsa-mir-6769a (MI0022614), hsa-mir-6769b (MI0022706), hsa-mir-6770-1 (MI0022615), hsa-mir-6770-2 (MI0026418), hsa-mir-6770-3 (MI0026419), hsa-mir-6771 (MI0022616), hsa-mir-6772 (MI0022617), hsa-mir-6773 (MI0022618), hsa-mir-6774 (MI0022619), hsa-mir-6775 (MI0022620), hsa-mir-6776 (MI0022621), hsa-mir-6777 (MI0022622), hsa-mir-6778 (MI0022623), hsa-mir-6779 (MI0022624), hsa-mir-6780a (MI0022625), hsa-mir-6780b (MI0022681), hsa-mir-6781 (MI0022626), hsa-mir-6782 (MI0022627), hsa-mir-6783 (MI0022628), hsa-mir-6784 (MI0022629), hsa-mir-6785 (MI0022630), hsa-mir-6786 (MI0022631), hsa-mir-6787 (MI0022632), hsa-mir-6788 (MI0022633), hsa-mir-6789 (MI0022634), hsa-mir-6790 (MI0022635), hsa-mir-6791 (MI0022636), hsa-mir-6792 (MI0022637), hsa-mir-6793 (MI0022638), hsa-mir-6794 (MI0022639), hsa-mir-6795 (MI0022640), hsa-mir-6796 (MI0022641), hsa-mir-6797 (MI0022642), hsa-mir-6798 (MI0022643), hsa-mir-6799 (MI0022644), hsa-mir-6800 (MI0022645), hsa-mir-6801 (MI0022646), hsa-mir-6802 (MI0022647), hsa-mir-6803 (MI0022648), hsa-mir-6804 (MI0022649), hsa-mir-6805 (MI0022650), hsa-mir-6806 (MI0022651), hsa-mir-6807 (MI0022652), hsa-mir-6808 (MI0022653), hsa-mir-6809 (MI0022654), hsa-mir-6810 (MI0022655), hsa-mir-6811 (MI0022656), hsa-mir-6812 (MI0022657), hsa-mir-6813 (MI0022658), hsa-mir-6814 (MI0022659), hsa-mir-6815 (MI0022660), hsa-mir-6816 (MI0022661), hsa-mir-6817 (MI0022662), hsa-mir-6818 (MI0022663), hsa-mir-6819 (MI0022664), hsa-mir-6820 (MI0022665), hsa-mir-6821 (MI0022666), hsa-mir-6822 (MI0022667), hsa-mir-6823 (MI0022668), hsa-mir-6824 (MI0022669), hsa-mir-6825 (MI0022670), hsa-mir-6826 (MI0022671), hsa-mir-6827 (MI0022672), hsa-mir-6828 (MI0022673), hsa-mir-6829 (MI0022674), hsa-mir-6830 (MI0022675), hsa-mir-6831 (MI0022676), hsa-mir-6832 (MI0022677), hsa-mir-6833 (MI0022678), hsa-mir-6834 (MI0022679), hsa-mir-6835 (MI0022680), hsa-mir-6836 (MI0022682), hsa-mir-6837 (MI0022683), hsa-mir-6838 (MI0022684), hsa-mir-6839 (MI0022685), hsa-mir-6840 (MI0022686), hsa-mir-6841 (MI0022687), hsa-mir-6842 (MI0022688), hsa-mir-6843 (MI0022689), hsa-mir-6844 (MI0022690), hsa-mir-6845 (MI0022691), hsa-mir-6846 (MI0022692), hsa-mir-6847 (MI0022693), hsa-mir-6848 (MI0022694), hsa-mir-6849 (MI0022695), hsa-mir-6850 (MI0022696), hsa-mir-6851 (MI0022697), hsa-mir-6852 (MI0022698), hsa-mir-6853 (MI0022699), hsa-mir-6854 (MI0022700), hsa-mir-6855 (MI0022701), hsa-mir-6856 (MI0022702), hsa-mir-6857 (MI0022703), hsa-mir-6858 (MI0022704), hsa-mir-6859-1 (MI0022705), hsa-mir-6859-2 (MI0026420), hsa-mir-6859-3 (MI0026421), hsa-mir-6860 (MI0022707), hsa-mir-6861 (MI0022708), hsa-mir-6862-1 (MI0022709), hsa-mir-6862-2 (MI0026415), hsa-mir-6863 (MI0022710), hsa-mir-6864 (MI0022711), hsa-mir-6865 (MI0022712), hsa-mir-6866 (MI0022713), hsa-mir-6867 (MI0022714), hsa-mir-6868 (MI0022715), hsa-mir-6869 (MI0022716), hsa-mir-6870 (MI0022717), hsa-mir-6871 (MI0022718), hsa-mir-6872 (MI0022719), hsa-mir-6873 (MI0022720), hsa-mir-6874 (MI0022721), hsa-mir-6875 (MI0022722), hsa-mir-6876 (MI0022723), hsa-mir-6877 (MI0022724), hsa-mir-6878 (MI0022725), hsa-mir-6879 (MI0022726), hsa-mir-6880 (MI0022727), hsa-mir-6881 (MI0022728), hsa-mir-6882 (MI0022729), hsa-mir-6883 (MI0022730), hsa-mir-6884 (MI0022731), hsa-mir-6885 (MI0022732), hsa-mir-6886 (MI0022733), hsa-mir-6887 (MI0022734), hsa-mir-6888 (MI0022735), hsa-mir-6889 (MI0022736), hsa-mir-6890 (MI0022737), hsa-mir-6891 (MI0022738), hsa-mir-6892 (MI0022739), hsa-mir-6893 (MI0022740), hsa-mir-6894 (MI0022741), hsa-mir-6895 (MI0022742), hsa-mir-7106 (MI0022957), hsa-mir-7107 (MI0022958), hsa-mir-7108 (MI0022959), hsa-mir-7109 (MI0022960), hsa-mir-7110 (MI0022961), hsa-mir-7111 (MI0022962), hsa-mir-7112-1 (MI0022963), hsa-mir-7112-2 (MI0026414), hsa-mir-7113 (MI0022964), hsa-mir-7114 (MI0022965), hsa-mir-7150 (MI0023610), hsa-mir-7151 (MI0023611), hsa-mir-7152 (MI0023612), hsa-mir-7153 (MI0023613), hsa-mir-7154 (MI0023614), hsa-mir-7155 (MI0023615), hsa-mir-7156 (MI0023616), hsa-mir-7157 (MI0023617), hsa-mir-7158 (MI0023618), hsa-mir-7159 (MI0023620), hsa-mir-7160 (MI0023621), hsa-mir-7161 (MI0023619), hsa-mir-7162 (MI0023623), hsa-mir-7515 (MI0024354), hsa-mir-7641-1 (MI0024975), hsa-mir-7641-2 (MI0024976), hsa-mir-7702 (MI0025238), hsa-mir-7703 (MI0025239), hsa-mir-7704 (MI0025240), hsa-mir-7705 (MI0025241), hsa-mir-7706 (MI0025242), hsa-mir-7843 (MI0025510), hsa-mir-7844 (MI0025514), hsa-mir-7845 (MI0025515), hsa-mir-7846 (MI0025516), hsa-mir-7847 (MI0025517), hsa-mir-7848 (MI0025518), hsa-mir-7849 (MI0025519), hsa-mir-7850 (MI0025520), hsa-mir-7851 (MI0025521), hsa-mir-7852 (MI0025522), hsa-mir-7853 (MI0025523), hsa-mir-7854 (MI0025524), hsa-mir-7855 (MI0025525), hsa-mir-7856 (MI0025526), hsa-mir-7973-1 (MI0025748), hsa-mir-7973-2 (MI0025749), hsa-mir-7974 (MI0025750), hsa-mir-7975 (MI0025751), hsa-mir-7976 (MI0025752), hsa-mir-7977 (MI0025753), hsa-mir-7978 (MI0025754), hsa-mir-8052 (MI0025888), hsa-mir-8053 (MI0025889), hsa-mir-8054 (MI0025890), hsa-mir-8055 (MI0025891), hsa-mir-8056 (MI0025892), hsa-mir-8057 (MI0025893), hsa-mir-8058 (MI0025894), hsa-mir-8059 (MI0025895), hsa-mir-8060 (MI0025896), hsa-mir-8061 (MI0025897), hsa-mir-8062 (MI0025898), hsa-mir-8063 (MI0025899), hsa-mir-8064 (MI0025900), hsa-mir-8065 (MI0025901), hsa-mir-8066 (MI0025902), hsa-mir-8067 (MI0025903), hsa-mir-8068 (MI0025904), hsa-mir-8069 (MI0025905), hsa-mir-8070 (MI0025906), hsa-mir-8071-1 (MI0025907), hsa-mir-8071-2 (MI0026417), hsa-mir-8072 (MI0025908), hsa-mir-8073 (MI0025909), hsa-mir-8074 (MI0025910), hsa-mir-8075 (MI0025911), hsa-mir-8076 (MI0025912), hsa-mir-8077 (MI0025913), hsa-mir-8078 (MI0025914), hsa-mir-8079 (MI0025915), hsa-mir-8080 (MI0025916), hsa-mir-8081 (MI0025917), hsa-mir-8082 (MI0025918), hsa-mir-8083 (MI0025919), hsa-mir-8084 (MI0025920), hsa-mir-8085 (MI0025921), hsa-mir-8086 (MI0025922), hsa-mir-8087 (MI0025923), hsa-mir-8088 (MI0025924), hsa-mir-8089 (MI0025925). See, e.g., pre-microRNAs listed on miRBase.org In varying embodiments, the pre-microRNA is not pre-miRNA-22, pre-miRNA-122, pre-miRNA-124-2, pre-miRNA-125-2, pre-miRNA-155 or pre-miRNA-221.

In varying embodiments, the hybrid molecules comprise the full-length native pre-micro-RNA. In some embodiments, the hybrid molecules comprise fragments or subsequences of the native pre-micro-RNA molecules. Fragments or subsequences of the native pre-micro-RNA molecules that find use will have one or more cleavage sites recognized by and accessible to an endoribonuclease (e.g., Dicer) such that an inserted RNA molecule (e.g., a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), an aptamer) can be cleaved out of or released from the hybrid tRNA/pre-microRNA molecule.

3. Inserted RNA Molecules

In varying embodiments, the hybrid tRNA/pre-microRNA molecules contain an inserted RNA sequence and serve as a scaffold for the high-level production of the inserted RNA sequence, which can be cleaved from the hybrid tRNA/pre-microRNA molecule, e.g., by an endoribonuclease, e.g., by Dicer. In varying embodiments, the inserted RNA molecule can be from about 18 nucleotides and up to about 200 nucleotides, e.g., at least about 18 nucleotides and up to about 150 nucleotides, e.g., at least about 18 nucleotides and up to about 125 nucleotides, e.g., at least about 18 nucleotides and up to about 100 nucleotides, e.g., at least about 18 nucleotides and up to about 75 nucleotides, e.g., at least about 18 nucleotides and up to about 50 nucleotides, e.g., at least about 18 nucleotides and up to about 40 nucleotides, e.g., at least about 18 nucleotides and up to about 30 nucleotides. In varying embodiments, the inserted RNA molecule can be about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

As appropriate or desired, the inserted RNA can be an inhibitory nucleic acid, that prevents, reduces or inhibits the transcription or translation of a target nucleic acid or protein. In varying embodiments, the inhibitory nucleic acid is a noncoding RNA (ncRNA), mature microRNA (miRNA), a small interfering RNA (siRNA), a short hairpin RNA (shRNA), a Piwi-interacting RNA (piRNA), a small nuclear RNA (snRNA), or a small nucleolar RNA (snoRNA). In some embodiments, the inserted RNA is a mature miRNA, e.g., that is derived from (e.g., is homologous to) or is heterologous to the pre-microRNA molecule in the hybrid tRNA/pre-microRNA scaffold. In varying embodiments, the inserted RNA is a mature miRNA selected from the group consisting of miR-21, miR-22, miR-27b, miR-33, miR-34a, miR 122, miR 124-1, miR-125-1, miR-1291 and let-7a. In varying embodiments, the inserted RNA is a noncoding RNA. In some embodiments, the noncoding RNA is Homeobox (HOX) antisense intergenic RNA (HOTAIR).

In some embodiments, the inserted RNA is an aptamer that binds to a target molecule or a target polypeptide.

In some embodiments, the target nucleic acid or polypeptide is selected from the group consisting of a fluorescent protein, a cytokine, a growth factor, a hormone, a kinase, a nuclear receptor, a G protein-coupled receptor, an epigenetic regulator, a transcription factor. In some embodiments, the target nucleic acid or polypeptide is a fluorescent protein selected from a violet fluorescent protein, a blue fluorescent protein (BFP), a cyan fluorescent protein, a green fluorescent protein (GFP), a yellow fluorescent protein (YFP), an orange fluorescent protein (OFP), a red fluorescent protein (RFP) and a sapphire-type fluorescent protein. In some embodiments, the target nucleic acid or polypeptide is a cytokine selected from interleukin (IL)-1a, IL-10, tumor necrosis factor (TNF)α, interferon (IFN)α, IFNβ, IFNγ, TGFβ1, IL-5, IL-6, IL-8, IL-10, IL-12, IL-17, IL-18, IL-22, IL-23 and migration inhibitory factor (MIF). In some embodiments, the target nucleic acid or polypeptide is a nuclear receptor selected from Peroxisome proliferator-activated receptor gamma (PPAR-γ or PPARG), retinoic acid receptor (RAR), vitamin D receptor, estrogen receptor (ER), androgen receptor (AR), glucocorticoid receptor (GR), thyroid hormone receptor (THR), farnesoid X receptor (FXR) or NR1H4 (nuclear receptor subfamily 1, group H, member 4), a liver X receptor (LXR), constitutive androstane receptor (CAR), and pregnane X receptor (PXR). In some embodiments, the target nucleic acid or polypeptide is a growth factor selected from vascular endothelial growth factor (VEGF), Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Healing factor, Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumor necrosis factor-alpha (TNF-α), wingless-type MMTV integration site (WNT) family members, placental growth factor (PGF), Somatotrophin (growth hormone or GH), IL-2, IL-3, IL-4, IL-5, IL-6, and IL-7.

a. Disease Markers and Targets

In some embodiments, the target nucleic acid or polypeptide is a biomarker associated with the progression or causative of cancer.

In the case of breast cancer, a target miRNA may be selected from human miRNAs including but not limited to miR-10b, miR-21, miR-29b, miR-17-5p, miR-125b, miR-145, miR-146, and miR-155. For detection of malignant lymphoma, a target miRNA may be selected from human miRNAs including but not limited to miR-155, miR-17, miR-18a, miR-19a, miR-20a, miR-19b, and miR-92. Breast tumors, moreover, comprise heterogeneous miRNA profiles and miRNA signature of, e.g., let-7 family, mir-10b, mir-18a, mir-106a, mir125-a, mir125-b, mir-126, mir-130a, mir-145, mir-155, mir-141, mir-214, mir-205, mir-206, mir-210, mir-126, mir-335, mir-213, mir-203, 17-5p, miR-30, mir-34, and mir-342, have been proposed to affect breast cancer outcomes. See, e.g., Wiemer, Eur. J Cancer 43: 1529-1544 (2007).

In colorectal cancer, a target miRNA may be selected from human miRNAs including but not limited to the let-7 family, miR-10a, miR-20a, miR-24, miR-29b, miR-31, miR-96, miR-133b, miR-135b, miR-143, miR-145, miR-183, miR-17, miR-18a, miR-19a, miR-19b and miR-92.

For hepatocellular carcinoma, the target miRNA may be selected from human miRNAs including but not limited to miR-18, miR-125a, miR-195, miR-199a, miR-200a, and miR-224. In varying embodiments, miR-16, miR-199a, and/or miR-195 can serve as target miRNA for various liver cancers.

In cases of pancreatic cancer, the target miRNA may be selected from human miRNAs including but not limited to miR-21, miR-24, miR-34a, miR-100, miR-101, miR-103, miR-107, miR-125b, miR-143, miR-145, miR-148b, miR-200, and miR-155. See Wiemer, Eur. J Cancer 43: 1529-1544 (2007); Zhao et al., Mol Cancer Ther. 2013 January; 12(1):83-93; Bao et al., "Anti-Tumor Activity of a Novel Compound-CDF Is Mediated by Regulating miR-21, miR-200, and PTEN in Pancreatic Cancer." PloS One, Vol. 6(3)| e17850 (2011); Qazi et al., "Restoration of E-cadherin expression in pancreatic ductal adenocarcinoma treated with microRNA-101." Surgery 152: 704-13 (2012); Pramanik et al., "Restitution of Tumor Suppressor MicroRNAs Using a Systemic Nanovector Inhibits Pancreatic Cancer Growth in Mice." Mol Cancer Ther; 10(8) (2011); Kaestner, "The FoxA factors in organogenesis and differentiation." Current Opinion in Genetics & Development, 20:527-532 (2010); and Brychtova, "Anterior gradient 2: A novel player in tumor cell biology." Cancer Letters 304, 1-7 (2011).

For prostate cancer, the target miRNA may be selected from human miRNAs including but not limited to let-7d, miR-128a, miR-195, and miR-203.

In cases of lung cancer, the target miRNA may be selected from human miRNAs including but not limited to the let-7 family, miR-17, miR-18a, miR-19a, miR-20a, miR-19b, miR 34, miR-92, miR-21, miR-126*, miR-155, miR-200b, miR-205, and miR-210.

Further, a number of additional miRNAs are differentially expressed in melanoma cells, and several of the over-expressed miRNAs appear to regulate melanoma cell invasiveness (Ma et al., 2009; Mueller and Bosserhoff, 2009; Mueller et al., 2009; Philippidou et al., 2010; Segura et al., 2010; Stark et al., 2010). The miRNAs miR-221/222 down-regulate p27Kip1/CDKN1B and the c-KIT receptor mRNA levels, thereby controlling the progression of neoplasia, leading to enhanced proliferation and reduced differentiation in such cancers cells (Felicetti et al., 2008). miR-137, moreover, down-regulates the expression of MITF, a master regulator of cell growth, maturation, and pigmentation in melanoma (Bemis et al., 2008). It has recently been shown that several miRNA genes are differentially regulated in melanoma cells, and therefore, lead to cancer. One such miRNA, miR-211, is consistently reduced in melanoma (see Mazar et al, 2010), which is associated with increased invasiveness and high proliferation rates in susceptible cells. A group of epigenetically regulated miRNA genes, moreover, has been associated with melanomas, e.g., miR-34b, -489, -375, -132, -142-3p, -200a, -145, -452, -21, -34c, -496, -let7e, -654, and -519b.

In some embodiments, the target nucleic acid or polypeptide is selected from the group consisting of miR-1291; AKT2; Cyclin Bl; MeCP2; FOXA2; AMPKal; Anterior gradient homolog 2 (AGR2); Argininosuccinate synthase (ArSS); Chain C, structure of the H3-H4 chaperone ASF1; Ornithine aminotransferase (OAT); Keratin, type II cyto-skeletal 8 (KRT8); Phosphoenolpyruvate carboxykinase 2 (PEPCK2); Enoyl-coenzyme A (Co A) hydratase (ECHS1); Phosphoserine aminotransferase isoform 1 (PSAT1); Dihydrolipoamide acetyltransferase (DLAT); Peroxiredoxin 3, isoform CRA a (PRDX3); Cysteine-rich protein 2 (CRIP2); Chain C, human PCNA; Fascin homolog 1, actin-bundling protein, isoform CRA a (FSCN1); Serpin HI precursor; Protein disulfide-isomerase precursor; Chain A, disulfide isomerase related chaperone ERP29; Triosephosphate isomerase isoform 2 (TPII); Peroxiredoxin-4 (PRDX4); and Isocitrate dehydrogenase [NAD] subunit beta (IDH3B); a-fetoprotein (AFP); AFP-L3%, des-gamma-carboxypro-thrombin (DCP); CDH1 (E-cadherin); trimethylated lysine 27 of H3 histone (H3K27me3); histone deacetylase-1; histone deacetylase-2; SIRT1; CD44; aldehyde dehydrogenase; KRAS2; or RREB1, an ABC transporter (e.g., ABCC1, ABCG2, ABCB1, ABCC2, ABCC3, and ABCC4) or any combination thereof.

4. High Level Production of Hybrid tRNA/Pre-microRNA and tRNA/shRNA Molecules in vitro The hybrid tRNA/pre-microRNA and tRNA/shRNA molecules can be produced by recombinant expression in a host cell, or can be synthetically prepared. Such recombinant and synthetic methods are well known in the art. When produced by recombinant expression in a host cell, the host cell can be eukaryotic or prokaryotic. In varying embodiments, the host cell is of the same species of cell as that of the tRNA molecule or the pre-microRNA or shRNA molecule used in the hybrid tRNA/pre-microRNA or tRNA/shRNA molecule. When producing a hybrid tRNA/pre-microRNA and tRNA/shRNA molecules comprising an inserted RNA sequence, a host cell that does not comprise an endoribonuclease that may cleave out the inserted RNA (e.g., Dicer) can be used. In varying embodiments, the host cell for the recombinant expression of a hybrid tRNA/pre-microRNA molecule is a prokaryotic cell, e.g., a bacterial cell, e.g., an *Escherichia coli* cell. In varying embodiments, the host cell for the recombinant expression of a hybrid tRNA/pre-microRNA or tRNA/shRNA molecule is a eukaryotic cell, e.g., a mammalian cell, a human cell, an insect cell, a plant cell or a yeast cell. Eukaryotic (e.g., mammalian or human) host cells which are deficient for Dicer are known in the art and find use for the high level expression for production of the hybrid tRNA/pre-microRNA and/or tRNA/shRNA molecules in a eukaryotic host cell, e.g., as described in Commins, et al. *Proc Natl Acad Sci USA,* (2006) 103(10):3687-3692; Murchison, et al., *Proc Natl Acad Sci USA,* (2005) 102(34): 12135-12140; and Kanellopoulou, et al., *Genes Dev.,* (2005) 19:489-501.

The hybrid tRNA/pre-microRNA and tRNA/shRNA scaffolds facilitate stable, consistent and reliable high level expression of a desired inserted RNA molecule in vivo and in vitro, as described herein. In varying embodiments, high levels of the hybrid tRNA/pre-microRNA and tRNA/shRNA scaffolds are produced in vitro by a host cell that does not comprise an endoribonuclease that may cleave out the inserted RNA (e.g., Dicer). In varying embodiments, at least about 5-100 mg, e.g., at least about 10-50 mg, of hybrid tRNA/pre-microRNA and tRNA/shRNA scaffold molecules can be produced in vitro from 1 liter of *E. coli* culture over 16-48 hours of time. In varying embodiments, at least about 5-100 mg, e.g., at least about 10-50 mg, of hybrid tRNA/pre-microRNA and tRNA/shRNA scaffold molecules can be produced in vitro from 1 liter of yeast cell culture. In some embodiments, the tRNA/pre-microRNA or tRNA/shRNA molecule produced comprises at least about 5%, e.g., at least about 6%, 7%, 8%, 9%, 10%, 11%, 12%, 15%, 20%, or more, of the total RNA.

In varying embodiments, the hybrid tRNA/pre-microRNA and tRNA/shRNA scaffolds are purified as part of the total RNA from the production host cells. Such methods of isolating or purifying total RNA from a host cell are established in the art. In some embodiments, the hybrid tRNA/pre-microRNA and tRNA/shRNA scaffolds are further substantially isolated or purified from the other RNA molecules and components of the production host cell. This can be done using any method in the art, including, e.g., separation by separation by gel electrophoresis, affinity chromatography, chromatography, FPLC and/or HPLC. The substantially isolated and/or purified hybrid tRNA/pre-microRNA and tRNA/shRNA scaffolds can then be transfected or delivered into a eukaryotic cell, which will then process the hybrid tRNA/pre-microRNA and tRNA/shRNA scaffolds to cleave or release the inserted RNA.

In varying embodiments, the hybrid tRNA/pre-microRNA scaffolds are contacted with or exposed to an endoribonuclease (e.g., Dicer) in vitro, under conditions sufficient to allow cleave or release of the inserted RNA. In varying embodiments, the efficiency of in vitro cleavage or release of the inserted RNA from the hybrid tRNA/pre-microRNA scaffolds can be facilitated by adding a RNase, ribozyme or DNAzyme site to the tRNA-pre-miRNA molecule.

5. Therapeutic Delivery of RNA Molecules in vivo

The hybrid tRNA/pre-microRNA and tRNA/shRNA scaffolds can be administered to a subject in need thereof for delivery of an inserted RNA of interest (e.g., an inhibitory nucleic acid, an aptamer) to interior of a target cell. Generally, the subject is a mammal and therefore comprises eukaryotic cells which express endoribonucleases (e.g., Dicer). Once the target eukaryotic cells of the subject have been transfected or transformed with the hybrid tRNA/pre-microRNA and tRNA/shRNA scaffolds, the endoribonucleases (e.g., Dicer) within the target cell cleave out or release the inserted RNA of interest.

In varying embodiments, the inserted RNA is an inhibitory nucleic acid (e.g., a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), an aptamer). In varying embodiments, the inhibitory RNA once released from the hybrid scaffold in a eukaryotic cell reduces the amount and/or activity of the target nucleic acid or polypeptide by at least about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including any percent within these ranges, such as but not limited to 15%, 20%, 25%, 30%, 35%, 40%, 45%, 50%, 55%, 60%, 65%, 70%, 75%, 80%, 85%, 90%, 95%, 96%, 97%, 98%, and 99%.

In certain embodiments, the hybrid tRNA/pre-microRNA and tRNA/shRNA scaffolds are expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application in a general, illustrative sense, and are not intended to limit the invention.

In one embodiment, an expression vector for expressing the hybrid tRNA/pre-microRNA and tRNA/shRNA scaffolds comprises a promoter "operably linked" to a polynucleotide encoding the hybrid tRNA/pre-microRNA and tRNA/shRNA scaffolds (e.g., containing an inserted RNA). The phrase "operably linked" or "under transcriptional control" as used herein means that the promoter is in the correct location and orientation in relation to a polynucleotide to control the initiation of transcription by RNA polymerase and expression of the polynucleotide.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Illustrative promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences include UTRs which include an Internal Ribosome Entry Site (IRES) present in the leader sequences of picornaviruses such as the encephalomyocarditis virus (EMCV) UTR (fang et al. J. Virol. (1989) 63:1651-1660. Other picornavirus UTR sequences that will also find use in the present invention include the polio leader sequence and hepatitis A virus leader and the hepatitis C IRES.

There are a number of ways in which expression vectors may be introduced into cells. In certain embodiments, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the available methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

The typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing the hybrid tRNA/pre-microRNA and tRNA/shRNA scaffolds (e.g., containing an inserted RNA) in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs in the present invention. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect cleavage and expression of inserted RNA, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Porter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the hybrid tRNA/pre-microRNA and tRNA/shRNA scaffolds, e.g., containing the inserted RNA of interest, may be positioned and expressed at different sites. In certain embodiments, the nucleic acid encoding the hybrid tRNA/pre-microRNA and tRNA/shRNA scaffolds may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ohosh and Bachhawat, 1991). Also contemplated are lipofectamine-DNA complexes.

In certain embodiments, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-I) (Kato et al., 1991). In yet further embodiments, the liposome may be complexed or employed in conjunction with both HVJ and HMG-I. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular lncRNA or inhibitor into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise an encapsulating particle and an external targeting ligand, e.g., that specifically binds to a tumor associated antigen. For example, Nicolau et al. (1987) employed lactosylceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties. Other tumor associated antigens of use for targeting include without limitation, e.g., include without limitation, melanoma associated antigens (MAGE-1, MAGE-3, TRP-2, melanosomal membrane glycoprotein gp100, gp75 and MUC-1 (mucin-1) associated with melanoma); CEA (carcinoembryonic antigen) which can be associated, e.g., with ovarian, melanoma or colon cancers; folate receptor alpha expressed by ovarian carcinoma; free human chorionic gonadotropin beta (hCGβ) subunit expressed by many different tumors, including but not limited to myeloma; HER-2/neu associated with breast cancer; encephalomyelitis antigen HuD associated with small-cell lung cancer; tyrosine hydroxylase associated with neuroblastoma; prostate-specific antigen (PSA) associated with prostate cancer; CA125 associated with ovarian cancer; and the idiotypic determinants of a B cell lymphoma can generate tumor-specific immunity (attributed to idiotype-specific humoral immune response). Moreover, antigens of human T cell leukemia virus type 1 have been shown to induce specific CTL responses and antitumor immunity against the virus-induced human adult T cell leukemia (ATL). See, e.g., Haupt, et al., Experimental Biology and Medicine (2002) 227:227-237; Ohashi, et al., Journal of Virology (2000) 74(20):9610-9616. Other TAAs are known and find use for the formulation and targeted delivery of the hybrid tRNA/pre-microRNA and tRNA/shRNA scaffolds.

In a particular example, the oligonucleotide may be administered in combination with a cationic lipid. Examples of cationic lipids include, but are not limited to, lipofectin, DOTMA, DOPE, and DOTAP. The publication of WO00/71096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Also encompassed are pharmaceutical compositions comprising the hybrid tRNA/pre-microRNA or tRNA/shRNA scaffolds and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the hybrid tRNA/pre-microRNA and tRNA/shRNA scaffolds described herein. Commercially available fat emulsions that are suitable for delivering the nucleic acids to tissues, such as cardiac muscle tissue and smooth muscle tissue, include Intralipid, Liposyn, Liposyn II, Liposyn III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

One will generally desire to employ appropriate salts and buffers to render delivery vehicles stable and allow for uptake by target cells. Buffers also will be employed when recombinant cells are introduced into a patient. Aqueous compositions of the present invention comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the nucleic acids of the compositions.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15$^{th}$ Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

The skilled artisan will be able to select and use an appropriate system for delivering the inhibitory nucleic acid or an expression vector to target cells in vitro or in vivo without undue experimentation.

The hybrid tRNA/pre-microRNA and tRNA/shRNA scaffolds (e.g., containing an inserted RNA) may be administered to a subject with cancer to enhance or increase the responsiveness to chemotherapy comprising a platinum coordination complex. In alternative embodiments, the cancer is resistant to treatment with a chemotherapy regime. By "resistant to chemotherapy" is meant that the cancer does not substantially respond to treatment with the chemotherapy. Identification of such resistant cancers and cancer In some embodiments, the hybrid tRNA/pre-microRNA and tRNA/shRNA scaffolds (e.g., containing an inserted RNA) may be used to treat subjects who have failed (relapsed) after standard chemotherapy or bone marrow transplantation or other emerging or novel targeted therapies. By "treat," "treatment" or "treating" is meant ameliorating symptoms associated with cancer, including preventing or delaying the onset of the disease symptoms and/or lessening the severity or frequency of the disease symptoms and/or prolonging remission and/or decreasing the frequency or severity of relapse. In varying embodiments, the hybrid tRNA/pre-microRNA and tRNA/shRNA scaffolds (e.g., containing an inserted RNA) can be administered to the subject in conjunction with chemotherapy comprising a platinum coordination complex (e.g., prior to or concurrently with chemotherapy comprising a platinum coordination complex.

The hybrid tRNA/pre-microRNA and tRNA/shRNA scaffolds (e.g., containing an inserted RNA) may be provided alone or in combination with other compounds (for example, chemotherapeutics), in the presence of a liposome, an adjuvant, or any pharmaceutically acceptable carrier, in a form suitable for administration to mammals, for example, humans, cattle, sheep, etc. If desired, treatment with the hybrid tRNA/pre-microRNA and tRNA/shRNA scaffolds (e.g., containing an inserted RNA) may be combined with traditional and existing, or emerging, therapies for cancer, e.g., targeted chemotherapies using cancer-specific peptides described, e.g., in Intl. Publ. No. 2011/038142.

The hybrid tRNA/pre-microRNA and tRNA/shRNA scaffolds (e.g., containing an inserted RNA) may be administered chronically or intermittently. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature. In alternative embodiments, the hybrid tRNA/pre-microRNA and tRNA/shRNA scaffolds (e.g., containing an inserted RNA) are administered to a subject in need of such inhibitors, e.g., a subject diagnosed with or suspected of having a cancer.

In alternative embodiments, a hybrid tRNA/pre-microRNA or tRNA/shRNA scaffold (e.g., containing an inserted RNA) may be effectively delivered to cancer cells, by a variety of methods known to those skilled in the art. Such methods include but are not limited to liposomal encapsulation/delivery, vector-based gene transfer, fusion to peptide or immunoglobulin sequences (peptides described, e.g., in Intl. Publ. No. 2011/038142) for enhanced cell targeting and other techniques. Suitable viral vectors include retroviral vectors such as lentiviral vectors, adenovirus vectors, adeno-associated virus vectors, etc. In alternative embodiments, a hybrid tRNA/pre-microRNA or tRNA/shRNA scaffold (e.g., containing an inserted RNA), may also be formulated in pharmaceutical compositions well known to those in the field. These include liposomal formulations and combinations with other agents or vehicles/excipients such as cyclodextrins which may enhance delivery of the inhibitory nucleic acid. In alternative embodiments, suitable carriers include lipid-based carriers such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In alternative embodiments, the carrier system is a cyclodextrin-based carrier system such as a cyclodextrin polymer-nucleic acid complex. In further embodiments, the carrier system is a protein-based carrier system such as a cationic peptide-nucleic acid complex.

Suitable carriers are known in the art and are described in, without limitation, United States Patent Application Nos. 20070173476 published Jul. 26, 2007; 20050008617 published Jan. 13, 2005; 20050014962 published Jan. 20, 2005; 20050064595 published Mar. 24, 2005; 20060008910 published Jan. 12, 2006; 20060051405 published Mar. 9, 2006; 20060083780 published Apr. 20, 2006; 20050008689 published Jan. 13, 2005; 20070172950 published Jul. 26, 2007; U.S. Pat. No. 7,101,995 issued Sep. 5, 2006 to Lewis, et al.; U.S. Pat. No. 7,220,400 issued May 22, 2007, to Monahan, et al.; U.S. Pat. No. 5,705,385 issued Jan. 6, 1998 to Bally, et al.; U.S. Pat. No. 5,965,542 issued Oct. 12, 1999 to Wasan, et al.; U.S. Pat. No. 6,287,591 issued Sep. 11, 2001 to Semple, et al., all of which are hereby incorporated by reference.

In one embodiment, the present invention contemplates a nucleic acid-lipid particle comprising a hybrid tRNA/pre-microRNA or tRNA/shRNA scaffold (e.g., containing an inserted RNA). In addition to the references described above, suitable nucleic acid-lipid particles and their use are described in U.S. Pat. Nos. 6,815,432, 6,586,410, and 6,534,484.

Conventional pharmaceutical practice may be employed to provide suitable formulations or compositions to administer the hybrid tRNA/pre-microRNA or tRNA/shRNA scaffolds (e.g., containing an inserted RNA) to subjects suffering from, at risk of, or presymptomatic for cancer. Suitable pharmaceutical compositions may be formulated by means known in the art and their mode of administration and dose determined by the skilled practitioner. Any appropriate route of administration may be employed, for example, parenteral, intravenous, subcutaneous, intramuscular, intraventricular, intraurethral, intraperitoneal, intranasal, aerosol, oral administration, or any mode suitable for the selected treatment. Therapeutic formulations may be in the form of liquid solutions or suspensions. For enteral administration, the compound may be administered in a tablet, capsule or dissolved in liquid form. The table or capsule may be enteric coated, or in a formulation for sustained release. For intranasal formulations, in the form of powders, nasal drops, or aerosols. For parenteral administration, a hybrid tRNA/pre-microRNA or tRNA/shRNA scaffold (e.g., containing an inserted RNA) may be dissolved in sterile water or saline or a pharmaceutically acceptable vehicle used for administration of non-water soluble hybrid tRNA/pre-microRNA or tRNA/shRNA scaffold (e.g., containing an inserted RNA) such as those used for vitamin K. Suitable formulations include those that have desirable pharmaceutical properties, such as targeted delivery to cancer cells, improved serum half-life/stability of a hybrid tRNA/pre-microRNA or tRNA/shRNA scaffold (e.g., containing an inserted RNA), improved intracellular penetration and cytoplasmic delivery, improved persistence of in-vivo activity, reduction in dose required for efficacy, reduction in required dosing frequency, etc. In alternative embodiments, a liposomal nanoparticle-based dosing formulation of a hybrid tRNA/pre-microRNA or tRNA/shRNA scaffold (e.g., containing an inserted RNA) may be prepared using methods well known to those skilled in the art and currently practiced for the preparation pharmaceutical formulations of other oligonucleotide-based reagents/therapeutics including anti-sense oligonucleotides and/or RNAi (siRNA)-based agents. In alternative embodiments, a gene therapy approach for transduction of hybrid tRNA/pre-microRNA and tRNA/shRNA scaffolds (e.g., containing an inserted RNA) to target cells (e.g. cancer cells) using for example lentiviral-based vectors, may be used.

Methods well known in the art for making formulations are found in, for example, Remington: the Science & Practice of Pharmacy, Loyd, et al., eds., $22^{nd}$ ed., Pharmaceutical Press, (2012). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the hybrid tRNA/pre-microRNA and tRNA/shRNA scaffolds (e.g., containing an inserted RNA) are administered to an individual in an amount sufficient to stop or slow a cancer, or to promote differentiation, or inhibit or decrease self-renewal, or inhibit or decrease engraftment or metastasis of cancer cells.

An "effective amount" of a hybrid tRNA/pre-microRNA or tRNA/shRNA scaffold (e.g., containing an inserted RNA) according to the invention includes a therapeutically effective amount or a prophylactically effective amount. A "therapeutically effective amount" refers to an amount effective, at dosages and for periods of time necessary, to achieve the desired therapeutic result, such as treatment of a cancer or promotion of differentiation, or inhibition or decrease of self-renewal or inhibition or decrease of engraftment or metastasis of a cancer cell. The increase or decrease may be between 10% and 90%, e.g., 10%, 20%, 30%, 40%, 50%, 60%, 70%, 80%, 90%, or may be over 100%, such as 200%, 300%, 500% or more, when compared with a control or reference subject, sample or compound.

A therapeutically effective amount of a hybrid tRNA/pre-microRNA or tRNA/shRNA scaffold (e.g., containing an inserted RNA) may vary according to factors such as the disease state, age, sex, and weight of the individual subject, and the ability of the hybrid tRNA/pre-microRNA and tRNA/shRNA scaffolds (e.g., containing an inserted RNA) to elicit a desired response in the individual. Dosage regimens may be adjusted to provide the optimum therapeutic response. A therapeutically effective amount is also one in which any toxic or detrimental effects of the hybrid tRNA/pre-microRNA or tRNA/shRNA scaffold (e.g., containing an inserted RNA) are outweighed by the therapeutically beneficial effects. A "prophylactically effective amount" refers to an amount effective, at dosages and for periods of time necessary, to achieve the desired prophylactic result, such as prevention or protection against a cancer or promotion of differentiation, inhibition or decrease of self-renewal or inhibition or decrease of engraftment or metastasis of cancer cells. Typically, a prophylactic dose is used in subjects prior to or at an earlier stage of disease, so that a prophylactically effective amount may be less than a therapeutically effective amount. In alternative embodiments, dosages may be adjusted depending on whether the subject is in remission from cancer or not. A preferred range for therapeutically or prophylactically effective amounts of a hybrid tRNA/pre-microRNA and tRNA/shRNA scaffolds (e.g., containing an inserted RNA) may be any integer from 0.1 nM-0.1M, 0.1 nM-0.05M, 0.05 nM-15 µM or 0.01 nM-10 µM. In alternative embodiments, a therapeutically or prophylactically effective amount that is administered to a subject may range from about 5 to about 3000 micrograms/kg if body weight of the subject, or any number therebetween.

In alternative embodiments, the hybrid tRNA/pre-microRNA or tRNA/shRNA scaffold (e.g., containing an inserted RNA) is provided in an amount that is from 10% to 99% greater than the amount of target nucleic acid or polypeptide present in cancer cells, or more generally at least 10%, 20%, 30%, 40%, 50, 55% or 60%, or at least 65%, 75%, 80%, 85%, 90%, or 95%, or as much as 96%, 97%, 98%, or 99% greater than the amount present in cancer cells. In alternative embodiments, the hybrid tRNA/pre-microRNA or tRNA/shRNA scaffold (e.g., containing an inserted RNA) is provided in an amount that is 0.5 to 50 fold greater than the amount present in cancer cells, or more generally at least 0.5, 1, 1.5, 2, 5, 10, 20, 25, 30, 35, 40, 45 fold greater than the amount present in cancer cells. In alternative embodiments, the hybrid tRNA/pre-microRNA or tRNA/shRNA scaffold (e.g., containing an inserted RNA) is provided in an amount that is equivalent to the amount present in non-cancerous bladder cells or the amount present in normal bladder cells.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

6. Kits

In varying embodiments, provided are kits comprising the hybrid tRNA/pre-microRNA and/or tRNA/shRNA scaffolds (e.g., containing an inserted RNA) described herein.

In varying embodiments, suitable formulations may be provided in a kit including one or more hybrid tRNA/premicroRNA and/or tRNA/shRNA scaffolds (e.g., containing an inserted RNA), together with instructions for using the hybrid tRNA/pre-microRNA scaffolds (e.g., containing an inserted RNA) to treat a cancer. The kit may contain additional agents such as a pharmaceutical carrier e.g, a liposomal carrier or additional active ingredients such as a chemotherapeutic agent. The additional agents may be provided in the same container as that containing the hybrid tRNA/pre-microRNA and/or tRNA/shRNA scaffolds (e.g., containing an inserted RNA) or may be provided in a container separate from that containing the hybrid tRNA/pre-microRNA and/or tRNA/shRNA scaffolds (e.g., containing an inserted RNA).

EXAMPLES

The following examples are offered to illustrate, but not to limit the claimed invention.

Example 1

A General Approach to High-yield Biosynthesis of Chimeric RNAs Bearing Various Types of Functional Small RNAs for Broad Applications RNA research and therapy relies primarily on synthetic RNAs. We employed recombinant RNA technology towards large-scale production of pre-miRNA agents in bacteria, but found the majority of target RNAs were not or negligibly expressed. We thus developed a novel strategy to achieve consistent high-yield biosynthesis of chimeric RNAs carrying various small RNAs (e.g., miRNAs, siRNAs and RNA aptamers), which was based upon an optimal noncoding RNA scaffold (OnRS) derived from tRNA fusion pre-miR-34a (tRNA/mir-34a). Multi-milligrams of chimeric RNAs (e.g., OnRS/miR-124, OnRS/GFP-siRNA, OnRS/Neg (scrambled RNA) and OnRS/MGA (malachite green aptamer)) were readily obtained from 1 L bacterial culture. Deep sequencing analyses revealed that mature miR-124 and target GFP-siRNA were selectively released from chimeric RNAs in human cells. Consequently, OnRS/miR-124 was active in suppressing miR-124 target gene expression and controlling cellular processes, and OnRS/GFP-siRNA was effective in knocking down GFP mRNA levels and fluorescent intensity in ES-2/GFP cells and GFP-transgenic mice. Furthermore, the OnRS/MGA sensor offered a specific strong fluorescence upon binding MG, which was utilized as label-free substrate to accurately determine serum Rnase activities in pancreatic cancer patients. These results demonstrate that OnRS-based bioengineering is a common, robust and versatile strategy to assemble various types of small RNAs for broad applications.

Introduction

RNA interference (RNAi) technologies have been widely utilized for genome function studies. There are also a number of RNAi-based therapies under clinical trials (1-3) in addition to an RNA aptamer (Pegaptanib) being approved by the U.S. Food and Drug Administration for the treatment of age-related macular degeneration (4). Currently RNAi agents and noncoding RNA (ncRNA) materials used for basic, translational and clinical research such as small interfering RNAs (siRNAs), short hairpin RNAs (shRNAs), RNA aptamers, and microRNAs (miRs or miRNAs) are mainly produced through chemical synthesis (5-9), while other virus and non-virus-vector based strategies literally utilize DNA agents. Although organic synthesis of oligonucleotides may be automated, a multi-milligram dose of 22-nt double-stranded siRNA or miRNA agents for in-vivo testing or projected therapy is very costly. It is also unclear to what extent chemical modifications would alter the structures, biological activities and safety profiles of these ncRNAs, despite that synthetic ncRNAs exhibit some favorable pharmacokinetic properties such as a longer half-life. In vitro transcription (10,11) is another way to produce RNA agents in variable lengths. However, in vitro transcription generally produces RNA molecules in a test tube on micrograms scale, thus the production of larger quantities of RNAs requires considerably more of the costly RNA polymerases.

With an interest in developing new strategies to bioengineer ready-to-use RNAi agents on a large scale, a successful example has been reported very recently for the generation of fully-processed siRNAs from p19-expressing bacteria (12). On the other hand, tRNA (13-15) and rRNA (16) have been employed as scaffolds to produce a number of chimeric RNAs in common strains of bacteria, given the fact that tRNAs and rRNAs are present as stable RNA molecules in the cells. The recombinant RNA chimeras are thus isolated, and the target RNAs may be released in demand by corresponding Rnase (13,14), Ribozyme (15) or DNAzyme (16) for structural and biophysical analyses. These recombinant RNA technologies provide a novel way for a cost-effective and fast production of large quantities of recombinant RNAs (e.g., milligrams of RNA chimeras from 1 L bacteria culture).

We had taken the initiative to produce pre-miRNA chimeras (FIG. 1a) in common strains of E. coli using tRNA scaffold (17). We hypothesized that fusion tRNA/pre-miRNA isolated from bacteria might act as a "prodrug" where pre-miRNA could be selectively processed to mature miRNA in human cells, and tRNA scaffold would be degraded to tRNA fragments (tRFs). In the present study, we demonstrated that the majority of tRNA/pre-miRNA chimeras did not accumulate in bacteria or only at a negligible level, thus we developed a novel optimal ncRNA scaffold (OnRS)-based strategy to achieve a consistent high-yield production of chimeric RNAs in E. coli that offers the versatility to carry various types of functional small RNAs of interests such as miRNAs, siRNAs and RNA aptamers (FIG. 1b). This approach is proven robust and shall have broad applications to engineering of target chimeric RNAi agents and RNA sensors that may be utilized as research tools and further developed as therapeutic agents and diagnostic tools.

Materials and Methods

Bacterial culture. All E. coli stains were cultured at 37° C. in LB broth supplemented with 100 µg/mL ampicillin. DH5α(Life Technologies, Grand Island, N.Y.) was used for cloning and HST08 (Clontech Laboratories, Mountain View, Calif.) was employed for the production of multi-milligrams of chimeric RNAs. Other strains such as DH5α, Top 10 (Life Technologies, Grand Island, N.Y.) and BL21 (Sigma-Aldrich, St. Louis, Mo.) were also used to evaluate ncRNA expression/accumulation.

Human cell culture. The human carcinoma cell line A549 was purchased from American Type Culture Collection (Manassas, Va.), and ES-2/GFP was from Cell Biolabs (San Diego, Calif.). Both cell lines were maintained in RPMI 1640 with 10% fetal bovine serum at 37° C. in a humidified atmosphere with 5% $CO_2$ and 95% air.

Prediction of RNA Secondary Structures. The secondary structures of chimeric ncRNAs were predicted using the CentroidFold (www.ncrna.org/centroidfold) (18) and CentroidHomfold (www.ncrna.org/centroidhomfold) (19).

Construction of plasmids. Individual tRNA/pre-miRNA expression plasmids were cloned as we reported (17), following PCR amplification of target sequences from human genomic DNA using gene specific primers (IDT, San Diego, Calif.). See, Table 1. To create OnRS/miR-124, OnRS/Neg, OnRS/GFP-siRNA and Trna-miR-155/GFP-siRNA expression plasmids, the oligonucleotides (Table 1) were annealed and amplified, then the amplicons were cloned into the vector pBSMrnaSeph (14) (kindly provided by Dr. Luc Ponchon, France) linearized by endonucleases SalI-HF® and AatII (New England Biolabs, Ipswich, Mass.). To construct OnRS/MGA5 and OnRS/MGA3 expression plasmids, Trna/mir-34a was used as a template for the amplification of target sequences using the oligonucleotides (Table 1), and then the amplicons were inserted into pBSMrnaSeph vector linearized by SacII and EagI (New England Biolabs) which removed the SEPHADEX™ aptamer from Trna scaffold at the same time. All inserts were confirmed by Sanger sequencing analyses at UC Davis Genome Center.

TABLE 1

| (a) Sequences of OnRS-based chimeric RNAs | |
|---|---|
| Target RNAs | Sequences (5'→3') |
| OnRS (tRNA/mir-34a) | GGCUACGUAGCUCAGUUGGUUAGAGCAGCGGCCGAGUAAUUUACGUCGACGUGGACCGGCCAGCUGUGAGUGUUUCUUUGGCAGUGU CUUAGCUGGUUGUUGUGAGCAAUAGUAAGGAAGCAAUCAGCAAGUAUACUGCCCUA- GAAGUGCUGCACGUUGUGGGGCCCAAGAGGG AAGATGACGUCGAUGGUUGCGGCCGCGGGUCACAGGUUCGAAUCCCGUCGUAGCCACCA (SEQ ID NO: 3) |
| OnRS/miR-124 | GGCUACGUAGCUCAGUUGGUUAGAGCAGCGGCCGAGUAAUUUACGUCGACCCGUGGACCGGCCAGCUGUGAGUGUUUCUUUAAGGCA CGCGGUGAAUGCCUGUGAGCAAUAGUAAGGAAGGCAUUCACGCUGUGCCUUCUA- GAAGUGCUGCACGUUGUGGGGCCCAAGAGGGAA GACGUCGAUGGUUGCGGCCGCGGGUCACAGGUUCGAAUCCCGUCGUAGCCACCA (SEQ ID NO: 28) |
| OnRS/Neg | GGCUACGUAGCUCAGUUGGUUAGAGCAGCGGCCGAGUAAUUUACGUCGACCCGUGGACCGGCCAGCUGUGAGUGUUUCUUCACCUAU AACAACGGUAGUUUUUGUGAGCAAUAGUAAGGAAGAAACUACCUUGUUUAUAGGUCUA- GAAGUGCUGCACGUUGUGGGGCCCAAGAG GGAAGACGUCGAUGGUUGCGGCCGCGGGUCACAGGUUCGAAUCCCGUCGUAGCCACCA (SEQ ID NO: 35) |
| OnRS/GFP-siRNA | GGCUACGUAGCUCAGUUGGUUAGAGCAGCGGCCGAGUAAUUUACGUCGACCCGUGGACCGGCCAGCUGUGAGUGUUUCUUAGUUGUA CUCCAGCUUGUGCCCUGUGAGCAAUAGUAAGGAAGGGCACAAGUGGUAGUACAACCUA- GAAGUGCUGCACGUUGUGGGGCCCAAGAG GGAAGACGUCGAUGGUUGCGGCCGCGGGUCACAGGUUCGAAUCCCGUCGUAGCCACCA (SEQ ID NO: 36) |
| OnRS/MGA5 | GGCUACGUAGCUCAGUUGGUUAGAGCAGCGGCCGGGAUCCCGACUGGCGAGAGCCAGGUAACGAAUGGAUCCGUGGACCGGCCAGCU GUGAGUGUUUCUUUGGCAGUGUCUUAGCUGGUUGUUGUGAGCAAUA- GUAAGGAAGCAAUCAGCAAGUAUACUGCCCUAGAAGUGCUG CACGUUGUGGGGCCCGGUCCACCCGCGGGUCACAGGUUCGAAUCCCGUCGUAGCCACCA (SEQ ID NO: 39) |
| OnRS/MGA3 | GGCUACGUAGCUCAGUUGGUUAGAGCAGCGGCCGGUGGACCGGCCAGCUGUGAGUGUUUCUUUGGCAGUGUCUUAGCUGGUUGUUGU GAGCAAUAGUAAGGAAGCAAUCAGCAAGUAUACUGCCCUAGAAGUGCUGCACGUU- GUGGGGCCCGGUCCACGGAUCCCGACUGGCGA GAGCCAGGUAACGAAUGGAUCCCCGCGGGUCACAGGUUCGAAUCCCGUCGUAGCCACCA (SEQ ID NO: 40) |

The underlined are the sequences of tRNA scaffold.
The rest is the has-miR-34a precursor with ~9 nt flanking sequence at each prime.
The sequence in red indicates the target sequence and the green part is the complementary sequence.
Sequence in bold indicates the MGA.

| (b) Oligonucleotides used for plasmid construction and qPCR analysis | |
|---|---|
| Plasmids | Primer sequences (5'→3') |
| tRNA/mir-27b | Fow-ACGCGTCGACCCAGCGATGACCTCTCTAAC (SEQ ID NO: 49)<br>Rev-CATCGACGTCCTTAACTGTCCCCATCTCACC (SEQ ID NO: 50) |
| tRNA/mir-34a | Fow-AGTAATTTACGTCGACGTGGACCGGCCAGCTGTGAGTGTT (SEQ ID NO: 51)<br>Rev-CGGCCGCAACCATCGACGTCATCTTCCCTCTTGGGCCCCACAACG (SEQ ID NO: 52) |
| tRNA/mir-122 | Fow-AGTAATTTACGTCGAC TTCGTGGCTACAGAGTTTCCTTAGCAG (SEQ ID NO: 53)<br>Rev-CGGCCGCAACCATCGACGTCCAAGACATTTATCGAGGGAAGGATTGC (SEQ ID NO: 54) |
| tRNA/mir-124-1 | Fow-AGTAATTTACGTCGACCTCCTTTCCTTCCTCAGGAG (SEQ ID NO: 55)<br>Rev-CGGCCGCAACCATCGACGTCCGCCGACCCACGGTGCTCA (SEQ ID NO: 56) |
| tRNA/mir-124-2 | Fow-AGTAATTTACGTCGACTACTTTCCGGATCAAGATTAG (SEQ ID NO: 57)<br>Rev-CGGCCGCAACCATCGACGTCTTGGTGTCCTTCAAGTGCAG (SEQ ID NO: 58) |
| tRNA/mir-125-1 | Fow-AGTAATTTACGTCGACAGAAAACATTGTTCGCTCCTCTC (SEQ ID NO: 59)<br>Rev-CGGCCGCAACCATCGACGTCAGGATGCAAAAGCACGACTCGC (SEQ ID NO: 60) |
| tRNA/mir-125-2 | Fow-AGTAATTTACGTCGACTCTACCGCATCAAACCAGACTTTTCC (SEQ ID NO: 61)<br>Rev-CGGCCGCAACCATCGACGTCCTGCTGGTTCCCCTCCGCC (SEQ ID NO: 62) |
| tRNA/mir-155 | Fow-AGTAATTTACGTCGACAGGCTTGCTGTAGGCTGTATGCTG (SEQ ID NO: 63)<br>Rev-CGGCCGCAACCATCGACGTC AATGCTAGTAACAGGCATCATACACTGTTA (SEQ ID NO: 64) |

TABLE 1-continued

| | |
|---|---|
| tRNA/mir-221 | Fow-AGTAATTTACGTCGACCTTGCAAGCTGAACATCCAGGTCTG (SEQ ID NO: 65)<br>Rev-CGGCCGCAACCATCGACGTCCAGCCAATGGAGAACATGTTTCCA (SEQ ID NO: 66) |
| tRNA/mir-1291 | Fow-ACGCGTCGACGAGTTCTGTCCGTGAGCCTTGG (SEQ ID NO: 67)<br>Rev-CATCGACGTCACAGCCAACAGACCACAGGAAG (SEQ ID NO: 68) |
| tRNA/let7a | Fow-AGTAATTTACGTCGACACCCTGGATGTTCTCTTCAC (SEQ ID NO: 69)<br>Rev-CGGCCGCAACCATCGACGTCGATGCAGACTTTTCTATCACG (SEQ ID NO: 70) |
| OnRS/miR-124-20 | Fow-AGTAATTTACGTCGACCCGTGGACCGGCCAGCTGTGAGTGTTTCTTTAAGGCACGCGGTGAATGCCTGTGAGCAATAGTAAG GAAGGC (SEQ ID NO: 71)<br>Rev-CGGCCGCAACCATCGACGTCTTCCCTCTTGGGCCCCACAACGTGCAGCACTTCTAGAAGGCACAGCGTGAATGCCTTCCTTA CTATTGC (SEQ ID NO: 72) |
| OnRS/Neg | Fow-AGTAATTTACGTCGACCCGTGGACCGGCCAGCTGTGAGTGTTTCTTCACCTATAACAACGGTAGTTTTTGTGAGCAATAGTA AGGAAGAA (SEQ ID NO: 73)<br>Rev-CGGCCGCAACCATCGACGTCTTCCCTCTTGGGCCCCACAACGTGCAGCACTTCTAGACCTATAAACAAGGTAGTTTCTTCCT TACTATTG (SEQ ID NO: 74) |
| OnRS/GFP-siRNA | Fow-AGTAATTTACGTCGACCCGTGGACCGGCCAGCTGTGAGTGTTTCTTAGTTGTACTCCAGCTTGTGCCCTGTGAGCAATAGTA AGGAAGGG (SEQ ID NO: 75)<br>Rev-CGGCCGCAACCATCGACGTCTTCCCTCTTGGGCCCCACAACGTGCAGCACTTCTAGGTTGTACTACCACTTGTGCC CTTCCTTACTATTG (SEQ ID NO: 76) |
| tRNA/miR-155/GFP-siRNA | Fow-AGTAATTTACGTCGACGAGGCTTGCTGAAGGCTGTATGCTGGTTGTACTCCAGCTTGTGC-CCGTTTTGGCCACTGACTGACGG (SEQ ID NO: 77)<br>Rev-CGGCCGCAACCATCGACGTCGAGTGCTAGTAACAGGCCTTGTGTCCTGGTTGTACTCCAT-TGTGCCCGTCAGTCAGTGGCCAA (SEQ ID NO: 78) |
| OnRS/MGA5 | Fow-GTTAGAGCAGCGGCCGGGATCCCGACTGGCGAGAGCCAGGTAACGAATGGATCCGTGGACCGGCCAGCTGTGAG (SEQ ID NO: 79)<br>Rev-GAACCTGTGACCCGCGGGTGGACCGGGCCCCACAACGTGCAGCA (SEQ ID NO: 80) |
| OnRS/MGA3 | Fow-GTTAGAGCAGCGGCCGGTGGACCGGCCAGCTGTGAG (SEQ ID NO: 81)<br>Rev-GAACCTGTGACCCGCGGGGATCCATTCGTTACCTGGCTCTCGCCAGTCGGGATCCGTGGACCGGGCCCCACAACGTGCAGCA (SEQ ID NO: 82) |

| has Primers used for RT-qPCR experiments | |
|---|---|
| Utility | Primer sequences (5'→3') |
| Universal rev | GCGCTAAGGCACGCGGTG (SEQ ID NO: 83) |
| U74 | RT-GTCGTATCCAGTGCAGGGTCCGAGGTATTCGCACTGGATACGACAATTGT (SEQ ID NO: 84)<br>Fow-CCTGTGGAGTTGATCCTAGTCTGGGTG (SEQ ID NO: 85) |
| miR-124 | RT-GTCGTATCCAGTGCAGGGTCCGAGGTATTCGCACTGGATACGACGGCATT (SEQ ID NO: 86)<br>Fow-GCGCTAAGGCACGCGGTG (SEQ ID NO: 87) |
| GFP-siRNA | RT-GTCGTATCCAGTGCAGGGTCCGAGGTATTCGCACTGGATACGAC GGGCAC (SEQ ID NO: 138)<br>Fow-GCGCGCAGTTGTACTCCAGCTT (SEQ ID NO: 89) |
| GFP mRNA | Fow-ACGTAAACGGCCACAAGTTC (SEQ ID NO: 90)<br>Rev-AAGTCGTGCTGCTTCATGTG (SEQ ID NO: 91) |
| PPIA | Fow-CCTAAAGCATACGGGTCCTG (SEQ ID NO: 92)<br>Rev-TTTCACTTTGCCAAACACCA (SEQ ID NO: 93) |
| 18s | Fow-GTAACCCGTTGAACCCCATT (SEQ ID NO: 94)<br>Rev-CCATCCAATCGGTAGTAGCG (SEQ ID NO: 95) |

Expression of chimeric RNAs in E. coli. Chimeric RNAs were expressed in HST08 on a large scale as described (13,14,17). Total RNAs were isolated from E. coli using the Tris-HCl-saturated phenol extraction method, quantitated with a NanoDrop 2000 spectrophotometer (Thermo Fisher Scientific, Rockford, Ill.) and analyzed by denaturing urea (8 M) polyacrylamide (8%) gel electrophoresis (PAGE). All images were acquired with ChemiDoc MP Imaging System (Bio-Rad, Hercules, Calif.). Intensities of bands were used to provide a rough estimation of relative levels of recombinant ncRNAs present in the total RNAs.

Purification of recombinant ncRNAs. Purification of recombinant ncRNAs was conducted with a NGC QUEST 10PLUS CHROM fast protein liquid chromatography (FPLC) System (Bio-Rad). Separation of recombinant ncRNAs from total RNAs was achieved on a UNO Q6 anion-exchange column (Bio-Rad), which was first equilibrated with Buffer A (10 mM sodium phosphate, pH=7.0) at a flow rate 5.0 mL/min for 0.5 min, followed by a gradient elution at the same flow rate, 0-56% Buffer B (Buffer A plus 1 M sodium chloride) in 0.5 min, 56% Buffer B for 2 min, 56-65% Buffer B in 10 min, and then 100% Buffer B for 2 min, 100-0% Buffer B in 0.5 min and 100% Buffer A for 5 min. FPLC traces were monitored at 260 nm using a UV/Vis detector. Peak areas were employed to estimate the relative levels of recombinant ncRNAs within the total RNAs, which agrees with those determined by urea-PAGE analyses. After analyzed on a denaturing PAGE gel, the fractions containing pure ncRNAs were pooled. Recombinant ncRNAs were precipitated with ethanol, reconstituted with nuclease-free water, and then desalted and concentrated with Amicon ultra-2 mL centrifugal filters (30 KD; EMD Millipore, Billerica, Mass.). The only exception was OnRS/MGA that was reconstituted with 10 mM HEPES (pH=7.4) buffer. The quantity of purified ncRNAs was determined using Nano-Drop and the quality was validated by PAGE analysis before other experiments.

Deep sequencing of small RNAs and data analysis. A549 cells were transfected with 50 nM FPLC-purified OnRS/miR-124 and tRNA/mir-34a (OnRS), and ES-2/GFP cells were transfected with OnRS/Neg and OnRS/GFP-siRNA using Lipofectamine 2000 (Life Technologies). Total RNAs were isolated using a Direct-zol RNA extraction kit (Zymo Research, Irvine, Calif.) at 48 h post-transfection, and small RNA libraries were generated using the Illumina Truseq™ Small RNA Preparation kit (Illumina, San Diego, Calif.) according to the instructions. The purified cDNA library was used for cluster generation on Illumina's Cluster Station and then sequenced on Illumina GAIIx following vendor's instructions. Raw sequencing reads (40 nt) were obtained using Illumina's Sequencing Control Studio software version 2.8 (SCS v2.8) following real-time sequencing image analysis and base-calling by Illumina's Real-Time Analysis version 1.8.70 (RTA v1.8.70). The extracted sequencing reads were used for the standard sequencing data analysis by following a proprietary pipeline script, ACGT101-miR v4.2 (LC Sciences, Houston, Tex.)(20,21). Cells were treated in triplicate and sequenced separately.

Reverse transcription quantitative real-time PCR (RT-qPCR). Cells were transfected with various doses of recombinant ncRNAs and harvested at particular time points. Total RNAs were isolated using Direct-zol RNA isolation kit (Zymo Research), and RNA concentrations were determined using NanoDrop 2000 spectrophotometer. RT was conducted with NxGen M-MuLV reverse transcriptase (Lucigen, Middleton, Wis.), and qPCR analysis was carried out on a CFX96 Touch real-time PCR system (Bio-Rad) using quantitative RT-PCR Master mix (New England Biolabs), as described(17,22). Levels of miRNAs were normalized to U74, and mRNA levels were normalized to PPIA. Gene specific primers were shown in Table 1. Each experiment was conducted in triplicate and each sample was measured 2-3 times. Similar results were obtained when the study was repeated.

Western blots. A549 cells were transfected with 100 nM OnRS/miR-124 or OnRS/Neg and harvested after 48 h. Cell lysates were prepared with RIPA lysis buffer (Rockland Immunochemical Inc., Limerick, Pa.) consisting of complete protease inhibitor cocktail (Roche, Nutley, N.J.). Protein concentrations were determined using the BCA Protein Assay Kit (Thermo Fisher Scientific). Whole-cell proteins (40 μs per lane) were separated on 10% SDS-PAGE gel, and electrophoretically transferred onto PVDF membranes (Bio-Rad). Membranes were then incubated with selective antibody against P-STAT-3, STAT-3 (Cell Signaling Technology, Danvers, Mass.) or GAPDH (Santa Cruz Biotech Inc., Texas, Tex.), and subsequently with peroxidase anti-rabbit (Jackson ImmunoResearch Inc., West Grove, Pa.) or anti-mouse IgG (Cell Signaling). The membranes were then incubated with ECL substrates (Bio-Rad), and images were acquired with ChemiDoc MP Imaging System (Bio-Rad). Cells were treated in triplicate and the same results were obtained when the whole study was repeated.

Apoptosis assay. The apoptosis assay was performed by using a FACS Annexin V assay kit (Trevigen, Inc., Gaithersburg, Md., USA) following the manufacturer's protocol. Briefly, A549 cells were transfected with 100 nM recombinant ncRNAs, harvested at 72 h post-transfection, incubated with Annexin V-FITC conjugate and propidium iodide solution, and then the samples were analyzed on a FACScan flow cytometer (BD Biosciences, San Jose, Calif.). Data analysis was performed using Flowjo (Ashland, Oreg.). Cells were treated in triplicate and similar results were obtained when the whole experiment was repeated.

Mtt assay. A549 cells were transfected with 20 or 100 nM chimeric RNAs. At 72 h post-transfection, cell viability was determined using MTT as we described previously (23). Cells were treated in triplicate and similar results were obtained when the whole study was repeated.

Real-time cell growth analysis. A549 cells were seeded 40,000/well on an 8-well E-Plate and treated with 20 or 100 nM recombinant ncRNA 24 h later. Cell growth was monitored using an iCELLigence system (ACEA Biosciences, San Diego, Calif.). Similar results were obtained when the whole experiment was repeated for three times.

In vitro knockdown of GFP. ES-2/GFP cells were seeded 8,000 cells/well on a 24-well plate and transfected with 5 or 15 nM FPLC-purified chimeric RNAs at 24 h later. The fluorescence was monitored with an Olympus IX81 microscope (Olympus, Center Valley, Pa.) at 24 h, 48 h and 72 h post-transfection. All images were acquired using the same settings at the same time. At the end of the study, total RNAs were isolated from the cells and subject to RT-qPCR evaluation of GFP mRNA and siRNA levels. Cells were treated in triplicate, and similar results were obtained when the whole experiment was repeated.

In vivo knockdown of GFP. All animal procedures were approved by the Institutional Animal Care and Use Committee at UC Davis. Six- to seven-week-old male GFP-transgenic (C57BL/6-Tg(CAG-EGFP)1Osb/J) mice (24) (The Jackson Laboratory, Bar Harbor, Me.) were injected i.v. with 75 μg FPLC-purified OnRS/Neg (N=3) or OnRS/GFP-siRNA (N=4) after formulated with in vivo-jetPEI (Polyplus-transfection Inc., New York, N.Y.) each day for consecutive 3 days. Three days after the last injection, mice were sacrificed and liver tissues were collected. Frozen sections (8 μm) were prepared after embedded in Tissue-Tek O.C.T. (Sakura Finetek, Torrance, Calif.) and examined directly using a Zeiss Axio Observer.zl Microscope coupled to a Zeiss LSM 710 Scanning Device (Zeiss, Oberkochen, Germany). Different batches of sections (8 μm) were fixed with 4% paraformaldehyde (Sigma-Aldrich, St. Louis, Mo.) and stained with 1 μg/mL 4',6-diamidino-2-phenylindole (DAPI; Sigma-Aldrich). GFP fluorescence and DAPI-stained nuclei images were recorded with confocal microscope sequentially and then merged together.

In addition, liver tissues were subject to RNA isolation and RT-qPCR analyses for GFP mRNA and siRNA levels against 18S and U74 was used as control, respectively. Gene specific primers were presented in Table 1.

Malachite green (MG) aptamer binding assays. Absorbance scanning was performed from 550 nm to 700 nm using a SpectraMax Microplate Reader (Molecular Devices, Sunnyvale, Calif.) after 32 μg purified ncRNAs or 80 μg total RNAs were incubated with 10 μM MG in 100 mM KCl, 5 mM $MgCl_2$, and 10 mM HEPES (pH=7.4) buffer in a total volume of 100 μL. Fluorescent intensity was determined at 630/650 nm (excitation/emission) with the same SpectraMax Microplate Reader for purified ncRNAs (32 μg) or total RNAs (80 μg) in the absence and presence of MG (10 μM).

To establish the linearity of MGA-bound MG fluorescent intensity vis-à-vis MG and MGA concentrations, the intensities of fluorescence were examined when 2.08 µM OnRS/MGA5 was exposed to 0-10 µM MG and 10 µM was incubated with 0-5.2 µM OnRS/MGA5, respectively, in 10 mM HEPES (pH=7.4) buffer in a total volume of 100 µL. Each assay was carried out in triplicate, and all experiments were repeated at least once that showed similar results.

Serum Rnase activity assay. Serum specimens from IRB-approved, prospectively-collected UC Davis Pancreas Registry bank were utilized. The serum has been processed uniformly within 4 h of blood collection, aliquoted and stored in a −80 0C freezer till usage with minimal freeze-thaw cycle. A total of 20 patients' serum from 10 pancreatic ductal adenocarcinoma (PDAC) (5 early-stage PDAC (American Joint Committee of Cancer, Stages 1 & 2)) and 10 benign/normal pancreas cases (5 chronic pancreatitis and 5 normal pancreases) were selected. The PDAC cases consisted of 4 males and 6 females, benign/normal of 5 males and 5 females. Age ranges were 51 to 80 (mean=67 y/o) in the PDAC and 37 to 85 (mean=60 y/o) in benign/normal groups. A normal pooled human serum sample (Fisher Scientific Inc., Waltham, Mass.), human recombinant Rnase A (Novoprotein, Summit, N.J.) and human recombinant angiogenin (R&D Systems, Minneapolis, Minn.) were used for method development.

To evaluate the change in MGA-bound MG fluorescent intensity in relationship to incubation time (0-30 min) after exposure to human serum, 2.08 µM OnRS/MGA5 was incubated with 0.4 or 2.0 µL normal pooled human serum in 10 mM HEPES (pH=7.4) buffer in a total volume of 90 µL, and then fluorescence was determined after the addition of 10 µL MG to a final 10 µM concentration. To assess the protection of MGA by in vivo-jetPEI, 2.08 µM OnRS/MGA5 and 1.0 µL pool human serum were incubated for 0-60 min. To determine the dose response, various volumes of the pooled human serum (0.01-10 µL) or concentrations of recombinant human Rnase A (0-$10^{-4}$ µg/µL) and angiogenin (0-$10^{-2}$ µg/µL) were incubated with 2.08 µM OnRS/MGA5 for 10 min. To define the influence of Rnase inhibitor, the pooled human serum (0, 1, 2 and 5 µL) was incubated with 2.08 µM OnRS/MGA5 for 10 min, with or without 0.4 Rnase inhibitor (Lucigen, Middleton, Wis.). Each incubation reaction was carried out in triplicate, and all experiments were repeated at least once that offered consistent findings.

Based upon the linearity of fluorescent intensity over MG and MGA concentrations, incubation time and quantity of human sera, 0.4 µL patient serum sample was incubated with 2.08 µM OnRS/MGA5 in 10 mM HEPES (pH=7.4) buffer in a total volume of 90 µL at 37° C. for 5 min and then 10 µL MG was added to give 10 µM final concentration for the determination of fluorescence at 630/650 nm (excitation/emission). Serum Rnase activity was calculated as the change in fluorescent intensity over time and quantity of serum sample, i.e., ΔA.U./min/µL. Each patient sample was assayed twice with <10% variations.

Statistical analysis. Values were expressed as mean±SD. According to the number of groups and variances, data were analyzed with unpaired Student's t-test, or one-way or two-way ANOVA (GraphPad Prism, San Diego, Calif.). Difference was considered as significant for P-value less than 0.05 (P<0.05).

Results

An OnRS is developed to achieve high-yield production of recombinant RNAi agents. We intended to bioengineer tRNA fusion pre-miRNA (tRNA/mir) agents in common strains of bacteria (FIG. 1a) on a large scale, i.e., milligrams of recombinant ncRNAs from 1 L bacterial culture. A series of plasmids were created and employed to transform E. coli. Surprisingly, we found that the levels of recombinant pre-miRNA chimeras expressed/accumulated in HST08 E. coli were largely variable when the same tRNA scaffold was used. The majority of tRNA/pre-miRNA chimeras were unfortunately not accumulated or at a negligible level (FIG. 1a). Use of other E. coli strains still offered no or even lower levels of target ncRNA chimeras. Nevertheless, given the findings that tRNA/mir-34a was accumulated to a high level in bacteria (e.g., ~15-20% of total RNAs) and chimeric tRNA/mir-34a was stable and selectively processed to mature has-miR-34a in various types of human carcinoma cells, we hypothesized that tRNA/mir-34a might be developed as an OnRS over the tRNA scaffold towards a consistent high-level production of target miRNAs (FIG. 1b).

We thus took up the challenge to assemble miR-124 using the OnRS (tRNA/mir-34a) platform, noticing that miR-124 differs much from miR-34a in size (20 vs. 22 nt) and arm of origin (3' vs. 5'). We replaced the 22-nt miR-34a-5p with 20-nt miR-124-3p and substituted their complementary sequences accordingly (Table 1), which indeed offered a high-level expression of OnRS/miR-124 chimera in HST08 E. coli (FIG. 1b). Recombinant OnRS/miR-124 was then readily purified to a high degree of homogeneity (>99%) using the anion-exchange FPLC method (FIG. 1c). Likewise, the OnRS was able to assemble other miRNAs (e.g., 21-nt miR-27b and 22-nt miR-22, etc.) and a 22-nt scrambled RNA sequence (chimeric RNA was named OnRS/Neg and used as a control in the following studies; Table 1), which were all consistently produced in HST08 E. coli at high yields and on a large scale, i.e., >15% of OnRS/miRNAs in total RNAs and >1.5 mg of FPLC-purified OnRS/miRNAs from 0.5 L bacterial culture at all times.

We further evaluated if we could utilize this OnRS-based approach to produce milligrams of functional siRNA agents in 1 L E. coli culture. A 22-nt GFP siRNA (25) was chosen as a model siRNA to assemble chimeric OnRS/GFP-siRNA (Table 1). In contrast to a minimal level of accumulation in bacteria when tRNA/mir-155 was utilized as a carrier, the use of OnRS (tRNA/mir-34a) provided a consistent high-level expression of OnRS/GFP-siRNA (FIG. 1b) and facilitated the FPLC purification of recombinant ncRNAs (FIG. 1d). As a result, we were able to produce 1.5-2.0 mg, >98% pure OnRS/GFP-siRNA from 0.5 L bacterial culture every time. These results indicate that target miRNA/siRNA agents can be assembled by using OnRS-based platform to offer a consistent high-level production of chimeric ncRNAs in bacteria.

Target miRNAs/siRNAs are selectively released from chimeric ncRNAs in human cells while tRNA scaffold is processed to tRNA fragments (tRFs). Next we assessed if mature miR-124 could be selectively produced from OnRS/miR-124 in human cells. An unbiased deep sequencing study was conducted after the preparation of small RNAs library from human lung carcinoma A549 cells at 48 h post-transfection with OnRS/miR-124 and OnRS (tRNA/mir-34a). The data showed that OnRS/miR-124 was selectively processed to large numbers (5,613±975 reads) of 20-nt miR-124 in A549 cells (FIG. 2a). In contrast, there was 0±1 reads of mature miR-124 identified in A549 cells treated with tRNA/mir-34a (OnRS) that actually offered 22-nt miR-34a. Other miR-124 isoforms including those of 21 nt in length, as well as some passenger strands, were also noted whereas at much lower levels. In addition, OnRS/miR-124 had no or relatively much smaller influence on other cellular miRNAs including the has-mir-34a-p3 fragment (FIG. 2a), while the tRNA scaffold was degraded to tRFs that actually exhibited similar patterns between OnRS/miR-124- and tRNA/mir-34a-treated cells (FIG. 2c).

Likewise, we conducted the unbiased deep sequencing analyses of cellular small RNAs in human ES-2/GFP cells at 48 h post-transfection with FPLC-purified OnRS/GFP-siRNA and OnRS/Neg. The data showed that GFP-siRNA levels were about 1,000-fold higher in ES-2/GFP cells treated with chimeric OnRS/GFP-siRNA than the control OnRS/Neg (FIG. 2b), which was mainly attributable to the increase in 22-, 23- and 21-nt isoforms and accompanied by lower levels of passenger strands. It was also noted that OnRS/Neg was indeed processed to a number of scrambled RNAs at 22-23 nt in length, but at much lower levels, which might be related to a lower stability of the scrambled RNAs or insufficient processing. Nevertheless, there were no or minimal differences in the levels of other cellular miRNAs between OnRS/GFP-siRNA- and OnRS/Neg-treated cells. Furthermore, the tRF patterns were also similar between OnRS/GFP-siRNA and OnRS/Neg-treated cells (FIG. 2d), despite that overall tRF levels were much lower in ES-2/GFP cells than A549 cells. Together, these results support the utility of OnRS for "stealth delivery" of target miRNAs and siRNAs into human cells beyond high-yield production of the chimeric ncRNAs in bacteria and the use of OnRS/Neg as a control to assess OnRS/siRNA activities.

OnRS-carried miR-124 is biologically/pharmacologically active in controlling target gene expression and cancer cellular processes. Then we evaluated the bioactivities of OnRS-carried miR-124, as miR-124 is known to regulate a number of target genes such as the oncogenic signal transducer and activator of transcription 3 (STAT3), enhance apoptosis, and inhibit cell proliferation (26-28). Consistent with deep sequencing data, selective stem-loop RT-qPCR analyses showed that mature miR-124 levels were around 1000-fold higher in A549 cells from day 1 to 4 after transfection with OnRS/miR-124, compared with OnRS/Neg (FIG. 3a). Increase in miR-124 in OnRS/miR-124-treated A549 cells led to a 60% reduction of STAT3 protein levels (FIG. 3b), and 1- to 2-fold greater degrees of early and late apoptosis as well as necrosis (FIG. 3c). Consequently, OnRS/miR-124 exhibited significantly greater antiproliferative activity than OnRS/Neg, as demonstrated by MTT assay and using a Real-Time Cell Analyzer (FIG. 3d-3e). These results demonstrate that chimeric OnRS/miR-124 is biologically/pharmacological active in regulating miR-124 target gene expression and controlling cancer cell growth after being processed to mature miR-124 in the cells.

OnRS-carried GFP siRNA is effective in knocking down GFP expression in vitro and in vivo. We also assessed the effectiveness of OnRS-carried GFP siRNA using GFP-expressing ES-2 cells and GFP-transgenic mouse models. In ES-2/GFP cells, OnRS/GFP-siRNA significantly suppressed the GFP fluorescence intensity and mRNA levels at 72 h post-transfection (FIG. 4a-4b), which was associated with 3 orders of magnitude increase in GFP siRNA levels (FIG. 4c). We then treated GFP-transgenic mice (24) with in vivo-jetPEI-formulated OnRS/GFP-siRNA. Compared to the GFP-transgenic mice treated with the same doses of in vivo-jetPEI-formulated OnRS/Neg, there was a remarkable reduction of hepatic GFP fluorescence intensity (FIG. 4d-4e) and mRNA levels (FIG. 4f) in GFP-transgenic mice treated with OnRS/GFP-siRNA, which was linked to an over 3,000-fold increase in GFP siRNA levels. These data indicate that chimeric GFP-siRNAs produced on large scale using the OnRS cargo are effective agents for in vitro and in vivo RNAi applications.

Utility of OnRS for high-level production of active RNA aptamer chimeras in bacteria. Encouraged by these findings, we further challenged the potential applications of OnRS to the production of functional RNA aptamers. A malachite green aptamer (MGA) (9) was chosen as a model aptamer and inserted at the 5' and 3' of miR-34a to offer OnRS/MGA5 and OnRS/MGA3, respectively (FIG. 6a). Both chimeras were revealed to be expressed at surprisingly high levels in bacteria, i.e., over 50% of OnRS/MGA in total RNAs (FIG. 6b). Thus we could use FPLC (FIG. 6c) to easily purify 5-6 mg OnRS/MGA from 15-20 mg total RNAs isolated from 0.5 L bacterial culture at all times.

Consistent with the reported property of MGA (9), we found that the wavelength of MG maximum absorbance was shifted from 618 to 630 nm upon binding the label-free, chimeric OnRS/MGA sensor (FIG. 6d). Interestingly, the use of FPLC-purified OnRS/MGA or total RNAs isolated from OnRS/MGA-expressing bacteria gave the same shift in wavelength, whereas a SEPHADEX™ aptamer (OnRS/Seph) and corresponding total RNAs did not, indicating the selectivity of MGA-MG interactions. The function of OnRS-carried MGA was further demonstrated by a strong fluorescent intensity at 630/650 nm (excitation/emission) upon binding MG (FIG. 6e). In contrast, label-free OnRS/MGA itself did not exhibit any fluorescence, and only minimal basal-level MG fluorescent intensity was shown in the absence or presence of non-MGA-containing total RNAs and HPLC-purified OnRS/Seph (FIG. 6e), supporting the specificity of MGA-bound-MG fluorescence. These results demonstrate that OnRS is also powerful for high-yield production of functional RNA aptamers of interests.

Application of label-free, OnRS-carried malachite green aptamer sensor to determine serum Rnase activities among human pancreatic cancer patients. Given the unique property of MGA-bound MG in exhibiting the fluorescence, we further developed an OnRS/MGA-based Rnase activity assay and employed the label-free chimeric OnRS/MGA to investigate and compare serum Rnase activities between human PDAC and benign (including chronic pancreatitis)/normal patients because pancreatic cancer patients were shown to have much higher serum Rnase activities (29). The intensity of the fluorescence increased with MG concentrations and nearly plateaued at 10 μM MG when OnRS/MGA concentration was fixed at 2.08 μM (or 0.16 μg/μL while a good linear range was shown for 0.04-5.2 μM OnRS/MGA when MG concentration was fixed at 10 μM (FIG. 7a). As expected, the intensity of OnRS/MGA-bound MG fluorescence was decreased over time (FIG. 7b) when OnRS-carried MGA was cleaved by the Rnases in a normal pooled human serum sample, and the response was dependent upon the doses of human sera (FIG. 7c) while sera themselves did not have any significant fluorescence. Indeed, use of in vivo-jetPEI provided good protection against the decrease in fluorescent intensity over time, and addition of Rnase inhibitor completely blocked the cleavage of OnRS/MGA by serum Rnases. These data indicate that OnRS/MGA may be utilized to directly determine Rnase activities.

To define the role of Rnase A (the major form Rnase in human serum) in the cleavage of chimeric ncRNAs, we directly compared the susceptibility of OnRS-carried MGA to cDNA-expressed Rnase A and angiogenin (Rnase 5). As manifested by the degrees of change in the intensity of MGA-bound MG fluorescence, 2.08 μM OnRS/MGA was completely cleaved by $5.0 \times 10^{-5}$ μg/μL Rnase A in 10 min, whereas only 40% OnRS/MGA was degraded by 500-fold higher concentration (0.01 μg/μL) of angiogenin in 30 min. Since Rnase A is the major form of Rnase in human serum (30), this assay would mainly indicate pancreas-derived Rnase A activity in human serum. Therefore, we utilized OnRS/MGA to evaluate the Rnase activities in a set of serum samples prospectively collected from PDAC and benign/normal patients. The data showed that serum Rnase activities (Δ.A.U./min/μL) were significantly (P<0.01) higher in PDAC (196±22) than benign/normal (118±8) patients. These results implicate that chimeric MGA sensor produced using the OnRS platform could be useful for determination of Rnase activities.

Discussion

A general approach has been established for a consistent, cost-effective production of multiple to tens of milligrams of chimeric ncRNAs in 1 L culture of a common strain of *E. coli*, bearing various types of small RNAs of interests. The OnRS used in this platform is based upon the tRNA fusion pre-miRNA-34a that is resistant to nucleolytic digestion in bacteria and thus accumulated to significantly high level (e.g., >15% of total RNAs) for an easy purification with the anion-exchange FPLC method. The miR-34a-5p/miR-34a-3p duplex within the OnRS cargo may be replaced by any target double-stranded small RNAs such as siRNA or miRNA/miRNA*duplex (FIG. 1b) to achieving high-yield production of corresponding chimeric siRNA or miRNA agents, as exemplified by successful production of >1.5 mg of OnRS/miR-124, OnRS/GFP-siRNA and control OnRS/Neg chimeras from 0.5 L bacterial culture in this report. In addition, single-stranded small RNAs such as RNA aptamers can be sprouting at particular sites on OnRS to offer the aptamer chimeras (FIG. 5a), which are nicely demonstrated by the assembling of OnRS/MGA5 and OnRS/MGA3 sensors. The robustness and versatility of OnRS-based platform is also supported by successful production of other target RNA agents (e.g., miR-27b, miR-22, and a vascular endothelial growth factor (VEGF) aptamer, etc.), whereas its application to bioengineer other types of biological RNAs such as catalytic RNAs (ribozymes) for biotransformation and guide RNAs (gRNAs) for genome editing warrants further investigations.

Chimeric OnRS/miRNAs and OnRS/siRNAs can act as "pro-drugs" for the "delivery" of target RNAi agents into the cells. Indeed they were selectively processed to large numbers of target miRNAs and siRNAs in human cells, as determined by unbiased deep sequencing studies (FIG. 2a-2b). So was the scrambled RNA from OnRS/Neg. The presence of small RNA isoforms differing in 1- or 2-nt at 5' or 3' within chimeric ncRNA- and vehicle-treated human cells may indicate the flexibilities of endoribonucleases in producing small RNAs from pre-miRNAs or shRNAs (31-33). As a result, selective stem-loop RT-qPCR assays revealed a three orders of magnitude increase in miR-124 in A549 cells and GFP siRNA in ES-2/GFP cells, respectively. The results are also in good agreement with our findings on the stability of tRNA/mir-34a chimera in human cells, i.e., the increases in target small RNAs levels were associated with higher levels of OnRS chimeras lasting as long as 4 days post-treatment, which highlights a favorable stability of OnRS chimeras within human cells. On the other hand, there were no or diminutive changes in the levels of other cellular miRNAs, and the tRNA-derived tRFs exhibited similar patterns in the same human cell lines (FIG. 2c-2d). Nevertheless, the levels of individual or total tRFs identified in ES-2/GFP cells were much lower than A549 cells, which is presumably due to the differences in generating, degrading, excreting and/or retaining tRFs in different types of cells. In addition, while the target miRNAs/siRNAs, tRFs and other small RNAs derived from chimeric ncRNA agents in human cells were fully elucidated, the roles of specific ribonucleases such as Dicer in the processes remain undefined.

The bioactivities of miRNAs (FIG. 3) and siRNAs (FIG. 4) released from the OnRS cargo are clearly demonstrated by the selective suppression of corresponding target gene expression in vitro and in vivo, using the OnRS/Neg as a control. The transcription factor STAT3, a known miR-124 target gene (27,28), plays an important role in many cellular processes such as cell proliferation and apoptosis. Reduction of STAT3 protein expression levels by miR-124 may at least partially provide an explanation for the enhanced apoptosis and repressed proliferation of A549 cells (FIG. 3). On the other hand, the suppression of GFP mRNA expression levels in GFP-expressing ES-2/GFP cells and GFP-transgenic mouse liver tissues by OnRS-delivered GFP siRNA explains the lower GFP fluorescent intensities (FIG. 4). While the advantages and disadvantages of using recombinant DNA agents, synthetic and recombinant RNAs to achieve RNAi are undoubtedly subjects of debate, the OnRS-based technology offers a new opportunity to readily and cost-effectively produce multi-milligrams of chimeric miRNA and siRNA agents in a research laboratory setting and allows one to utilize biological RNAs to perform RNA actions in vitro and in vivo. Nevertheless, the relative selectivity, efficiency and safety of OnRS-carried RNAi agents, as compared to existing agents or methods, await more extensive evaluation.

The utility of OnRS was further extended to consistent high-yield production of RNA aptamers. A priori it is unknown whether aptamer activity would still be present in the tRNA (13-15) and 5S rRNA (16) scaffolds, although ribozyme activity was observed in the context of the tRNA scaffold when Hammerhead ribozyme sequences were inserted together with the target RNA to be produced (15). The OnRS-resembled RNA aptamer MGA sensor indeed interacted with MG to produce a specific strong fluorescence at 630/650 nm (excitation/emission; FIG. 5e), as it was originally discovered (9), which was further employed for the determination of serum Rnase activities in clinical samples (FIG. 7e). The Rnase activity assay using label-free MGA sensor developed in this study is different from current methods. The Kunitz Rnase activity assay (29,34-36) is based upon the ultraviolet absorbance of label-free nucleic acids at 260 nm or nucleosides at 280 nm, which is relatively less selective and sensitive. Recent and current Rnase activity assays including those commercially-available kits rely on isotope- or fluorophore-labeled RNAs or antibodies (37-40), and thus offer greater sensitivities to determine very low levels of Rnase activities or indicate Rnase protein levels. However, human serum is comprised of much higher Rnase activities. Without extensive dilutions (e.g., 1:1,000) of the serum sample that might affect the Rnase activity assay including linear range, larger quantities (e.g., >10 μg) of labeled synthetic RNA agents are needed, and thus the assays become costly. After careful examination of the linearity in relation to MG and OnRS/MGA concentrations as well as the quantity of human serum and incubation time, we were able to establish a fluorescence-based Rnase assay using label-free OnRS/MGA sensor. Consistent with previous findings (29,36,38), our assays revealed a significantly higher serum Rnase activity in PDAC patients which may be attributable to the major form Rnase A released from the cancerous pancreases.

In summary, we presented a novel OnRS-based general approach for a consistent high-yield production of chimeric RNAs in common *E. coli* strains that carry functional small RNAs of interests such as miRNAs, siRNAs and RNA aptamers. This approach is proven robust and versatile and shall have broad applications to engineer chimeric ncRNAs, which may be utilized as in vitro and in vivo research tools and further developed as diagnostic and therapeutic agents.

References for Example 1

1. Dykxhoorn, D. M. and Lieberman, J. (2006) Knocking down disease with siRNAs. Cell, 126, 231-235.
2. Burnett, J. C. and Rossi, J. J. (2012) RNA-based therapeutics: current progress and future prospects. Chemistry & biology, 19, 60-71.
3. Kole, R., Krainer, A. R. and Altman, S. (2012) RNA therapeutics: beyond RNA interference and antisense oligonucleotides. Nature reviews. Drug discovery, 11, 125-140.
4. Ulrich, H., Trujillo, C. A., Nery, A. A., Alves, J. M., Majumder, P., Resende, R. R. and Martins, A. H. (2006) DNA and RNA aptamers: from tools for basic research towards therapeutic applications. Combinatorial chemistry & high throughput screening, 9, 619-632.
5. Kelnar, K., Peltier, H. J., Leatherbury, N., Stoudemire, J. and Bader, A. G. (2014) Quantification of therapeutic miRNA mimics in whole blood from non-human primates. Analytical chemistry, 86, 1534-1542.
6. Ling, H., Fabbri, M. and Calin, G. A. (2013) MicroRNAs and other non-coding RNAs as targets for anticancer drug development. Nature reviews. Drug discovery, 12, 847-865.
7. Takahashi, M., Yamada, N., Hatakeyama, H., Murata, M., Sato, Y., Minakawa, N., Harashima, H. and Matsuda, A. (2013) In vitro optimization of 2'-Ome-4'-thioribonucleoside-modified anti-microRNA oligonucleotides and its targeting delivery to mouse liver using a liposomal nanoparticle. Nucleic acids research, 41, 10659-10667.
8. Gebert, L. F., Rebhan, M. A., Crivelli, S. E., Denzler, R., Stoffel, M. and Hall, J. (2014) Miravirsen (SPC3649) can inhibit the biogenesis of miR-122. Nucleic acids research, 42, 609-621.
9. Babendure, J. R., Adams, S. R. and Tsien, R. Y. (2003) Aptamers switch on fluorescence of triphenylmethane dyes. Journal of the American Chemical Society, 125, 14716-14717.
10. Beckert, B. and Masquida, B. (2011) Synthesis of RNA by in vitro transcription. Methods in molecular biology, 703, 29-41.
11. Huang, F., He, J., Zhang, Y. and Guo, Y. (2008) Synthesis of biotin-AMP conjugate for 5' biotin labeling of RNA through one-step in vitro transcription. Nature protocols, 3, 1848-1861.
12. Huang, L., Jin, J., Deighan, P., Kiner, E., McReynolds, L. and Lieberman, J. (2013) Efficient and specific gene knockdown by small interfering RNAs produced in bacteria. Nature biotechnology, 31, 350-356.
13. Ponchon, L. and Dardel, F. (2007) Recombinant RNA technology: the tRNA scaffold. Nature methods, 4, 571-576.
14. Ponchon, L., Beauvais, G., Nonin-Lecomte, S. and Dardel, F. (2009) A generic protocol for the expression and purification of recombinant RNA in *Escherichia coli* using a tRNA scaffold. Nature protocols, 4, 947-959.
15. Nelissen, F. H., Leunissen, E. H., van de Laar, L., Tessari, M., Heus, H. A. and Wijmenga, S. S. (2012) Fast production of homogeneous recombinant RNA—towards large-scale production of RNA. Nucleic acids research, 40, e102.
16. Liu, Y., Stepanov, V. G., Strych, U., Willson, R. C., Jackson, G. W. and Fox, G. E. (2010) DNAzyme-mediated recovery of small recombinant RNAs from a 5S rRNA-derived chimera expressed in *Escherichia coli*. BMC biotechnology, 10, 85.
17. Li, M. M., Wang, W. P., Wu, W. J., Huang, M. and Yu, A. M. (2014) Rapid Production of Novel Pre-MicroRNA Agent has-mir-27b in *Escherichia coli* Using Recombinant RNA Technology for Functional Studies in Mammalian Cells. Drug metabolism and disposition: the biological fate of chemicals, 42, 1791-1795.
18. Sato, K., Hamada, M., Asai, K. and Mituyama, T. (2009) CENTROIDFOLD: a web server for RNA secondary structure prediction. Nucleic acids research, 37, W277-280.
19. Hamada, M., Yamada, K., Sato, K., Frith, M. C. and Asai, K. (2011) CentroidHomfold-LAST: accurate prediction of RNA secondary structure using automatically collected homologous sequences. Nucleic acids research, 39, W100-106.
20. Meyer, C., Grey, F., Kreklywich, C. N., Andoh, T. F., Tirabassi, R. S., Orloff, S. L. and Streblow, D. N. (2011) Cytomegalovirus microRNA expression is tissue specific and is associated with persistence. Journal of virology, 85, 378-389.
21. Wei, Z., Liu, X., Feng, T. and Chang, Y. (2011) Novel and conserved micrornas in Dalian purple sea urchin (Strongylocentrotus *nudus*) identified by next generation sequencing. International journal of biological sciences, 7, 180-192.
22. Bi, H. C., Pan, Y. Z., Qiu, J. X., Krausz, K. W., Li, F., Johnson, C. H., Jiang, C. T., Gonzalez, F. J. and Yu, A. M. (2014) N-methylnicotinamide and nicotinamide N-methyltransferase are associated with microRNA-1291-altered pancreatic carcinoma cell metabolome and suppressed tumorigenesis. Carcinogenesis, 35, 2264-2272.
23. Pan, Y. Z., Zhou, A., Hu, Z. and Yu, A. M. (2013) Small nucleolar RNA-derived microRNA has-miR-1291 modulates cellular drug disposition through direct targeting of ABC transporter ABCC1. Drug metabolism and disposition: the biological fate of chemicals, 41, 1744-1751.
24. Okabe, M., Ikawa, M., Kominami, K., Nakanishi, T. and Nishimune, Y. (1997) 'Green mice' as a source of ubiquitous green cells. FEBS letters, 407, 313-319.
25. Boudreau, R. L. and Davidson, B. L. (2012) Generation of hairpin-based RNAi vectors for biological and therapeutic application. Methods in enzymology, 507, 275-296.
26. Cao, X., Pfaff, S. L. and Gage, F. H. (2007) A functional study of miR-124 in the developing neural tube. Genes & development, 21, 531-536.
27. Cai, B., Li, J., Wang, J., Luo, X., Ai, J., Liu, Y., Wang, N., Liang, H., Zhang, M., Chen, N. et al. (2012) microRNA-124 regulates cardiomyocyte differentiation of bone marrow-derived mesenchymal stem cells via targeting STAT3 signaling. Stem cells, 30, 1746-1755.
28. Hatziapostolou, M., Polytarchou, C., Aggelidou, E., Drakaki, A., Poultsides, G. A., Jaeger, S. A., Ogata, H., Karin, M., Struhl, K., Hadzopoulou-Cladaras, M. et al. (2011) An HNF4alpha-miRNA inflammatory feedback circuit regulates hepatocellular oncogenesis. Cell, 147, 1233-1247.
29. Reddi, K. K. and Holland, J. F. (1976) Elevated serum ribonuclease in patients with pancreatic cancer. Proceedings of the National Academy of Sciences of the United States of America, 73, 2308-2310.
30. Akagi, K., Murai, K., Hirao, N. and Yamanaka, M. (1976) Purification and properties of alkaline ribonuclease from human serum. Biochimica et biophysica acta, 442, 368-378.
31. Gu, S., Jin, L., Zhang, Y., Huang, Y., Zhang, F., Valdmanis, P. N. and Kay, M. A. (2012) The loop position of shRNAs and pre-miRNAs is critical for the accuracy of dicer processing in vivo. Cell, 151, 900-911.

32. Castellano, L. and Stebbing, J. (2013) Deep sequencing of small RNAs identifies canonical and non-canonical miRNA and endogenous siRNAs in mammalian somatic tissues. Nucleic acids research, 41, 3339-3351.

33. Dueck, A., Ziegler, C., Eichner, A., Berezikov, E. and Meister, G. (2012) microRNAs associated with the different human Argonaute proteins. Nucleic acids research, 40, 9850-9862.

34. Kunitz, M. (1950) Crystalline desoxyribonuclease; isolation and general properties; spectrophotometric method for the measurement of desoxyribonuclease activity. The Journal of general physiology, 33, 349-362.

35. Crook, E. M., Mathias, A. P. and Rabin, B. R. (1960) Spectrophotometric assay of bovine pancreatic ribonuclease by the use of cytidine 2':3'-phosphate. The Biochemical journal, 74, 234-238.

36. Peterson, L. M. (1979) Serum Rnase in the diagnosis of pancreatic carcinoma. Proceedings of the National Academy of Sciences of the United States of America, 76, 2630-2634.

37. Potenza, N., Salvatore, V., Migliozzi, A., Martone, V., Nobile, V. and Russo, A. (2006) Hybridase activity of human ribonuclease-1 revealed by a real-time fluorometric assay. Nucleic acids research, 34, 2906-2913.

38. Kottel, R. H., Hoch, S. O., Parsons, R. G. and Hoch, J. A. (1978) Serum ribonuclease activity in cancer patients. British journal of cancer, 38, 280-286.

39. Vlassov, A., Florentz, C., Helm, M., Naumov, V., Buneva, V., Nevinsky, G. and Giege, R. (1998) Characterization and selectivity of catalytic antibodies from human serum with Rnase activity. Nucleic acids research, 26, 5243-5250.

40. Nakata, D. (2014) Increased N-glycosylation of Asn (8)(8) in serum pancreatic ribonuclease 1 is a novel diagnostic marker for pancreatic cancer. Scientific reports, 4, 6715.

Example 2

Chimeric Mir-1291 Biosynthesized Efficiently in *E. coli* is Effective to Reduce Target Gene Expression in Human Carcinoma Cells and Improve Chemosensitivity This Example demonstrates a high-yield expression of chimeric pre-miR-1291 in common *E. coli* strains using the same tRNA scaffold. The tRNA fusion pre-miR-1291 (tRNA/mir-1291) was then purified to high homogeneity using affinity chromatography, whose primary sequence and posttranscriptional modifications were directly characterized by mass spectrometric analyses. Chimeric tRNA/mir-1291 was readily processed to mature miR-1291 in human carcinoma MCF-7 and PANC-1 cells. Consequently, recombinant tRNA/mir-1291 reduced the protein levels of miR-1291 target genes including ATP-binding cassette transporter ABCC1, and forkhead box protein FOXA2, and methyl CpG binding protein MeCP2, as compared with cells transfected with the same doses of control tRNA scaffold (tRNA/MSA). In addition, tRNA-carried pre-miR-1291 suppressed the growth of MCF-7 and PANC-1 cells in a dose dependent manner, and significantly enhanced the sensitivity of ABCC1-overexpressing PANC-1 cells to doxorubicin. These results indicate that recombinant miR-1291 agent is effective in the modulation of target gene expression and chemosensitivity, which may provide insights into high-yield bioengineering new ncRNA agents for pharmacoepigenetics research.

Introduction

The discovery of genomically-encoded, functional non-coding RNAs (ncRNAs) such as microRNAs (miRNAs or miRs) and long noncoding RNAs in the control of various cellular processes including drug disposition and cell proliferation has expanded our knowledge of "genes" in the cells. Some miRNAs (e.g., miR-519c, -328, -326, -379, -1291 and -124) (To et al., 2008; Pan et al., 2009; Liang et al., 2010; Haenisch et al., 2011; Pan et al., 2013; Markova and Kroetz, 2014) that negatively regulate the expression of ATP-binding cassette (ABC) efflux transporters (e.g., ABCC1, ABCC2, ABCC4 and ABCG2) may be employed to improve the sensitivity of human carcinoma cells to anticancer drugs. Furthermore, a number of oncogenic miRNAs dysregulated in tumor tissues may be directly targeted to manage tumor progression (Trang et al., 2008; Bader et al., 2010). These approaches are indeed under active investigations towards an improved understanding of miRNA pharmacoepigenetics and development of novel miRNA-based therapies.

However, research on miRNA pharmacoepigenetics and therapies is hampered by the lack of an efficient method for producing large quantities of inexpensive and natural miRNA agents. The broadly used viral or non-viral vector-based miRNA expression systems utilize DNA agents rather than RNAs, and this approach relies on the host cells or organisms to transcribe DNA to miRNA precursors before getting into the cytoplasmic miRNA machinery. The other major group of miRNA agents consists of miRNA mimics, precursors and antagomirs that are all produced via chemical synthesis. Although organic synthesis of oligonucleotides may be automated, a projected dose of miRNA mimics or precursors for in vivo studies is very costly. It is also unclear to what extent chemical modifications would alter miRNA structure, folding, biological activity and safety profile despite that artificial miRNA mimics show some favorable pharmacokinetic properties such as a longer half-life. In vitro transcription may be employed to produce target RNA agents, whereas it normally generates RNA molecules in a test tube on microgram scale, and the production of larger quantities of RNAs requires more and costly RNA polymerases. Recently, tRNA (Ponchon and Dardel, 2007; Ponchon et al., 2009; Nelissen et al., 2012) and rRNA (Liu et al., 2010) have been successfully employed as scaffolds to biosynthesize recombinant RNAs for structural and biophysical analyses, given the fact that tRNAs and rRNAs are present as stable RNA molecules in the cells. This recombinant RNA technology provides a novel way for cost-effective and rapid production of large quantities of recombinant RNAs (e.g., milligrams of target RNAs from 1 L bacterial culture).

In an effort to produce natural miRNA agents to perform miRNA actions, we had demonstrated that the tRNA scaffold could be used to produce chimeric pre-miR-27b (tRNA/mir-27b) agents in *E. coli* to study miR-27b functions in the modulation of drug metabolism in human cells (Li et al., 2014). However, the yield of recombinant tRNA/mir-27b is extremely low (e.g., <2% of chimeric tRNA/mir-27b in total RNAs). Herein we show that various lengths of human pre-miR-1291 chimera could be assembled using the same tRNA scaffold, and much expected high-level expression (e.g., >10% of fusion tRNA/mir-1291 in total RNAs) was identified for pre-miR-1291 around 120-nt in length in a common *E coli* strain HST08, which may be employed to investigate the functions of relatively less understood miR-1291 (Pan et al., 2013; Bi et al., 2014). Sephadex aptamer tagged recombinant tRNA/mir-1291 was purified by affinity chromatography, and mapped/sequenced through mass spectrometry (MS)-based studies, including the characterization of posttranscriptional modifications. Furthermore, chimeric tRNA/mir-1291 was processed to mature miR-1291 in human carcinoma MCF-7 and PANC-1 cells.

Compared with the control tRNA scaffold (tRNA/MSA), tRNA/mir-1291 reduced the protein expression levels of miR-1291 target genes (e.g., ABCC1), and sensitized the ABCC1-overexpressing human carcinoma cells to anticancer drug doxorubicin (a known substrate of transporter ABCC1). These findings provide insight into developing recombinant miRNA agents for pharmacoepigenetic and therapeutic studies.

Materials and Methods

Chemicals and Materials. Doxorubicin was purchased from LC Laboratories (Woburn, Mass.). Lipofectamine 2000, Trizol reagent and BCA Protein Assay Kit were bought from Thermo Fisher Scientific Inc. (Waltham, Mass.). RIPA lysis buffer was purchased from Rockland Immunochemicals (Limerick, Pa.), and the complete protease inhibitor cocktail was bought from Roche Diagnostics (Mannheim, Germany). The antibody against methyl CpG binding protein 2 (MeCP2) was purchased from Cell Signaling (Danvers, Mass.), the antibodies against ABCC1 and forkhead box protein A2 (FOXA2) were purchased from Abcam (Cambridge, Mass.), and the antibody against glyceraldehyde-3-phosphate dehydrogenase (GAPDH) was bought from Santa Cruz Biotechnologies (Santa Cruz, Calif.). The horseradish peroxidase goat anti-rabbit or mouse secondary antibodies were bought from Jackson Immuno-Research Laboratories (West Grove, Pa.). ECL substrate and PVDF membrane were obtained from Bio-Rad (Hercules, Calif.). All other chemicals and organic solvents of analytical grade were purchased from Sigma-Aldrich (St. Louis, Mo.) or Thermo Fisher Scientific Inc. (Waltham, Mass.).

Prediction of RNA Secondary Structure. The secondary structures of Sephadex aptamer tagged methionyl-tRNA scaffold (tRNA/MSA), pre-miRNAs, and chimeric RNAs (FIG. 11A) were predicted using the CentroidFold (http://www.ncrna.org/centroidfold) and CentroidHomfold (http://www.ncrna.org/centroidhomfold).

Construction of Plasmids. To express pre-miR-1291 using the tRNA scaffold (FIG. 11A), the DNA fragments encoding 123-nt, 164-nt and 197-nt pre-miR-1291 were amplified by PCR with the primers 5'-ACGCGTCGACGAGTTCTGTC-CGTGAGCCTTGG-3' (SEQ ID NO:67) and 5'- CATC-GACGTCACAGCCAACAGACCACAGGAAG-3' (SEQ ID NO:68), 5'-ACGCGTCGACAGCCTTGGGTAGAAT-TCCAG-3' (SEQ ID NO:96) and 5'-CATCGACGTC-GAGCTGTAGGTTGTTTCTTCC-3' (SEQ ID NO:97), and 5'-ACGCGTCGACGAGTTCTGTCCGTGAGCCTTG-3' (SEQ ID NO:98) and 5'-CATCGACGTCCCTCTTC-CAATGGGATGGTGAG-3' (SEQ ID NO:99), respectively, and then cloned into the vector pBSMrnaSeph (kindly provided by Dr. Luc Ponchon, Université Paris Descartes, France) (Ponchon and Dardel, 2007; Ponchon et al., 2009) (FIG. 11B) that was linearized by restriction endonucleases SalI and AatII (New England Biolabs, Ipswich, MA). All inserts were confirmed by Sanger sequencing analysis.

Expression of Chimeric RNAs in E. coli. Expression of tRNA/mir-1291 chimeras and the control tRNA/MSA was performed as described (Ponchon and Dardel, 2007; Ponchon et al., 2009; Li et al., 2014). Briefly, freshly transformed HST08 E. coli cells (Clontech, Mountain View, Calif.) were plated on LB agar plate containing 100 µg/mL of ampicillin. After grown overnight at 37° C., a single colony was picked up to inoculate an overnight culture with 5 mL LB media containing 100 µg/mL of ampicillin at 37° C. For large-scale RNA expression, fresh transformants were directly incubated in 1 L LB medium containing 100 µg/mL of ampicillin at 37° C. overnight. Total RNAs were isolated from bacteria using Tris-HCl-saturated phenol extraction method, which were quantitated using a Nano-Drop spectrophotometer (Thermo Fisher Scientific) and analyzed by denaturing urea (8 M) polyacrylamide (8%) gel electrophoresis (PAGE) to examine recombinant ncRNA expression.

Purification of Recombinant ncRNAs. Purification of recombinant ncRNAs consisting of Sephadex aptamer tag was conducted as reported (Ponchon and Dardel, 2007; Ponchon et al., 2009) with minor modifications. Briefly, one gram of Sephadex G-100 beads (Sigma-Aldrich) were incubated in 10 mL buffer A consisting of 50 mM potassium phosphate, 5 mM $MgCl_2$, and 100 mM NaCl, pH 7.5, at 90° C. for 5 h, and then washed twice with buffer A before use. The E. coli cell pellets were sonicated and cellular debris was removed by centrifugation at 10,000 g for 10 min. The supernatant was loaded onto the Sephadex column, washed three times with buffer A, and eluted with buffer A consisting of 50 mg/mL soluble dextran B512 (average molecular weight 9,000-11,000 Da, Sigma-Aldrich). The dextran was removed through buffer exchange using Ultra-0.5 mL Centrifugal Filters (30 KD for tRNA/MSA, 50 KD for tRNA/mir-1291; Millipore, Billerica, Mass.). The purity of isolated RNAs was estimated based on the band intensity after resolving on denaturing PAGE gels and the quantity was determined by NanoDrop. Purified recombinant RNAs were stored in DEPC-treated water at −80° C. before further analyses.

Analysis of Intact Recombinant ncRNA by Electrospray Ionization-Mass Spectrometry (ESI-MS). The procedure described previously (Taucher and Breuker, 2010) was followed for ESI-MS analysis of intact ncRNAs. In particular, the electrospray solution consisted of 1 µM ncRNA, 25 mM imidazole and 25 mM piperidine in 1:1 water/methanol. The flow rate for direct infusion was 3.0 µL/min. The mass spectra were acquired in negative ion mode using Thermo LTQ XL-ion trap mass spectrometer over an m/z range of 600-2000. The spray voltage was 4.2 kV with a capillary temperature at 275° C., capillary voltage of −38 V and tube lens voltage of −95 V. Sheath gas, auxiliary gas and sweep gas were set at 20, 5 and 2 arbitrary units, respectively. The instrumental settings were optimized by automatic tuning with poly d(T)80. The instrument was calibrated as per the manufacturer's instructions (error ~100 ppm). ESI mass spectra of intact ncRNAs were deconvoluted using ProMass software for Xcalibur (Novatia LLC, www.enovatia.com) to determine the average molecular weights (MWs) of recombinant RNAs.

Nucleoside Analysis of Recombinant ncRNAs by Liquid Chromatography Coupled with Ultraviolet and Mass Spectrometry Detection (LC-UV-MS). The hydrolysates of recombinant RNAs were prepared by heating the RNAs at 95° C. for 5 min followed by chilling on ice for 3 min. The RNA was initially digested, as described (Russell and Limbach, 2013), with Nuclease P1 (2 U/0.5 A260 unit) (Sigma-Aldrich) in the presence of 1/10 volume of 0.1 M ammonium acetate (pH 5.3) at 45° C. for 2 h. The mixture was further treated with 0.002 units of snake venom phosphodiesterase (Worthington Biochemicals Lakewood, Lakewood, N.J.) and 0.5 units of 95Ibany95yl phosphatase (New England Biolabs) in 1/10 volume of 1 M ammonium bicarbonate at 37° C. for 2 h to release nucleosides from oligonucleotides. These nucleosides were resolved on a 2.1 mm×250 mm Supelcosil LC-18-S(5 µm particle) reversed phase column fitted with a 2.1 mm×20 mm Supelguard LC-18-S guard column at flow rate of 250 µL/min by using Hitachi D-7000 HPLC equipped with diode array detector. The post-column flow was split between UV-detector (2/3 volume) and mass spectrometer (1/3 volume) to record the UV trace and m/z values of analyte ions, respectively. Mobile phases were 5 mM ammonium acetate (pH 5.3) (mobile phase A) and 40% aqueous acetonitrile (mobile phase B) with multilinear gradients as described (Pomerantz and McCloskey, 1990). Mass spectra were recorded using a Thermo LTQ-XL ion trap mass spectrometer equipped with an ion max electrospray source in the positive ion mode over an m/z range of 100-1000. The electrospray conditions included a capillary temperature of 275° C., spray voltage of 4.2 kV, capillary voltage of 35 V and tube lens voltage of 85 V, sheath gas, auxiliary gas and sweep gas of 25, 15 and 10 arbitrary units, respectively. Data-dependent collision-induced dissociation (CID) tandem mass spectrometry (MS/MS) was performed on the two most abundant ions observed at a given time during the entire chromatographic run.

Mapping and Sequencing of ncRNAs by LC Tandem MS (LC-MS/MS) Analysis. Mapping of recombinant ncRNAs and identification of nucleoside modifications were achieved by LC-MS/MS analysis of Rnase T1-digested RNA fragments (Krivos et al., 2011). Briefly, the ammonium acetate precipitated recombinant ncRNAs (3 µg) were treated with Rnase T1 (25 U/µg of RNA, Roche Molecular Biochemicals, Indianapolis, Ind.) and bacterial alkaline phosphatase (0.0001 U/µg of RNA, Worthington Biochemical Corporation) at 37° C. for 2 h. The digests were subsequently dried in a Speedvac and stored at 4° C. Just before LC-MS/MS, the sample was resuspended with mobile phase C (400 mM hexafluoroisopropanol (HFIP) and 16.3 mM 96Ibany96ylamine (TEA) in water, pH 7.0). The RNA digestion products were resolved on an Xbridge C18 column (Waters, Milford, Mass.) (1.0 mm×150 mm) by a 70-min gradient elution with mobile phase C and mobile phase D (50% mobile phase C, 50% methanol) at a flow rate of 30 µL/min using a Thermo Surveyor HPLC system and a Thermo Micro AS autosampler. The tuning and MS method were essentially the same as described (Wong et al., 2013). Mass values were restricted to a scan range of m/z 600-2000, and data-dependent CID MS/MS was performed for the top four most abundant ions before keeping them in the exclusion list for 30 s.

An in silico analysis of Rnase T1 digestion of unmodified version of each recombinant ncRNA was performed using the Mongo Oligo Mass Calculator (http://mods.rna.albany.edu/masspec/Mongo-Oligo). This helped in identification of the appropriate m/z values that are common to tRNA/MSA and tRNA/mir-1291, as well as those unique to tRNA/mir-1291. The observed deviation of m/z values from the predicted values was recorded following manual data analysis.

Human Cell Culture and Transfection. Human pancreatic carcinoma PANC-1 and breast cancer MCF-7 cells were purchased from American Type Culture Collection (Manassas, Va.). PANC1 and MCF-7 cells were cultured in DMEM and RPMI1640 medium, respectively, containing 10% fetal bovine serum, 100 U/mL of penicillin sodium, and 100 mg/mL streptomycin sulfate at 37° C. in a humidified atmosphere of 5% carbon dioxide. Cells were transfected with purified recombinant ncRNAs using Lipofectamine 2000.

Reverse Transcription (RT) Quantitative Real-Time PCR (qPCR). MCF-7 and PANC-1 cells were harvested at different time points after transfection with various doses of recombinant ncRNAs using Lipofectamine 2000. Total RNAs were isolated using Direct-zol RNA extraction kit (Zymo Research, Irvine, Calif.). RT-qPCR analysis was conducted on a CFX96 Touch real-time PCR system (Bio-Rad, Hercules, Calif.). Quantification of pre-miR-1291 was performed with GoTaq 2-Step RT-qPCR system (Promega, Madison, Wis.) using gene selective primers, and stem-loop RT-qPCR analysis of mature miR-1291 was conducted with the TaqMan small RNA assay kit (Thermo Fisher Scientific), as reported (Li et al., 2011; Pan et al., 2013). The cycle number (CT) at which the amplicon concentration crossed a defined threshold was determined for each analyte. The relative expression was calculated using the formula 2-$\Delta$CT, where $\Delta$CT was the difference in CT value between the analyte (pre-miR-1291 or miR-1291) and internal standard (18S and U6), and then normalized to the control treatment.

Immunoblot Analysis. MCF-7 and PANC-1 cells were transfected with 20 nM tRNA/mir-1291 or tRNA/MSA using Lipofectamine 2000 and then harvested after 48 h. Cell lysates were prepared with RIPA lysis buffer supplemented with the complete protease inhibitor cocktail, and protein concentrations were determined with the BCA Protein Assay Kit. Whole-cell proteins (40 µg per lane) were separated on 10% SDS-PAGE gel, and electrophoretically transferred onto PVDF membranes which were then incubated with selective antibody against MeCP2, FOXA2, MRP1 or GAPDH. After blotting with peroxidase goat anti-rabbit or mouse IgG, the membranes were incubated with ECL substrates and images were acquired with Chemi-Doc MP Imaging System (Bio-Rad). All experiments were conducted in triplicate using different transfections (N=3) and repeated at least twice.

Cytotoxicity Assays. MCF-7 and PANC-1 cells were seeded at 10,000 cells/well in a 24-well culture plate or 3,000 cells/well in a 96-well culture plate. At different time points after transfection with the recombinant tRNA/mir-1291 or tRNA/MSA at specific concentrations using Lipofectamine 2000, cell viability was determined using MTT (Sigma-Aldrich) assay as described (Pan et al., 2009; Pan et al., 2013) using an Infinite M200 Pro Microplate reader (Tecan, Durham, N.C.). To examine the influence of ncRNA on doxorubicin cytotoxicity, PANC-1 cells were first transfected with 20 nM ncRNAs or just Lipofectamine 2000 (vehicle control) for 48 h. After incubated with various concentrations of doxorubicin or drug vehicle (0.1% DMSO) for another 48 h, cell viability was determined by MTT assays. Doxorubicin cytotoxicity data were fit to a normalized, inhibitory dose-response model with variable slope, $Y=100/(1+10^{((LogIC50-X) \times Hill\ Slope)})$ (GraphPad Prism, San Diego, Calif.). The effects of recombinant ncRNAs on cell growth were better estimated by fitting to a normalized, inhibitory dose-response model, $Y=Bottom+(Top-Bottom)/(1+10^{((LogEC50-X) \times Hill\ Slope)})$, where the bottom and top were defined as 40% and 100%, respectively.

Statistical Analysis. All values were mean±standard deviation (SD). According to the number of groups and variances, data were compared by unpaired Student's t-test, one-way or two-way ANOVA using GraphPad Prism. Difference was considered as significant when the probability was less than 0.05 ($P<0.05$).

Results

Design and Construction of tRNA/Mir-1291 Expression Plasmids. To better maintain the hairpin structure of pre-miR-1291 (87 nt), we extended both 5' and 3' flanking sequences to 123 nt, 164 nt and 197 nt whose corresponding DNA segments were thus cloned (FIG. 11B). Construction of ncRNA expression plasmids consisting of various lengths of pre-miR-1291 sequences also would allow us to evaluate the impact of length of oligonucleotides on recombinant ncRNA expression. The predicted secondary structures of tRNA/MSA, pre-miR-1291 and tRNA/mir-1291 (FIG. 11A) suggested that tRNA/mir-1291 chimeras containing 164-nt and 197-nt pre-miR-1291 might be able to maintain the tRNA D-loop and T-loop structures, and the 123-nt pre-miR-1291 would form a more stable, intramolecular stem-loop structure at the T-loop arm (FIG. 11A). Nevertheless, the basic stem-loop structure of pre-miR-1291 retained within all three tRNA/mir-1291 chimeras, suggesting that they would be accessible by endoribonucleases for the production of mature miR-1291 in human cells.

Expression and Purification of Recombinant tRNA/Mir-1291. To examine the expression of tRNA/mir-1291 chimeras, total RNAs were isolated from $E.$ $coli$ and subjected to RNA electrophoretic mobility assay. The appearance of new RNA bands at the expected sizes (200-300 nt; FIG. 11C) in $E.$ $coli$ cells transformed with tRNA/mir-1291 expression plasmids, as compared with the cells transformed with tRNA/MSA expression plasmids, indicated a successful expression of recombinant tRNA/mir-1291 agents. It is noted that the electrophoretic mobility of chimeric tRNA/pre-miRNAs looked greater than that indicated by the single-stranded RNA markers. This is likely due to the presence of "double-stranded" stem structures in these ncRNAs (FIG. 11A). It appeared that the tRNA/mir-1291-123nt (totally 227 nt in length) was accumulated at much higher level (e.g., >10% in total RNAs) than other longer tRNA/mir-1291-164nt and tRNA/mir-1291-197nt species (totally 268 nt and 301 nt, respectively; <2% in total RNAs) under the same conditions (FIG. 11C).

The recombinant tRNA/mir-1291-123nt and tRNA/MSA bearing a Sephadex aptamer tag were isolated by affinity chromatography (FIG. 11D). Other cellular components such as rRNA, tRNA, DNA and proteins were readily removed during loading and washing processes, and the recombinant ncRNAs bound to Sephadex G-100 were isolated after elution with dextran. A good purity (>85%; based on gel electrophoresis) and reasonable yield (around 2% of recombinant ncRNA/total RNAs or 2-3 mg ncRNAs from 1 L bacterial culture; based on the quantitation using Nano-Drop) was achieved for tRNA/mir-1291-123nt and tRNA/MSA. In contrast, the purity of tRNA/mir-1291-164nt and −197nt chimeras was less than 60%, which was likely related to their low expression levels. Therefore, only the tRNA/mir-1291-123nt was utilized for the following studies, which was simply referred as tRNA/mir-1291.

Structural Characterization of Recombinant ncRNAs. The sequence of purified tRNA/mir-1291 was initially confirmed by Sanger sequencing after the preparation of cDNAs. To directly determine the primary sequence of recombinant tRNA/mir-1291 and possible posttranscriptional modifications, several studies were conducted using MS techniques. First, the intact tRNA/mir-1291 was analyzed by ESI-MS to measure the MW of constituent RNA species. Deconvolution of the multiply charged ESI data indicated the presence of multiple species of RNA. The most abundant (~70%; based on peak areas) experimentally-determined MWs were found to be 73,422.4 Da for tRNA/mir-1291 (FIG. 12A). The differences between measured and predicted MWs (162.4 Da) suggest the presence of modified nucleosides. Additional components were also noted, whose MWs correspond to unmodified RNA species or truncated RNA species of lower MWs than tRNA/mir-1291.

To identify possible posttranscriptional modifications which are common for natural RNAs produced in living cells, LC-UV-MS analysis was conducted to define the nucleosides in hydrolysates prepared from tRNA/mir-1291 and compared with the scaffold tRNA/MSA. A number of modified nucleosides such as dihydrouridine (D), pseudouridine ($\Psi$)7-methylguanosine (m7G), 4-thiouridine ($s^4$U), 3-(3-amino-3-carboxypropyl)uridine ($acp^3$U), 5-methyluridine ($m^5$U), 2'-O-methylguanosine (Gm), and 1-methylguanosine ($m^1$G) were found for both tRNA/mir-1291 and tRNA/MSA samples (FIG. 12B). While some modified nucleosides (e.g., D and $\Psi$) were clearly identified by both the UV and MS data, others (e.g., Gm and $m^1$G in tRNA/mir-1291) were less obviously determined by UV detection but readily discerned by corresponding MS data.

To further localize the nucleoside modifications, the ncRNAs were treated with guanosine-specific ribonuclease T1 and bacterial alkaline phosphatase. The resulting digestion products were resolved on an ion-pairing reversed phase C18 column, identified and sequenced by tandem MS (FIG. 12C). The majority of modified nucleosides (e.g., D, $\Psi$, $m^7$G, $s^4$U, $acp^3$U and $m^5$U) obviously identified by the LC-UV analysis (FIG. 12B) could be mapped to Rnase T1 digestion products and assigned to the tRNA scaffold, whereas the unassigned modification (e.g., $m^1$G) might be attributed to co-purified nucleic acids or prior carry-over. These results not only validated the primary sequences of purified tRNA/mir-1291 but also demonstrated the presence of natural modifications of the tRNA scaffold influencing ncRNA stability.

Chimeric tRNA/Mir-1291 is Processed to Mature miR-1291 in Human Carcinoma Cells. To delineate if mature miR-1291 can be produced from recombinant tRNA/mir-1291 chimera in human cells, we employed selective Taq-Man stem-loop RT-qPCR small RNA assay kit to quantify mature miR-1291 and regular RT-qPCR to determine pre-miR-1291 levels. Our data showed that pre-miR-1291 levels were sharply increased in human carcinoma MCF-7 cells treated with the tRNA/mir-1291 (FIG. 13A), indicating a successful transfection of tRNA/mir-1291. Meanwhile, the levels of mature miR-1291 were elevated remarkably in a dose dependent manner (FIG. 13B). Interestingly, a three and two orders of magnitude increase in pre-miR-1291 and mature miR-1291, respectively, persisted in MCF-7 cells for 72 h after transfection (FIG. 13C-D). Similarly, there were around three orders of magnitude increase in pre-miR-1291 and two orders of magnitude increase in mature miR-1291 in PANC-1 cells at 24 h and 72 h post-transfection of 20 nM of recombinant tRNA/mir-1291. These results suggest that recombinant tRNA/mir-1291 is readily processed to mature miR-1291 within human carcinoma cells.

Recombinant tRNA/mir-1291 is Effective to Control miR-1291 Target Gene Expression in Human Carcinoma Cells. To evaluate whether chimeric tRNA/mir-1291 is pharmacologically active in the modulation of miR-1291 target gene expression in human carcinoma cells, we first examined the impact of recombinant tRNA/mir-1291 on the protein levels of transporter ABCC1, a validated target for miR-1291 (Pan et al., 2013). Immunoblot analysis using protein-selective antibody revealed that 20 nM of tRNA/mir-1291 reduced ABCC1 protein expression by 90% in PANC-1 cells, as compared with control tRNA/MSA treatment (FIG. 14A). We thus evaluated the effects of tRNA/mir-1291 and tRNA/MSA on two other targets, MeCP2 and FOXA2, which were identified by TargetScan algorithm (www.targetscan.org/) and validated in our laboratory. MeCP2 and FOXA2 are overexpressed in MCF-7 (Lin and Nelson, 2003) and PANC-1 cells (Song et al., 2010), respectively. Both cell lines had relatively lower levels of miR-1291, as compared with other cell lines such as MCF-7/MX100 and HepG2. Our data showed that tRNA/mir-1291 led to a 30% reduction of FOXA2 protein levels in PANC-1 cells (FIG. 14B) and 50% decrease of MeCP2 in MCF-7 cells (FIG. 14C), as compared with control tRNA/MSA treatments. These results demonstrate that recombinant tRNA/mir-1291 is effective to regulate miR-1291 target gene expression in human carcinoma cells, which may be attributable to the actions of mature miR-1291 produced from chimeric tRNA/mir-1291 in the cells (FIG. 13).

tRNA-Carried Pre-miR-1291 Suppresses the Growth of Human Carcinoma Cells. We thus assessed the impact of Chimeric miR-1291 on cancer cell growth because miR-1291 has been revealed to act as a tumor suppressor by our studies (Yu et al., 2013; Bi et al., 2014) and others (Hidaka et al., 2012; Yamasaki et al., 2013). Our pilot studies showed that, compared with the control tRNA/MSA, a greater extent of inhibition by tRNA/mir-1291 was shown at 48 h post-transfection in MCF-7 cells and 72 h post-treatment in PANC-1 cells. Thus we examined the dose response relationship of tRNA/mir-1291 in the suppression of MCF-7 and PANC-1 cell growth at 48 h and 72 h, respectively. Our data showed that recombinant tRNA/mir-1291 remarkably inhibited PANC-1 and MCF-7 cell proliferation in a dose dependent manner and to a significantly ($P<0.01$, two-way ANOVA) greater degree than the control tRNA/MSA (FIG. 15A-B). This was also manifested by lower EC50 values for tRNA/mir-1291 (2.59±1.30 nM in MCF-7 cells and 1.61±1.29 nM in PANC-1 cells) than those for tRNA/MSA (1160±1026 nM in MCF-7 cells and 7.09±1.22 nM in PANC-1 cells) (FIG. 15C). These results indicate that tRNA-carried pre-miR-1291 is functional to inhibit the proliferation of human cancer cells.

Chimeric tRNA/Mir-1291 Sensitizes Human Carcinoma PANC-1 Cells to Doxorubicin. Because miR-1291 is able to enhance chemosensitivity through down-regulation of ABCC1 transporter (Pan et al., 2013) and tRNA-carried pre-miR-1291 is effective to reduce ABCC1 protein levels in human carcinoma PANC-1 cells (FIG. 14A), we investigated if recombinant tRNA/mir-1291 could alter the sensitivity of ABCC1-overexpressing PANC-1 cells to doxorubicin, an ABCC1 substrate anticancer drug. Doxorubicin cytotoxicity against PANC-1 cells was determined by MTT assays after transfection with tRNA/mir-1291, the control tRNA/MSA and vehicle. Our data showed that tRNA/mir-1291-transfected cells were more sensitive to doxorubicin than the control tRNA/MSA- and vehicle-treated cells (FIG. 16A). The improved sensitivity was also indicated by a significantly lower EC50 value in cells transfected with tRNA/mir-1291 (133±21 nM) than tRNA/MSA (297±42 nM) and vehicle control (325±50 nM) (FIG. 16B). These results suggest that co-administration of recombinant tRNA/mir-1291 enhances the antiproliferative effects of doxorubicin.

Discussion

A new way to efficiently produce multi-milligrams of chimeric pre-miR-1291 agents from 1 L bacterial culture was demonstrated in this study, which utilizes a tRNA-based recombinant RNA technology. Pre-miR-1291 fused to the tRNA was protected against nucleolytic digestion in bacteria and thus accumulated to a high level for further purification. This stable tRNA scaffold was revealed to comprise a number of posttranscriptionally-modified nucleosides, which were directly identified and mapped to specific sites through MS analyses of the purified ncRNAs. Our data also showed that tRNA-carried pre-miR-1291 was readily processed to mature miR-1291 in different types of human carcinoma cells, and consequently suppressed miR-1291 target gene expression (e.g., ABCC1), inhibited human MCF-7 and PANC-1 cell growth, and enhanced the chemosensitivity of PANC-1 cells.

Human miR-1291 is shown to regulate the expression of transporter ABCC1, modulate intracellular drug accumulation and affect chemosensitivity (Pan et al., 2013). In addition, miR-1291 is revealed to act as a tumor suppressor in various human carcinoma cell lines by our studies (Yu et al., 2013; Bi et al., 2014) as well as others (Hidaka et al., 2012; Yamasaki et al., 2013). Motivated by the idea to produce natural miRNA agents to perform miRNA actions, we had made large efforts to biosynthesize pre-miR-1291 agents using the tRNA scaffold to examine miR-1291 biological functions and therapeutic implications in vitro and in vivo (Li et al., 2014; Chen et al., 2015). The success and efficiency in producing recombinant RNAs relies on the structure and metabolic stability of target RNA in the organism. It is obvious that any target RNAs labile to bacterial Rnase digestion is undoubtedly subjected to nucleolytic cleavage and thus there will be a limited or no accumulation of recombinant RNAs (e.g., pre-miR-27b) (Li et al., 2014; Chen et al., 2015). Recombinant pre-miR-1291 chimeras were revealed to be expressed successfully in a number of common E. coli strains, and a high-level accumulation was observed in HST08 and DH5α cells, similar as pre-miR-34a (Chen et al., 2015). Consistent with previous findings (Ponchon and Dardel, 2007; Ponchon et al., 2009), lower levels of recombinant RNAs were found for longer pre-miR-1291 species, which is presumably due to an increase of unstructured regions that are misfolded and/or cleaved by bacterial Rnases. High-level expression also facilitated the purification of recombinant tRNA/mir-1291-123nt, which was consistently produced in multi-milligrams quantity from 1 L fermentation that would allow us to assess miR-1291 activities in vivo, as we have done with other efficiently expressed ncRNAs (Chen et al., 2015). Despite that the purification yields using Sephadex G-100 were relatively low (e.g., 2-3%), this method is simple and the Sephadex-tagged recombinant ncRNAs that failed to bind to Sephadex in the first round (e.g., flow-through and wash 1-3) may be combined for re-purification to offer a much improved total yield (e.g., 5-10%) close to anion exchange fast protein liquid chromatography method (Li et al., 2014; Chen et al., 2015).

Posttranscriptional modification of RNA molecules is ubiquitous in a living organism and it greatly increases the chemical diversity. As a result, the modified RNAs may exhibit different structures via alternative folding, as well as physicochemical properties and biological functions. Over 100 different base modifications such as methylation, pseudouridylation, thiolation and reduction of uracil to dihydrouracil have been identified for various classes of natural RNAs, and around 85% are present in tRNAs (Limbach et al., 1994; Cantara et al., 2011). Using mass spectrometry analyses of isolated tRNA/mir-1291 and tRNA/MSA, we were able to determine the modified nucleosides and map them to the specific sites in tRNA scaffold. A number of modified nucleosides occurred on the D- and T-loop, including D20, D21, [$m^7G$]77, [$acp^3U$]78,

[m⁵U]85 and Ψ86, which may be important for the stability (Alexandrov et al., 2006) and function of natural methionyl tRNA. Nevertheless, not all modifications detected by LC-UV-MS-based nucleoside analysis could be assigned to the recombinant ncRNAs, which might be attributed to the small fraction of co-purified bacterial tRNAs (Hossain and Limbach, 2007; 2009).

In the whole cell system, three orders of magnitude increase of pre-miR-1291 levels was shown at 72 h post-transfection, highlighting a successful introduction of tRNA/mir-1291 chimera into human cells and most importantly a favorable stability of recombinant ncRNAs within human cells. Consequently, mature miR-1291 levels were increased by two orders of magnitude, indicating a successful processing of tRNA/mir-1291 to mature miR-1291. It is noteworthy that all recombinant ncRNAs such as tRNA/mir-27 (Li et al., 2014), tRNA/mir-1291 (this study) and tRNA/mir-34a (Chen et al., 2015) showed favorable cellular stability and selective generation of target mature miRNAs, suggesting that tRNA carrier also offers a "stealth delivery" of target miRNAs into human cells beyond the production of chimeric ncRNAs in bacteria. Nevertheless, further studies are warranted to define the specific Rnases involved in the processing of recombinant ncRNAs in human cells.

The production of mature miR-1291 from chimeric RNAs led to a significant suppression of protein levels of miR-1291 target genes such as ABCC1 and FOXA2 in PANC-1 cells, and MeCP2 in MCF-7 cells. Overexpression of efflux transporter ABCC1 is associated with multidrug resistance (Filipits et al., 2005; Haber et al., 2006; Faggad et al., 2009), and down-regulation or inhibition of such transporters may represent an effective means to overcome multidrug resistance (Choi and Yu, 2014). Consistent with our recent studies (Pan et al., 2013), tRNA-carried pre-miR-1291 were able to suppress ABCC1 protein expression, and consequently led to an improved sensitivity of PANC-1 cells to doxorubicin. On the other hand, MeCP2 is the first methyl-CpG-binding domain protein discovered in its family which acts as a chromatin regulator of transcription and is encoded by the gene mutated in the neurodevelopmental disorder Rett syndrome (LaSalle and Yasui, 2009). MeCP2, usually overexpressed in human carcinomas, promotes the growth and invasiveness of many types of cancer cells including breast carcinoma cells (Billard et al., 2002; Ray et al., 2013) and may modulate ABCB1/MDR1 expression (El-Osta and Wolffe, 2001). FOXA2, a transcription factor belonging to the forkhead class of DNA-binding proteins, is revealed as an important regulator in promoting pancreatic/hepatic/colorectal cell differentiation and organ development (Gao et al., 2008; Song et al., 2010), and regulating the expression of some (proto-)oncogenes (Zhang et al., 2010) and a number of ABC transporters (Bochkis et al., 2008; Bochkis et al., 2012). Therefore, reduction of MeCP2 and FOXA2 protein levels may at least partially provide an explanation for miR-1291 in suppressing cancer cell proliferation (Yu et al., 2013; Bi et al., 2014) and enhancing chemosensitivity. Together, these findings indicate the potential utility of recombinant miR-1291 agent for examining miR-1291 functions and sensitizing human carcinoma cells to anticancer drugs.

In summary, this study demonstrated a rapid and efficient method for the production of multi-milligrams chimeric miR-1291 agents from 1 L bacterial culture in a research lab setting, which was achieved by using a methionyl tRNA scaffold. Our data showed the tRNA scaffold consisted of a number of natural posttranscriptional modifications, and the tRNA-carried pre-miR-1291 was effective to modulate miR-1291 target gene (e.g., ABCC1) expression in human carcinoma cells and improve chemosensitivity. The results offer clues to the production of new miRNA agents for studying pharmacoepigenetic and developing ncRNA therapeutics.

References for Example 2

Alexandrov, A., I. Chernyakov, W. Gu, S. L. Hiley, T. R. Hughes, E. J. Grayhack and E. M. Phizicky (2006). Rapid tRNA decay can result from lack of nonessential modifications. Mol Cell 21: 87-96.

Bader, A. G., D. Brown and M. Winkler (2010). The promise of microRNA replacement therapy. Cancer Res 70: 7027-7030.

Bi, H. C., Y. Z. Pan, J. X. Qiu, K. W. Krausz, F. Li, C. H. Johnson, C. T. Jiang, F. J. Gonzalez and A. M. Yu (2014). N-methylnicotinamide and nicotinamide N-methyltransferase are associated with microRNA-1291-altered pancreatic carcinoma cell metabolome and suppressed tumorigenesis. Carcinogenesis 35: 2264-2272.

Billard, L. M., F. Magdinier, G. M. Lenoir, L. Frappart and R. Dante (2002). MeCP2 and MBD2 expression during normal and pathological growth of the human mammary gland. Oncogene 21: 2704-2712.

Bochkis, I. M., N. E. Rubins, P. White, E. E. Furth, J. R. Friedman and K. H. Kaestner (2008). Hepatocyte-specific ablation of Foxa2 alters bile acid homeostasis and results in endoplasmic reticulum stress. Nat Med 14: 828-836.

Bochkis, I. M., J. Schug, D. Z. Ye, S. Kurinna, S. A. Stratton, M. C. Barton and K. H. Kaestner (2012). Genome-wide location analysis reveals distinct transcriptional circuitry by paralogous regulators Foxa1 and Foxa2. PloS Genet 8: e1002770.

Cantara, W. A., P. F. Crain, J. Rozenski, J. A. McCloskey, K. A. Harris, X. Zhang, F. A. Vendeix, D. Fabris and P. F. Agris (2011). The RNA Modification Database, RNAMDB: 2011 update. Nucleic Acids Res 39: D195-201.

Chen, Q. X., W. P. Wang, S. Zeng, S. Urayama and A. M. Yu (2015). A general approach to high-yield biosynthesis of chimeric RNAs bearing various types of functional small RNAs for broad applications. Nucleic Acids Res 43: 3857-3869.

Choi, Y. H. and A. M. Yu (2014). ABC transporters in multidrug resistance and pharmacokinetics, and strategies for drug development. Curr Pharm Des 20: 793-807.

El-Osta, A. and A. P. Wolffe (2001). Analysis of chromatin-immunopurified MeCP2-associated fragments. Biochem Biophys Res Commun 289: 733-737.

Faggad, A., S. Darb-Esfahani, R. Wirtz, B. Sinn, J. Sehouli, D. Konsgen, H. Lage, A. Noske, W. Weichert and A. C. Buckendahl (2009). Expression of multidrug resistance-associated protein 1 in invasive ovarian carcinoma: implication for prognosis. Histopathology 54: 657-666.

Filipits, M., G. Pohl, M. Rudas, 0. Dietze, S. Lax, R. Grill, R. Pirker, C. C. Zielinski, H. Hausmaninger and E. Kubista (2005). Clinical role of multidrug resistance protein 1 expression in chemotherapy resistance in early-stage breast cancer: the Austrian Breast and Colorectal Cancer Study Group. Journal of Clinical Oncology 23: 1161-1168.

Gao, N., J. LeLay, M. Z. Vatamaniuk, S. Rieck, J. R. Friedman and K. H. Kaestner (2008). Dynamic regulation of Pdx1 enhancers by Foxa1 and Foxa2 is essential for pancreas development. Genes Dev 22: 3435-3448.

Haber, M., J. Smith, S. B. Bordow, C. Flemming, S. L. Cohn, W. B. London, G. M. Marshall and M. D. Norris (2006). Association of high-level MRP1 expression with poor clinical outcome in a large prospective study of primary neuroblastoma. Journal of Clinical Oncology 24: 1546-1553.

Haenisch, S., S. Laechelt, H. Bruckmueller, A. Werk, A. Noack, 0. Bruhn, C. Remmler and I. Cascorbi (2011). Down-regulation of ATP-binding cassette C2 protein expression in HepG2 cells after rifampicin treatment is mediated by microRNA-379. Molecular pharmacology 80: 314-320.

Hidaka, H., N. Seki, H. Yoshino, T. Yamasaki, Y. Yamada, N. Nohata, M. Fuse, M. Nakagawa and H. Enokida (2012). Tumor suppressive microRNA-1285 regulates novel molecular targets: aberrant expression and functional significance in renal cell carcinoma. Oncotarget 3: 44-57.

Hossain, M. and P. A. Limbach (2007). Mass spectrometry-based detection of transfer RNAs by their signature endonuclease digestion products. RNA 13: 295-303.

Hossain, M. and P. A. Limbach (2009). Multiple endonucleases improve MALDI-MS signature digestion product detection of bacterial transfer RNAs. Anal Bioanal Chem 394: 1125-1135.

Krivos, K. L., B. Addepalli and P. A. Limbach (2011). Removal of 3'-phosphate group by bacterial alkaline phosphatase improves oligonucleotide sequence coverage of Rnase digestion products analyzed by collision-induced dissociation mass spectrometry. Rapid Commun Mass Spectrom 25: 3609-3616.

LaSalle, J. M. and D. H. Yasui (2009). Evolving role of MeCP2 in Rett syndrome and autism. Epigenomics 1: 119-130.

Li, M. M., W. P. Wang, W. J. Wu, M. Huang and A. M. Yu (2014). Rapid Production of Novel Pre-MicroRNA Agent has-mir-27b in *Escherichia coli* Using Recombinant RNA Technology for Functional Studies in Mammalian Cells. Drug Metab Dispos 42: 1791-1795

Li, X., Y. Z. Pan, G. M. Seigel, Z. H. Hu, M. Huang and A. M. Yu (2011). Breast cancer resistance protein BCRP/ABCG2 regulatory microRNAs (has-miR-328, -519c and −520 h) and their differential expression in stem-like ABCG2+ cancer cells. Biochem Pharmacol 81: 783-792.

Liang, Z., H. Wu, J. Xia, Y. Li, Y. Zhang, K. Huang, N. Wagar, Y. Yoon, H. T. Cho, S. Scala and H. Shim (2010). Involvement of miR-326 in chemotherapy resistance of breast cancer through modulating expression of multidrug resistance-associated protein 1. Biochem Pharmacol 79: 817-824.

Limbach, P. A., P. F. Crain and J. A. McCloskey (1994). Summary: the modified nucleosides of RNA. Nucleic Acids Res 22: 2183-2196.

Lin, X. and W. G. Nelson (2003). Methyl-CpG-binding domain protein-2 mediates transcriptional repression associated with hypermethylated GSTP1 CpG islands in MCF-7 breast cancer cells. Cancer Res 63: 498-504.

Liu, Y., V. G. Stepanov, U. Strych, R. C. Willson, G. W. Jackson and G. E. Fox (2010). DNAzyme-mediated recovery of small recombinant RNAs from a 5S rRNA-derived chimera expressed in *Escherichia coli*. BMC Biotechnol 10: 85.

Markova, S. M. and D. L. Kroetz (2014). ABCC4 is regulated by microRNA-124a and microRNA-506. Biochem Pharmacol 87: 515-522.

Nelissen, F. H., E. H. Leunissen, L. van de Laar, M. Tessari, H. A. Heus and S. S. Wijmenga (2012). Fast production of homogeneous recombinant RNA—towards large-scale production of RNA. Nucleic Acids Res 40: e102.

Pan, Y. Z., M. E. Morris and A. M. Yu (2009). MicroRNA-328 negatively regulates the expression of breast cancer resistance protein (BCRP/ABCG2) in human cancer cells. Mol Pharmacol 75: 1374-1379.

Pan, Y. Z., A. Zhou, Z. Hu and A. M. Yu (2013). Small nucleolar RNA-derived microRNA has-miR-1291 modulates cellular drug disposition through direct targeting of ABC transporter ABCC1. Drug Metab Dispos 41: 1744-1751.

Pomerantz, S. C. and J. A. McCloskey (1990). Analysis of RNA hydrolyzates by liquid chromatography-mass spectrometry. Methods Enzymol 193: 796-824.

Ponchon, L., G. Beauvais, S. Nonin-Lecomte and F. Dardel (2009). A generic protocol for the expression and purification of recombinant RNA in *Escherichia coli* using a tRNA scaffold. Nat Protoc 4: 947-959.

Ponchon, L. and F. Dardel (2007). Recombinant RNA technology: the tRNA scaffold. Nat Methods 4: 571-576.

Ray, B. K., S. Dhar, C. Henry, A. Rich and A. Ray (2013). Epigenetic regulation by Z-DNA silencer function controls cancer-associated ADAM-12 expression in breast cancer: cross-talk between MeCP2 and NF1 transcription factor family. Cancer Res 73: 736-744.

Russell, S. P. and P. A. Limbach (2013). Evaluating the reproducibility of quantifying modified nucleosides from ribonucleic acids by LC-UV-MS. J Chromatogr B Analyt Technol Biomed Life Sci 923-924: 74-82.

Song, Y., M. K. Washington and H. C. Crawford (2010). Loss of FOXA1/2 is essential for the epithelial-to-mesenchymal transition in pancreatic cancer. Cancer Res 70: 2115-2125

Taucher, M. and K. Breuker (2010). Top-down mass spectrometry for sequencing of larger (up to 61 nt) RNA by CAD and EDD. J Am Soc Mass Spectrom 21: 918-929.

To, K. K., Z. Zhan, T. Litman and S. E. Bates (2008). Regulation of ABCG2 expression at the 3' untranslated region of its mRNA through modulation of transcript stability and protein translation by a putative microRNA in the 51 colon cancer cell line. Mol Cell Biol 28: 5147-5161.

Trang, P., J. B. Weidhaas and F. J. Slack (2008). MicroRNAs as potential cancer therapeutics. Oncogene 27 Suppl 2: S52-57.

Wong, S. Y., B. Javid, B. Addepalli, G. Piszczek, M. B. Strader, P. A. Limbach and C. E. Barry, 3' (2013). Functional role of methylation of G518 of the 16S rRNA 530 loop by GidB in *Mycobacterium tuberculosis*. Antimicrob Agents Chemother 57: 6311-6318.

Yamasaki, T., N. Seki, H. Yoshino, T. Itesako, Y. Yamada, S. Tatarano, H. Hidaka, T. Yonezawa, M. Nakagawa and H. Enokida (2013). Tumor-suppressive microRNA-1291 directly regulates glucose transporter 1 in renal cell carcinoma. Cancer Sci 104: 1411-1419.

Zhang, Y., T. Z. Ali, H. Zhou, D. R. D'Souza, Y. Lu, J. Jaffe, Z. Liu, A. Passaniti and A. W. Hamburger (2010). ErbB3 binding protein 1 represses metastasis-promoting gene anterior gradient protein 2 in prostate cancer. Cancer Res 70: 240-248.

Example 3

Bioengineering Novel Chimeric Microrna-34a for Prodrug Cancer Therapy: High-Yield Expression and Purification, and Structural and Functional Characterization Development of microRNA (miRNA or miR) based treatments such as miR-34a replacement therapy is limited to the use of synthetic RNAs with artificial modifications. This example demonstrates the high-yield and large-scale biosynthesis of chimeric miR-34a agent in *Escherichia coli* using tRNA scaffold, which can act as a prodrug for cancer therapy. The recombinant tRNA fusion pre-miR-34a (tRNA/mir-34a) was quickly purified to a high degree of homogeneity (>98%) using anion-exchange fast protein liquid chromatography (FPLC), whose primary sequence and posttranscriptional modifications were directly characterized by mass spectrometric analyses. Chimeric tRNA/mir-34a showed favorable cellular stability while it was degradable by several ribonucleases. Deep sequencing and qPCR studies revealed that tRNA-carried pre-miR-34a was precisely processed to mature miR-34a within human carcinoma cells, whereas the same tRNA fragments were produced from tRNA/mir-34a and the control tRNA scaffold (tRNA/MSA). Consequently, tRNA/mir-34a inhibited the proliferation of various types of human carcinoma cells in a dose dependent manner and to much greater degrees than the control tRNA/MSA, which was mechanistically attributable to the reduction of miR-34a target genes. Furthermore, tRNA/mir-34a significantly suppressed the growth of human non-small cell lung cancer A549 and hepatocarcinoma HepG2 xenograft tumors in mice, compared to the same dose of tRNA/MSA. In addition, recombinant tRNA/mir-34a had no or minimal effects on blood chemistries and IL-6 levels in mouse models, suggesting that recombinant RNAs were well tolerated. These findings demonstrate feasible production of biological miRNAs to perform miRNA actions, and miRNA-based therapies.

Introduction

MicroRNAs have been revealed as a large family of genomically-encoded noncoding RNAs (ncRNAs) that are critical factors in the control of cancer cell proliferation, apoptosis and invasion, and tumor initiation and progression (Kasinski and Slack, 2011; Bader, 2012), as well as drug disposition (Yu, 2009; Ingelman-Sundberg et al., 2013) and pathogenesis of other diseases (Yao and Li, 2015). Research on miRNA biological functions has offered clues to develop novel cancer treatments, and a number of miRNA-based therapies are indeed under or moving towards clinical trials. In particular, oncogenic miRNAs such as miR-10b, which are upregulated in cancer cells, may be targeted to achieve the control of cancer cell proliferation and tumor growth (Ma et al., 2007). On the other hand, tumor suppressive miRNAs such as miR-34a showing a loss-of-function in cancerous tissues may be reintroduced into cancer cells to suppress tumor progression (He et al., 2007; Welch et al., 2007). The later approach, namely "miRNA replacement therapy", is distinguished from the former miRNA antagonism strategy. The miRNA or pre-miRNAs used in miRNA replacement therapy have the same sequences as genomically-encoded miRNAs or pre-miRNAs, and therefore unlikely to produce "off-target" effects. Meanwhile, because miRNAs are normal constituents of healthy cells, reintroduction of therapeutic miRNAs is unlikely to cause major toxicity (Bader, 2012).

Human miR-34a is one of the most promising tumor suppressive miRNAs for cancer treatment. Loss of miR-34a expression has been documented in a wide range of solid tumors and hematological malignancies, including lung, prostate, breast, pancreas, liver, colon, kidney, bladder, skin, esophagus, brain, cervix, ovary, urothelium and lymphoid systems (see review (Bader, 2012)). While the biogenesis of miR-34a is directly controlled by tumor protein p53 at the transcriptional level (Chang et al., 2007; He et al., 2007), ectopic expression of miR-34a leads to a dramatic reprogramming of a set of target genes such as cyclin-dependent kinase 6 (CDK6), hepatocyte growth factor receptor MET, platelet-derived growth factor receptor-alpha (PDGFRA) and GTPase KRAS, and consequently inhibits cancer cell proliferation, induces cell cycle arrest and enhances apoptosis (Chang et al., 2007; He et al., 2007; Sun et al., 2008; Yamakuchi et al., 2008; Li et al., 2009; Kasinski and Slack, 2012). Meanwhile, miR-34a can stimulate endogenous p53 activity in a positive feedback-loop by targeting the NAD-dependent deacetylase sirtuin-1 (SIRT1) that deactivates p53, and the transcriptional repressor Yin Yang 1 (YY1) that binds to p53 and promotes p53 ubiquitination and degradation (Yamakuchi et al., 2008). Moreover, miR-34a suppresses clonogenic expansion, tumor regeneration and metastasis through targeting CD44 and cancer stem cells or tumor-initiating cells (Liu et al., 2011). The anticancer activity of miR-34a has been nicely demonstrated in various types of human carcinoma cells in vitro including lung, liver, pancreas, colon, brain, skin, prostate, bone, ovary, as well as lymphoma and leukemia. In addition, although the performance of miR-34a replacement therapy in animal models depends heavily on the delivery system used, a number of successful examples have illustrated the effectiveness of miR-34a in inhibiting progression of many types of xenograft tumors, including non-small cell lung cancer (Wiggins et al., 2010; Kasinski and Slack, 2012), prostate cancer (Liu et al., 2011), pancreatic cancer (Pramanik et al., 2011) and lymphomas (Craig et al., 2012). As a result, "MRX34", a liposome-formulated miR-34a, has entered Phase I clinical trials for the treatment of unresectable primary liver cancer (Kelnar et al., 2014).

Nevertheless, research on miRNA pharmacology and therapeutics rely primarily on the use of synthetic RNAs (e.g., miRNA mimics and antagomirs, and pre-miRNAs (mir)) and recombinant DNA agents (e.g., viral or non-viral vector-based miRNA or "decoy" antisense RNA expression plasmids). The use of DNA materials may complicate the RNA-based processes, and this approach also relies on the host cells or organisms to transcribe the gene to miRNA precursors before the generation of mature miRNAs. Despite that organic synthesis of oligonucleotides may be automated, a multi-milligram dose of 22-nt double-stranded miRNA mimics projected for in-vivo testing or therapy is very costly. In addition, it is unknown how artificial modifications may alter the folding, biological activities and safety profiles, even though synthetic miRNAs exhibit some favorable pharmacokinetic properties such as a longer half-life.

Motivated by the idea to deploy biological RNAs to perform RNA actions for pharmacotherapy, we aimed to bioengineer pre-miRNA (mir) agents in common strains of bacteria on a large scale using the tRNA scaffold (Ponchon and Dardel, 2007; Ponchon et al., 2009; Nelissen et al., 2012). We hypothesized that the tRNA fusion pre-miRNA (tRNA/mir) could act as a prodrug where pre-miRNA might be selectively processed to mature miRNA in human cells, and tRNA scaffold would be metabolized or degraded to tRNA fragments (tRFs). In contrast to a low-yield production of pre-miR-27b (Li et al., 2014), we present herein an optimal expression and rapid purification of multi-milligrams of tRNA fusion pre-miR-34a (tRNA/mir-34a) from 1 L bacterial culture in a research laboratory setting. The molecular weight, primary sequence, and posttranscriptional modifications of recombinant tRNA/mir-34a were directly characterized by mass spectrometry (MS) studies. Furthermore, unbiased deep sequencing study and targeted qPCR analyses showed that tRNA-carried pre-miR-34a was indeed processed precisely into mature miR-34a in human carcinoma cells, leading to a 70- to 100-fold increase in cellular miR-34a levels. Consequently, tRNA/mir-34a significantly suppressed the protein levels of miR-34a target genes (e.g., CDK6, SIRT1, and MET) and proliferation of human lung (A549 and H460) and liver (HepG2 and Huh-7) cancer cells in vitro in a dose-dependent manner, as compared to the control tRNA scaffold (tRNA/MSA). In addition, we demonstrated that recombinant tRNA/mir-34a was well tolerated in animal models, and remarkably repressed A549 and HepG2 xenograft tumor growth in vivo. These findings indicate that biological RNA agents engineered in bacteria serve as a new category of RNA agents for drug discovery as well as basic and translational research.

Materials and Methods

Chemicals and Materials. Lipofectamine 2000, Trizol reagent and BCA Protein Assay Kit were purchased from Thermo Fisher Scientific Inc. (Waltham, Mass.). RIPA lysis buffer was bought from Rockland Immunochemicals (Limerick, Pa.), and the complete protease inhibitor cocktail was purchased from Roche Diagnostics (Mannheim, Germany). The antibodies against CDK6 (C-21), SIRT1 (H-300), Met (C-28) and glyceraldehyde-3-phosphate dehydrogenase (GAPDH) were purchased from Santa Cruz Biotech Inc. (Texas, Tex.), and peroxidase goat anti-rabbit IgG was from Jackson ImmunoResearch Inc. (West Grove, Pa.). ECL substrate and PVDF membrane were bought from Bio-Rad (Hercules, Calif.). All other chemicals and organic solvents of analytical grade were purchased from Sigma-Aldrich (St. Louis, Mo.) or Thermo Fisher Scientific Inc. (Waltham, Mass.).

Bacterial Culture. All $E.$ $coli$ stains were cultured at 37° C. in LB broth supplemented with 100 μg/mL ampicillin. DH5α and TOP10 (Life Technologies, Grand Island, N.Y.) were used for cloning as well as screening for recombinant ncRNA expression. BL21 (Sigma-Aldrich, St. Louis, Mo.) and HST08 (Clontech Laboratories, Mountain View, Calif.) were also used to screen ncRNA accumulation. HST08 was identified and utilized for large-scale production of recombinant ncRNAs.

Human Cell Culture. The human carcinoma cell lines HepG2, Huh-7, A549 and H460 were purchased from American Type Culture Collection (Manassas, Va.). HepG2 cells were cultured in EMEM medium, A549 and H460 cells in RPMI 1640 medium, and Huh-7 cells in DMEM medium supplemented with 10% fetal bovine serum (GBICO BRL, Rockville, Md.), at 37° C. in a humidified atmosphere containing 5% $CO_2$. Cells in the logarithmic growth phase were used for experiments.

Prediction of RNA Secondary Structure. The secondary structures of various sizes of human pre-miR-34a, tRNA scaffold, and the chimeric ncRNAs were predicted using the CentroidFold (http://www.ncrna.org/centroidfold), CentroidHomfold (http://www.ncrna.org/centroidhomfold), and RNAstructure (http://rna.urmc.rochester.edu/RNAstructureWeb/Servers/Predict 1/Predict 1.html).

Construction of tRNA/mir-34a Expression Plasmids. The DNA fragments encoding 112-nt and 129-nt human pre-miR-34a (miRBase ID: MI0000268) were amplified from human genomic DNA by PCR using the primers 5'-AGT AAT TTA CGT CGA CGG CCA GCT GTG AGT GTT TCT TTG G-3' (SEQ ID NO:100) and 5'-CGG CCG CAA CCA TCG ACG TCT GGG CCC CAC AAC GTG CAG CAC TT-3' (SEQ ID NO:101), and 5'-AGT AAT TTA CGT CGA CGT GGA CCG GCC AGC TGT GAG TGT T-3' (SEQ ID NO:51) and 5'-CGG CCG CAA CCA TCG ACG TCA TCT TCC CTC TTG GGC CCC ACA ACG-3' (SEQ ID NO:52) (IDT, San Diego, CA), respectively. The amplicons were inserted into the pBSMrnaSeph vector (kindly provided by Dr. Luc Ponchon at the Université Paris Descartes) (Ponchon et al., 2009) linearized with SalI-HF® and AatII (New England Biolabs, Ipswich, MA). Target tRNA/mir-34a expression plasmids were confirmed by Sanger sequencing analyses at UC Davis Genome Center.

Expression of Recombinant ncRNAs in $E.$ $coli.$ Recombinant ncRNAs were expressed in HST08 as described (Ponchon and Dardel, 2007; Ponchon et al., 2009; Li et al., 2014). Total RNAs were isolated using the Tris-HCl-saturated phenol extraction method, quantitated with a NanoDrop 2000 spectrophotometer (Thermo Fisher Scientific, Rockford, Ill.), and analyzed by denaturing urea (8 M) polyacrylamide (8%) gel electrophoresis (PAGE) to assess the expression of recombinant ncRNAs. We usually loaded 0.2-1.0 μg RNAs per lane for the urea-PAGE analysis. The ssRNA ladder and siRNA marker were purchased from New England Biolabs. Images were acquired with ChemiDo MP Imaging System (Bio-Rad, Hercules, Calif.), and intensities of bands were used to provide a rough estimation of relative levels of recombinant ncRNAs present in the total RNAs.

Affinity Purification of Recombinant ncRNAs. Purification of sephadex aptamer-tagged ncRNAs using Sephadex G-100 beads (Sigma-Aldrich) was conducted as reported (Ponchon et al., 2009; Li et al., 2015), and RNA fractions were analyzed by urea-PAGE.

FPLC Purification of Recombinant ncRNAS. Recombinant tRNA/mir-34a was purified from total RNAs on a UNO Q6 anion-exchange column (Bio-Rad) using a NGC QUEST 10PLUS CHROM FPLC System (Bio-Rad). After the samples were loaded, the column was first equilibrated with Buffer A (10 mM sodium phosphate, pH=7.0) at a flow rate 6.0 mL/min for 0.5 min, followed by a gradient elution at the same flow rate, 0-56% Buffer B (Buffer A plus 1 M sodium chloride) in 0.5 min, 56% Buffer B for 2 min, 56-65% Buffer B in 10 min, and then 100% Buffer B for 2 min, 100-0% Buffer B in 0.5 min and 100% Buffer A for 5 min. The salt gradient elution condition for the control tRNA/MSA was essentially the same as reported (Li et al., 2014). FPLC traces were monitored at 260 nm using a UV/Vis detector. Peak areas were also utilized to estimate the relative levels of recombinant ncRNAs within the total RNAs, which were consistent with those determined by urea-PAGE analyses. After analyzed by urea-PAGE, the fractions containing pure ncRNAs were pooled. Recombinant ncRNAs were precipitated with ethanol, reconstituted with nuclease-free water, and then desalted and concentrated with Amicon ultra-2 mL centrifugal filters (30 KD; EMD Millipore, Billerica, Mass.). The quantity of ncRNAs was determined using a NanoDrop 2000 spectrophotometer and the quality was validated by PAGE and HPLC analysis before other experiments.

HPLC Analysis of Purified ncRNAs. HPLC analysis was conducted using an) (Bridge OST C18 column (2.1×50 mm, 2.5 μm particle size; Waters, Milford, Mass.) on a Shimadzu LC-20AD HPLC system. The flow rate was 0.2 mL/min, and the column was maintained at 60° C. Mobile phase A consisted of 8.6 mM triethylamine (TEA) and 100 mM hexafluoroisopropanol (HFIP, pH 8.3) in water, and mobile phase B consisted of 8.6 mM TEA and 100 mM HFIP in methanol. The LC gradient was as follows: 0-1 min, 16% mobile phase B; 21 min, 22% mobile phase B. RNA was monitored at 260 nm using a photodiode array detector.

Removal and Detection of Endotoxin. Endotoxin was further removed from FPLC-purified ncRNAs using the CleanAll DNA/RNA Clean-up Kit (Norgen Biotek, Thorold, ON, Canada) and Endotoxin-free Water (Lonza, Walkersville, Md.), as instructed by the manufacturer. Endotoxin activities in total RNAs as well as the FPLC-purified and CleanAll Kit-processed ncRNA samples were determined using the Pyrogent-5000 kinetic LAL assay (Lonza) by following the instructions. In particular, a SpectraMax3 plate reader (Molecular Devices, Sunnyvale, Calif.) was used to measure turbidity at a 340 nm wavelength. Provided endotoxin standards were used to generate a standard curve, and endotoxin levels in RNA samples were expressed in EU/µg RNA (endotoxin units/µg RNA).

Electrospray Ionization-Mass Spectrometry (ESI-MS) Analysis of Intact Recombinant ncRNAs. The procedures described by Taucher and Breuker (Taucher and Breuker, 2010) were followed. The instrumental settings were optimized by automatic tuning with poly d(T)80. The mass spectra were acquired in negative ion mode using a Thermo LTQ XL-ion trap mass spectrometer over an m/z range of 600-2000. ESI mass spectra of intact ncRNAs were deconvoluted using ProMass software for Xcalibur (Version 2.8 rev. 2) (Novatia LLC, Newtown, Pa.) to determine the average molecular weights (MWs) of recombinant RNAs.

Nucleoside Analysis by LC-UV-MS. The hydrolysates were prepared with Nuclease P1 (Sigma-Aldrich), snake venom phosphodiesterase (Worthington Biochemicals Lakewood, Lakewood, N.J.) and antarctic phosphatase (New England Biolabs), resolved on a 5 µm, 2.1 mm×250 mm Supelcosil LC-18-S column using a Hitachi D-7000 HPLC system, and analyzed by a diode array detector and a Thermo LTQ-XL ion trap mass spectrometer, as described by Russell and Limbach (Russell and Limbach, 2013).

RNA Mapping by LC-MS/MS. RNA mapping and assignment of modifications using a Thermo Surveyor HPLC system coupled to a Thermo LTQ XL ion trap mass spectrometer and a Thermo Micro AS autosampler after the digestion with RNase T1 (Roche Molecular Biochemicals, Indianapolis, Ind.) and bacterial alkaline phosphatase (Worthington Biochemical Corporation) was carried out as described (Krivos et al., 2011). Collision-induced dissociation tandem mass spectrometry (CID MS/MS) was used to obtain sequence information from the RNase digestion products.

Susceptibility to RNases. Recombinant ncRNAs were digested by individual RNases in provided buffer or HEPES (100 mM KCl, 5 mM $MgCl_2$, 10 mM HEPES, pH 7.4) at 37° C. for 1 h. In particular, 12 µg ncRNAs were incubated with 1 µg/mL human recombinant RNase I (Novoprotein, Summit, N.J.), 12 µg ncRNAs with 10 µg/mL Human Recombinant Angiogenin (R&D Systems, Minneapolis, Minn.), 1 µg ncRNAs with 1 U of recombinant Dicer (Genlantis Inc., San Diego, Calif.), 6 µg ncRNAs with 5 U of bacterial RNase III (Life Technologies), and 5 µg ncRNAs with 5 U of RNase R (Epicentre, Madison, Wis.). Likewise, 4 µg RNA was formulated with 0.64 µL in vivo-jetPEI (Polyplus-transfection Inc., New York, N.Y.) delivery agent to a 5% final glucose concentration, and then added to OptiMEM with or without 1 µL human serum (Thermo Scientific) to a 100 µL volume and incubated at 37° C. for 20 min. The digestion products were analyzed by 8% urea PAGE.

Reverse Transcription Quantitative Real-Time PCR (RT-qPCR). Total RNA was isolated from cells using Direct-zol RNA MiniPrep kit (Zymo Research, Irvine, CA), and reverse transcribed with NxGen M-MuLV reverse transcriptase (Lucigen, Middleton, WI) and stem-loop primer 5'-GTC GTA TCC AGT GCA GGG TCC GAG GTA TTC GCA CTG GAT ACG ACA CAA CC-3' (SEQ ID NO:139) for miR-34a, or iScript reverse-transcription Supermix (Bio-Rad) for chimeric ncRNAs, pre-miR-34a and U6. Quantitative real-time PCR (qPCR) was conducted with quantitative RT-PCR Master mix (New England Biolabs) on a CFX96 Touch real-time PCR system (Bio-Rad), as described (Bi et al., 2014; Li et al., 2014). The primers were as follows: 5'-GGC TAC GTA GCT CAG TTG GT-3' (SEQ ID NO:103) (forward) and 5'-TGG TGG CTA CGA CGG GAT TC-3' (SEQ ID NO:104) (reverse) for chimeric ncRNAs; 5'-GGC CAG CTG TGA GTG TTT CTT TGG-3' (SEQ ID NO:105) (forward) and 5'-GGG CCC CAC AAC GTG CAG-3' (SEQ ID NO:106) (reverse) for pre-miRNA mir-34a; 5'-CGC GCT GGC AGT GTC TTA GCT-3' (SEQ ID NO:107) (forward) and 5'-GTG CAG GGT CCG AGG T-3' (SEQ ID NO:108) (reverse) for mature miR-34a; and 5'-CTC GCT TCG GCA GCA CA-3' (SEQ ID NO:109) (forward) and 5'-AAC GCT TCA CGA ATT TGC GT-3' (SEQ ID NO:110) (reverse) for U6. The relative expression was calculated by using the comparative threshold cycle (Ct) method with the formula 2-ΔΔCt.

Small RNA Library Construction. Total RNAs were isolated with Trizol reagent (Invitrogen) from A549 cells harvested at 48 h post-treatment with highly purified ncRNAs or Lipofectamine 2000 (Life Technologies) itself, and the small RNA library was generated using the Illumina Truseq™ Small RNA Preparation kit (Illumina, San Diego, Calif.) according to the instructions.

Deep Sequencing and Data Analysis. The purified cDNA library was used for cluster generation on Illumina's Cluster Station and then sequenced on Illumina GAIIx following vendor's instructions. Raw sequencing reads (40 nt) were obtained using Illumina's Sequencing Control Studio software version 2.8 (SCS v2.8) following real-time sequencing image analysis and base-calling by Illumina's Real-Time Analysis version 1.8.70 (RTA v1.8.70). The extracted sequencing reads were used for the standard sequencing data analysis by following a proprietary pipeline script, ACGT101-miR v4.2 (LC Sciences, Houston, Tex.).

Immunoblot Analysis. The cell lysates were prepared using RIPA buffer (Rockland Immunochemical Inc., Limerick, Pa.) supplemented with the complete protease inhibitor cocktail (Roche, Nutley, N.J.). Protein concentrations were determined using the BCA Protein Assay Kit (Thermo Fisher Scientific). Proteins were separated on a 10% SDS-PAGE gel and electro-transferred onto PVDF membranes using Trans-Blot Turbo Transfer System (Bio-Rad). Membranes were incubated with CDK6 (C-21), SIRT1 (H-300), or Met (C-28) rabbit polyclonal antibody (Santa Cruz Biotech Inc., Texas, Tex.) and subsequently with a peroxidase goat anti-rabbit IgG (Jackson ImmunoResearch Inc., West Grove, Pa.). The membranes were then incubated with Clarity Western ECL substrates (Bio-Rad) and visualized with the ChemiDoc MP Imaging System (Bio-Rad).

Cytotoxicity. The effects of tRNA/mir-34a on the proliferation of cancer cells were determined using an MTT assay, as described (Pan et al., 2013; Li et al., 2015). Cells were seeded in 96-well plates at 3,000 or 5,000 cells per well, and transfected with various concentrations of tRNA/mir-34a using Lipofectamine 2000 for 72 h. Cells transfected with the same doses of tRNA/MSA or Lipofectamine 2000 were used as controls. The EC50 and Hill slope values were estimated by fitting the data to a normalized inhibitory dose-response model (GraphPad Prism, San Diego, Calif.).

Xenograft Tumor Mouse Models. All animal procedures were approved by the Institutional Animal Care and Use Committee at UC Davis. A549 and HepG2 cells were collected, counted, and mixed with Matrigel (BD Biosciences, San Jose, Calif.) in a 1:1 ratio by volume. Cells ($5 \times 10^6$) in 100 µL of medium/Matrigel solution were injected s.c. into the lower back region of 5- to 6-week-old male nude mice (The Jackson Laboratory, Bar Harbor, Me.). Tumor volumes were measured with a caliper and calculated according to the formula, tumor volume ($mm^3$)=0.5µ (length (mm)×width (mm$^2$)). Recombinant tRNA/mir-34a and control tRNA/MSA were formulated with in vivo-jetPEI (Polyplus-transfection Inc.) and administered intratumorally (i.t.) once tumors reached 150-200 mm$^3$. Tumors were collected, fixed in 10% formalin and cut for histological verification by pathologist.

Safety Profiles in Mouse Models. Male BALB/c mice at five to six weeks of age (The Jackson Laboratory) were administered i.v. via tail vein with 100 µg of ncRNAs formulated with in vivo-jetPEI. Separate groups of animals were treated with in vivo-jetPEI vehicle as a negative control or 20 µg of lipopolysaccharide (LPS) as a positive control for cytokine induction (Wiggins et al., 2010; Bodeman et al., 2013; Wang et al., 2015). Blood was collected at various time points and serum was isolated using the serum separator (BD Biosciences). Serum cytokine IL-6 levels were quantitated using a mouse IL-6 assay kit (Pierce Thermo Scientific) on a SpectraMax M3 Multi-Mode Spectrophotometer (Molecular Devices), and mouse blood chemistry profiles were determined at the Comparative Pathology Laboratory at UC Davis.

Statistical Analysis. All data were presented as mean±SD. According to the number of groups and variances, data were analyzed with unpaired Student's t-test, or one-way or two-way ANOVA (GraphPad Prism). Any difference was considered as significant if the probability was less than 0.05 ($P<0.05$).

Results

Chimeric tRNA/mir-34a can be efficiently biosynthesized in a common strain of E. coli on a large scale and rapidly purified to a high degree of homogeneity. To achieve high-yield production of pre-miR-34a agents in E. coli, we chose to use the tRNA scaffold (Ponchon and Dardel, 2007; Ponchon et al., 2009) to assemble a fusion ncRNA namely tRNA/mir-34a (FIG. 17A). The secondary structures predicted by different computational algorithms all indicated that the stem-loop structure of pre-miR-34a consisting of Dicer cleavage sites would be retained within tRNA/mir-34a chimeras. Thus the pre-miR-34a coding sequences were cloned to offer tRNA/mir-34a expression plasmids. Our data showed that slight change in the length of pre-miR-34a did not alter the levels of recombinant tRNA/mir-34a accumulated (FIG. 18A). Target tRNA/mir-34a agents were expressed in different common E. coli strains and the highest accumulation levels were found in HST08 cells (FIG. 17B) at 9-14 h post-transformation (FIG. 18B). In addition, use of HST08 competent cells prepared within our laboratory offered similar levels of recombinant tRNA/mir-34a (FIG. 18C), and the high-level expression (e.g., ~15% of recombinant ncRNAs in total RNAs) was retained when bacterial cultures were scaled up to 0.5 L, and different batches of cultures were carried out (FIG. 18D), demonstrating a consistent and efficient expression of biological tRNA/mir-34a agents.

Next, we aimed to purify the recombinant tRNA/mir-34a to a high degree of homogeneity (e.g., >98%). Affinity purification was originally carried out for tRNA/mir-34a and the control tRNA/MSA bearing a Sephadex aptamer tag. Although affinity chromatography offered a good purity (>90%), overall yield was not very satisfactory (around 2% of recombinant ncRNA/total RNAs) which may be attributed to an unexpected but obvious inefficient binding (FIG. 18E). Thus we developed an anion exchange FPLC method for the isolation of tRNA/mir-34a and tRNA/MSA from total RNAs using a salt gradient elution. This FPLC method not only enabled rapid isolation of target ncRNAs 25 min per run; FIG. 17C) to a high degree of homogeneity (e.g., >98% purity, as demonstrated by gel electrophoresis and HPLC analysis (FIG. 17D) but also offered much higher purification yield (e.g., 67% according to the 15% target ncRNA present in total RNAs, or 10% recombinant ncRNA/ total RNAs loaded on column). This FPLC method largely facilitated the purification process which allows us to readily obtain milligrams of ncRNAs, i.e., ~1.5 mg of >98% pure tRNA/mir-34a from 15 mg of total RNAs isolated from 0.5 L bacterial culture at all times.

Recombinant ncRNAs carry posttranscriptional modifications. To delineate if the recombinant tRNA/mir-34a are comprised of any posttranscriptional modifications, which are common for natural RNAs produced in living cells (Novoa et al., 2012), we employed several mass spectrometry-based techniques to analyze the purified ncRNAs after confirming their primary sequences by Sanger sequencing of reversely-transcribed cDNAs. First, we determined the molecular weights (MWs) through electrospray ionization mass spectrometry (ESI-MS) analyses of the intact ncRNAs, which were 73,422.4 Da for tRNA/mir-34a and 34,765.2 Da for tRNA/MSA. The differences between the measured and predicted MWs (146.8 Da for tRNA/mir-34a, and 149.2 Da for tRNA/MSA; FIG. 19A) suggest the presence of modified nucleosides. We then conducted a LC-UV-MS analysis of ncRNA hydrolysates and identified a number of modified nucleosides for the tRNA scaffold (existing in both tRNA/ mir-34a and tRNA/MSA), such as dihydrouridine (D), pseudouridine (Ψ), 7-methylguanosine (m$^7$G), 4-thiouridine (s$^4$U), 2'-O-methylguanosine (Gm) and 3-(3-amino-3-carboxypropyl)uridine (acp$^3$U) (FIG. 19B). We thus carried out LC-MS/MS analyses (FIG. 19C) of RNA fragments produced from recombinant ncRNAs by RNase T1, which allowed us to successfully map the ncRNA sequences and localize all modified nucleosides for the tRNA scaffold (FIG. 17E). The deoxyadenosine (dA) found in tRNA/mir-34a hydrolysates (FIG. 19B) was not mapped to its RNase T1 digestions, which might be attributable to prior carry-over or co-purified nucleic acid. Together, these data indicate that recombinant ncRNAs obtained from E. coli indeed consist of various posttranscriptional modifications that may be critical for RNA folding and metabolic stability.

tRNA-Carried Pre-miR-34a is selectively processed to mature miR-34a in human carcinoma cells while the tRNA scaffold is degraded to tRNA fragments. To assess whether chimeric tRNA/mir-34a can be selectively processed to mature miR-34a in human cells, we first conducted unbiased deep sequencing study. The RNAseq data revealed that the tRNA/mir-34a chimera was precisely processed to mature miR-34a in A549 cells, leading to a 70-fold increase in miR-34a levels than the cells treated with tRNA/MSA or vehicle (FIG. 20A-B). In contrast, there was no or limited changes in other cellular miRNAs, except a few undefined small RNAs (e.g., hsa-miR-30c-5p_R+1 and hsa-mir-7641-1-p5_1ss6TC, etc.; FIG. 20A-B) which might be secondary effects that were caused by the changes in miR-34a target gene expression. Furthermore, the increase in miR-34a levels was attributed to the 22- and 23-nt isoforms that arose in tRNA/mir-34a-, tRNA/MSA- and vehicle-treated cells. In addition, the common tRNA scaffold was degraded in the cells to offer the same tRFs that exhibited similar patterns between tRNA/mir-34a- and tRNA/MSA-treated cells, whereas at much lower levels than mature miR-34a (FIG. 20B, supporting the use of tRNA/MSA as a proper control to distinguish the activities of pre-miR-34a.

Recombinant tRNA/Mir-34a exhibits a favorable cellular stability and is degradable by human RNases. Consistent with deep sequencing data, selective stem-loop RT-qPCR analyses revealed a 70- to 100-fold increase in mature miR-34a levels in human lung (A549 and H460) and liver (HepG2 and Huh-7) carcinoma cells after the transfection with tRNA/mir-34a (FIG. 21A). Moreover, mature miR-34a and pre-miR-34a levels were elevated in tRNA/mir-34a-treated A549 cells in a dose dependent manner; whereas there was no change of miR-34a levels in cells treated with tRNA/MSA where tRNA/MSA levels were actually increased (FIG. 21B). Most importantly, a high level of recombinant tRNA/mir-34a and tRNA/MSA persisted for 6 days in the cells post-transfection with levels gradually decreasing from day 3 (FIG. 21C), indicating a favorable cellular stability. In addition, the change of pre-miR-34a and mature miR-34a levels over time were solely dependent upon the tRNA/mir-34a treatment. Further biochemical experiments demonstrated that tRNA/mir-34a and tRNA/MSA were readily processed by RNase A (or RNase I, the major form of ribonuclease in human serum) and Dicer (RNase III) but to a relatively lower degree by angiogenin (RNase 5) (FIG. 21D), suggesting their involvement in the processing and degradation of recombinant ncRNAs. In contrast, bacterial RNase R was unable to cleave chimeric ncRNAs, providing a good explanation for why such ncRNAs were accumulated to high levels within bacteria.

tRNA-carried pre-miR-34a is active to reduce miR-34a target gene expression and to inhibit cancer cell proliferation, equally or more effective than synthetic miR-34a agents. We thus assessed the efficacy of tRNA-carried pre-miR-34a in the control of miR-34a target gene expression and cancer cell growth, using tRNA/MSA as a critical control. Recombinant tRNA/mir-34a showed a dose dependent inhibition against the proliferation of all types of cancer cells tested in our studies, to a much greater degree than the control tRNA/MSA (FIG. 22A and FIG. 23). The higher efficacy in suppressing cancer cell growth by tRNA/mir-34a was also indicated by the estimated EC50 values (Table 2). Inhibition of A549 and HepG2 carcinoma cell proliferation by tRNA/mir-34a was associated with a remarkable repression of a number of well-defined miR-34a target genes such as CDK6, SIRT1 and MET, as compared to the tRNA/MSA or vehicle treatments (FIG. 22B). In addition, we compared side-by-side the effectiveness of biological and synthetic miR-34a agents in human cell line models. Interestingly, our data showed that recombinant tRNA/mir-34a was relatively more effective to suppress the proliferation of A549 and HepG2 cells and the protein levels of miR-34a target genes (e.g., CDK6, SIRT1 and MET) than the same doses of synthetic pre-miR-34a and miR-34a mimics bearing artificial modifications, as compared to corresponding controls (FIG. 24A-B). These results indicate that tRNA-carried pre-miR-34a is biologically/pharmacologically active in the modulation of miR-34a target gene expression and cancer cell proliferation.

TABLE 2

Estimated EC50 and Hill slope values for the suppression of human carcinoma cell proliferation by recombinant tRNA/mir-34a and control tRNA/MSA

| Cell lines | EC50 (nM) | | Hill slope | |
|---|---|---|---|---|
| | tRNA/MSA | tRNA/mir-34a | tRNA/MSA | tRNA/mir-34a |
| A549 | Not fitted | 7.80 ± 1.19 | Not fitted | −2.18 ± 0.59 |
| H460 | 158 ± 1 | 5.72 ± 1.09* | −0.86 ± 0.20 | −1.32 ± 0.14* |
| HepG2 | 87.9 ± 1.1 | 4.75 ± 1.21* | −1.74 ± 0.40 | −0.96 ± 0.18* |
| Huh-7 | Not fitted | 11.1 ± 1.2 | Not fitted | −0.66 ± 0.07 |

(Goodness of Fit $R^2 > 0.75$).
"Not fitted" means that the Goodness of Fit is less than 0.50.
*Significantly ($P < 0.05$) different from the control tRNA/MSA in the same cell line.

Recombinant pre-miR-34a is effective to suppress xenograft tumor progression in mouse models. We thus evaluated the therapeutic effects of tRNA/mir-34a in vivo using human lung carcinoma A549 and hepatic carcinoma HepG2 xenograft tumor mouse models. When A549 xenograft tumors reached ~150 mm3 typically within 3 weeks after inoculation, we treated male nude mice intratumorally with 20 or 100 μg of in vivo-jetPEI-formulated tRNA/mir-34a, which would not be complicated by tissue distribution. Separate groups of animals were administered with the same doses of in vivo-jetPEI-formulated tRNA/MSA or only the in vivo-jetPEI vehicle as controls. Our data showed that, compared to the vehicle treatment or the same dose of tRNA/MSA, the higher dose (100 μg) of tRNA/mir-34a led to a complete disappearance of the A549 xenograft tumors (3 out of 6) and an overall significant repression of the outgrowth of viable tumors (FIG. 25A). The same dose (100 μg) of tRNA/mir-34a also significantly suppressed the growth of HepG2-derived xenografts (FIG. 25B), although to a lower degree than its effects on A549 xenografts. These findings indicate that recombinant tRNA-carried pre-miR-34a is effective to control xenograft tumor progression in vivo.

Chimeric ncRNAs are well tolerated in mouse models. We further investigated the safety profiles of recombinant tRNA/mir-34a agents produced in E. coli. The Limulus Amebocyte Lysate (LAL) assay was first conducted to evaluate whether these biological ncRNAs contain significant levels of endotoxin that may cause immune response or toxicity in mammalian cells. While total RNAs isolated from E. coli showed variable levels of endotoxin (100-1,000 EU/μg RNA), endotoxin activities were minimal for the ncRNAs purified with FPLC (<10 EU/μg RNA) and those further processed with an endotoxin removal kit (<3.0 EU/μg RNA). Despite the lack of an endotoxin safety standard for RNA agents and the uncertainty of whether RNAs influence (the mechanism of the) LAL assay, endotoxin activities in our purified ncRNAs measured much lower than 2,000 EU/μg DNA that is required to significantly inhibit transfection and cell proliferation (Butash et al., 2000).

After verifying that in vivo-jetPEI-loaded tRNA/mir-34a and tRNA/MSA were protected against degradation by serum RNases (FIG. 26A), we directly assessed the effects of in vivo-jetPEI-formulated ncRNAs on the immune response as well as hepatic and renal functions in immunocompetent BALB/c male mouse models. The activation of immune response is often indicated by the increase of blood levels of various cytokines, among which the pro- and anti-inflammatory cytokine IL-6 is the most sensitive in response to nucleic acids (Wiggins et al., 2010). As a positive control, LPS-treated mice showed an immediate sharp surge of serum IL-6 levels in 1-6 h after injection (FIG. 26B), in addition to obvious signs of stress (e.g., hunched posture and labored movement), and then fully recovered within 24 h. In contrast, serum IL-6 levels were just elevated slightly in mice in 6 h after intravenous administration of 100 µg tRNA/mir-34a or tRNA/MSA. The change was very mild as compared to the LPS treatment and it was similar to that reported for synthetic miR-34a mimics (Wiggins et al., 2010) that might not indicate an adverse drug response. Furthermore, mouse blood chemistry profiles including the levels of alanine aminotransferase (ALT), aspartate aminotransferase (AST), albumin, alkaline phosphatase (ALP), total bilirubin, blood urea nitrogen (BUN), creatinine and total protein were not significantly altered by recombinant tRNA/mir-34a (FIG. 7C), suggesting that the biological ncRNA agents did not induce acute liver or kidney toxicity.

Discussion

In contrast to the large efforts to develop miRNA-based therapies, translational and clinical research is often hampered by the access to large quantities of inexpensive natural miRNA agents. Motivated by the concept of deploying biological RNA agents to perform RNA actions and the principle of "prodrug", we established a novel strategy to cost-effectively produce multi-milligrams of tRNA fusion miR-34a biological agents in one liter cultures of a common strain of $E.$ $coli$ in a research laboratory setting. The better expression of recombinant ncRNA in HST08 strain may be related to the lack of gene clusters in HST08 cells for digesting methylated DNA or a lower capacity to polyadenylate ncRNA for degradation. It is noteworthy that our strategy is different from a newly report approach to generate fully-processed siRNAs using p19-expressing bacteria (Huang et al., 2013). A high-yield accumulation of recombinant tRNA/mir-34a in bacteria (~15% of total RNAs) also facilitated the purification by anion-exchange FPLC method to a high degree (>98%) of homogeneity. In addition, we were able to characterize the primary structures and modified nucleosides of recombinant ncRNAs through LC-UV-MS analyses of hydrolysates and LC-MS/MS analyses of RNase T1-cleaved fragments. Our findings illustrate fundamental posttranscriptional modifications of the tRNA scaffold that are critical for its stability (Alexandrov et al., 2006).

Chimeric tRNA/mir-34a showed a rather surprisingly favorable stability within human carcinoma cells, suggesting that the tRNA carrier also offered a "stealth delivery" of target pre-miR-34a into human cells beyond the high-yield production of chimeric tRNA/mir-34a in bacteria. As expected, chimeric tRNA/mir-34a acted as a "prodrug" in human carcinoma cells, where pre-miR-34a was selectively processed to mature miR-34a by intrinsic miRNA processing machinery and the tRNA carrier was degraded to tRFs (Lee et al., 2009; Li et al., 2012). The 70-fold higher levels of mature miR-34a were also accompanied by 60-fold increase in miR-34a-p3 small RNA derived from pre-miR-34a. Therefore, chimeric tRNA/mir-34a may serve as an optimal carrier to assemble small RNAs of interests (Chen et al., 2015) that cannot be produced with tRNA scaffold. In addition, these results offer a good understanding of the fate of recombinant ncRNAs in human cells and the susceptibility to a few commercially-available human RNases, despite that the precise contribution of specific RNases to the metabolism and pharmacokinetics of biological tRNA/mir-34a warrants further investigation. While the effects of these tRFs are unknown, the same tRFs were produced from tRNA/MSA and tRNA/mir-34a at comparable levels in human cells, supporting the validity of using tRNA/MSA expressed in the same strain of $E.$ $coli$ and purified in the same manner as a control for the assessment of bioactivities of tRNA-carried pre-miR-34a.

The functions of tRNA-carried pre-miR-34a were nicely demonstrated by the selective reduction of protein expression levels of a number of previously verified miR-34a target genes such as CDK6, MET and SIRT1 in both A549 and HepG2 cells, as compared to tRNA/MSA. These genes are critical for many cellular processes such as cell cycle and apoptosis. Therefore, the suppression of miR-34a target genes by recombinant pre-miR-34a provides a mechanistic explanation for its anti-proliferative activities. The broad anticancer activities of recombinant pre-miR-34a against various types of cancer cells are consistent with previous findings on miR-34a functions in targeting multiple oncogenes and oncogenic pathways among different types of cancer cells (Chang et al., 2007; He et al., 2007; Sun et al., 2008; Yamakuchi et al., 2008; Li et al., 2009; Liu et al., 2011; Kasinski and Slack, 2012). Meanwhile, different human carcinoma cell lines did exhibit variable sensitivities to tRNA/mir-34a, which may be due to the variability in genome and gene expression profiles as well as the apparent effects of pre-miR-34a on target gene expression in different cell lines. While we posit that the activities of tRNA-carried pre-miR-34a in the modulation of miR-34a target gene expression and cancer cell growth is attributable to the mature miR-34a selectively produced from chimeric tRNA/mir-34a, we cannot exclude the possibility that pre-miR-34a itself is responsible for some of the effects noted.

Non-small cell lung cancer A549 cells consisting of KRAS mutant, wild-type p53 and wild-type EGFR commonly found in human lung carcinomas are proper models for human lung carcinogenesis and tumor progression (Lehman et al., 1991; Nomoto et al., 2006). By contrast, the hepatocellular carcinoma (HCC) HepG2 cell line represents a pure human liver carcinoma cell line free of viral infections, is comprised of a NRAS mutant, and is often used as a HCC model (Hsu et al., 1993; Charette et al., 2010; Costantini et al., 2013). Therefore, the A549 and HepG2 cells were utilized to produce xenograft tumors in mouse models to evaluate the effectiveness of recombinant pre-miR-34a in the control of tumor growth in vivo. Our study revealed a significant suppression of both A549 and HepG2 xenograft tumor growth by the higher dose (100 µg) of tRNA/mir-34a, compared to the vehicle treatment or the same dose of tRNA/MSA. After monitoring tumor growth for 6 weeks, our data demonstrated that tRNA/mir-34a strikingly eradicated A549 tumors (3 out of 6 mice) while it is unknown whether and when recurrence would occur. Although we did not measure the half-life of tRNA/mir-34a in vivo, we have demonstrated that expression levels persisted until day 6 in A549 and HepG2 cell lines after single dose transfection. Meanwhile, our data showed a much greater degree of inhibition against A549 xenografts than HepG2 by tRNA/mir-34a, which is in agreement with the efficacy of tRNA/mir-34a defined with cancer cell line models in vitro. While this study is limited to an intratumoral drug administration, it provides direct evidence to support the effectiveness of biological miR-34a agents in vivo. Nevertheless, the utility of recombinant miR-34a agents for cancer treatments should be challenged using targeted drug delivery systems and/or more clinically-relevant tumor animal models before clinical investigations.

Our study also illustrated that a relatively higher dose intravenous bolus, FPLC-purified chimeric miR-34a biological agents did not cause any stress to the mice (e.g., hunched posture and labored movement) within 48 h after drug administration or alter the liver and kidney functions which were manifested by the unchanged blood chemistry profiles. The levels of serum IL-6, the most sensitive cytokine in response to nucleic acids, were only slightly perturbed by chimeric ncRNAs as compared with the LPS treatment. The minor change in IL-6 levels caused by recombinant tRNA/mir-34 and tRNA/MSA within a short period (6 h) was actually comparable to those reported for synthetic miR-34a mimics (Wiggins et al., 2010). Due to unchanged ALT, AST, bilirubin, albumin, BUN, creatinine, and total proteins levels in tRNA/mir-34a treated mice 48 h post-injection, these findings indicate that recombinant ncRNAs are well tolerated in mouse models and do not induce any acute toxicity. Nevertheless, further studies are needed to critically define the safety profiles following chronic administration of biological ncRNAs in different species of animal models before clinical studies.

It is also noteworthy that recombinant tRNA/mir-34a, as first described in the current study, was proven to be equally or more effective than synthetic pre-miR-34a and miR-34a mimics in the regulation of target gene expression and suppression of cancer cell proliferation, compared to corresponding controls. This might be related to the differences in their secondary structures and metabolic stabilities within the cells, and consequently the efficiencies of miRNA processing machinery and RISC complex in utilizing these agents for the regulation of target gene expression and control of cellular processes.

In conclusion, our results demonstrate that chimeric pre-miR-34a agents could be produced efficiently in a common strain of E. coli on a large scale. The biological tRNA/mir-34a bearing natural modifications exhibited a favorable cellular stability and was degradable by RNases. Furthermore, tRNA-carried pre-miR-34a was pharmacologically active to suppress human carcinoma cell proliferation through the regulation of miR-34a target gene expression after being selectively processed to mature miR-34a. In addition, chimeric miR-34a was effective to control xenograft tumor progression while it was well tolerated in mouse models. Our findings indicate that chimeric miRNA agents engineered in bacteria are useful tools for the discovery and development of novel pharmacotherapies.

References for Example 3

Alexandrov, A., I. Chernyakov, W. Gu, S. L. Hiley, T. R. Hughes, E. J. Grayhack and E. M. Phizicky (2006). Rapid tRNA decay can result from lack of nonessential modifications. Mol Cell 21: 87-96.

Bader, A. G. (2012). miR-34—a microRNA replacement therapy is headed to the clinic. Frontiers in genetics 3: 120.

Bi, H. C., Y. Z. Pan, J. X. Qiu, K. W. Krausz, F. Li, C. H. Johnson, C. T. Jiang, F. J. Gonzalez and A. M. Yu (2014). N-methylnicotinamide and nicotinamide N-methyltransferase are associated with microRNA-1291-altered pancreatic carcinoma cell metabolome and suppressed tumorigenesis. Carcinogenesis 35: 2264-2272.

Bodeman, C. E., A. L. Dzierlenga, C. M. Tally, R. M. Mulligan, A. D. Lake, N. J. Cherrington and S. C. McKarns (2013). Differential regulation of hepatic organic cation transporter 1, organic anion-transporting polypeptide 1a4, bile-salt export pump, and multidrug resistance-associated protein 2 transporter expression in lymphocyte-deficient mice associates with interleukin-6 production. J Pharmacol Exp Ther 347: 136-144.

Butash, K. A., P. Natarajan, A. Young and D. K. Fox (2000). Reexamination of the effect of endotoxin on cell proliferation and transfection efficiency. Biotechniques 29: 610-614, 616, 618-619.

Chang, T. C., E. A. Wentzel, O. A. Kent, K. Ramachandran, M. Mullendore, K. H. Lee, G. Feldmann, M. Yamakuchi, M. Ferlito, C. J. Lowenstein, D. E. Arking, M. A. Beer, A. Maitra and J. T. Mendell (2007). Transactivation of miR-34a by p53 broadly influences gene expression and promotes apoptosis. Mol Cell 26: 745-752.

Charette, N., C. De Saeger, V. Lannoy, Y. Horsmans, I. Leclercq and P. Starkel (2010). Salirasib inhibits the growth of hepatocarcinoma cell lines in vitro and tumor growth in vivo through ras and mTOR inhibition. Mol Cancer 9: 256.

Chen, Q. X., W. P. Wang, S. Zeng, S. Urayama and A. M. Yu (2015). A general approach to high-yield biosynthesis of chimeric RNAs bearing various types of functional small RNAs for broad applications. Nucleic Acids Res 43: 3857-3869.

Costantini, S., G. Di Bernardo, M. Cammarota, G. Castello and G. Colonna (2013). Gene expression signature of human HepG2 cell line. Gene 518: 335-345.

Craig, V. J., A. Tzankov, M. Flori, C. A. Schmid, A. G. Bader and A. Muller (2012). Systemic microRNA-34a delivery induces apoptosis and abrogates growth of diffuse large B-cell lymphoma in vivo. Leukemia 26: 2421-2424.

He, L., X. He, L. P. Lim, E. de Stanchina, Z. Xuan, Y. Liang, W. Xue, L. Zender, J. Magnus, D. Ridzon, A. L. Jackson, P. S. Linsley, C. Chen, S. W. Lowe, M. A. Cleary and G. J. Hannon (2007). A microRNA component of the p53 tumour suppressor network. Nature 447: 1130-1134.

Hsu, I. C., T. Tokiwa, W. Bennett, R. A. Metcalf, J. A. Welsh, T. Sun and C. C. Harris (1993). p53 gene mutation and integrated hepatitis B viral DNA sequences in human liver cancer cell lines. Carcinogenesis 14: 987-992.

Huang, L., J. Jin, P. Deighan, E. Kiner, L. McReynolds and J. Lieberman (2013). Efficient and specific gene knockdown by small interfering RNAs produced in bacteria. Nat Biotechnol 31: 350-356.

Ingelman-Sundberg, M., X. B. Zhong, O. Hankinson, S. Beedanagari, A. M. Yu, L. Peng and Y. Osawa (2013). Potential role of epigenetic mechanisms in the regulation of drug metabolism and transport. Drug Metab Dispos 41: 1725-1731.

Kasinski, A. L. and F. J. Slack (2011). Epigenetics and genetics. MicroRNAs en route to the clinic: progress in validating and targeting microRNAs for cancer therapy. Nature reviews. Cancer 11: 849-864.

Kasinski, A. L. and F. J. Slack (2012). miRNA-34 prevents cancer initiation and progression in a therapeutically resistant K-ras and p53-induced mouse model of lung adenocarcinoma. Cancer Res 72: 5576-5587.

Kelnar, K., H. J. Peltier, N. Leatherbury, J. Stoudemire and A. G. Bader (2014). Quantification of therapeutic miRNA mimics in whole blood from non-human primates. Anal Chem 86: 1534-1542.

Krivos, K. L., B. Addepalli and P. A. Limbach (2011). Removal of 3'-phosphate group by bacterial alkaline phosphatase improves oligonucleotide sequence coverage of RNase digestion products analyzed by collision-induced dissociation mass spectrometry. Rapid Commun Mass Spectrom 25: 3609-3616.

Lee, Y. S., Y. Shibata, A. Malhotra and A. Dutta (2009). A novel class of small RNAs: tRNA-derived RNA fragments (tRFs). Genes Dev 23: 2639-2649.

Lehman, T. A., W. P. Bennett, R. A. Metcalf, J. A. Welsh, J. Ecker, R. V. Modali, S. Ullrich, J. W. Romano, E. Appella, J. R. Testa and et al. (1991). p53 mutations, ras mutations, and p53-heat shock 70 protein complexes in human lung carcinoma cell lines. Cancer Res 51: 4090-4096.

Li, M. M., B. Addepalli, M. J. Tu, Q. X. Chen, W. P. Wang, P. A. Limbach, J. M. LaSalle, S. Zeng, M. Huang and A. M. Yu (2015). Chimeric miR-1291 biosynthesized efficiently in *E. coli* is effective to reduce target gene expression in human carcinoma cells and improve chemosensitivity. Drug Metab Dispos: (in press).

Li, M. M., W. P. Wang, W. J. Wu, M. Huang and A. M. Yu (2014). Rapid Production of Novel Pre-MicroRNA Agent hsa-mir-27b in *Escherichia coli* Using Recombinant RNA Technology for Functional Studies in Mammalian Cells. Drug Metab Dispos 42: 1791-1795.

Li, Y., F. Guessous, Y. Zhang, C. Dipierro, B. Kefas, E. Johnson, L. Marcinkiewicz, J. Jiang, Y. Yang, T. D. Schmittgen, B. Lopes, D. Schiff, B. Purow and R. Abounader (2009). MicroRNA-34a inhibits glioblastoma growth by targeting multiple oncogenes. Cancer Res 69: 7569-7576.

Li, Z., C. Ender, G. Meister, P. S. Moore, Y. Chang and B. John (2012). Extensive terminal and asymmetric processing of small RNAs from rRNAs, snoRNAs, snRNAs, and tRNAs. Nucleic Acids Res 40: 6787-6799.

Liu, C., K. Kelnar, B. Liu, X. Chen, T. Calhoun-Davis, H. Li, L. Patrawala, H. Yan, C. Jeter, S. Honorio, J. F. Wiggins, A. G. Bader, R. Fagin, D. Brown and D. G. Tang (2011). The microRNA miR-34a inhibits prostate cancer stem cells and metastasis by directly repressing CD44. Nat Med 17: 211-215.

Ma, L., J. Teruya-Feldstein and R. A. Weinberg (2007). Tumour invasion and metastasis initiated by microRNA-10b in breast cancer. Nature 449: 682-688.

Nelissen, F. H., E. H. Leunissen, L. van de Laar, M. Tessari, H. A. Heus and S. S. Wijmenga (2012). Fast production of homogeneous recombinant RNA—towards large-scale production of RNA. Nucleic Acids Res 40: e102.

Nomoto, K., K. Tsuta, T. Takano, T. Fukui, T. Fukui, K. Yokozawa, H. Sakamoto, T. Yoshida, A. M. Maeshima, T. Shibata, K. Furuta, Y. Ohe and Y. Matsuno (2006). Detection of EGFR mutations in archived cytologic specimens of non-small cell lung cancer using high-resolution melting analysis. Am J Clin Pathol 126: 608-615.

Novoa, E. M., M. Pavon-Eternod, T. Pan and L. Ribas de Pouplana (2012). A role for tRNA modifications in genome structure and codon usage. Cell 149: 202-213.

Pan, Y. Z., A. Zhou, Z. Hu and A. M. Yu (2013). Small nucleolar RNA-derived microRNA hsa-miR-1291 modulates cellular drug disposition through direct targeting of ABC transporter ABCC1. Drug Metab Dispos 41: 1744-1751.

Ponchon, L., G. Beauvais, S. Nonin-Lecomte and F. Dardel (2009). A generic protocol for the expression and purification of recombinant RNA in *Escherichia coli* using a tRNA scaffold. Nat Protoc 4: 947-959.

Ponchon, L. and F. Dardel (2007). Recombinant RNA technology: the tRNA scaffold. Nat Methods 4: 571-576.

Pramanik, D., N. R. Campbell, C. Karikari, R. Chivukula, O. A. Kent, J. T. Mendell and A. Maitra (2011). Restitution of tumor suppressor microRNAs using a systemic nanovector inhibits pancreatic cancer growth in mice. Mol Cancer Ther 10: 1470-1480.

Russell, S. P. and P. A. Limbach (2013). Evaluating the reproducibility of quantifying modified nucleosides from ribonucleic acids by LC-UV-MS. J Chromatogr B Analyt Technol Biomed Life Sci 923-924: 74-82.

Sun, F., H. Fu, Q. Liu, Y. Tie, J. Zhu, R. Xing, Z. Sun and X. Zheng (2008). Downregulation of CCND1 and CDK6 by miR-34a induces cell cycle arrest. FEBS Lett 582: 1564-1568.

Taucher, M. and K. Breuker (2010). Top-down mass spectrometry for sequencing of larger (up to 61 nt) RNA by CAD and EDD. J Am Soc Mass Spectrom 21: 918-929.

Wang, Y., X. Shan, Y. Dai, L. Jiang, G. Chen, Y. Zhang, Z. Wang, L. Dong, J. Wu, G. Guo and G. Liang (2015). Curcumin analog L48H37 prevents LPS-induced TLR4 signaling pathway activation and sepsis via targeting MD2. J Pharmacol Exp Ther.

Welch, C., Y. Chen and R. L. Stallings (2007). MicroRNA-34a functions as a potential tumor suppressor by inducing apoptosis in neuroblastoma cells. Oncogene 26: 5017-5022.

Wiggins, J. F., L. Ruffino, K. Kelnar, M. Omotola, L. Patrawala, D. Brown and A. G. Bader (2010). Development of a lung cancer therapeutic based on the tumor suppressor microRNA-34. Cancer Res 70: 5923-5930.

Yamakuchi, M., M. Ferlito and C. J. Lowenstein (2008). miR-34a repression of SIRT1 regulates apoptosis. Proc Natl Acad Sci USA 105: 13421-13426.

Yao, H. W. and J. Li (2015). Epigenetic modifications in fibrotic diseases: implications for pathogenesis and pharmacological targets. J Pharmacol Exp Ther 352: 2-13.

Yu, A. M. (2009). Role of microRNAs in the regulation of drug metabolism and disposition. Expert Opin Drug Metab Toxicol 5: 1513-1528.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

INFORMAL SEQUENCE LISTING

Underlined are tRNA sequences, and the italic are pre-miRNA sequences. Italic bold sequences are extended 5' and 3' sequences of pre-miRNA. Underlined italic bold represents mutated nucleotides. The boxed are aptamer (e.g., MGA) sequences.

SEQ ID NO: 1 - tRNA/MSA (107 nt)
5'-GGCUACGUAGCUCAGUUGGUUAGAGCAGCGGCCGAGUAAUUUACGUCGACGGUGACGU
CGAUGGUUGCGGCCGCGGGUCACAGGUUCGAAUCCCGUCGUAGCCACCA-3'

SEQ ID NO: 2 - Human Pre-miR-34a (hsa-mir-34a; MI0000268)
5'-*GGCCAGCUGUGAGUGUUUCUUUGGCAGUGUCUUAGCUGGUUGUGUGAGCAAUAGUAA
GGAAGCAAUCAGCAAGUAUACUGCCCUAGAAGUGCUGCACGUUGUGGGGCCC*-3'

-continued

INFORMAL SEQUENCE LISTING

Underlined are tRNA sequences, and the italic are pre-miRNA sequences. Italic bold sequences are extended 5' and 3' sequences of pre-miRNA. Underlined italic bold represents mutated nucleotides. The boxed are aptamer (e.g., MGA) sequences.

SEQ ID NO: 3 - OnRS-1 or tRNA/mir-34a (233 nt)
5'-<u>GGCUACGUAGCUCAGUUGGUUAGAGCAGCGGCCGAGUAAUUUACGUCGA</u>-*GUGGACCG*
*GCCAGCUGUGAGUGUUUCUUUGGCAGUGUCUUAGCUGGUUGUUGUGAGCAAUAGUAAGGAA*
*GCAAUCAGCAAGUAUACUGCCCUAGAAGUGCUGCACGUUGUGGGCCC**AAGAGGGAAGAUG*
<u>ACGUCGAUGGUUGCGGCCGCGGGUCACAGGUUCGAAUCCCGUCGUAGCCACCA</u>-3'

SEQ ID NO: 4 - OnRS-2 or tRNA/mir-34a-2 (195 nt)
5'-<u>GGCUACGUAGCUCAGUUGGUUAGAGCAGCGGCCG</u>*GUGGACC**GGCCAGCUGUGAGUGUU*
*UCUUUGGCAGUGUCUUAGCUGGUUGUUGUGAGCAAUAGUAAGGAAGCAAUCAGCAAGUAUA*
*CUGCCCUAGAAGUGCUGCACGUUGUGGGGCCC**GGUCCAC**C*<u>CGCGGGUCACAGGUUCGAAUC</u>
<u>CCGUCGUAGCCACCA</u>-3

SEQ ID NO: 5 - OnRS-3 or tRNA/mir-34a-3 (198 nt)
5'-<u>GGCUACGUAGCUCAGUUGGUUAGAGCAGCGGCCG</u>*GGCCAGCUGUGAGUGUUUCUUUGG*
*CAGUGUCUUAGCUGGUUGUUGUGAGCAAUAGUAAGGAAGCAAUCAGCAAGUAUACUGCCCU*
*AGAAGUGCUGCACGUUGUGGGGCCC*<u>GACGUCGAUGGUUGCGGCCGCGGGUCACAGGUUCGA</u>
<u>AUCCCGUCGUAGCCACCA</u>-3'

SEQ ID NO: 6 - OnRS-4a or tRNA/mir-34a-4a (181 nt):
5'-<u>GGCUACGUAGCUCAGUUGGUUAGAGCAGCGGCCG</u>*GGCCAGCUGUGAGUGUUUCUUUGG*
*CAGUGUCUUAGCUGGUUGUUGUGAGCAAUAGUAAGGAAGCAAUCAGCAAGUAUACUGCCCU*
*AGAAGUGCUGCACGUUGUGGGGCCC*<u>CCGCGGGUCACAGGUUCGAAUCCCGUCGUAGCCACC</u>
<u>A</u>-3'

SEQ ID NO: 7 - OnRS-4b or tRNA/mir-34a-4b (180 nt):
5'-<u>GGCUACGUAGCUCAGUUGGUUAGAGCAGCGGCCG</u>*GGCCAGCUGUGAGUGUUUCUUUGG*
*CAGUGUCUUAGCUGGUUGUUGUGAGCAAUAGUAAGGAAGCAAUCAGCAAGUAUACUGCCCU*
*AGAAGUGCUGCACGUUGU**<u>U</u>**GGCCCCCGCGGGUCACAGGUUCGAAUCCCGUCGUAGCCACCA*-
3'

SEQ ID NO: 8 - OnRS-5 or tRNA/mir-34a-5 (181 nt):
5'-<u>GGCUACGUAGCUCAGUUGGUUAGAGCAGCGGCCG</u>*GGCC**CC**GCGUGAGUGUUUCUUUG*
*GCAGUGUCUUAGCUGGUUGUUGUGAGCAAUAGUAAGGAAGCAAUCAGCAAGUAUACUGCCC*
*UAGAAGUGCUGCACGUUGUGGGGCCC*<u>CCGCGGGUCACAGGUUCGAAUCCCGUCGUAGCCACC</u>
<u>A</u>-3'

SEQ ID No: 9 - Human Pre-miR-1291 (hsa-mir-1291; MI0006353)
5'-*GGUAGAAUUCCAGUGGCCCUGACUGAAGACCAGCAGUUGUACUGUGGCUGUUGGUUUC*
*AAGCAGAGGCCUAAAGGACUGUCUUCCUG*-3'

SEQ ID No: 10 - tRNA/mir-1291 or OnRS-6 (227 nt)
5'-<u>GGCUACGUAGCUCAGUUGGUUAGAGCAGCGGCCGAGUAAUUUACGUCGAC</u>*GAGUUCUG*
*UCCGUGAGCCUU**GGGUAGAAUUCCAGUGGCCCUGACUGAAGACCAGCAGUUGUACUGUGGC*
*UGUUGGUUUCAAGCAGAGGCCUAAAGGACUGUCUUCCUG**UGGUCUGUUGGCUGUGACGUCG*
*AUGGUUGCGG*<u>CCGCGGGUCACAGGUUCGAAUCCCGUCGUAGCCACCA</u>-3'

SEQ ID No: 11 - tRNA/mir-1291-2 or OnRS-7 (175 nt)
5'-<u>GGCUACGUAGCUCAGUUGGUUAGAGCAGCGGCCGAGUAAUUUACGUCGAC</u>*GGGUAGAA*
*UUCCAGUGGCCCUGACUGAAGACCAGCAGUUGUACUGUGGCUGUUGGUUUCAAGCAGAGGC*
*CUAAAGGACUGUCUUCCUGCC*<u>GCGGGUCACAGGUUCGAAUCCCGUCGUAGCCACCA</u>-3'

SEQ ID No: 12 - tRNA/mir-1291-3a or OnRS-8a (159 nt)
5'-<u>GGCUACGUAGCUCAGUUGGUUAGAGCAGCGGCCG</u>*GGGUAGAAUUCCAGUGGCCCUGAC*
*UGAAGACCAGCAGUUGUACUGUGGCUGUUGGUUUCAAGCAGAGGCCUAAAGGACUGUCUUC*
*CUGCCGCGGG*<u>UCACAGGUUCGAAUCCCGUCGUAGCCACCA</u>-3'

SEQ ID No: 13 - tRNA/mir-1291-3b or OnRS-8b (159 nt)
5'-<u>GGCUACGUAGCUCAGUUGGUUAGAGCAGCGGCCG</u>*GGG**<u>A</u>**AGAAUUCCAGUGGCCCUGAC*
*UGAAGACCAGCAGUUGUACUGUGGCUGUUGGUUUCAAGCAGAGGCCUAAAGGACUGUCUUC*
*CUGCCGCGGG*<u>UCACAGGUUCGAAUCCCGUCGUAGCCACCA</u>-3'

INFORMAL SEQUENCE LISTING

Underlined are tRNA sequences, and the italic are pre-miRNA sequences. Italic bold sequences are extended 5' and 3' sequences of pre-miRNA. Underlined italic bold represents mutated nucleotides. The boxed are aptamer (e.g., MGA) sequences.

SEQ ID No: 14 - tRNA/mir-1291-3c or OnRS-8c (159 nt)
5'-GGCUACGUAGCUCAGUUGGUUAGAGCAGCGGCCGGGGUAGAAUUCCAGUGGCCCUGAC
UGAAGACCAGCAGUUGUACUGUGGCUGUUGGUUUCAAGCAGAGGCCUAAAGGACUGUCUAC
CUGCCGCGGGUCACAGGUUCGAAUCCCGUCGUAGCCACCA-3'

SEQ ID No: 15 - tRNA/mir-1291-3d or OnRS-8d (158 nt)
5'-GGCUACGUAGCUCAGUUGGUUAGAGCAGCGGCCGGGGAAGAAUGCCAGUGGCCCUGAC
UGAAGACCAGCAGUUGUACUGUGGCUGUUGGUUUCAAGCAGAGGCCUAAAGGACUUCUUCC
UGCCGCGGGUCACAGGUUCGAAUCCCGUCGUAGCCACCA-3'

SEQ ID No: 16 - tRNA/mir-1291-3e or OnRS-8e (158 nt)
5'-GGCUACGUAGCUCAGUUGGUUAGAGCAGCGGCCGGGGUAGAAUUCCAGUGGCCCUGAC
UGAAGACCAGCAGUUGUACUGUGGCUGUUGGUUUCAAGCAGAGGCCUAAAGGAAUUCUACC
UGCCGCGGGUCACAGGUUCGAAUCCCGUCGUAGCCACCA-3'

SEQ ID No: 17 - Pre-miR-125b-1 (hsa-mir-125b-1; MI0000446)
5'-*UGCGCUCCUCUCAGUCCCUGAGACCCUAACUUGUGAUGUUUACCGUUUAAAUCCACGG
GUAGGCUCUUGGGAGCUGCGAGUCGUGCU*-3'

SEQ ID No: 18 - tRNA/mir-125b-1 or OnRS-9 (216 nt)
5'-GGCUACGUAGCUCAGUUGGUUAGAGCAGCGGCCGAGUAAUUUACGUCGAC*GAGAAAAC*
*AUUGU*U*GCGCUCCUCUCAGUCCCUGAGACCCUAACUUGUGAUGUUUACCGUUUAAAUCCAC
GGGUUAGGCUCUUGGGAGCUGCGAGUCGUGCU**UUUGCAUCCUUGACGUCGAUGGUUGCGG**C
CGCGGGUCACAGGUUCGAAUCCCGUCGUAGCCACCA-3'

SEQ ID No: 19 - tRNA/mir-125b-2 or OnRS-10 (159 nt)
5'-GGCUACGUAGCUCAGUUGGUUAGAGCAGCGGCCGUGCGCUCCUCUCAGUCCCUGAGAC
CCUAACUUGUGAUGUUUACCGUUUAAAUCCACGGGUUAGGCUCUUGGGAGCUGCGAGUCGU
GCUCCGCGGGUCACAGGUUCGAAUCCCGUCGUAGCCACCA-3'

SEQ ID No: 20 - tRNA/mir-125b-2a or OnRS-10a (159 nt)
5'-GGCUACGUAGCUCAGUUGGUUAGAGCAGCGGCCGA GCGCUCCUCUCAGUCCCUGAGAC
CCUAACUUGUGAUGUUUACCGUUUAAAUCCACGGGUUAGGCUCUUGGGAGCUGCGAGUCGU
GCUCCGCGGGUCACAGGUUCGAAUCCCGUCGUAGCCACCA-3'

SEQ ID No: 21 - tRNA/mir-125b-2b or OnRS-10b (159 nt)
5'-GGCUACGUAGCUCAGUUGGUUAGAGCAGCGGCCGUGCGCUCCUCUCAGUCCCUGAGAC
CCUAACUUGUGAUGUUUACCGUUUAAAUCCACGGGUUAGGCUCUUGGGAGCUGCGAGUCGU
GCACCGCGGGUCACAGGUUCGAAUCCCGUCGUAGCCACCA-3'

SEQ ID No: 22 - tRNA/mir-125b-2c or OnRS-10c (159 nt)
5'-GGCUACGUAGCUCAGUUGGUUAGAGCAGCGGCCGA GCGCGACUCUCAGUCCCUGAGAC
CCUAACUUGUGAUGUUUACCGUUUAAAUCCACGGGUUAGGCUCUUGGGAGCUGCGAGUCGU
GCUCCGCGGGUCACAGGUUCGAAUCCCGUCGUAGCCACCA-3'

SEQ ID No: 23 - tRNA/mir-125b-2d or OnRS-10d (159 nt)
5'-GGCUACGUAGCUCAGUUGGUUAGAGCAGCGGCCGUGCGCUCCUCUCAGUCCCUGAGAC
CCUAACUUGUGAUGUUUACCGUUUAAAUCCACGGGUUAGGCUCUUGGGAGCUGCGAGGAGU
GCACCGCGGGUCACAGGUUCGAAUCCCGUCGUAGCCACCA-3'

SEQ ID No: 24 - tRNA/mir-125b-2e or OnRS-10e (159 nt)
5'-GGCUACGUAGCUCAGUUGGUUAGAGCAGCGGCCGA GCGCGACUCGCAGUCCCUGAGAC
CCUAACUUGUGAUGUUUACCGUUUAAAUCCACGGGUUAGGCUCUUGGGAGCUGCGAGUCGU
GCUCCGCGGGUCACAGGUUCGAAUCCCGUCGUAGCCACCA-3'

SEQ ID No: 25 - tRNA/mir-125b-2f or OnRS-10f (159 nt)
5'-GGCUACGUAGCUCAGUUGGUUAGAGCAGCGGCCGUGCGCUCCUCUCAGUCCCUGAGAC
CCUAACUUGUGAUGUUUACCGUUUAAAUCCACGGGUUAGGCUCUUGGGAGCUGA GAGGAGU
GCACCGCGGGUCACAGGUUCGAAUCCCGUCGUAGCCACCA-3'

-continued

INFORMAL SEQUENCE LISTING

Underlined are tRNA sequences, and the italic are pre-miRNA sequences. Italic bold sequences are extended 5' and 3' sequences of pre-miRNA. Underlined italic bold represents mutated nucleotides. The boxed are aptamer (e.g., MGA) sequences.

SEQ ID No: 26 - Pre-miR-124-1 (hsa-mir-124-1; MI0000443)
5'-AGGCCUCUCUCUCCGUGUUCACAGCGGACCUUGAUUUAAAUGUCCAUACAAUUAAGGC
ACGCGGUGAAUGCCAAGAAUGGGGCUG-3'

SEQ ID No: 27 - tRNA/mir-124-1 (232 nt): A hybrid molecule of methionyl tRNA and pre-miR-124-1 with extended sequences.
5'-GGCUACGUAGCUCAGUUGGUUAGAGCAGCGGCCGAGUAAUUUACGUCGAC*CUCCUUUC*

*CUUCCUCAGGAGAA*AGGCCUCUCUCUCCGUGUUCACAGCGGACCUUGAUUUAAAUGUCCAU

ACAAUUAAGGCACGCGGUGAAUGCCAAGAAUGGGGCUG*GCUGAGCACCGUGGGUCGGCGGA*

*CGUCGAUGGUUGCGG*CCGCGGGUCACAGGUUCGAAUCCCGUCGUAGCCACCA-3'

SEQ ID No: 28 - OnRS/miR-124 (228 nt): A hybrid molecule of methionyl tRNA and pre-miR-34a in which miR-34a sequences (mature and guide) are replaced by miR-124 (-3p and guide) sequences.
5'-GGCUACGUAGCUCAGUUGGUUAGAGCAGCGGCCGAGUAAUUUACGUCGAC*CCGUGGAC*

*CGGCCAGCUGUGAGUGUUUCUU*__UAAGGCACGCGGUGAAUGC__*CUGUGAGCAAUAGUAAGGAA*

*GGCAUUCACGCUGUGCCUUCUAGAAGUGCUGCACGUUGUGGGGCCCAAGAGGGAAGACGUC*

*GAUGGUUGCGG*CCGCGGGUCACAGGUUCGAAUCCCGUCGUAGCCACCA-3'
Double underline is the mature miR-124 sequence, and bold underline is the guide miR-124 sequence.

SEQ ID No: 29 - Pre-miR-27b (hsa-mir-27b; MI0000440)
5'- *ACCUCUCUAACAAGGUGCAGAGCUUAGCUGAUUGGUGAACAGUGAUUGGUUUCCGCUU
UGUUCACAGUGGCUAAGUUCUGCACCUGAAGAGAAGGUG*-3'

SEQ ID No: 30 - tRNA/mir-27b (227 nt): A hybrid molecule of methionyl tRNA and pre-miR-27b with extended sequences.
5'-GGCUACGUAGCUCAGUUGGUUAGAGCAGCGGCCGAGUAAUUUACGUCGAC*CCAGCGAU*

*GA**CCUCUCUAACAAGGUGCAGAGCUUAGCUGAUUGGUGAACAGUGAUUGGUUUCCGCUUUG*

*UUCACAGUGGCUAAGUUCUGCACCUGAAGAGAAGGUG**AGAUGGGGACAGUUAAGGACGUCG*

*AUGGUUGCGG*CCGCGGGUCACAGGUUCGAAUCCCGUCGUAGCCACCA-3'

SEQ ID No: 31 - OnRS/miR-27b (230 nt): A hybrid molecule of methionyl tRNA and pre-miR-34a in which miR-34a sequences (mature and guide) are replaced by miR-27b (mature and guide) sequences.
5'-GGCUACGUAGCUCAGUUGGUUAGAGCAGCGGCCGAGUAAUUUACGUCGAC*CCGUGGAC*

*CGGCCAGCUGUGAGUGUUUCUU*__UUCACAGUGGCUAAGUUCUGC__*CUGUGAGCAAUAGUAAGGA*

*AGCAGAACUAGCUCACUGUGAC*UAGAAGUGCUGCACGUUGUGGGGCCCAAGAGGGAAGACG

*UCGAUGGUUGCGG*CCGCGGGUCACAGGUUCGAAUCCCGUCGUAGCCACCA-3'
Double underline is the mature miR-27b sequence, and bold underline is the guide sequence.

SEQ ID No: 32 - Pre-miR-22 (hsa-mir-22; MI0000078)
5'-GGCUGAGCCGCAGUAGUUCUUCAGUGGCAAGCUUUAUGUCCUGACCCAGC
UAAAGCUGCCAGUUGAAGAACUGUUGCCCUCUGCC-3'

SEQ ID No: 33 - tRNA/mir-22 (210 nt): A hybrid molecule of methionyl tRNA and pre-miR-22 with extended sequences.
5'-GGCUACGUAGCUCAGUUGGUUAGAGCAGCGGCCGAGUAAUUUACGUCGAC*UUCCUCUC*

*ACGCCCUCACCU**GGCUGAGCCGCAGUAGUUCUUCAGUGGCAAGCUUUAUGUCCUGACCCAG*

*CUAAAGCUGCCAGUUGAAGAACUGUUGCCCUCUGCC**CCUGGCUUCGAGGAGGAG*CCGCGGG

UCACAGGUUCGAAUCCCGUCGUAGCCACCA-3'

SEQ ID No: 34 - OnRS/miR-22 (232 nt): A hybrid molecule of methionyl tRNA and pre-miR-34a in which the miR-34a (mature and guide) sequences are substituted by miR-22 (mature and guide) sequences.
5'-GGCUACGUAGCUCAGUUGGUUAGAGCAGCGGCCGAGUAAUUUACGUCGAC*CCGUGGAC*

*CGGCCAGCUGUGAGUGUUUCUU*__AAGCUGCCAGUUGAAGAACUGUUG__*UGAGCAAUAGUAAGG*

*AAGCAGUUCUUAACUUGGCAGCUC*UAGAAGUGCUGCACGUUGUGGGGCCCAAGAGGGAAGA

INFORMAL SEQUENCE LISTING

Underlined are tRNA sequences, and the italic are pre-miRNA sequences. Italic bold sequences are extended 5' and 3' sequences of pre-miRNA. Underlined italic bold represents mutated nucleotides. The boxed are aptamer (e.g., MGA) sequences.

*CGUCGAUGGUUGCGG*CCGCGGGUCACAGGUUCGAAUCCCGUCGUAGCCACCA-3'
Double underline is the mature miR-22 sequence, and bold underline is the guide miR-22 sequence.

SEQ ID No: 35 - OnRS/Neg (232 nt): A hybrid molecule of methionyl tRNA and pre-miR-34a in which the miR-34a (mature and guide) sequences are substituted by the gRNA (mature and guide) sequences.
5'-GGCUACGUAGCUCAGUUGGUUAGAGCAGCGGCCGAGUAAUUUACGUCGAC*CCGUGGAC*
*CGGCCAGCUGUGAGUGUUUCUU*CACCUAUAACAACGGUAGUUUUU*GUGAGCAAUAGUAAGG*

*AAG*AAACUACCUUGUUUAUAGG*UCUAGAAGUGCUGCACGUUGUGGG*GCCCAAGAGGGAAGA*

*CGUCGAUGGUUGCGG*CCGCGGGUCACAGGUUCGAAUCCCGUCGUAGCCACCA-3'
Double underline is the scrambled sRNA sequence, and bold underline is the guide sRNA sequence.

SEQ ID No: 36 - OnRS/GFP-siRNA (232 nt): A hybrid molecule of methionyl tRNA and pre-miR-34a in which the miR-34a (mature and guide) sequences are substituted by the GFP-siRNA (mature and guide) sequences.
5'-GGCUACGUAGCUCAGUUGGUUAGAGCAGCGGCCGAGUAAUUUACGUCGACCCGUGGAC
CGGCCAGCUGUGAGUGUUUCUUAGUUGUACUCCAGCUUGUGCCCUGUGAGCAAUAGUAAGG

AAGGGCACAAGUGGUAGUACAACCUAGAAGUGCUGCACGUUGUGGGGCCCAAGAGGGAAGA

CGUCGAUGGUUGCGGCCGCGGGUCACAGGUUCGAAUCCCGUCGUAGCCACCA-3'
Double underline is the GFP siRNA sequence, and bold underline is the guide siRNA sequence.

SEQ ID No: 37 - tRNA/mir-155/GFP-siRNA (216 nt): A hybrid molecule of methionyl tRNA and pre-miR-155 in which the miR-155 (mature and guide) sequences are substituted by the GFP-siRNA (mature and guide) sequences.
5'-GGCUACGUAGCUCAGUUGGUUAGAGCAGCGGCCGAGUAAUUUACGUCGAC*GAGGCUUG*
*CUGAAGGCUGUAUGCUG*GUUGUACUCCAGCUUGUGCCC*GUUUUGGCCACUGACUGACGGGC*

*ACAAUGGAGUACAACC*AGGACACAAGGCCUGUUACUAGCACUCGACGUCGAUGGUUGCGGC

CGCGGGUCACAGGUUCGAAUCCCGUCGUAGCCACCA-3'

SEQ ID NO: 38 - Malachite Green Aptamer (MGA) (38 nt):
5'-[GGAUCCCGACUGGCGAGAGCCAGGUAACGAAUGGAUCC]-3'

SEQ ID NO: 39 - OnRS-2/MGA5 (233 nt): A hybrid molecule of methionyl tRNA, pre-miR-34a and MGA where the MGA is inserted upstream of pre-miR-34a.
5'-GGCUACGUAGCUCAGUUGGUUAGAGCAGCGGCCG[GGAUCCCGACUGGCGAGAGCCAGG
UAACGAAUGGAUCC]*GUGGACC*GGCCAGCUGUGAGUGUUUCUUUGGCAGUGUCUUAGCUGGU UGUUGUGAGCAAUAGUAAGGAAGCAAUCAGCAAGUAUACUGCCCUAGAAGUGCUGCACGUU
GUGGGGCCC*GGUCCAC*CCGCGGGUCACAGGUUCGAAUCCCGUCGUAGCCACCA-3'

SEQ ID NO: 40 - OnRS-2/MGA3 (233 nt): A hybrid molecule of methionyl tRNA, pre-miR-34a and MGA where the MGA is inserted downstream of pre-miR-34a.
5'-GGCUACGUAGCUCAGUUGGUUAGAGCAGCGGCCG*GUGGACC*GGCCAGCUGUGAGUGUU UCUUUGGCAGUGUCUUAGCUGGUUGUUGUGAGCAAUAGUAAGGAAGCAAUCAGCAAGUAUA
CUGCCCUAGAAGUGCUGCACGUUGUGGGGCCC*GGUCCAC*[GGAUCCCGACUGGCGAGAGCCA

GGUAACGAAUGGAUCC]CCGCGGGUCACAGGUUCGAAUCCCGUCGUAGCCACCA-3'

SEQ ID No: 41 - tRNA/shRNA-1a or OnRS-11a/siRNA (miRNA)
5'-GGCUACGUAGCUCAGUUGGUUAGAGCAGCGGCCGAGUAAUUUACGUCGAC
GAUCCCNNNNNNNNNNNNNNNNNNNNNNUUCAAGAGANNNNNNNNNNNNNNN
NNNNNNNUUUUUGGAAACCGCGGGUCACAGGUUCGAAUCCCGUCGUAGCCACC
A-3'
Double underline is the siRNA or miRNA sequence.

SEQ ID No: 42 - tRNA/shRNA-1b or OnRS-11b/siRNA (miRNA)
5'-GGCUACGUAGCUCAGUUGGUUAGAGCAGCGGCCGAGUAAUUUACGUCGAC
GAUCCNNNNNNNNNNNNNNNNNNNNNNUUCAAGAGANNNNNNNNNNNNNNNNN

INFORMAL SEQUENCE LISTING

Underlined are tRNA sequences, and the italic are pre-miRNA sequences. Italic bold sequences are extended 5' and 3' sequences of pre-miRNA. Underlined italic bold represents mutated nucleotides. The boxed are aptamer (e.g., MGA) sequences.

NNNNNGACCGCGGGUCACAGGUUCGAAUCCCGUCGUAGCCACCA-3'
Double underline is the siRNA or miRNA sequence.

SEQ ID No: 43 - tRNA/shRNA-1c or OnRS-11c/siRNA (miRNA)
5'-GGCUACGUAGCUCAGUUGGUUAGAGCAGCGGCCGAGUAAUUUACGUCGAC
GNNNNNNNNNNNNNNNNNNNNNUUCAAGAGANNNNNNNNNNNNNNNNNNNNN
NUUCCGCGGGUCACAGGUUCGAAUCCCGUCGUAGCCACCA-3'
Double underline is the siRNA or miRNA sequence.

SEQ ID No: 44 - tRNA/shRNA-1d or OnRS-11d/siRNA (miRNA)
5'-GGCUACGUAGCUCAGUUGGUUAGAGCAGCGGCCGAGUAAUUUACGUCGAC
GAUCCCCNNNNNNNNNNNNNNNNNNNNNNUCAAGAGANNNNNNNNNNNNNNNNN
NNNNNNUUUUUGGAAACCGCGGGUCACAGGUUCGAAUCCCGUCGUAGCCACCA-3'
Double underline is the siRNA or miRNA sequence.

SEQ ID No: 45 - tRNA/shRNA-1e or OnRS-11e/siRNA (miRNA)
5'-GGCUACGUAGCUCAGUUGGUUAGAGCAGCGGCCGAGUAAUUUACGUCGAC
GAUCCNNNNNNNNNNNNNNNNNNNNNNNUCAAGAGANNNNNNNNNNNNNNNNNN
NNNNUGAACCGCGGGUCACAGGUUCGAAUCCCGUCGUAGCCACCA-3'
Double underline is the siRNA or miRNA sequence.

What is claimed is:

1. A polynucleotide comprising a tRNA operably linked to a pre-microRNA (pre-miRNA), wherein all or part of the stem-loop anticodon of the tRNA is replaced with the pre-miRNA, and wherein the pre-miRNA comprises a nucleotide sequence having at least 90% sequence identity to the nucleotide sequence of a pre-miRNA selected from the group consisting of: pre-miRNA-1291, pre-miRNA-34a, pre-miRNA-125b, pre-miRNA-124, hsa-let-7c, hsa-mir-92a-1, hsa-mir-218-1, and hsa-mir-7-1.

2. The polynucleotide of claim 1, wherein the tRNA is a methionyl tRNA.

3. The polynucleotide of claim 1, wherein the tRNA is a mammalian tRNA.

4. The polynucleotide of claim 1, wherein the pre-miRNA is naturally or artificially derived.

5. The polynucleotide of claim 1, wherein the tRNA and/or pre-miRNA are further operably linked to one or more inserted RNA molecules.

6. The polynucleotide of claim 5, wherein the inserted RNA molecule is inserted at, abutted with or operably linked to:
a) the 5' end of the pre-miRNA;
b) the 3' end of the pre-miRNA;
c) 5' of a dicer cleavage site of the pre-miRNA; or
d) 3' of a dicer cleavage site of the pre-miRNA.

7. The polynucleotide of claim 5, wherein the inserted RNA has at least 18 nucleotides and up to 200 nucleotides.

8. The polynucleotide of claim 5, wherein the inserted RNA is selected from the group consisting of a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), a guide RNA (gRNA), a catalytic RNA, a riboswitch, and an RNA aptamer.

9. The polynucleotide of claim 5, wherein the inserted RNA reduces or inhibits the expression of a target polypeptide or a target polynucleotide.

10. An expression cassette or viral vector comprising the polynucleotide of claim 1.

11. A liposome, a polymer or a nanoparticle comprising the polynucleotide of claim 1.

12. An isolated host cell comprising a polynucleotide of claim 1.

13. The isolated host cell of claim 12, wherein the isolated host cell is selected from the group consisting of: a bacterial cell, a mammalian cell, an insect cell, and a plant cell.

14. A kit comprising the polynucleotide of claim 1.

15. A method of producing a hybrid tRNA/pre-microRNA, comprising expressing in a population of host cells the tRNA/pre-microRNA polynucleotide of claim 1.

16. A method of producing an RNA molecule, comprising expressing in a population of host cells the RNA molecule from the tRNA/pre-microRNA polynucleotide of claim 1.

17. A method of reducing or inhibiting the expression of a target polynucleotide in a subject in need thereof, comprising administering to the subject the polynucleotide of claim 1.

* * * * *

UNITED STATES PATENT AND TRADEMARK OFFICE
CERTIFICATE OF CORRECTION

| | | |
|---|---|---|
| PATENT NO. | : 10,619,156 B2 | Page 1 of 1 |
| APPLICATION NO. | : 15/313555 | |
| DATED | : April 14, 2020 | |
| INVENTOR(S) | : Aiming Yu | |

It is certified that error appears in the above-identified patent and that said Letters Patent is hereby corrected as shown below:

In the Specification

Column 1, after Line 13, before Line 15 should read:
-- STATEMENT OF GOVERNMENT SUPPORT
This invention was made with government support under contract numbers R01CA225958, U01CA175315, and R01GM113888 awarded by the National Institutes of Health. The government has certain rights in the invention. --.

Column 35, Line 65:
Delete "(IL)-1a, IL-10" and replace with -- (IL)-1$\alpha$, IL-1$\beta$ --.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 166

<210> SEQ ID NO 1
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
ggcuacguag cucaguuggu uagagcagcg gccgaguaau uuacgucgac ggugacgucg    60
augguugcgg ccgcgggucacagguucgaa ucccgucgua gccacca                  107

<210> SEQ ID NO 2
<211> LENGTH: 110
<212> TYPE: RNA
<213> ORGANISM: Homo sapiens

<400> SEQUENCE: 2
ggccagcugu gaguguuucu uuggcagugu cuuagcuggu uguugugagc aauaguaagg    60
aagcaaucag caaguauacu gcccuagaag ugcugcacgu ugugggggccc             110

<210> SEQ ID NO 3
<211> LENGTH: 232
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
ggcuacguag cucaguuggu uagagcagcg gccgaguaau uuacgucgag uggaccggcc    60
agcugugagu guucuuugg caguucuua gcugguuguu gugagcaaua guaaggaagc    120
aaucagcaag uauacugccc uagaagugcu gcacguugug gggccaaga gggaagauga    180 cgucgauggu ugcggccgcg ggucacaggu ucgaaucccg ucguagccac ca            232

<210> SEQ ID NO 4
<211> LENGTH: 195
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
ggcuacguag cucaguuggu uagagcagcg gccgguggac cggccagcug ugaguguuuc    60
uuuggcagug ucuuagcugg uuguguguag caauaguaag gaagcaauca gcaaguauac   120
ugcccuagaa gugcugcacg uugugggggcc ggu ccaccc gcggucaca gguucgaauc   180 ccgucguagc cacca                                                    195

<210> SEQ ID NO 5
<211> LENGTH: 198
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
ggcuacguag cucaguuggu uagagcagcg gccgggccag cugugagugu uucuuuggca    60
gugucuuagc ugguuguugu gagcaauagu aaggaagcaa ucagcaagua uacugcccua   120
gaagugcugc acguuguggg gcccgacguc gaugguugcg ccgcgggguc acagguucga   180
aucccgucgu agccacca                                                 198

<210> SEQ ID NO 6
<211> LENGTH: 181
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
ggcuacguag cucaguuggu uagagcagcg gccgggccag cugugagugu uucuuuggca    60
gugucuuagc ugguuguugu gagcaauagu aaggaagcaa ucagcaagua uacugcccua   120
gaagugcugc acguugugggg gccccgcgg gucacagguu cgaaucccgu cguagccacc   180
a                                                                   181

<210> SEQ ID NO 7
<211> LENGTH: 180
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
ggcuacguag cucaguuggu uagagcagcg gccgggccag cugugagugu uucuuuggca    60
gugucuuagc ugguuguugu gagcaauagu aaggaagcaa ucagcaagua uacugcccua   120
gaagugcugc acguuguggg ccccgcggg ucagguuc gaaucccguc guagccacca     180

<210> SEQ ID NO 8
<211> LENGTH: 181

```
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
ggcuacguag cucaguuggu uagagcagcg gccgggcccc gcugugagug uuucuuggc      60 agugucuuag cugguuguug ugagcaauag uaaggaagca aucagcaagu auacugcccu    120
agaagugcug cacguugugg ggccccgcgg gucacagguu cgaaucccgu cguagccacc    180
a                                                                   181

<210> SEQ ID NO 9
<211> LENGTH: 87
<212> TYPE: RNA
<213> ORGANISM: Homo sapiens

<400> SEQUENCE: 9
gguagaauuc caguggcccu gacugaagac cagcaguugu acuggcug uugguuucaa      60 gcagaggccu aaaggacugu cuuccug                                        87

<210> SEQ ID NO 10
<211> LENGTH: 227
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10
ggcuacguag cucaguuggu uagagcagcg gccgaguaau uuacgucgac gaguucuguc    60
cgugagccuu ggguagaauu ccaguggccc ugacugaaga ccagcaguug uacuguggcu    120
guugguuuca agcagaggcc uaaaggacug ucuuccugug gucuguuggc ugacgucg     180 auggugcgg ccgcggguca cagguucgaa ucccgucgua gccacca                  227

<210> SEQ ID NO 11
<211> LENGTH: 175
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
ggcuacguag cucaguuggu uagagcagcg gccgaguaau uuacgucgac ggguagaauu    60
ccaguggccc ugacugaaga ccagcaguug uacuguggcu guugguuuca agcagaggcc    120
uaaaggacug ucuuccugcc gcgggucaca gguucgaauc ccgucguagc cacca       175

<210> SEQ ID NO 12
<211> LENGTH: 159
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 12
ggcuacguag cucaguuggu uagagcagcg gccggguag aauuccagug gcccugacug    60
aagaccagca guuguacugu ggcuguuggu uucaagcaga ggccuaaagg acugucuucc   120
```

```
ugccgcgggu cacagguucg aaucccgucg uagccacca                             159
```

<210> SEQ ID NO 13
<211> LENGTH: 159
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13

```
ggcuacguag cucaguuggu uagagcagcg gccggggaag aauuccagug gcccugacug       60
aagaccagca guuguacugu ggcuguuggu uucaagcaga ggccuaaagg acugucuucc      120
ugccgcgggu cacagguucg aaucccgucg uagccacca                             159
```

<210> SEQ ID NO 14
<211> LENGTH: 159
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 14

```
ggcuacguag cucaguuggu uagagcagcg gccggguag aauuccagug gcccugacug        60
aagaccagca guuguacugu ggcuguuggu uucaagcaga ggccuaaagg acugucuacc      120
ugccgcgggu cacagguucg aaucccgucg uagccacca                             159
```

<210> SEQ ID NO 15
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 15

```
ggcuacguag cucaguuggu uagagcagcg gccggggaag aaugccagug gcccugacug       60
aagaccagca guuguacugu ggcuguuggu uucaagcaga ggccuaaagg acuucuuccu      120
gccgcggguc acagguucga aucccgucgu agccacca                              158
```

<210> SEQ ID NO 16
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16

```
ggcuacguag cucaguuggu uagagcagcg gccgggguag aauuccagug gcccugacug       60
aagaccagca guuguacugu ggcuguuggu uucaagcaga ggccuaaagg aauucuaccu      120
gccgcggguc acagguucga aucccgucgu agccacca                              158
```

<210> SEQ ID NO 17
<211> LENGTH: 87
<212> TYPE: RNA
<213> ORGANISM: Homo sapiens

<400> SEQUENCE: 17

```
ugcgcccuc ucagucccug agacccuaac uugugauguu uaccguuuaa auccacgggu        60
```
aggcucuugg gagcugcgag ucgugcu                                          87

<210> SEQ ID NO 18
<211> LENGTH: 216
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 18
ggcuacguag cucaguuggu uagagcagcg gccgaguaau uuacgucgac gagaaaacau      60
uguugcgcuc cucucagucc cugagacccu aacuugugau guuuaccguu uaaauccacg     120
gguuaggcuc uugggagcug cgagucgugc uuuugcaucc uugacgucga gguugcggc     180 cgcgggucac agguucgaau cccgucuag ccacca                                216

<210> SEQ ID NO 19
<211> LENGTH: 159
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19
ggcuacguag cucaguuggu uagagcagcg gccgugcgcu ccucucaguc ccugagaccc      60
uaacuuguga uguuuaccgu uuaaauccac ggguuaggcu cuuggagcu gcgagucgug     120 cuccgcgggu cacagguucg aaucccgucg uagccacca                            159

<210> SEQ ID NO 20
<211> LENGTH: 159
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 20
ggcuacguag cucaguuggu uagagcagcg gccgagcgcu ccucucaguc ccugagaccc      60
uaacuuguga uguuuaccgu uuaaauccac ggguuaggcu cuuggagcu gcgagucgug     120 cuccgcgggu cacagguucg aaucccgucg uagccacca                            159

<210> SEQ ID NO 21
<211> LENGTH: 159
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 21
ggcuacguag cucaguuggu uagagcagcg gccgugcgcu ccucucaguc ccugagaccc      60
uaacuuguga uguuuaccgu uuaaauccac ggguuaggcu cuuggagcu gcgagucgug     120 caccgcgggu cacagguucg aaucccgucg uagccacca                            159

<210> SEQ ID NO 22
<211> LENGTH: 159
<212> TYPE: RNA
<213> ORGANISM: Artificial Sequence
<220> FEATURE:

<223> OTHER INFORMATION: Description of Artificial Sequence: Synthetic
polynucleotide

<400> SEQUENCE: 22

```
ggcuacguag cucaguuggu uagagcagcg gccgagcgcg acucucaguc ccugagaccc      60
uaacuuguga uguuuaccgu uuaaauccac ggguuaggcu cuugggagcu gcgagucgug     120
cuccgcgggu cacagguucg aaucccgucg uagccacca                            159
```

<210> SEQ ID NO 23
<211> LENGTH: 159
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 23

```
ggcuacguag cucaguuggu uagagcagcg gccgugcgcu ccucucaguc ccugagaccc      60
uaacuuguga uguuuaccgu uuaaauccac ggguuaggcu cuugggagcu gcgaggagug     120
caccgcgggu cacagguucg aaucccgucg uagccacca                            159
```

<210> SEQ ID NO 24
<211> LENGTH: 159
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 24

```
ggcuacguag cucaguuggu uagagcagcg gccgagcgcg acucgcaguc ccugagaccc      60
uaacuuguga uguuuaccgu uuaaauccac ggguuaggcu cuugggagcu gcgagucgug     120
cuccgcgggu cacagguucg aaucccgucg uagccacca                            159
```

<210> SEQ ID NO 25
<211> LENGTH: 159
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 25

```
ggcuacguag cucaguuggu uagagcagcg gccgugcgcu ccucucaguc ccugagaccc      60
uaacuuguga uguuuaccgu uuaaauccac ggguuaggcu cuugggagcu gagaggagug     120
caccgcgggu cacagguucg aaucccgucg uagccacca                            159
```

<210> SEQ ID NO 26
<211> LENGTH: 85
<212> TYPE: RNA
<213> ORGANISM: Homo sapiens

<400> SEQUENCE: 26

```
aggccucucu cuccguguuc acagcggacc uugauuuaaa uguccauaca auuaaggcac      60
gcggugaaug ccaagaaugg ggcug                                            85
```

<210> SEQ ID NO 27
<211> LENGTH: 232
<212> TYPE: RNA
<213> ORGANISM: Artificial Sequence

```
<220> FEATURE:
<223> OTHER INFORMATION: Description of Artificial Sequence: Synthetic
      polynucleotide

<400> SEQUENCE: 27
ggcuacguag cucaguuggu uagagcagcg gccgaguaau uuacgucgac cuccuuuccu      60
uccucaggag aaaggccucu cucuccgugu ucacagcgga ccuugauuua aauguccaua    120
caauuaaggc acgcggugaa ugccaagaau ggggcuggcu gagcaccgug gucggcgga    180 cgucgauggu ugcggccgcg ggucacaggu ucgaaucccg ucuagccac ca             232

<210> SEQ ID NO 28
<211> LENGTH: 228
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 28
ggcuacguag cucaguuggu uagagcagcg gccgaguaau uuacgucgac ccguggaccg      60
gccagcugug aguguuucuu uaaggcacgc ggugaaugcc ugagcaauu aguaaggaag    120 gcauucacgc ugugccuucu agaagugcug cacguugugg ggcccaagag ggaagacguc    180
gauuguugcg gccgcgdgguc acagguucga aucccgucgu agccacca                 228

<210> SEQ ID NO 29
<211> LENGTH: 97
<212> TYPE: RNA
<213> ORGANISM: Homo sapiens

<400> SEQUENCE: 29
accucucuaa caaggugcag agcuuagcug auuggugaac agugauuggu uccgcuuug      60 uucacagugg cuaaguucug caccugaaga gaaggug                              97

<210> SEQ ID NO 30
<211> LENGTH: 227
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 30
ggcuacguag cucaguuggu uagagcagcg gccgaguaau uuacgucgac ccagcgauga      60
ccucucuaac aaggugcaga gcuuagcuga uuggugaaca gugauugguu uccgcuuugu    120
ucacaguggc uaaguucugc accugaagag aaggugagau ggggcaguu aaggacgucg    180 auuguugcgg ccgcggguca cagguucgaa ucccgucgua gccacca                   227

<210> SEQ ID NO 31
<211> LENGTH: 230
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 31
ggcuacguag cucaguuggu uagagcagcg gccgaguaau uuacgucgac ccguggaccg      60
gccagcugug aguguuucuu uucacagugg cuaaguucug cugugagcaa uaguaaggaa    120
```

```
gcagaacuag cucacuguga cuagaagugc ugcacguugu ggggcccaag agggaagacg    180
ucgaugguug cggccgcggg ucacagguuc gaaucccguc guagccacca              230

<210> SEQ ID NO 32
<211> LENGTH: 85
<212> TYPE: RNA
<213> ORGANISM: Homo sapiens

<400> SEQUENCE: 32
ggcugagccg caguaguucu ucaguggcaa gcuuuauguc cugacccagc uaaagcugcc    60
aguugaagaa cuguugcccu cugcc                                        85

<210> SEQ ID NO 33
<211> LENGTH: 210
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 33
ggcuacguag cucaguuggu uagagcagcg gccgaguaau uuacgucgac uuccucucac    60
gcccucaccu ggcugagccg caguaguucu ucaguggcaa gcuuuauguc cugacccagc   120
uaaagcugcc aguugaagaa cuguugcccu cugccccugg cuucgaggag gagccgcggg   180
ucacagguuc gaaucccguc guagccacca                                   210

<210> SEQ ID NO 34
<211> LENGTH: 232
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 34
ggcuacguag cucaguuggu uagagcagcg gccgaguaau uuacgucgac ccguggaccg    60
gccagcugug aguguuucuu aagcugccag uugaagaacu guugagca auaguaagga    120 agcaguucuu aacuuggcag cucuagaagu gcugcacguu gugggcccca agagggaaga   180
cgucgauggu ugcggccgcg ggucacaggu ucgaaucccg ucuagccac ca            232

<210> SEQ ID NO 35
<211> LENGTH: 232
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 35
ggcuacguag cucaguuggu uagagcagcg gccgaguaau uuacgucgac ccguggaccg    60
gccagcugug aguguuucuu caccuauaac aacgguaguu uuugugagca auaguaagga   120
agaaacuacc uuguuuauag gucuagaagu gcugcacguu gugggcccca agagggaaga   180
cgucgauggu ugcggccgcg ggucacaggu ucgaaucccg ucuagccac ca            232

<210> SEQ ID NO 36
<211> LENGTH: 232
<212> TYPE: RNA
<213> ORGANISM: Artificial Sequence
<220> FEATURE:
```

```
<223> OTHER INFORMATION: Description of Artificial Sequence: Synthetic
      polynucleotide

<400> SEQUENCE: 36
ggcuacguag cucaguuggu uagagcagcg gccgaguaau uuacgucgac ccguggaccg    60
gccagcugug aguguuucuu aguguacuc cagcuugugc ccugugagca auaguaagga    120
agggcacaag ugguaguaca accuagaagu gcugcacguu gugggccca agagggaaga   180 cgucgauggu ugcggccgcg ggucacaggu ucgaaucccg ucguagccac ca           232

<210> SEQ ID NO 37
<211> LENGTH: 216
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 37
ggcuacguag cucaguuggu uagagcagcg gccgaguaau uuacgucgac gaggcuugcu    60
gaaggcugua ugcugguugu acuccagcuu gucccguuu uggccacuga cugacgggca    120
caauggagua caaccaggac acaaggccug uuacuagcac ucgacgucga gguugcggc    180 cgcgggucac agguucgaau cccgucguag ccacca                             216

<210> SEQ ID NO 38
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggaucccgac uggcgagagc cagguaacga auggaucc                           38

<210> SEQ ID NO 39
<211> LENGTH: 233
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 39
ggcuacguag cucaguuggu uagagcagcg gccgggaucc cgacuggcga gagccaggua    60
acgaauggau ccguggaccg gccagcugug aguguuucuu uggcagugu uuagcugguu   120 guugugagca auaguaagga agcaaucagc aaguauacug cccuagaagu gcugcacguu   180 gugggcccg guccacccgc gggucacagg uucgaauccc gucguagcca cca           233

<210> SEQ ID NO 40
<211> LENGTH: 233
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 40
ggcuacguag cucaguuggu uagagcagcg gccgguggac cggccagcug ugaguguuuc    60
uuuggcagug ucuuagcugg uuguugugag caauaguaag gaagcaauca gcaaguauac   120
```
ugcccuagaa gugcugcacg uuguggggcc cgguccacgg aucccgacug gcgagagcca    180
gguaacgaau ggaucccgc gggucacagg uucgaauccc gucguagcca cca    233

<210> SEQ ID NO 41
<211> LENGTH: 157
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (58)..(79)
<223> OTHER INFORMATION: a, c, u, g, unknown or other
<220> FEATURE:
<221> NAME/KEY: misc_feature
<222> LOCATION: (58)..(79)
<223> OTHER INFORMATION: n is a, c, g, or u
<220> FEATURE:
<221> NAME/KEY: modified_base
<222> LOCATION: (89)..(110)
<223> OTHER INFORMATION: a, c, u, g, unknown or other
<220> FEATURE:
<221> NAME/KEY: misc_feature
<222> LOCATION: (89)..(110)
<223> OTHER INFORMATION: n is a, c, g, or u

<400> SEQUENCE: 41
ggcuacguag cucaguuggu uagagcagcg gccgaguaau uuacgucgac gaucccnnn    60 nnnnnnnnnn nnnnnnnnnu ucaagagann nnnnnnnnnn nnnnnnnnnn uuuuuggaaa    120 ccgcgggca cagguucgaa ucccgucgua gccacca    157

<210> SEQ ID NO 42
<211> LENGTH: 147
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (56)..(77)
<223> OTHER INFORMATION: a, c, u, g, unknown or other
<220> FEATURE:
<221> NAME/KEY: misc_feature
<222> LOCATION: (56)..(77)
<223> OTHER INFORMATION: n is a, c, g, or u
<220> FEATURE:
<221> NAME/KEY: modified_base
<222> LOCATION: (87)..(108)
<223> OTHER INFORMATION: a, c, u, g, unknown or other
<220> FEATURE:
<221> NAME/KEY: misc_feature
<222> LOCATION: (87)..(108)
<223> OTHER INFORMATION: n is a, c, g, or u

<400> SEQUENCE: 42
ggcuacguag cucaguuggu uagagcagcg gccgaguaau uuacgucgac gaucnnnnn    60 nnnnnnnnnn nnnnnnuuc aagagannnn nnnnnnnnn nnnnnnnga ccgcgggca    120 cagguucgaa ucccgucgua gccacca    147

<210> SEQ ID NO 43
<211> LENGTH: 143
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:

```
<221> NAME/KEY: modified_base
<222> LOCATION: (52)..(73)
<223> OTHER INFORMATION: a, c, u, g, unknown or other
<220> FEATURE:
<221> NAME/KEY: misc_feature
<222> LOCATION: (52)..(73)
<223> OTHER INFORMATION: n is a, c, g, or u
<220> FEATURE:
<221> NAME/KEY: modified_base
<222> LOCATION: (83)..(104)
<223> OTHER INFORMATION: a, c, u, g, unknown or other
<220> FEATURE:
<221> NAME/KEY: misc_feature
<222> LOCATION: (83)..(104)
<223> OTHER INFORMATION: n is a, c, g, or u

<400> SEQUENCE: 43
ggcuacguag cucaguuggu uagagcagcg gccgaguaau uuacgucgac gnnnnnnnnn      60
nnnnnnnnnn nnnuucaaga gannnnnnnn nnnnnnnnnn nnnnuuccgc gggucacagg     120
uucgaauccc gucguagcca cca                                            143

<210> SEQ ID NO 44
<211> LENGTH: 156
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (58)..(79)
<223> OTHER INFORMATION: a, c, u, g, unknown or other
<220> FEATURE:
<221> NAME/KEY: misc_feature
<222> LOCATION: (58)..(79)
<223> OTHER INFORMATION: n is a, c, g, or u
<220> FEATURE:
<221> NAME/KEY: modified_base
<222> LOCATION: (88)..(109)
<223> OTHER INFORMATION: a, c, u, g, unknown or other
<220> FEATURE:
<221> NAME/KEY: misc_feature
<222> LOCATION: (88)..(109)
<223> OTHER INFORMATION: n is a, c, g, or u

<400> SEQUENCE: 44
ggcuacguag cucaguuggu uagagcagcg gccgaguaau uuacgucgac gaucccnnn      60 nnnnnnnnnn nnnnnnnnnu caagagannn nnnnnnnnnn nnnnnnnnnu uuuggaaac     120 cgcgggucac agguucgaau cccgucguag ccacca                              156

<210> SEQ ID NO 45
<211> LENGTH: 148
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (56)..(77)
<223> OTHER INFORMATION: a, c, u, g, unknown or other
<220> FEATURE:
<221> NAME/KEY: misc_feature
<222> LOCATION: (56)..(77)
<223> OTHER INFORMATION: n is a, c, g, or u
<220> FEATURE:
<221> NAME/KEY: modified_base
<222> LOCATION: (86)..(107)
<223> OTHER INFORMATION: a, c, u, g, unknown or other
<220> FEATURE:
<221> NAME/KEY: misc_feature
```

```
<222> LOCATION: (86)..(107)
<223> OTHER INFORMATION: n is a, c, g, or u

<400> SEQUENCE: 45
ggcuacguag cucaguuggu uagagcagcg gccgaguaau uuacgucgac gauccnnnnn    60
nnnnnnnnnn nnnnnnnuca agagannnnn nnnnnnnnnn nnnnnnnuga accgcggguc   120
acagguucga aucccgucgu agccacca                                      148

<210> SEQ ID NO 46
<211> LENGTH: 15
<212> TYPE: RNA
<213> ORGANISM: Homo sapiens

<400> SEQUENCE: 46
cacguugugg ggccc                                                     15

<210> SEQ ID NO 47
<211> LENGTH: 233
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<223> OTHER INFORMATION: Description of Combined DNA/RNA Molecule:
      Synthetic oligonucleotide

<400> SEQUENCE: 47
ggcuacguag cucaguuggu uagagcagcg gccgaguaau uuacgucgac guggaccggc    60
cagcugugag uguuucuuug gcagugucuu agcugguugu ugugagcaau aguaaggaag   120
caaucagcaa guauacugcc cuagaagugc ugcacguug ggggcccaag agggaagatg    180
acgucgaugg uugcggccgc gggucacagg uucgaauccc gucuagccha cca          233

<210> SEQ ID NO 48
<211> LENGTH: 232
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 48
ggcuacguag cucaguuggu uagagcagcg gccgaguaau uuacgucgac ccguggaccg    60
gccagcugug aguguuucuu caccuauaac aacgguaguu uuugugagca auaguaagga   120
agaaacuacc uuguuuauag gucuagaagu gcugcacguu gugggcccca agagggaaga   180
cgucgauggu ugcggccgcg ggucacaggu ucgaauccog ucuagccac ca             232

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgcgtcgac ccagcgatga cctctctaac                                     30

<210> SEQ ID NO 50
<211> LENGTH: 31
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
catcgacgtc cttaactgtc cccatctcac c                                    31

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agtaatttac gtcgacgtgg accggccagc tgtgagtgtt                           40

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cggccgcaac catcgacgtc atcttccctc ttgggcccca caacg                     45

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agtaatttac gtcgacttcg tggctacaga gtttccttag cag                       43

<210> SEQ ID NO 54
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cggccgcaac catcgacgtc caagacattt atcgagggaa ggattgc                   47

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agtaatttac gtcgacctcc tttccttcct caggag                               36

<210> SEQ ID NO 56
<211> LENGTH: 39
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 56
cggccgcaac catcgacgtc cgccgaccca cggtgctca                                    39

<210> SEQ ID NO 57
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
agtaatttac gtcgactact ttccggatca agattag                                      37

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
cggccgcaac catcgacgtc ttggtgtcct tcaagtgcag                                   40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
agtaatttac gtcgacagaa aacattgttg cgctcctctc                                   40

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
cggccgcaac catcgacgtc aggatgcaaa agcacgactc gc                                42

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
agtaatttac gtcgactcta ccgcatcaaa ccagactttt cc                                42

<210> SEQ ID NO 62
<211> LENGTH: 39
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 62
cggccgcaac catcgacgtc ctgctggttc ccctccgcc                           39

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
agtaatttac gtcgacaggc ttgctgtagg ctgtatgctg                          40

<210> SEQ ID NO 64
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cggccgcaac catcgacgtc aatgctagta acaggcatca tacactgtta              50

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agtaatttac gtcgaccttg caagctgaac atccaggtct g                       41

<210> SEQ ID NO 66
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cggccgcaac catcgacgtc cagccaatgg agaacatgtt tcca                    44

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acgcgtcgac gagttctgtc cgtgagcctt gg                                 32

<210> SEQ ID NO 68
<211> LENGTH: 32
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 68
catcgacgtc acagccaaca gaccacagga ag                                    32

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agtaatttac gtcgacaccc tggatgttct cttcac                                36

<210> SEQ ID NO 70
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cggccgcaac catcgacgtc gatgcagact tttctatcac g                          41

<210> SEQ ID NO 71
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
agtaatttac gtcgacccgt ggaccggcca gctgtgagtg tttctttaag gcacgcggtg      60
aatgcctgtg agcaatagta aggaaggc                                        88

<210> SEQ ID NO 72
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cggccgcaac catcgacgtc ttccctcttg ggccccacaa cgtgcagcac ttctagaagg      60
cacagcgtga atgccttcct tactattgc                                       89

<210> SEQ ID NO 73
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
agtaatttac gtcgacccgt ggaccggcca gctgtgagtg tttcttcacc tataacaacg      60
gtagtttttg tgagcaatag taaggaagaa                                      90

```
<210> SEQ ID NO 74
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cggccgcaac catcgacgtc ttccctcttg ggccccacaa cgtgcagcac ttctagacct    60
ataaacaagg tagtttcttc cttactattg                                     90

<210> SEQ ID NO 75
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
agtaatttac gtcgacccgt ggaccggcca gctgtgagtg tttcttagtt gtactccagc    60
ttgtgccctg tgagcaatag taaggaaggg                                     90

<210> SEQ ID NO 76
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cggccgcaac catcgacgtc ttccctcttg ggccccacaa cgtgcagcac ttctaggttg    60
tactaccact tgtgcccttc cttactattg                                     90

<210> SEQ ID NO 77
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agtaatttac gtcgacgagg cttgctgaag gctgtatgct ggttgtactc cagcttgtgc    60
ccgttttggc cactgactga cgg                                            83

<210> SEQ ID NO 78
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cggccgcaac catcgacgtc gagtgctagt aacaggcctt gtgtcctggt tgtactccat    60
tgtgcccgtc agtcagtggc caa                                            83

<210> SEQ ID NO 79
<211> LENGTH: 74
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 79
gttagagcag cggccgggat cccgactggc gagagccagg taacgaatgg atccgtggac    60
cggccagctg tgag                                                      74

<210> SEQ ID NO 80
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gaacctgtga cccgcgggtg gaccgggccc cacaacgtgc agca                      44

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gttagagcag cggccggtgg accggccagc tgtgag                               36

<210> SEQ ID NO 82
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gaacctgtga cccgcgggga tccattcgtt acctggctct cgccagtcgg gatccgtgga    60
ccgggcccca caacgtgcag ca                                             82

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcgctaaggc acgcggtg                                                   18

<210> SEQ ID NO 84
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gtcgtatcca gtgcagggtc cgaggtattc gcactggata cgacaattgt                50

<210> SEQ ID NO 85
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cctgtggagt tgatcctagt ctgggtg                                        27

<210> SEQ ID NO 86
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gtcgtatcca gtgcagggtc cgaggtattc gcactggata cgacggcatt              50

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gcgctaaggc acgcggtg                                                 18

<210> SEQ ID NO 88
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtcgtatcca gtgcagggtc cgaggtattc gcactggata cgac                   44

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gcgcgcagtt gtactccagc tt                                           22

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acgtaaacgg ccacaagttc                                              20

<210> SEQ ID NO 91
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aagtcgtgct gcttcatgtg                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cctaaagcat acgggtcctg                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tttcactttg ccaaacacca                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gtaacccgtt gaaccccatt                                              20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ccatccaatc ggtagtagcg                                              20

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
acgcgtcgac agccttgggt agaattccag                                   30

<210> SEQ ID NO 97
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 97
catcgacgtc gagctgtagg ttgtttcttc c                                      31

<210> SEQ ID NO 98
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
acgcgtcgac gagttctgtc cgtgagcctt g                                      31

<210> SEQ ID NO 99
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
catcgacgtc cctcttccaa tgggatggtg ag                                     32

<210> SEQ ID NO 100
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
agtaatttac gtcgacggcc agctgtgagt gtttctttgg                             40

<210> SEQ ID NO 101
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cggccgcaac catcgacgtc tgggccccac aacgtgcagc actt                        44

<210> SEQ ID NO 102
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gtcgtatcca gtgcagggtc cgaggtattc gcactggata cgacacaacc                  50

<210> SEQ ID NO 103
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 103
ggctacgtag ctcagttggt                                                    20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tggtggctac gacgggattc                                                    20

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ggccagctgt gagtgtttct ttgg                                               24

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gggccccaca acgtgcag                                                      18

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cgcgctggca gtgtcttagc t                                                  21

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gtgcagggtc cgaggt                                                        16

<210> SEQ ID NO 109
<211> LENGTH: 17
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 109
ctcgcttcgg cagcaca                                                        17

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aacgcttcac gaatttgcgt                                                     20

<210> SEQ ID NO 111
<211> LENGTH: 161
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (53)..(109)
<223> OTHER INFORMATION: a, c, u, g, unknown or other
<220> FEATURE:
<221> NAME/KEY: misc_feature
<222> LOCATION: (53)..(109)
<223> OTHER INFORMATION: n is a, c, g, or u

<400> SEQUENCE: 111
ggcuacguag cucaguuggu uagagcagcg gccgaguaau uuacgucgag ugnnnnnnnn          60
nnnnnnnnnn nnnnnnnnnn nnnnnnnnnn nnnnnnnnnn nnnnnnnnnc gucgaugguu        120
gcggccgcgg gucacagguu cgaaucccgu cguagccacc a                            161

<210> SEQ ID NO 112
<211> LENGTH: 63
<212> TYPE: RNA
<213> ORGANISM: Homo sapiens
<220> FEATURE:
<221> NAME/KEY: misc_feature
<222> LOCATION: (37)..(38)
<223> OTHER INFORMATION: Nucleotides at these positions are
      non-consecutive and are seperated by a non-disclosed sequence

<400> SEQUENCE: 112
ggcuacguag cucaguuggu uagagcagcg gccgaguagg uucgaauccc gucguagcca         60
cca                                                                       63

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
aguugguuag agcagcggc                                                      19

<210> SEQ ID NO 114
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 114
aguugguuag agcagcggcc                                                    20

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
aguugguuag agcagcggcc g                                                  21

<210> SEQ ID NO 116
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
aguugguuag agcagcggcc gag                                                23

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
aaucccgucg uagccacca                                                     19

<210> SEQ ID NO 118
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
aucccgucgu agccacca                                                      18

<210> SEQ ID NO 119
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cccgucguag ccacca                                                        16

<210> SEQ ID NO 120
<211> LENGTH: 15
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 120
aaucccgucg uagcc                                                          15

<210> SEQ ID NO 121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121 gaucccguc guagccacca                                                      20

<210> SEQ ID NO 122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
guucgaaucc cgucguagcc                                                     20

<210> SEQ ID NO 123
<211> LENGTH: 56
<212> TYPE: RNA
<213> ORGANISM: Homo sapiens
<220> FEATURE:
<221> NAME/KEY: misc_feature
<222> LOCATION: (32)..(33)
<223> OTHER INFORMATION: Nucleotides at these positions are
      non-consecutive and are seperated by a non-disclosed sequence

<400> SEQUENCE: 123
ggcuacguag cucaguuggu uagagcagcg gcguucgaau cccgucguag ccacca             56

<210> SEQ ID NO 124
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ggcuacguag cucaguuggu uagagcagcg gc                                       32

<210> SEQ ID NO 125
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ggcuacguag cucaguuggu uagagcagcg                                          30

<210> SEQ ID NO 126
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 126
guucgaaucc cgucguagcc                                                    20

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
cgaaucccgu cguagccacc a                                                  21

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gaaucccguc guagccacca                                                    20

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129 aauccgucg uagccacca                                                      19

<210> SEQ ID NO 130
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
aucccgucgu agccacca                                                      18

<210> SEQ ID NO 131
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
cccgucguag ccacca                                                        16

<210> SEQ ID NO 132
<211> LENGTH: 140
<212> TYPE: RNA
<213> ORGANISM: Artificial Sequence
```

```
<220> FEATURE:
<223> OTHER INFORMATION: Description of Artificial Sequence: Synthetic
      polynucleotide

<400> SEQUENCE: 132
gaguucuguc cgugagccuu ggguagaauu ccaguggccc ugacugaaga ccagcaguug    60
uacuguggcu guugguuuca agcagaggcc uaaaggacug ucuuccugug gucuguuggc   120
ugugacgucg augguugcgg                                                140

<210> SEQ ID NO 133
<211> LENGTH: 233
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 133
ggcuacguag cucaguuggu uagagcagcg gccgaguaau uuacgucgac guggaccggc    60
cagcugugag uguuucuuug gcagugucuu agcugguugu ugugagcaau aguaaggaag   120
caaucagcaa guauacugcc cuagaagugc ugcacguug gggggcccaag agggaagaug   180 acgucgaugg uugcggccgc gggucacagg uucgaauccc gucguagcca cca           233

<210> SEQ ID NO 134
<211> LENGTH: 67
<212> TYPE: RNA
<213> ORGANISM: Homo sapiens
<220> FEATURE:
<221> NAME/KEY: misc_feature
<222> LOCATION: (32)..(33)
<223> OTHER INFORMATION: Nucleotides at these positions are
      non-consecutive and are seperated by a non-disclosed sequence

<400> SEQUENCE: 134
ggcuacguag cucaguuggu uagagcagcg gccgagucac aagguucgaa ucccgucgua    60
gccacca                                                              67

<210> SEQ ID NO 135
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ccacagguuc gaaucccguc guagccacca                                     30

<210> SEQ ID NO 136
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uucgaauccc gucguagcca cc                                             22

<210> SEQ ID NO 137
<211> LENGTH: 28
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 137
acagguucga aucccgucgu agccacca                                            28

<210> SEQ ID NO 138
<211> LENGTH: 50
<212> TYPE: DNA
<213> ORGANISM: Artificial Sequence
<220> FEATURE:
<223> OTHER INFORMATION: Synthetic sequence

<400> SEQUENCE: 138
gtcgtatcca gtgcagggtc cgaggtattc gcactggata cgacgggcac                    50

<210> SEQ ID NO 139
<211> LENGTH: 50
<212> TYPE: DNA
<213> ORGANISM: Artificial Sequence
<220> FEATURE:
<223> OTHER INFORMATION: Synthetic sequence

<400> SEQUENCE: 139
gtcgtatcca gtgcagggtc cgaggtattc gcactggata cgacacaacc                    50

<210> SEQ ID NO 140
<211> LENGTH: 63
<212> TYPE: DNA
<213> ORGANISM: Artificial Sequence
<220> FEATURE:
<223> OTHER INFORMATION: Synthetic sequence

<400> SEQUENCE: 140
ggcuacguag cucaguuggu uagagcagcg gccgaguagg uucgaauccc gucguagcca         60
cca                                                                       63

<210> SEQ ID NO 141
<211> LENGTH: 19
<212> TYPE: DNA
<213> ORGANISM: Artificial Sequence
<220> FEATURE:
<223> OTHER INFORMATION: Synthetic sequence

<400> SEQUENCE: 141
aguugguuag agcagcggc                                                      19

<210> SEQ ID NO 142
<211> LENGTH: 20
<212> TYPE: DNA
<213> ORGANISM: Artificial Sequence
<220> FEATURE:
<223> OTHER INFORMATION: Synthetic sequence

<400> SEQUENCE: 142
aguugguuag agcagcggcc                                                     20

<210> SEQ ID NO 143
<211> LENGTH: 21
<212> TYPE: DNA
<213> ORGANISM: Artificial Sequence
<220> FEATURE:
<223> OTHER INFORMATION: Synthetic sequence

<400> SEQUENCE: 143
```

-continued aguugguuag agcagcggcc g                                     21

<210> SEQ ID NO 144
<211> LENGTH: 23
<212> TYPE: DNA
<213> ORGANISM: Artificial Sequence
<220> FEATURE:
<223> OTHER INFORMATION: Synthetic sequence

<400> SEQUENCE: 144
aguugguuag agcagcggcc gag                                   23

<210> SEQ ID NO 145
<211> LENGTH: 19
<212> TYPE: DNA
<213> ORGANISM: Artificial Sequence
<220> FEATURE:
<223> OTHER INFORMATION: Synthetic sequence

<400> SEQUENCE: 145
aaucccgucg uagccacca                                        19

<210> SEQ ID NO 146
<211> LENGTH: 18
<212> TYPE: DNA
<213> ORGANISM: Artificial Sequence
<220> FEATURE:
<223> OTHER INFORMATION: Synthetic sequence

<400> SEQUENCE: 146
aucccgucgu agccacca                                         18

<210> SEQ ID NO 147
<211> LENGTH: 16
<212> TYPE: DNA
<213> ORGANISM: Artificial Sequence
<220> FEATURE:
<223> OTHER INFORMATION: Synthetic sequence

<400> SEQUENCE: 147
cccgucguag ccacca                                           16

<210> SEQ ID NO 148
<211> LENGTH: 14
<212> TYPE: DNA
<213> ORGANISM: Artificial Sequence
<220> FEATURE:
<223> OTHER INFORMATION: Synthetic sequence

<400> SEQUENCE: 148
aauccgucgu agcc                                             14

<210> SEQ ID NO 149
<211> LENGTH: 20
<212> TYPE: DNA
<213> ORGANISM: Artificial Sequence
<220> FEATURE:
<223> OTHER INFORMATION: Synthetic sequence

<400> SEQUENCE: 149
gaaucccguc guagccacca                                       20

<210> SEQ ID NO 150
<211> LENGTH: 20
<212> TYPE: DNA

<213> ORGANISM: Artificial Sequence
<220> FEATURE:
<223> OTHER INFORMATION: Synthetic sequence

<400> SEQUENCE: 150
guucgaaucc cgucguagcc                                              20

<210> SEQ ID NO 151
<211> LENGTH: 56
<212> TYPE: DNA
<213> ORGANISM: Artificial Sequence
<220> FEATURE:
<223> OTHER INFORMATION: Synthetic sequence

<400> SEQUENCE: 151
ggcuacguag cucaguuggu uagagcagcg gcguucgaau cccgucguag ccacca       56

<210> SEQ ID NO 152
<211> LENGTH: 32
<212> TYPE: DNA
<213> ORGANISM: Artificial Sequence
<220> FEATURE:
<223> OTHER INFORMATION: Synthetic sequence

<400> SEQUENCE: 152
ggcuacguag cucaguuggu uagagcagcg gc                                32

<210> SEQ ID NO 153
<211> LENGTH: 30
<212> TYPE: DNA
<213> ORGANISM: Artificial Sequence
<220> FEATURE:
<223> OTHER INFORMATION: Synthetic sequence

<400> SEQUENCE: 153
ggcuacguag cucaguuggu uagagcagcg                                   30

<210> SEQ ID NO 154
<211> LENGTH: 20
<212> TYPE: DNA
<213> ORGANISM: Artificial Sequence
<220> FEATURE:
<223> OTHER INFORMATION: Synthetic sequence

<400> SEQUENCE: 154
guucgaaucc cgucguagcc                                              20

<210> SEQ ID NO 155
<211> LENGTH: 21
<212> TYPE: DNA
<213> ORGANISM: Artificial Sequence
<220> FEATURE:
<223> OTHER INFORMATION: Synthetic sequence

<400> SEQUENCE: 155
cgaaucccgu cguagccacc a                                            21

<210> SEQ ID NO 156
<211> LENGTH: 19
<212> TYPE: DNA
<213> ORGANISM: Artificial Sequence
<220> FEATURE:
<223> OTHER INFORMATION: Synthetic sequence

<400> SEQUENCE: 156
gaauccgucg uagccacca                                               19

<210> SEQ ID NO 157
<211> LENGTH: 19
<212> TYPE: DNA
<213> ORGANISM: Artificial Sequence
<220> FEATURE:
<223> OTHER INFORMATION: Synthetic sequence

<400> SEQUENCE: 157
aaucccgucg uagccacca                                                    19

<210> SEQ ID NO 158
<211> LENGTH: 18
<212> TYPE: DNA
<213> ORGANISM: Artificial Sequence
<220> FEATURE:
<223> OTHER INFORMATION: Synthetic sequence

<400> SEQUENCE: 158
aucccgucgu agccacca                                                     18

<210> SEQ ID NO 159
<211> LENGTH: 16
<212> TYPE: DNA
<213> ORGANISM: Artificial Sequence
<220> FEATURE:
<223> OTHER INFORMATION: Synthetic sequence

<400> SEQUENCE: 159
cccgucguag ccacca                                                       16

<210> SEQ ID NO 160
<211> LENGTH: 107
<212> TYPE: DNA
<213> ORGANISM: Artificial Sequence
<220> FEATURE:
<223> OTHER INFORMATION: Synthetic sequence

<400> SEQUENCE: 160
ggcuacguag cucaguuggu uagagcagcg gccgaguaau uuacgucgac ggugacgucg       60
augguugcgg ccgcgggucu cagguucgaa ucccgucgua gccacca                    107

<210> SEQ ID NO 161
<211> LENGTH: 67
<212> TYPE: DNA
<213> ORGANISM: Artificial Sequence
<220> FEATURE:
<223> OTHER INFORMATION: Synthetic sequence

<400> SEQUENCE: 161
ggcuacguag cucaguuggu uagagcagcg gccgagucac aagguucgaa ucccgucgua       60
gccacca                                                                 67

<210> SEQ ID NO 162
<211> LENGTH: 30
<212> TYPE: DNA
<213> ORGANISM: Artificial Sequence
<220> FEATURE:
<223> OTHER INFORMATION: Synthetic sequence

<400> SEQUENCE: 162
ccacagguuc gaaucccguc guagccacca                                        30

<210> SEQ ID NO 163

```
<211> LENGTH: 15
<212> TYPE: DNA
<213> ORGANISM: Artificial Sequence
<220> FEATURE:
<223> OTHER INFORMATION: Synthetic sequence

<400> SEQUENCE: 163
aaucccgucg uagcc                                                    15

<210> SEQ ID NO 164
<211> LENGTH: 22
<212> TYPE: DNA
<213> ORGANISM: Artificial Sequence
<220> FEATURE:
<223> OTHER INFORMATION: Synthetic sequence

<400> SEQUENCE: 164
uucgaauccc gucguagcca cc                                            22

<210> SEQ ID NO 165
<211> LENGTH: 28
<212> TYPE: DNA
<213> ORGANISM: Artificial Sequence
<220> FEATURE:
<223> OTHER INFORMATION: Synthetic sequence

<400> SEQUENCE: 165
acagguucga aucccgucgu agccacca                                      28

<210> SEQ ID NO 166
<211> LENGTH: 38
<212> TYPE: DNA
<213> ORGANISM: Artificial Sequence
<220> FEATURE:
<223> OTHER INFORMATION: Synthetic sequence

<400> SEQUENCE: 166
ggaucccgac uggcgagagc cagguaacga auggaucc                           38
```